(12) United States Patent
Sellergren et al.

(10) Patent No.: US 12,038,447 B2
(45) Date of Patent: Jul. 16, 2024

(54) LIPID BILAYER MEMBRANE MIMIC

(71) Applicant: Börje Sellergren, Helsingborg (SE)

(72) Inventors: Börje Sellergren, Helsingborg (SE); Sing Yee Yeung, Bentley (AU); Yulia Sergeeva, Veberöd (SE)

(73) Assignee: Börje Sellergren, Helsingborg (SE)

( * ) Notice: Subject to any disclaimer, the term of this patent is extended or adjusted under 35 U.S.C. 154(b) by 506 days.

(21) Appl. No.: 16/762,207

(22) PCT Filed: Nov. 9, 2018

(86) PCT No.: PCT/SE2018/051141
§ 371 (c)(1),
(2) Date: May 7, 2020

(87) PCT Pub. No.: WO2019/093953
PCT Pub. Date: May 16, 2019

(65) Prior Publication Data
US 2020/0355707 A1    Nov. 12, 2020

(30) Foreign Application Priority Data
Nov. 7, 2017 (SE) .................................. 1730306-6

(51) Int. Cl.
*G01N 33/92* (2006.01)
*G01N 33/53* (2006.01)
*G01N 33/569* (2006.01)

(52) U.S. Cl.
CPC ......... *G01N 33/92* (2013.01); *G01N 33/5308* (2013.01); *G01N 33/56983* (2013.01); *G01N 2333/11* (2013.01); *G01N 2333/62* (2013.01)

(58) Field of Classification Search
CPC ............... G01N 33/92; G01N 2333/11; G01N 33/56983; G01N 33/53
See application file for complete search history.

(56) References Cited

U.S. PATENT DOCUMENTS 6,444,321 B1    9/2002   Arnebrant et al.

FOREIGN PATENT DOCUMENTS

| WO | WO-0126800 A1 * | 4/2001 | ......... B01J 19/0046 |
| WO | 2014039493 A1 | 3/2014 | |

OTHER PUBLICATIONS

Sing Yee Yeung, "Stimuli-Responsive Lipid Bilayer Mimics for Protein, Virus and Cell Recognition", 2018 ( Year: 2018).*
Jean-Paul Douliez, "Self-Assembly of Hollow Cones in a Bola-amphiphile/Hexadiamine Salt Solution", Oct. 21, 2005 (Year: 2005).*
Yeung, S.Y. et al., "Reversible Self-Assembled Monolayers (rSAMs) as Robust and Fluidic Lipid Bilayer Mimics," Langmuir 2018, Published online on Mar. 19, 2018, vol. 34 (13), pp. 4107-4115.

(Continued)

*Primary Examiner* — Maurice C Smith
(74) *Attorney, Agent, or Firm* — Colson Law Group, PLLC

(57) ABSTRACT

The present invention discloses a new approach to produce membrane or lipid bilayer mimicking surfaces, their use in the aforementioned areas of application, a kit of parts and a sensor.

18 Claims, 51 Drawing Sheets

(56) References Cited

OTHER PUBLICATIONS

Yeung, S.Y. et al., "Reversible Self-Assembled Monolayers (rSAMs): Adaptable Surfaces for Enhanced Multivalent Interactions and Ultrasensitive Virus Detection," ACS Central Science 2017, Published online on Nov. 10, 2017, vol. 3, Issue 11, pp. 1198-1207.

Sun, XL. et al., "Membrane-Mimetic Films of Asymmetric Phosphatidylcholine Lipid Bolaamphiphiles," Langmuir 2006, Published in issue Jan. 1, 2006, vol. 22, Issue 3, doi: 10.1021/la052125t, pp. 1201-1208.

Benvengu, T. et al., "Novel bolaamphiphiles with saccharidic polar headgroups: synthesis and supramolecular self-assemblies," Ploymer internationals (2003), First published Mar. 21, 2003, vol. 52, Issue 4, doi: 10.1002/pi.1056, pp. 500-506.

Jacquemet, A. et al., "Archaeal tetraether bipolar lipids: Structures, functions and applications," Biochimie, available online Jan. 27, 2009, vol. 91, Issue 6, doi:10.1016/j.biochi.2009.01.006, pp. 711-717.

Chong, P.LG., "Archaebacterial bipolar tetraether lipids: Physicochemical and membrane properties," Chemistry and Physics of Lipids, available online Jan. 12, 2010, vol. 163, Issue 3, doi:10.1016/j.chemphyslip.2009.12.006, pp. 253-265.

International Search Report of the International Searching Authority for PCT/SE2018/051141 with mailing date of Feb. 12, 2019.

\* cited by examiner

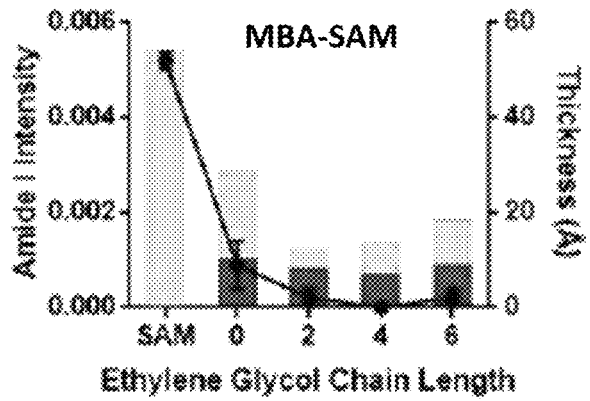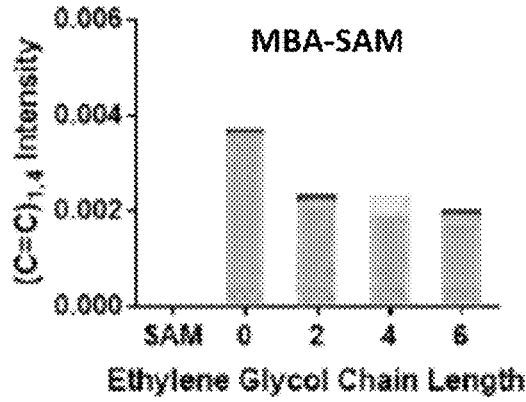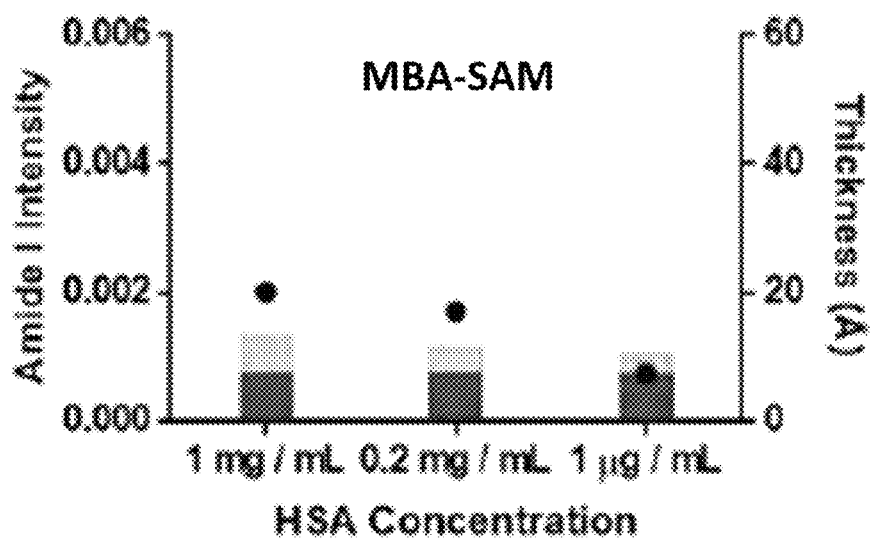

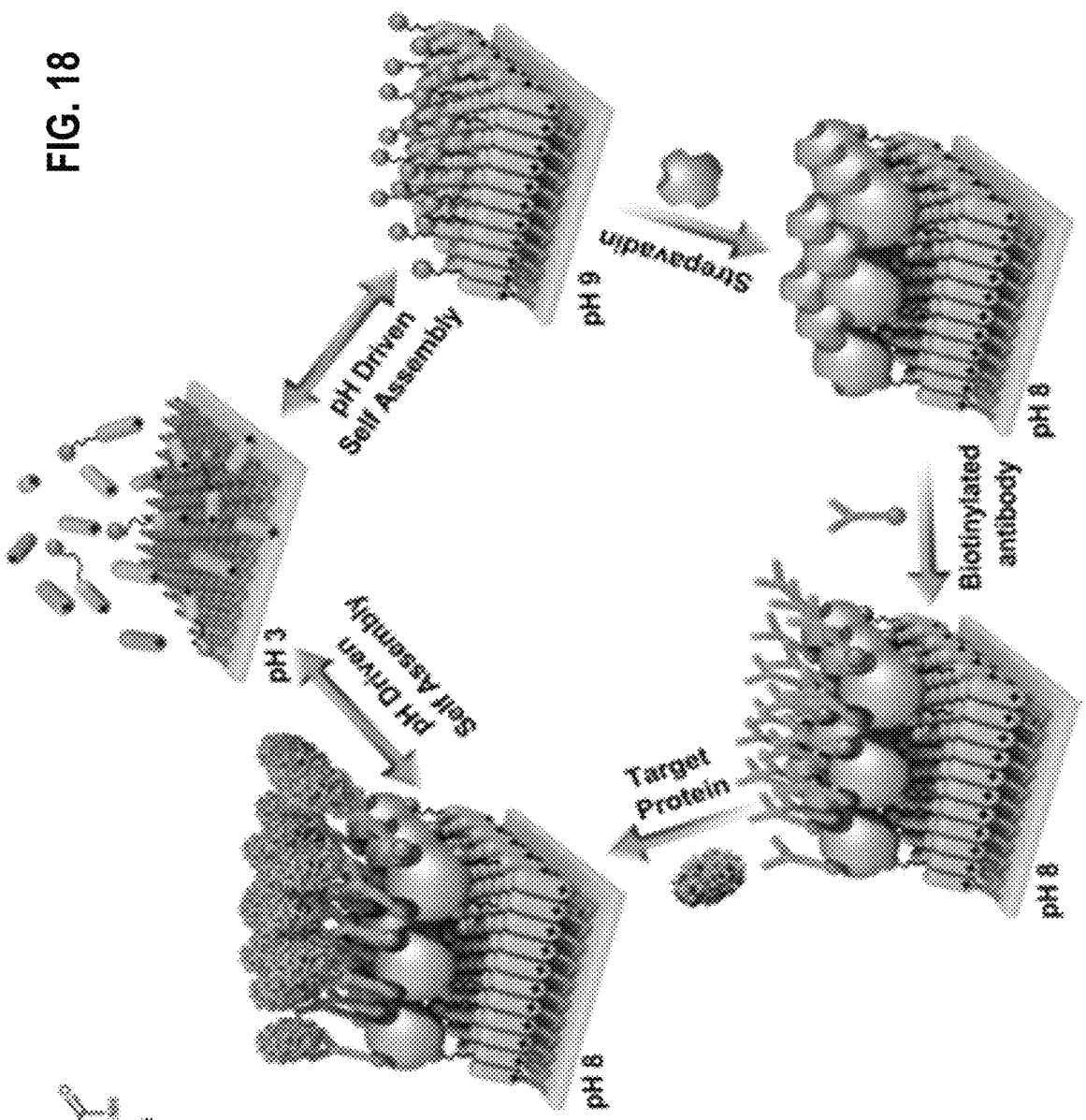
FIG. 18
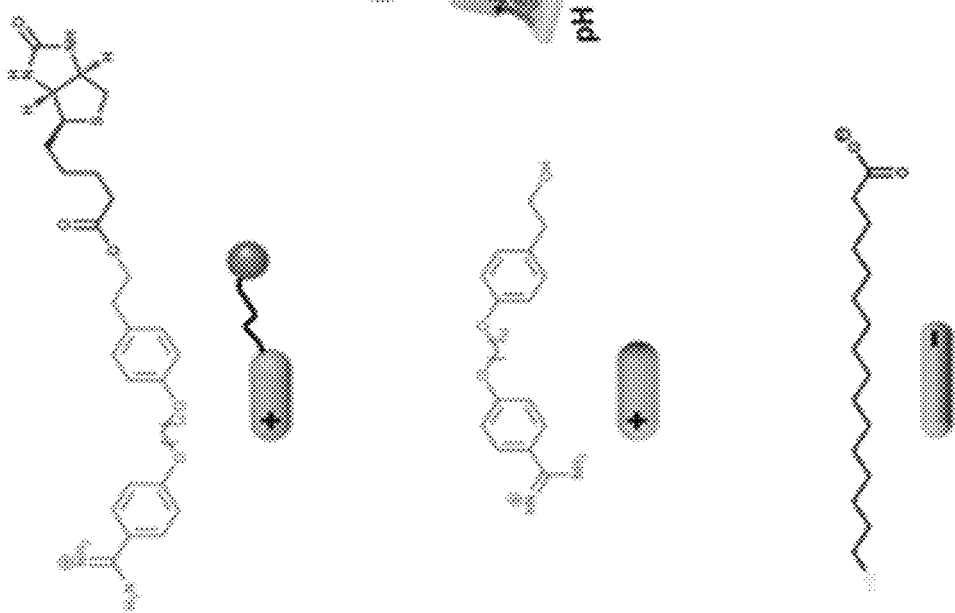

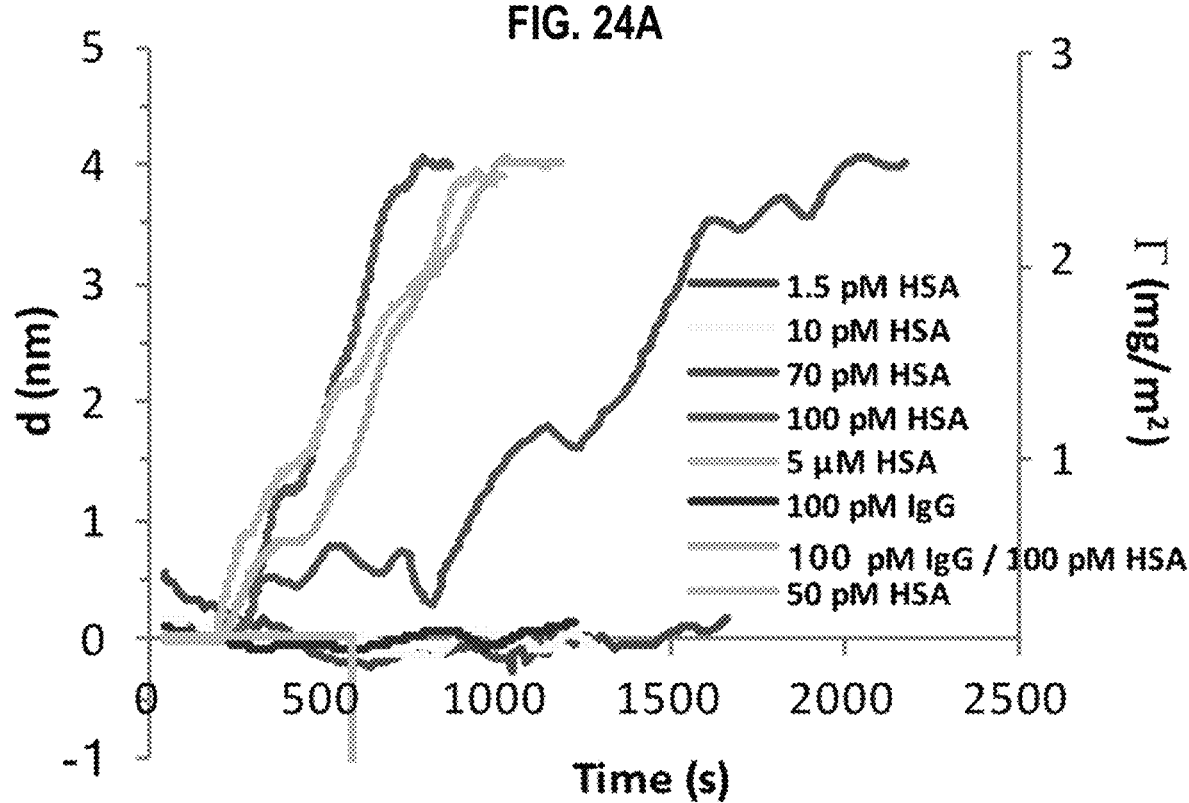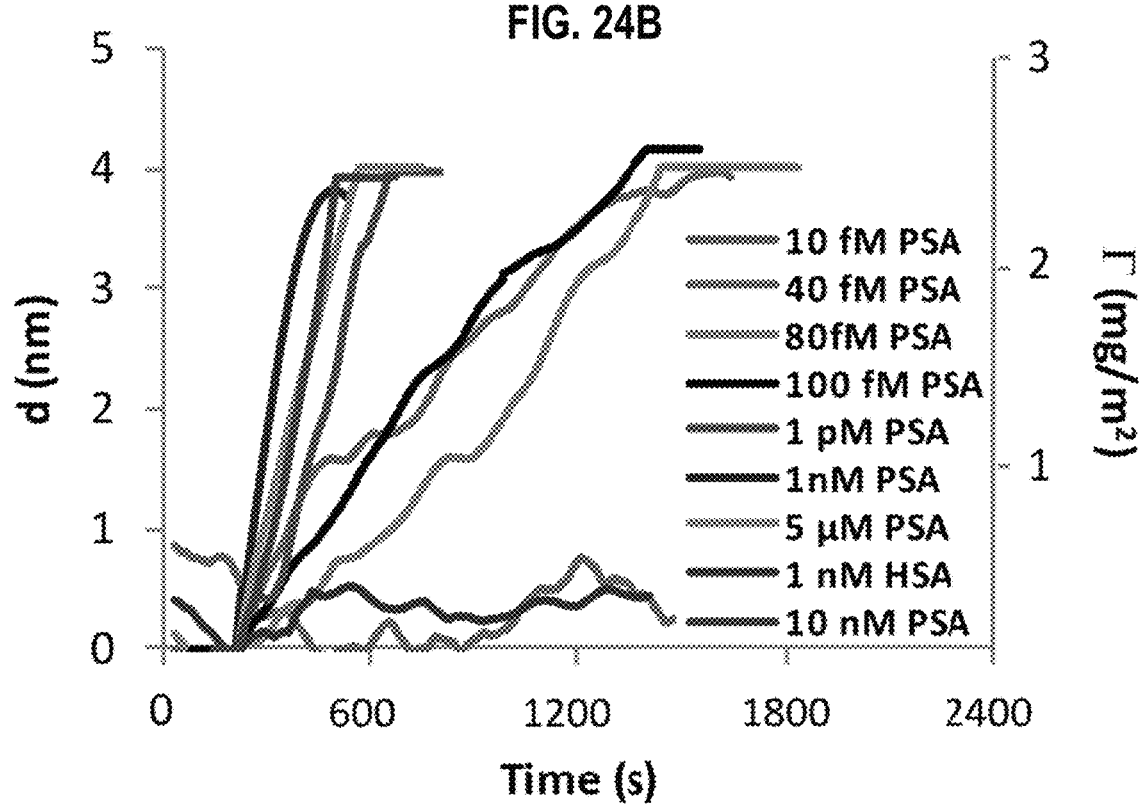

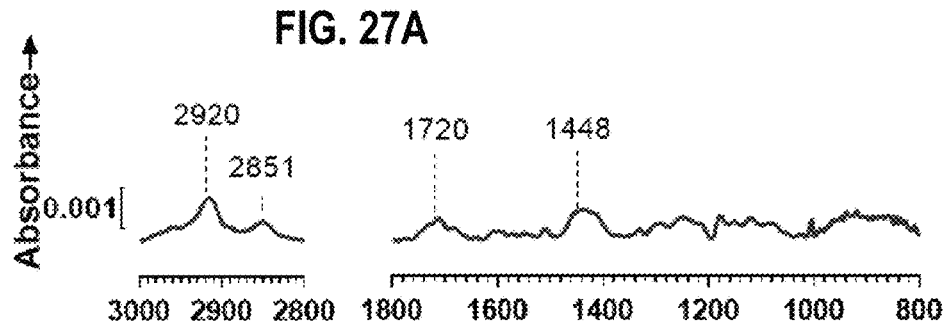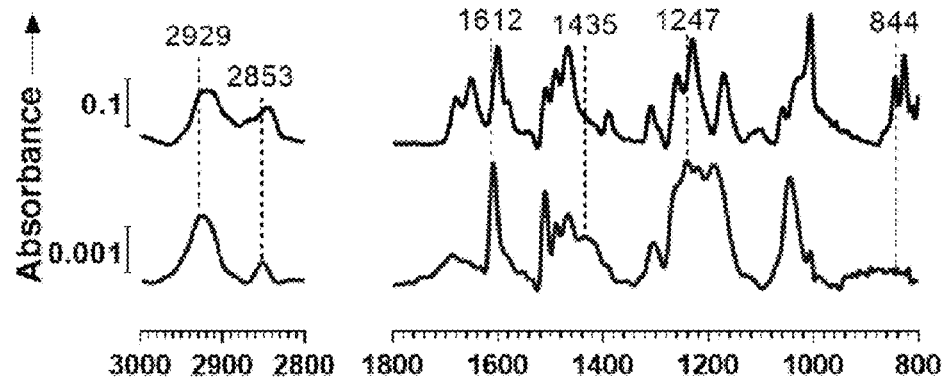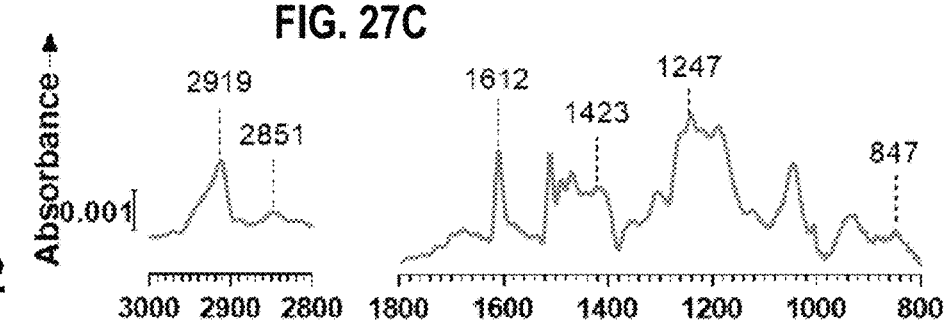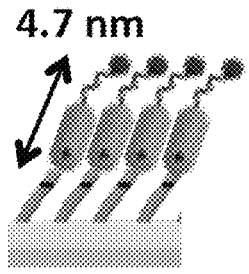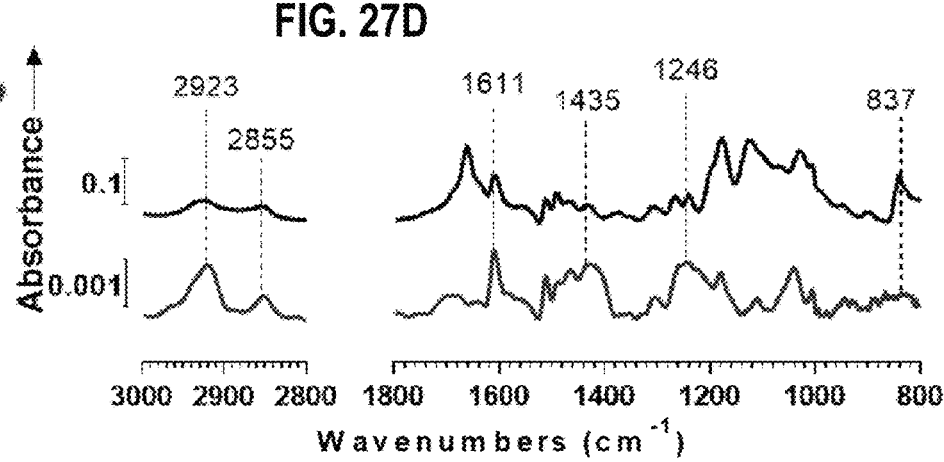

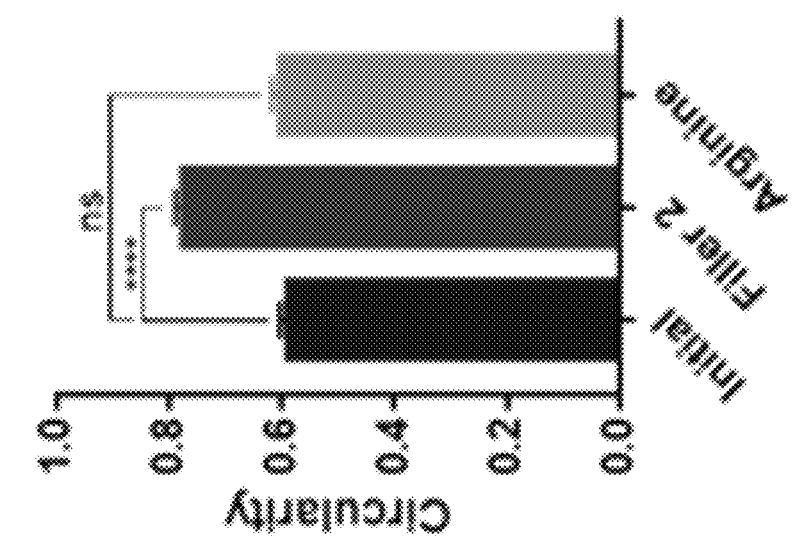
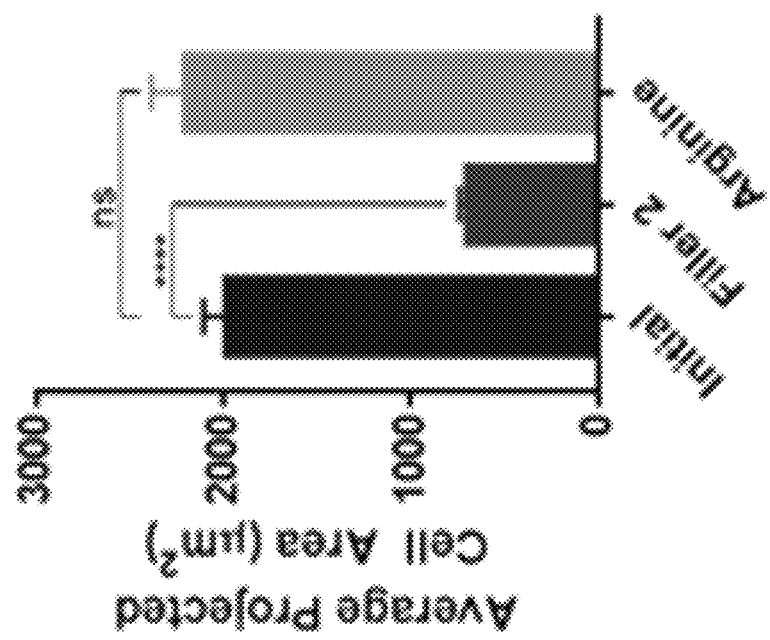
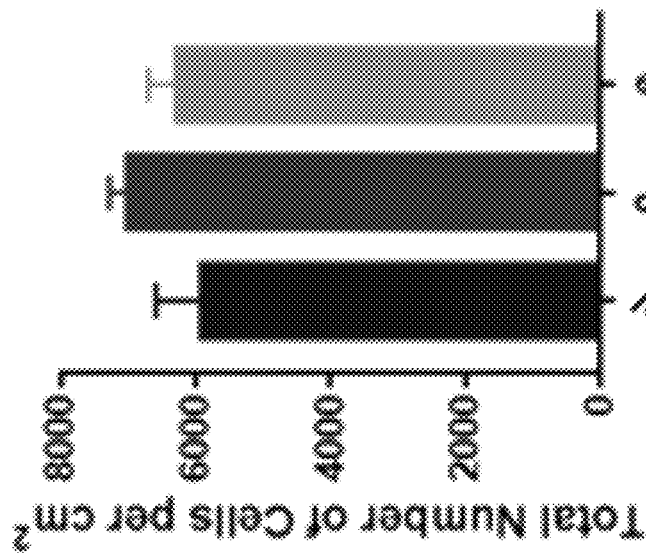

LIPID BILAYER MEMBRANE MIMIC

TECHNICAL FIELD

The present invention describes membrane mimicking surfaces comprising lipid bilayer of self-assembled Bolaform amphiphiles on a surface, their use and a method for their production.

TECHNICAL BACKGROUND

As drug delivery, therapy, and medical imaging become more target specific, there is a critical need for high fidelity and high-throughput screening methods for cell surface interactions. This has led to development of membrane mimicking surfaces.

The most well studied two-dimensional biomimetic cellular membrane models are self-assembled monolayers (Ulman, A., *An Introduction of Ultrahin Organic Films. From Langmuir-Blodgett to Self-assembly.* 1 ed. 1991, New York: Academic Press, Inc) and supported lipid bi-layers (Deng, Y. et al. Fluidic and Air-Stable Supported Lipid Bilayer and Cell-Mimicking Microarrays. J. Am. Chem. Soc. 2008, 130, 6267). The former has the advantage of control over ligand density, homogeneity and orientation, allowing unambiguous interaction studies. It however lacks lateral mobility, which is one of the most important aspects of cellular membranes. Supported lipid bilayers are laterally mobile but they are not robust enough to be used as biosensors. The layers formed are often not air stable and prone to exchange with proteins. Air stable and robust alternatives such as hybrid lipid bilayers often lose their lateral mobility. Literature examples that contain both characteristics are rare and typically requires extensive laboratory skills to fabricate. Membrane mimicking surfaces that feature the fluidic nature of lipid bi-layers combined with the robustness of chemisorbed self-assembled monolayers are thus far not known. Such systems would find important applications in the following areas.

Virus and Pathogen Sensing

Rapid diagnosis of influenza viruses and bacterial pathogens during an outbreak is critical for disease control (Gopinath et al. *Sensing strategies for influenza surveillance.* Biosensors and Bioelectronics 2014, 61, 357-369). There are currently 3 types of diagnostic tests for influenza viruses: virus isolation, antigen capture immunoassays and molecular diagnostic tests. Although effective and sensitive, these methods require trained personnel and a long testing time. Hence, development of probes and sensors capable of rapid typing and subtyping of influenza virus are highly desirable. Antibodies and aptamers are the most common probes for virus recognition offering excellent specificity for virus subtypes. Nevertheless, for the development of robust biosensors, avoiding labile and expensive biomolecular recognition elements offer clear advantages. In this context, biomimetic sensors employing glycans as recognition elements are highly interesting.

This relates to the multivalent binding essential for the adhearence of bacteria or virus particles onto host cell surfaces (M. Mammen, S.-K. Choi and G. M. Whitesides, *Angewandte Chemie International Edition,* 1998, 37, 2754-2794). In this context, the adhearence of influenza virus particles to the surfaces of bronchial epithelium cells have been extensively studied. The virus particles are 80-120 nanometers in diameter and of roughly spherical shape. Their viral envelope contain two main proteins, the lectin hemagglutinin (HA) and the enzyme neuraminidase (NA), each playing a distinctive role during infection. HA mediates binding to and entry into the target cells while NA is involved in the release of new virions from infected cells.

The adhesion is driven by interactions between several trimers of HA on the virus surface and several sialic acids (SAs) preferentially $\alpha$-2,6 and $\alpha$-2,3 sialic acids on human and bird cells, respectively, of the glycoproteins on the surface of the target cell. In support of this adhesion mechanism, Whitesides et al. showed that polymers or liposomes modified with sialic acids could inhibit this process (M. Mammen, S.-K. Choi and G. M. Whitesides, *Angewandte Chemie International Edition,* 1998, 37, 2754-2794). Moreover biomimetic virus sensors have been constructed based on this principle.

The recognition here relies on multivalent interactions between the glycan decorated surface and the virus particles. However, the glycans are typically covalently anchored on the surface by thiol gold chemistry precluding a dynamic adaptation of the glycan head groups to the guest surface. Moreover, in spite of successful subtyping using this approach, it has been limited to discrimination between avian and human virus strains. This highlights a general need to develop a dynamic and reversible surface modification allowing the reversible introduction of affinity reagents on sensor surfaces.

Dynamic Glycan Arrays

A major branch of glycobiology and glycan-focused biomedicine studies the interaction between carbohydrates and glycan-binding proteins e.g. lectins, enzymes and antibodies. (A. Geissner and P. H. Seeberger, *Annual Review of Analytical Chemistry,* 2016, 9, 223-247). Today, research into glycan-biopolymer interaction is unthinkable without glycan arrays, tools that enable high-throughput analysis of carbohydrate interaction partners. Glycan arrays offer many applications in basic biochemical research, for example, defining the specificity of glycosyltransferases and lectins such as immune receptors. Biomedical applications include the characterization and surveillance of influenza strains, identification of biomarkers for cancer and infection, and profiling of immune responses to vaccines. As for glycan based sensors (see above) most glycan arrays rely on covalent fixation of the glycans on a given support. Hence they are poor mimics of ligand receptor interactions occurring in the dynamic framework of biological membranes. A need exists therefore for practical means of preparing dynamic but robust glycan arrays.

Close Packed Protein Multilayers and Ultrasensitive Biosensors

Biosensing is one area where dynamic reversible platforms could be highly beneficial (Turner, A. P. F *Biosensors. Sense and sensibility.* Chem. Soc. Rev., 2013, 42, 3184-3196). Chemisorbed self assembled monolayers (SAMs) are commonly used to anchor receptor layers to the sensor transducers. One drawback of the forementioned modifications is that they are irreversible, commonly precluding surface regeneration and reuse. This problem often occurs upon surface fouling caused by strongly bound analytes such as in immunosensors or strongly adhering matrix components. Reversible surface modifications could offer a solution to this problem. Such platforms may also promote recognition events driven by multivalent interactions. One example is the interaction between biotin and tetravalent streptavidine (SA) which is commonly exploited in immunosensors as a versatile "glue" for antibody immobilization. The biotin-SA interaction is of high affinity ($K_d \approx 10^{-14}$ M) and specificity allowing SA to act as a multivalent linker to bind to surface biotins and to biotinylated affinity reagents in the solution phase. The efficiency of this surface functionalization depends on the residual valency, i.e. the amount of biotin-binding sites that remain after immobilization. This in turn depends on the nature of the biotinylated anchoring surface i.e. whether the biotin groups are irreversibly fixed to the sensor surface by covalent interactions (SAMs) or reside in fluid bilayers such as in supported lipid bilayer assemblies. In the former, the layer components are unable to readily diffuse laterally to adapt to the multivalent target whereas two dimensional fluidic assemblies (e.g. lipid bilayers) lead to denser SA coverage at the expense however of stability, rendering them unsuitable for robust biosensing. This highlights the need for molecular architectures that combine robustness with the dynamic nature of cellular membranes. It can be anticipated that such platforms would allow the preparation of dense oriented protein films leading in turn to more sensitive biosensors.

Smart Surfaces for Controlled Cell Adhesion

Cellular processes are crucially dependent on dynamic receptor-ligand interactions occurring at the interface between the cell membrane and the extracellular matrix (ECM) (J. Robertus, W. R. Browne, B. L. Feringa, *Chem. Soc. Rev.* 2010, 39, 354-378.) Changes in these interactions as a consequence of ECM remodeling, give rise to specific cell signaling and intracellular cascades. These processes are central in the physiology and pathological processes like tissue self-repair and tumorigenesis. As mimics of such dynamic interactions, artificial matrices with reversible display of bioactive ligands have attracted much attention. Surfaces capable of modulating cell-biomaterial interactions are commonly exploited for in-situ cell biology experimentation and in tissue engineering. Furthermore, a dynamic material interface with reversibly immobilized ligands has also shown great promise in drug targeting and isolation methods for therapeutics and diagnostics.

Current methods to control reversible ligand presentation on biomaterial interfaces mainly rely on surface functionalization with reversible linkers (e.g., noncovalent or reversible covalent interactions) to which the bioactive ligand is tethered. For example, by means of host-guest chemistry, reversible covalent chemistry, molecular assembly or other multiple non-covalent interactions, the integrin-targeted cell adhesive peptide RGD (Arg-Gly-Asp) could be dynamically and reversibly immobilized on the biointerfaces to regulate cell adhesion behavior. These approaches towards simulating the reversible ligand presentation in a biological system have greatly promoted the development of dynamic biointerfaces and a new generation of artificial ECM materials. To date, only a few reversible linkage chemistries have been exploited and new approaches are warranted.

SUMMARY OF THE INVENTION

The present invention discloses a new approach to produce membrane or lipid bilayer mimicking surfaces, their use in the aforementioned areas of application, a kit of parts and a sensor.

In a first aspect the present invention relates to a lipid bilayer mimic comprising self-assembled Bola-form amphiphiles on a surface, wherein the amphiphile comprises a hydrocarbon chain with hydrophilic end-groups at both the termini consisting of the α- and ω-ends. The advantages of such rSAMs over static SAMs and supported lipid bilayers have been outlined in the introduction at the end of each paragraph. Higher stability, ease and cost of production, higher affinity, lower detection limits in sensors, reversibility and reuse of sensor substrates. Hence, this lead to a possibility to be able to adjust the stability and hence lateral mobility of the rSAM. This is to a large degree controlled by the length of the chain reflecting the Van der Waal contact area between the amphiphiles.

In one embodiment according to the present invention the hydrocarbon chain contains a number of carbons between 2 and 16.

In another embodiment according to the present invention at least one of the hydrophilic groups is an amidine functional group. In yet another embodiment according to the present invention, the amidine is a benzamidine. Amidines and especially benzamidines are key to the stability of the rSAM.

In another embodiment according to the present invention the Bola-form amphiphile is an α-(4-amidinophenoxy)-ω-(3- or 4-substituted phenoxy)alkane. It is the 3- or 4-position on the terminating phenoxy group that may be varied.

In another embodiment according to the present invention the Bola-form amphiphile has a hydrocarbon chain is a spacer comprising a defined number of repeating units of ethylene glycol. In yet another embodiment according to the present invention, the number of ethylenglycol repeating units range between 1 and 5. The oligo ethylenglycol chain is key to reduce nonspecific binding of matrix components and this can be varied to adjust the nonspecific binding (NSB). This may be done independently from the variation of the hydrocarbon chain length.

In another embodiment according to the present invention the Bola-form amphiphile is any of Amino(4-(10-(4-(2-hydroxyethyl)phenoxy)decyloxy)phenyl)methaniminium chloride (Chart 2, structure 1); 4-[10-(4-{2-[2-(2-Hydroxy-ethoxy)-ethoxy]-ethyl}-phenoxy)-decyloxy]-benzamidine (Chart 5, structure 15 or Chart 8, structure E2); or 4-(10-{4-[2-(2-{2-[2-(2-Hydroxy-ethoxy)-ethoxy]-ethoxy}-ethoxy)-ethyl]-phenoxy}-decyloxy)-benzamidine (Chart 8, structure E4); 4-{10-[4-(2-{2-[2-(2-{2-[2-(2-Hydroxy-ethoxy)-ethoxy]-ethoxy}-ethoxy)-ethoxy]-ethoxy}-ethyl)-phenoxy]-decyloxy}-benzamidine (Chart 8, structure E6).

In one embodiment according to the present invention the Bola-form amphiphile is Amino(4-(10-(4-(2-hydroxyethyl)phenoxy)decyloxy)phenyl)methaniminium chloride (Chart 2, structure 1).

In one embodiment according to the present invention the Bola-form amphiphile is 4-[10-(4-{2-[2-(2-Hydroxy-ethoxy)-ethoxy]-ethyl}-phenoxy)-decyloxy]-benzamidine (Chart 5, structure 15 or Chart 8, structure E2).

In one embodiment according to the present invention the Bola-form amphiphile is 4-(10-{4-[2-(2-{2-[2-(2-Hydroxy-ethoxy)-ethoxy]-ethoxy}-ethoxy)-ethyl]-phenoxy}-decyloxy)-benzamidine (Chart 8, structure E4); 4-{10-[4-(2-{2-[2-(2-{2-[2-(2-Hydroxy-ethoxy)-ethoxy]-ethoxy}-ethoxy)-ethoxy]-ethoxy}-ethyl)-phenoxy]-decyloxy}-benzamidine (Chart 8, structure E6).

In another embodiment according to the present invention the terminus at the ω-end is a ligand, typically a monosaccharide, disaccharide, glycan, peptide.

In another embodiment according to the present invention the Bola-form amphiphile is substituted at the ω-end with a monosaccharide group.

In another embodiment according to the present invention the monosaccharide group is a sialic acid. The sialic acids are ligands for detecting virus e.g. influenza virus and can be used as membrane mimics for drug development e.g. cancer. In one embodiment according to the present invention, the sialic acid is N-acetylneuraminic acid or N-glycolylneuraminic acid.

In one embodiment according to the present invention the Bola-form amphiphile is 5-Acetylamino-2-[2-(1-{2-[2-(2-{4-[10-(4-carbamimidoyl-phenoxy)-decyloxy]-phenyl}-ethoxy)-ethoxy]-ethyl}-1H-[1,2,3]triazol-4-yl)-ethoxy]-4-hydroxy-6-(1,2,3-trihydroxy-propyl)-tetrahydro-pyran-2-carboxylic acid (Chart 2, structure 2).

In one embodiment according to the present invention the monosaccharide group is any of galactose or mannose. Galactose act as a ligand for antibiotic resistant bacterial strains whereas mannose is for HIV antibodies as potential vaccines.

In one embodiment according to the present invention the Bola-form amphiphile is substituted at the ω-end with a disaccharide group.

In one embodiment according to the present invention the disaccharide group is selected from the group consisting of Siaα2-6GalNAc (Sialyl Tn), Siaα2,3-Galβ, Siaα2,6-Galβ, GlcA2SO$_3$-1,4-Glc2NSO$_3$, GlcA2SO$_3$-1,4-Glc2NSO$_3$6SO$_3$.

In another embodiment according to the present invention the Bola-form amphiphile is substituted at the ω-end with a glycan group.

In one embodiment according to the present invention the glycan group is selected from the group consisting of Siaα 2-3Galβ 1-3GalNAc (Sialyl T), Siaα2,3-N-acetyllactosamine, Siaα2,6-N-acetyllactosamine. The disaccharides and glycans are tumor specific sugars for use in development of model surfaces or drug discovery.

In another embodiment according to the present invention the Bola-form amphiphile is substituted at the w-end with a peptide group. These peptides are key to cell adhesion and modulation of cell behavior.

In one embodiment according to the present invention the peptide group is containing the amino acid sequence RGD.

In one embodiment according to the present invention the Bola-form amphiphile is (2S,5S,11S)-16-(1-((2-(4-((10-(4-carbamimidoylphenoxy)decyl)oxy)phenethoxy)ethoxy)methyl)-1H-1,2,3-triazol-4-yl)-5-(carboxymethyl)-11-(3-guanidinopropyl)-2-(hydroxymethyl)-4,7,10,15-tetraoxo-3,6,9,12,13-pentaazaheptadec-16-enoic acid (Chart 17, structure GRGDS 3).

In another embodiment according to the present invention the Bola-form amphiphile is substituted at the ω-end with a biotin-containing group. The biotinylated rSAM is key to dock streptavidine in an ordered way for building immunosensors showing an enhanced and more sensitive detection.

In one embodiment according to the present invention the Bola-form amphiphile is 5-(2-Oxo-hexahydro-thieno[3,4-d]imidazol-6-yl)-pentanoic acid 2-{4-[10-(4-carbamimidoyl-phenoxy)-decyloxy]-phenyl}-ethyl ester trifluoroacetate (Chart 19, structure 2).

In yet another embodiment according to the present invention the Bola-form amphiphile is substituted at the ω-end with a neuraminidase inhibitor group. Hence, two cooperative ligands for binding the influenza virus is incorporated in the structure, this will lead to more specific and sensitive detection of different strains.

In one embodiment according to the present invention the neuraminidase inhibitor group is selected from the group consisting of zanamivir, oseltamivir and peramivir.

In yet another embodiment according to the present invention the Bola-form amphiphile or amphiphiles are bound to the surface by polar interactions between cationic groups of the Bola-form amphiphile and anionic groups of the surface.

In another embodiment according to the present invention the polar interaction between the Bola-form amphiphile and the surface is pH dependent. By this binding to the surface may be switched by pH control.

In another embodiment according to the present invention the self-assembled Bola-form amphiphiles are reversibly attached to the surface.

In another embodiment according to the present invention the self-assembled Bola-form amphiphiles are comprising one single amphiphile.

In another embodiment according to the present invention the self-assembled Bola-form amphiphiles are comprising a mixture of two or more amphiphiles. The Use of single or mixed amphiphiles gives a possibility to fine-tune the lipid bilayer mimic.

In another embodiment according to the present invention the self-assembled Bola-form amphiphiles possess lateral diffusion coefficients of 0.1-10 $\mu m^2 s^{-1}$.

In one embodiment of the present invention the surface is selected from the group consisting of gold, silver, glass or quartz. In one embodiment of the present invention the surface made of gold. In a further embodiment of the present invention the surface is made of silver. In even a further embodiment of the present invention the surface is made of glass or quartz.

In one embodiment of the present invention the surface is either concave such as a porous material or convex such as spherical microparticles or nanoparticles. The curvature is an important aspect for applications in therapeutics and cell and tissue engineering. The microparticles or nanoparticles may be made of different materials. In one embodiment of the present invention the nanoparticles are made of gold or silver.

In one embodiment of the present invention the surface is coated with a self-assembled monolayer comprising anionic groups. The surface is coated with oxyanionic groups for the possibility to interact with the hydrophilic end-groups of the amphiphiles.

In one embodiment of the present invention the surface is gold coated with a self-assembled monolayer selected from the group consisting of mercaptobenzoic acid (MBA), mercaptohexadecanoic acid (MHA) and mercaptoundecane sulfonic acid (MDSA).

In one embodiment of the present invention the surface is glass or quartz coated with a self-assembled monolayer selected from the group consisting of silane functionalized benzoic acid, silane functionalized decanoic acid, silane functionalized hexadecanoic and silane functionalized benzoic acid.

In another embodiment of the present invention the hydrophilic biotin end-group at the ω-end of the Bola-form amphiphile interacts with streptavidine. In one embodiment of the present invention the streptavidine further interacts with a biotinylated antibody.

In one embodiment of the present invention the ligand is coupled to the amphiphile by Huisgen/Sharpless click coupling of an ω-azide α-amidine amphiphile and an alkyne functionlized ligand or of an ω-alkyne α-amidine amphiphile and an azide-functionlized ligand.

A second aspect of the present invention relates to a method for detecting a target by using the lipid bilayer according to the present invention.

In one embodiment according to the present invention the target is a biological target selected from the group consisting of biopolymers, typically proteins, saccharides or nucleic acids; microorganisms; cells, typically cancer cells or stem cells; virus, typically an influenza virus, more specifically an influenza virus of the type H5N1; bacteria and pathogens. In another embodiment according to the present invention the protein is any of human serum albumin, prostate specific antigen, hemagluttinine or neuraminidase.

In yet another embodiment according to the present invention the detection is performed by at least one of the techniques selected from the group consisting of fluorescence measurements, optical techniques, ellipsometry, surface plasmon resonance, electrochemical techniques and gravimetri.

Another aspect of the present invention relates to the use of the lipid bilayer mimic as a sensor to detect biological targets.

Another aspect of the present invention relates to the use of the lipid bilayer mimic to control the reversible adhesion of cells.

Another aspect of the present invention relates to the use of the lipid bilayer mimic as an antibacterial or antiviral agent to inhibit pathogen adhesion.

Another aspect of the present invention relates to the use of the lipid bilayer mimic as a vaccin.

Another aspect of the present invention relates to the use of the lipid bilayer mimic as dynamic supports for glycans in glycan arrays.

In one embodiment according to the present invention the glycan arrays are used for surveillance of influenza strains, identification of biomarkers for cancer and infection, and profiling of immune responses to vaccines.

Another aspect of the present invention relates to a kit of parts comprising:
a. the lipid bilayer mimic according to the present invention;
b. streptavidine;
c. biotinylated antibody or biotinylated antibodies; and
d. optionally a surface.

Another aspect of the present invention relates to a sensor comprising the lipid bilayer mimic according to the present invention. In a specific embodiment the sensor of the present invention comprises the lipid bilayer mimic of the present invention, streptavidine and biotinylated antibody or biotinylated antibodies.

BRIEF DESCRIPTION OF THE DRAWINGS

The invention will now be described in more detail with reference to the accompanying drawings, where:

FIGS. 3A-3D show film thickness, (d), and adsorbed amount, (I) estimated by ellipsometry for FIG. 3A: a bare MHA-SAM on gold, rSAM of OH-terminated amidine 1 or rSAM of sialic acid terminated amidine 2 after exposure to solutions of hemagluttinine (HA), concanavaline A (ConA), human serum albumin (HSA), HA preincubated with (1% v/w) mucin or 0.005% (w/v) mucin until stable A and W values were obtained or for a maximum duration of 5000 s (whichever came first); FIG. 3B: rSAM-2 upon addition of incremental amounts of HA (squares), ConA (triangles) or HSA (circles); FIG. 3C: MHA-SAM (circles) or rSAM-2 (squares) or SAM-14 (triangles), prepared using covalently linked sialic acids) upon addition of deactivated influenza virus H5N1 (0.20-33 HAU) and rSAM 2 upon addition of deactivated influenza virus H5N1 preincubated with 1% (w/v) mucin (triangles). Nonlinear curve fitting resulted in Kd=5.1 nM for HA and Kd=$2.1 \times 10^{-13}$ M for influenza virus H5N1; and, FIG. 3D: Surface topography of an rSAM of 2 on MHA modified gold after exposure to deactivated H5N1 (14 HAU) followed by rinsing with pH 8 HEPES buffer. Identified virus particles are indicated by arrows.

FIG. 9A shows real time in situ ellipsometric thickness and rate constant, $K_{on}$ of MHA modified gold surfaces upon exposure to E0-6 (50 µM, pH 9 borate buffer); FIG. 9B shows in situ ellipsometric thickness after equilibration, $D_{ads}$ and after pH 8 HEPES buffer rinsing, $D_{rinse}$. For E6, only layers with stable equilibrium thickness were included in the calculations; FIG. 9C shows baseline corrected E2 bulk ATR spectrum and E2 modified MHA gold IRAS spectrum (top) and E4 bulk ATR spectrum and E4 modified MHA gold IRAS spectrum (bottom); and, FIG. 9D shows atomic force microscopy (AFM) topographic images and cross sectional profile of E0 and E2 layers.

FIG. 10A show real time in situ ellipsometric thickness and rate constants, $K_{on}$ of MHA modified gold surfaces upon exposure to E2 (50 µM, pH 9 borate, pH 8 or pH 7.4 HEPES buffer); FIG. 10B shown in situ ellipsometric thickness at equilibrium, $D_{ads}$ and after rinsing with the corresponding buffer, $D_{rinse}$; and, FIG. 10C show baseline corrected IRAS spectra of the layers after rinsing. The dotted lines in FIGS. 10A and 10B indicate the theoretical thickness of E2.

FIGS. 12A-12F generally illustrate protein stability and resistivity of E0-6 rSAMs on MHA or 4-mercaptobenzoic acid (MBA) modified gold: FIG. 12A show baseline corrected IRAS spectra of E2 on MBA-gold and after exposure to human serum albumin (HSA) or lysozyme (LYZ) (1 mg/ml) at pH 8; FIG. 12B show baseline corrected IRAS amide I intensity (ca. 1690 $cm^{-1}$) of E0-6 rSAMs on MHA or MBA modified gold before and after exposure to HSA or LYZ (1 mg/ml) pH 8; FIG. 12C show baseline corrected IRAS aromatic $(C{=}C)_{1,4}$ intensity (ca. 1611 $cm^{-1}$) of E0-6 rSAMs on MHA or MBA modified gold before and after exposure to HSA or LYZ (1 mg/mL) at pH 8; FIGS. 12D-12E show ethylene glycol chain length; and, FIG. 12F generally show HAS concentration.

FIG. 13A shows ellipsometric thickness after rinsing versus pH for rSAMs of E2 amidine 15 on SAMs of MHA (red symbols) and MBA (green symbols) on gold; FIG. 13B shows baseline corrected IRAS spectra of E0-6 on MHA-gold after one cycle of rinsing and drying using nitrogen (blue trace) and after 2 cycle of rinsing and drying using nitrogen (red trace); and, FIG. 13C shows FRAP curve for a 1 mol % fluorescein (FAM) tagged amidine in E2 on COOH terminated quartz surface.

FIG. 17 generally illustrate a schematic illustration of modulating cell adhesion behaviour on reversible self-assembled monolayers (rSAMs) functionalized with GRGDS peptide. i. Incubation of 4-mercaptobenzoic acid (MBA) or 10-mercaptoundecanesulfonic acid (MDSA) self-assembled monolayers (SAMs) with pH 8 HEPES buffer solution containing varying mole fraction of GRGDS 3 in filler 1 or 2, $X_{GRGDS3}$=0-0.25, followed by rinsing in pH 8 HEPES buffer. ii. Seeding of 3T3 fibroblasts on surface. iii. Incubation of cells on surface for 5 hrs. iv. Molecular exchange with filler 2 and quantification of cell detachment.

FIG. 18 shows pH-switchable adaptable mixed monolayers of α-benzamidine, ω-hydroxy or biotin Bola amphiphiles promote close packing and enhanced order in three consecutive protein layers. The concept is used to construct highly sensitive biosensors FIG. 19 illustrates synthetic pathway of biotin-terminated amphiphile 2: (a) $H_2O$/THF (1:1), 3M NaOH, $BOC_2O$ 10 eq., 0° C., 3 h, 67%; (b) biotin chloride 4 1.1 eq., acetone/toluene (1.5:1), $K_2CO_3$ 6.5 eq., 50° C., 12 h (c) DCM, TFA, 0° C., 2 h, 34% in steps (b) and (c).

FIG. 20 shows film thickness (d) estimated by air ellipsometry for mixed rSAMs of 1 and 2 (50 μM) (black diamonds) assembled on MHA modified gold in borate buffer (pH 9), rinsed with the same buffer and blown dried with nitrogen. Also shown is the increment in film thickness for the same surfaces after exposure (16 h) to a dilute solution of streptavidine (SA) (0.5 μM solutions) in borate buffer (pH 9), rinsing and drying in the same manner. The values are averages of 10 measurements at three different spots on each surface. The dashed line corresponds to the theoretical thickness assuming a layer of perpendicularly ordered molecules assuming an extended conformation. Adsorption of SA on the bare MHA SAM resulted in a thickness of 9±2 Å, nearly identical to the thickness value measured for SA on the rSAM of 1 alone.

FIGS. 21A-21B show a stepwise assembly of 50 μM mixed biotinylated amidin (1+2, $X_2$=0.1), 5 μM streptavidin (SA), 5 μM biotinylated Anti-HSA and 5 μM HSA, disassembly with pH 3, another assembly cycle with 50 μM mixed biotinylated amidin, 5 μM SA, 5 μM biotinylated Anti-HSA and mixed HSA/IgG 100 pM/100 pM, and pH switching of a multilayered assembly comprising 50 μM mixed biotinylated amidin (1+2, $X_2$=0.1), 5 μM SA, 5 μM biotinylated anti-PSA and 5 μM PSA, respectively. The assembly was followed by pH adjustment to pH 3 followed by pH adjustment to pH 8 by addition of 0.1M HCl and 0.1M NaOH to the cuvette. Each addition in FIG. 21A was preceeded by a ca 4 min rinse with pH 9 (addition of 1+2) or pH 8 (addition of proteins) buffer.

FIG. 22 shows a topographical atomic force microscopy (AFM) images (2 μm×2 μm) ordered according to the step-wise build-up of the quadruple layered structure. Starting from the upper left corner following the arrows are depicted A a SAM of MHA on a gold-mica surface, B rSAM-1+2, C rSAM-SA; D rSAM-SA-antiHSA; E rSAM-SA-antiHSA-HSA and F rSAM-SA-antiHSA-HSA after rinsing with acid at pH 3. The images were obtained in the tapping mode in air. The change in ellipsometric thickness as well as the roughness factor have been indicated.

FIG. 23 illustrates film thickness (d) estimated by air ellipsometry, IR signal intensity of the amide I band from IRAS measurements ($A_{1664}$), and contact angles (Theta in air for mixed rSAMs of 1 and 2 (50 μM), the rSAM after adsorption of SA and subsequent incubation with antiHSA and HSA.

FIGS. 24A-24D: FIGS. 24A-B show film thickness, (d), and amount adsorbed, (I) versus time on anti-HSA (FIG. 24A) or anti-PSA (FIG. 24B) modified rSAM in contact with pH 8 solutions containing different concentrations of HSA (FIG. 24A) or PSA (FIG. 24B) as indicated; and, FIGS. 24C-24D show the corresponding limiting thickness or slope of the thickness curves for HSA (FIG. 24C) and PSA (FIG. 24D) (squares) are shown in FIGS. 24C-24D. The circles in FIG. 24D refer to measurements on dilute serum samples.

FIG. 25 illustrates A Synthetic pathway of OH-terminated amphiphile 1 and sialic acid-terminated amphiphile 2 and B use of 1 and 2 to form an adaptable rSAM. Reagents and conditions in A: (a)1,10-dibromodecane 3 10 eq., K2CO3 2 eq., acetone, 80° C., 24 h, 81%; (b) 4-(2-hydroxy-ethyl)-phenol 6 2.0 eq., K2CO3 2.0 eq., acetone, 80° C., 24 h, ~99%; (c) 2-chloroethyl ether 8 43 eq., tetrabutylammonium hydrogen sulfate (THS) 2.0 eq., NaOH solution (50% w/w), rt, 18 h, 56%; (d) HCl gas, 1,4-dioxane, 0° C. à rt, 24 h, then $NH_3$ in MeOH, rt, 24 h, 82%, (e) $NaN_3$ 4.0 eq., DMF, 90 °C, 24 h, 47% (f) NaAsc 3.0 eq, Cu(II)$SO_4$ 0.3 eq, $H_2O$/2- butanol (1:2), rt, 4 h, 60%, (g) HCl gas, 1,4-dioxane, 0° C. à rt, 24 h, then NH₃ in MeOH, rt, 24 h, 53%.

Figure 26A:
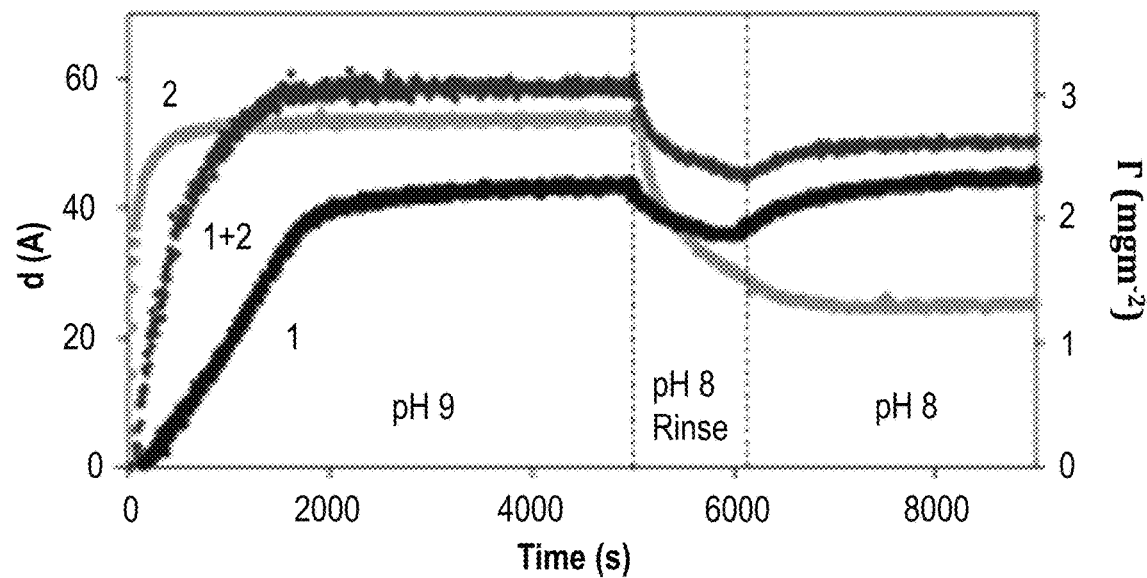
Figure 26B:
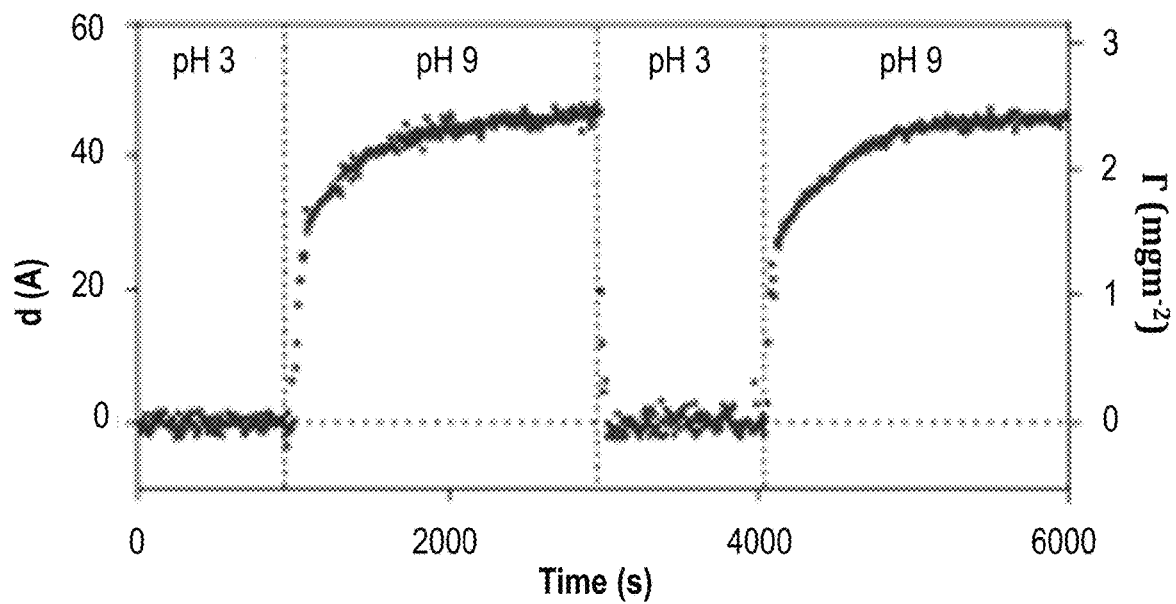

FIGS. 26A-26B: FIG. 26A shows film thickness, (d), and amount adsorbed, (Γ) estimated by in situ ellipsometry, versus time during adsorption of 1, 2 or a mixture of 1 and 2 ($\chi_2$=0.2) (50 µM in buffer) on MHA modified gold at pH 9, thickness values after pH 9 adsorption, $d_{ads}$ (Å) and after rinsing in pH 8 buffer, $d_{rinse}$ (Å) are tabulated Table 1; FIG. 26B shows film thickness, (d), and amount adsorbed, (Γ) measured during the pH-driven self-assembly of 2 on MHA modified gold at pH 9 followed by cycling the pH between 9 and 3 in borate buffer (0.01M). The desired pH was adjusted using 0.1 M NaOH or 0.1 M HCl solution in a discontinuous system.

Figure 27E:
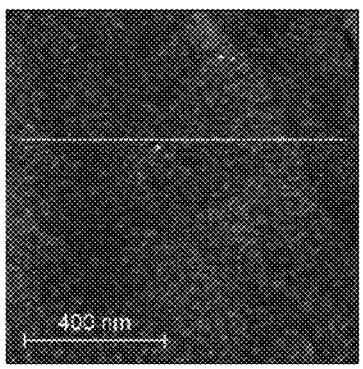
Figure 27E:
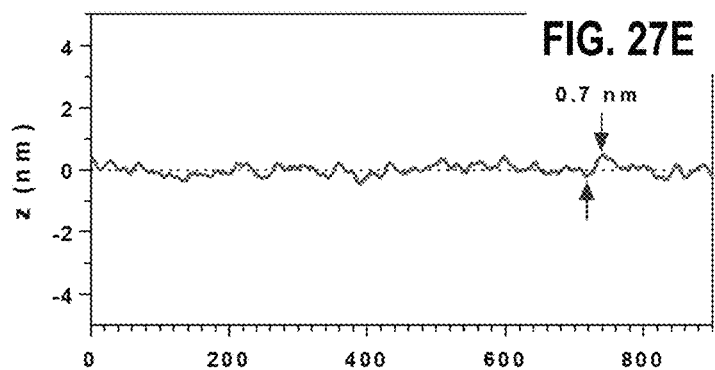
Figure 27F:
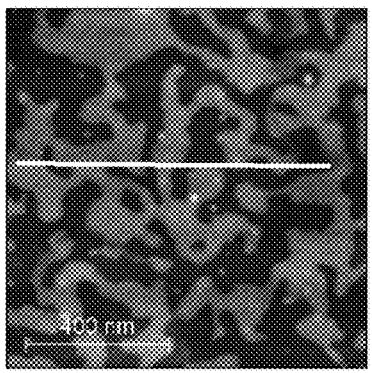
Figure 27F:
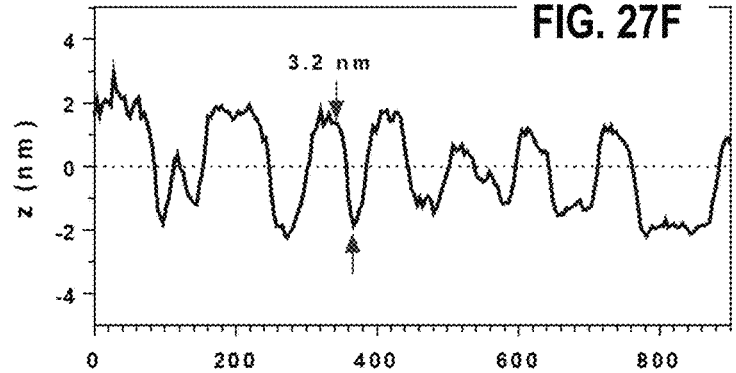
Figure 27G:
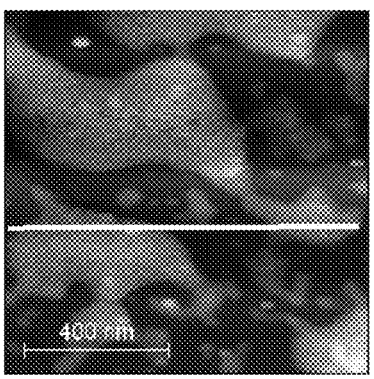
Figure 27G:
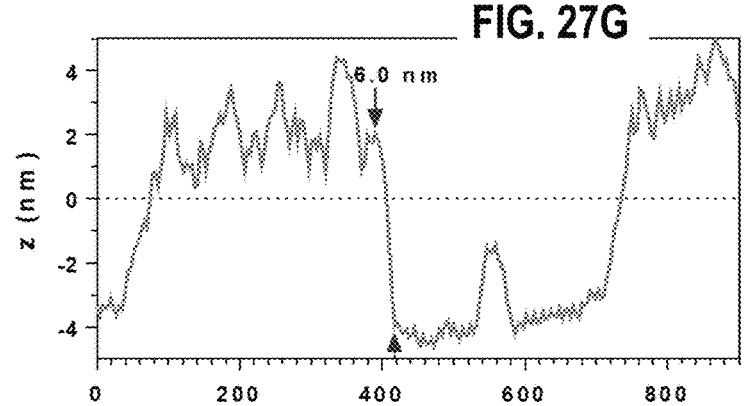
Figure 27H:
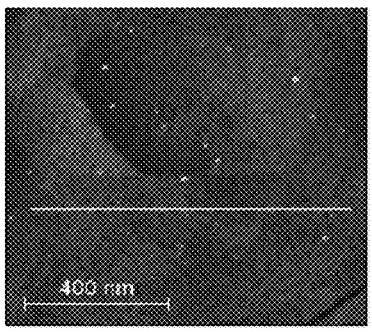
Figure 27H:
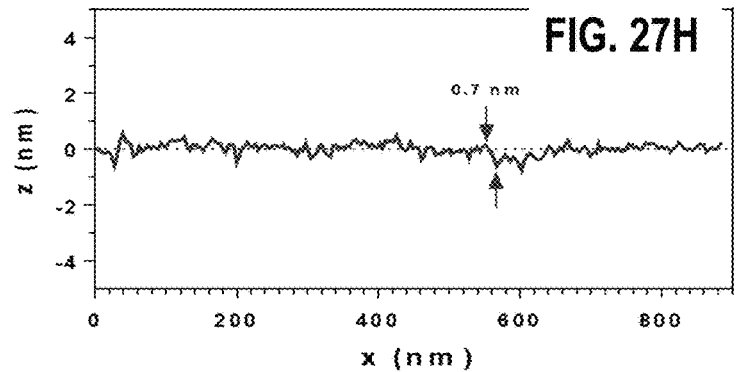

FIGS. 27A-27H: FIGS. 27A-27D show baseline-corrected IR reflection-absorption (IRAS) spectra of MHA on gold (FIG. 27A), rSAM-1 (FIG. 27B), rSAM-1+2 (FIG. 27C) and rSAM-2 (FIG. 27D), the black traces in FIGS. 27B and 27D correspond to spectra of bulk 1 and 2 their salt forms; FIGS. 27E-27H show topographical atomic force microscopy (AFM) images (1 µm×1 µm) of a SAM of MHA on a gold-mica surface (FIG. 27E), rSAM-1 (FIG. 27F), rSAM-1+2 (FIG. 27G) and rSAM-2 (FIG. 27H). The images were obtained in quantitative nanoscale mechanical (QNM) mode in air. The height difference between valley and peak are obtained from a section analysis as indicated by red arrows.

Figure 28A:
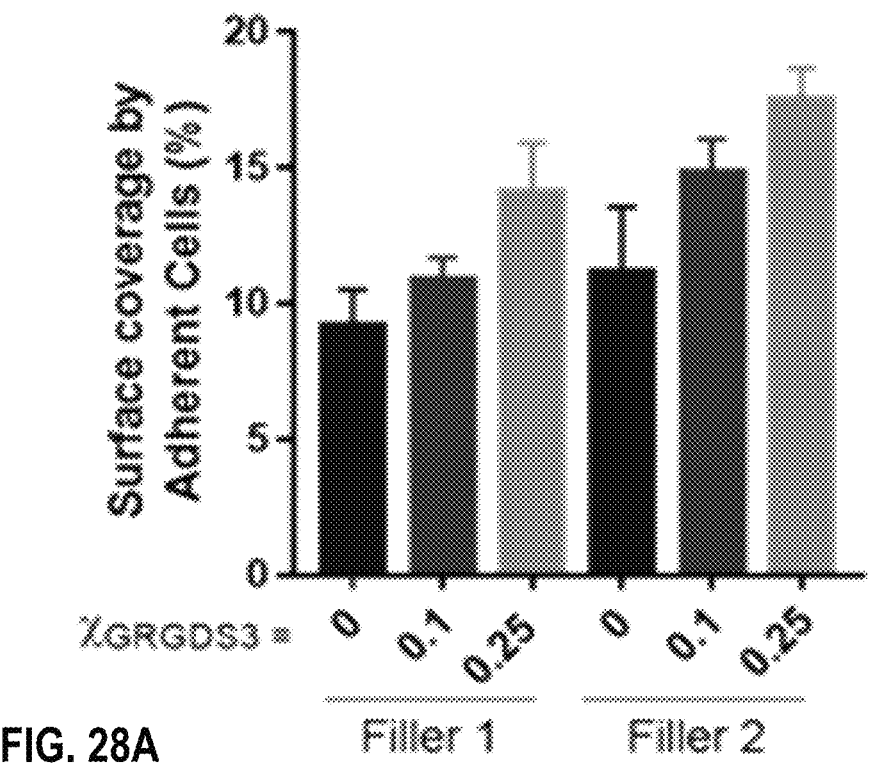
Figure 28B:
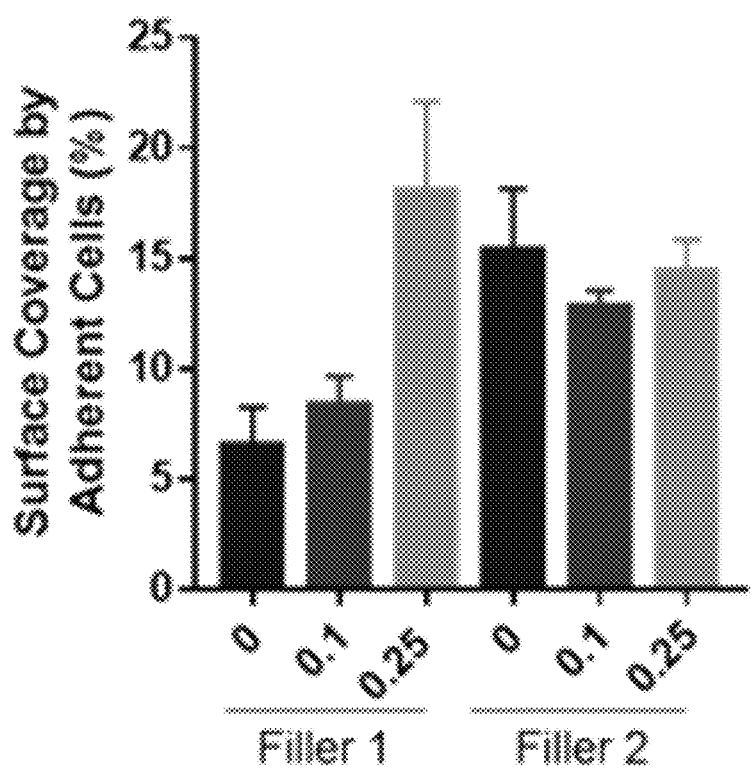
Figure 28C:
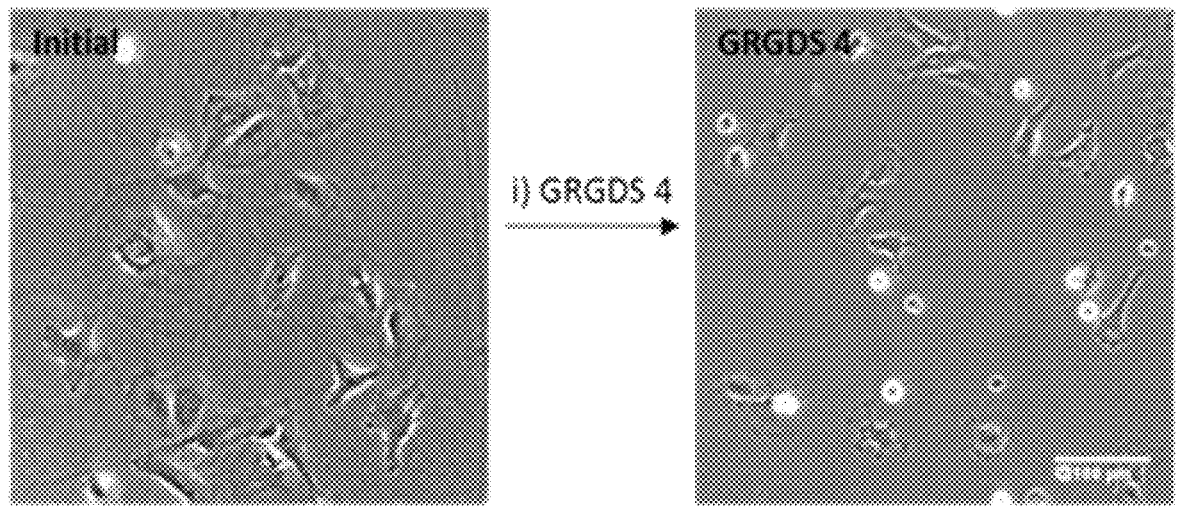
Figure 28D:
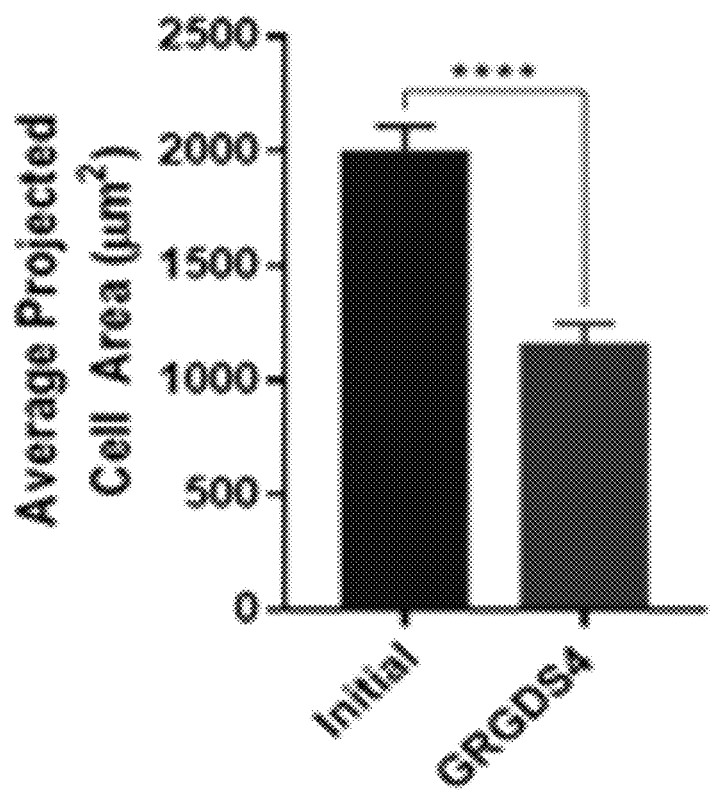

FIGS. 28A-28D show influence of filler length (filler 1 or 2) and GRGDS 3 density on MC3T3-E1 adhesion: FIG. 28A show a percentage surface coverage by adherent MC3T3-E1(%) as presented in brightfield micrographs of MC3T3-E1 after culture for 5 hours on MBA SAMs modified with vary mole fractions of GRGDS 3 in Filler 1 or 2, $X_{GRGDS3}$=0-0.25 as presented in FIG. 28B percentage surface coverage by adherent MC3T3-E1(%) as presented in brightfield micrographs of MC3T3-E1 after culture for 5 hours on MDSA SAMs modified with vary mole fractions of GRGDS 3 in Filler 1 or 2, $X_{GRGDS3}$=0-0.25 as presented in Chart 32; FIG. 28C show representative brightfield micrographs of MC3T3-E1 after culture for 5 hours on MBA SAMs modified with $X_{GRGDS3}$=0.25 (left) and after incubating with 100 µM GRGDS 4 for 2 hrs (right); and, FIG. 28D show specificity of GRGDS-integrin binding for cell adhesion determined by calculating the average projected cell area per cell in FIG. 28C. (*** p<0.0001).

Figure 29A:
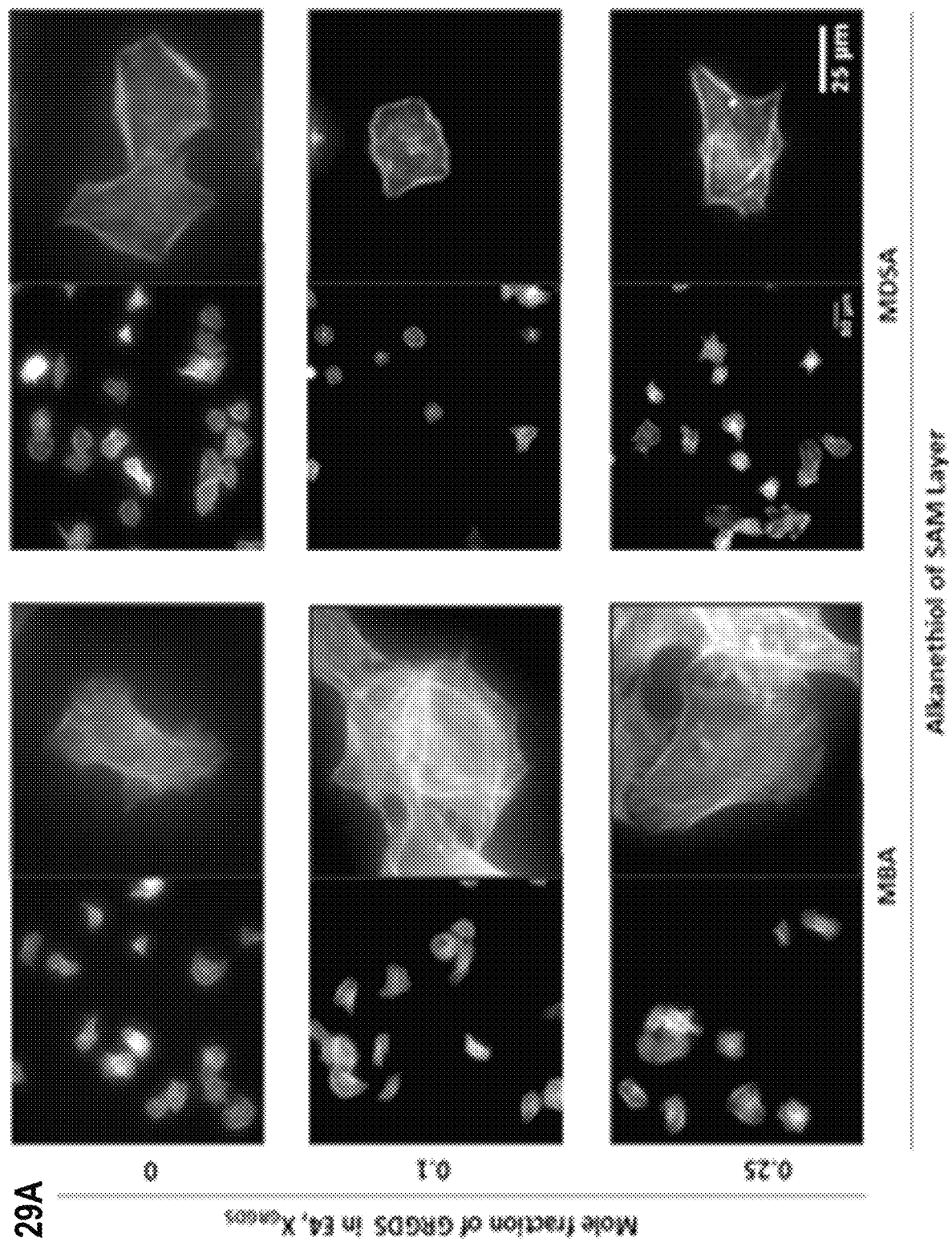
Figure 29B:
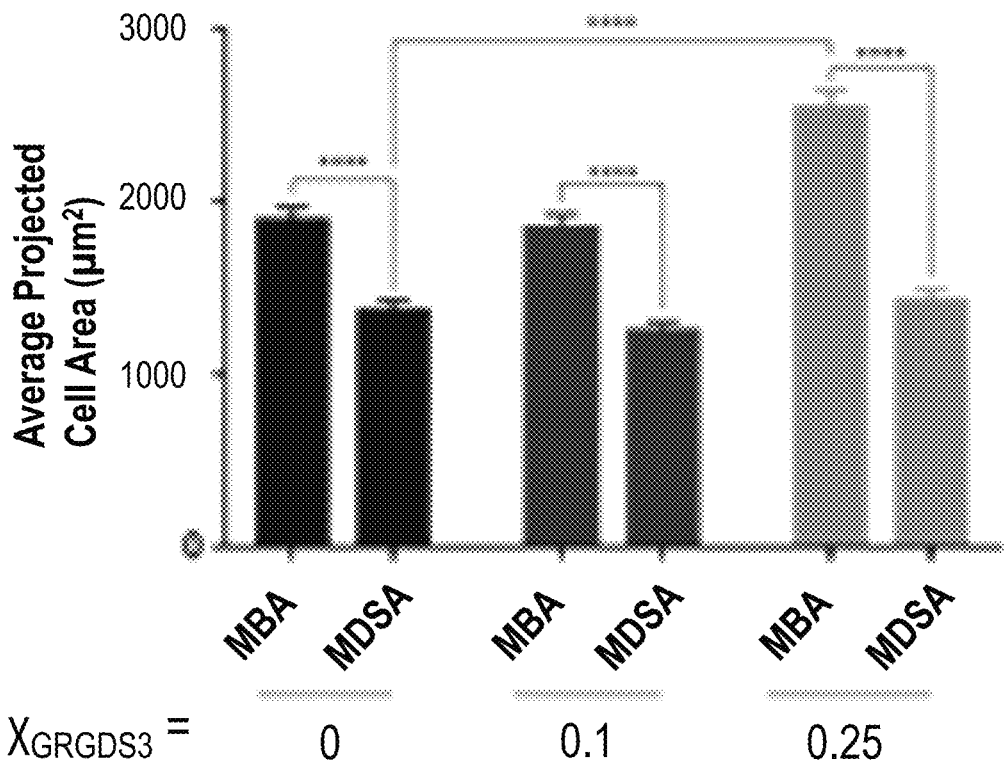
Figure 29C:
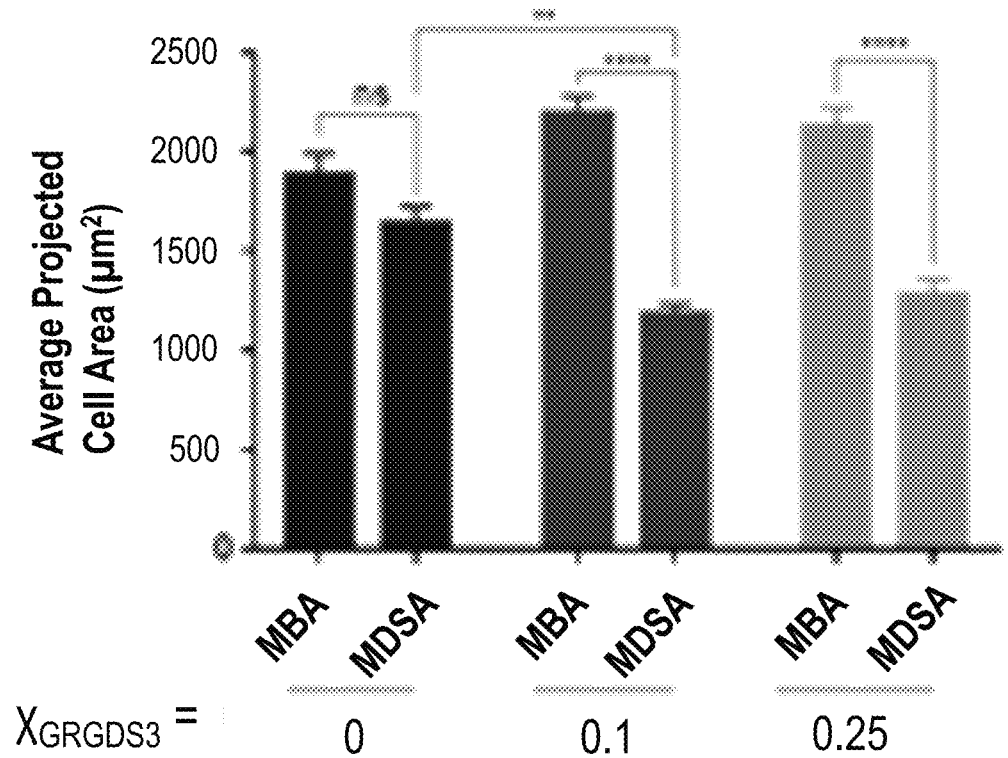

FIGS. 29A-29C show binding isotherm of filler 2 on either MBA (FIG. 29B) or MDSA (FIG. 29C)-SAMs determined by in situ ellipsometry.

Figure 30:
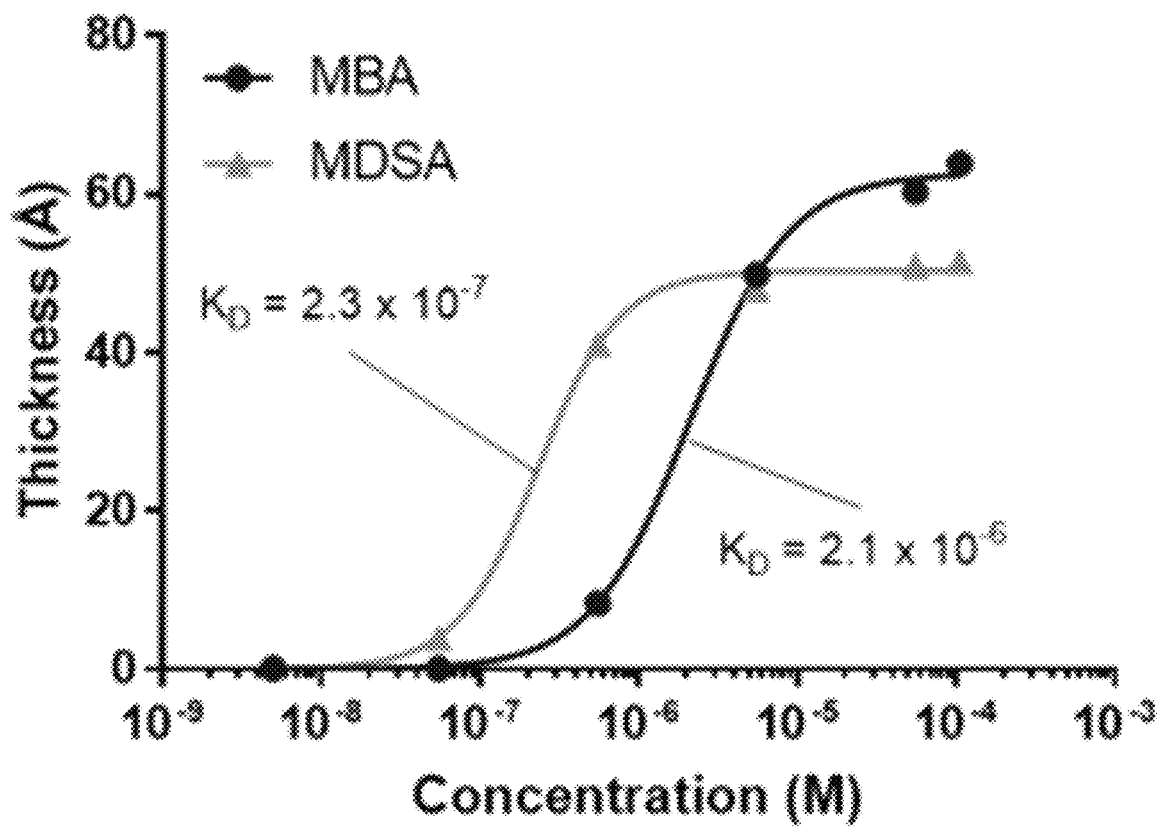

FIG. 30 show differences in cell morphology on MBA or MDSA anchored rSAMs. A Fluorescence micrographs of actin-stained MC3T3-E1 after culture for 5 hours on MBA or MDSA SAMs modified with varying mole fraction of GRGDS 3 and filler 2, $X_{GRGDS3, filler2}$. B Average projected cell area of MC3T3-E1 attached on surface modified with varying mole fraction of GRGDS 3 and filler 1, $X_{GRGDS3, filler1}$ on either MBA or MDSA SAMs described in Chart 33. C Average projected cell area of MC3T3-E1 attached on surface with varying mole fraction of GRGDS 3 and filler 2, $X_{GRGDS3, filler2}$ on either MBA or MDSA SAMs in FIG. 4A. (** p<0.0001;  p<0.01)

Figure 31A:
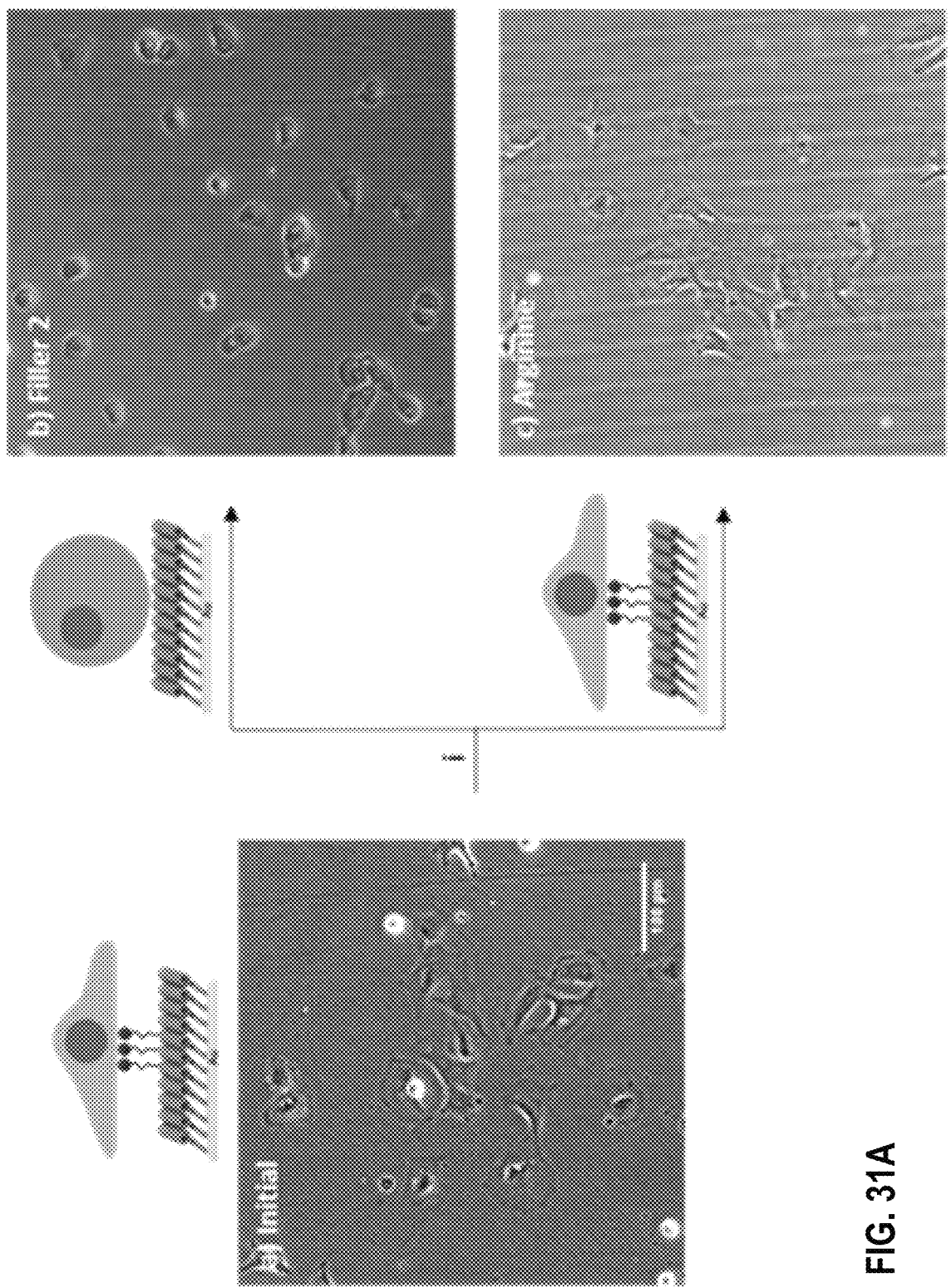

FIGS. 31A-31D show reversible cell adhesion induced by molecular exchange: FIG. 31A shows a representative brightfield micrograph a) initial of MC3T3-E1 after culture for 5 hours on MBA modified with $X_{GRGDS3}$=0.25 in filler 2 and i) 30 mins after addition of 100 µM of b) filler 2 or c) arginine; FIG. 31B shows a total number of cells per cm² attached on the surface described in A; FIG. 31C shows an average projected cell area of MC3T3-E1 attached on surface described in A; and, FIG. 31D shows circularity of MC3T3-E1 attached on surface described in A. (**** p<0.0001).

Figure 32:
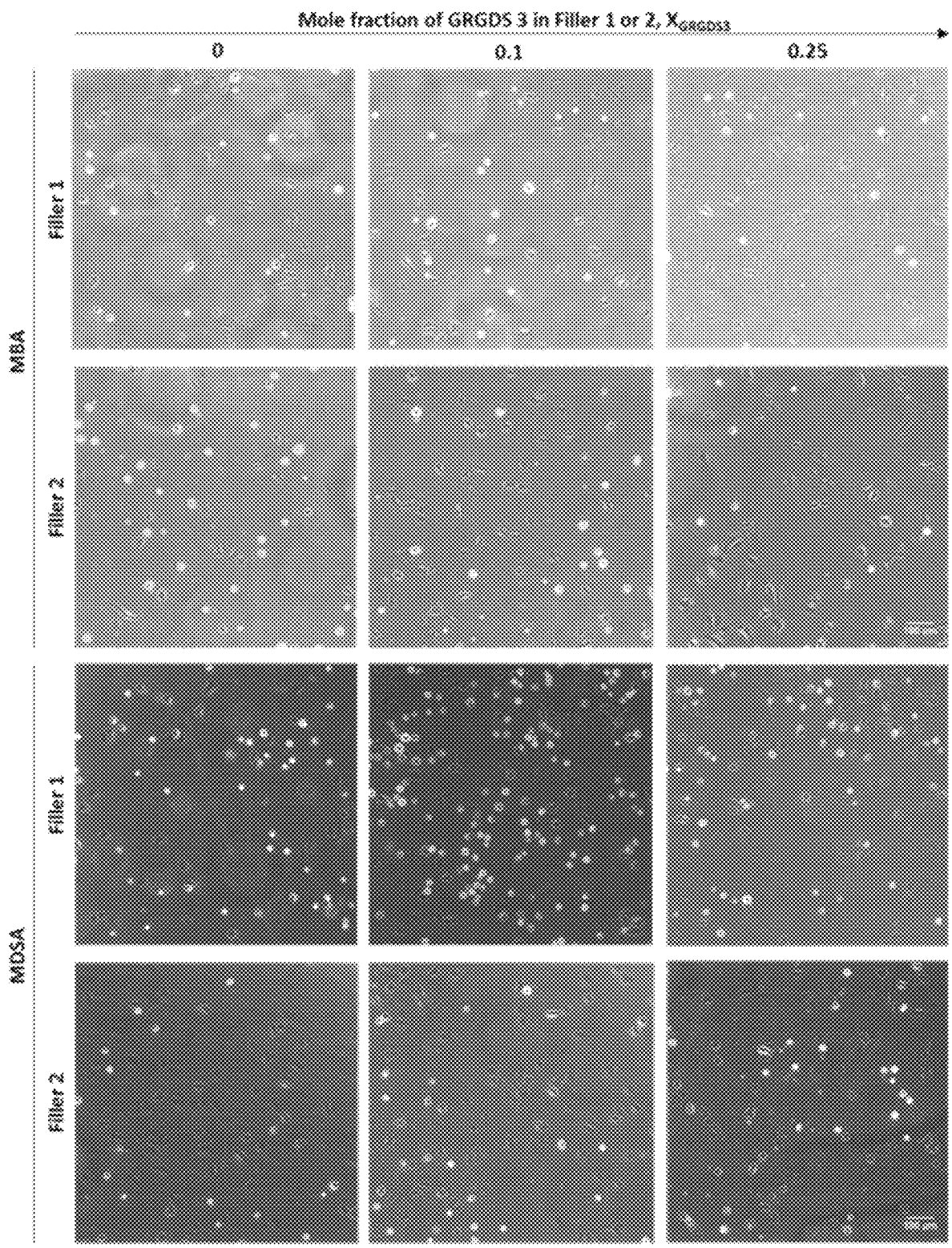

FIG. 32 is a brightfield micrographs of MC3T3-E1 adhered on surfaces modified with varying mole fraction of GRGDS3 in either filler 1 or 2, $X_{GRGDS3}$ on either MBA or MDSA SAMs.

Figure 33:
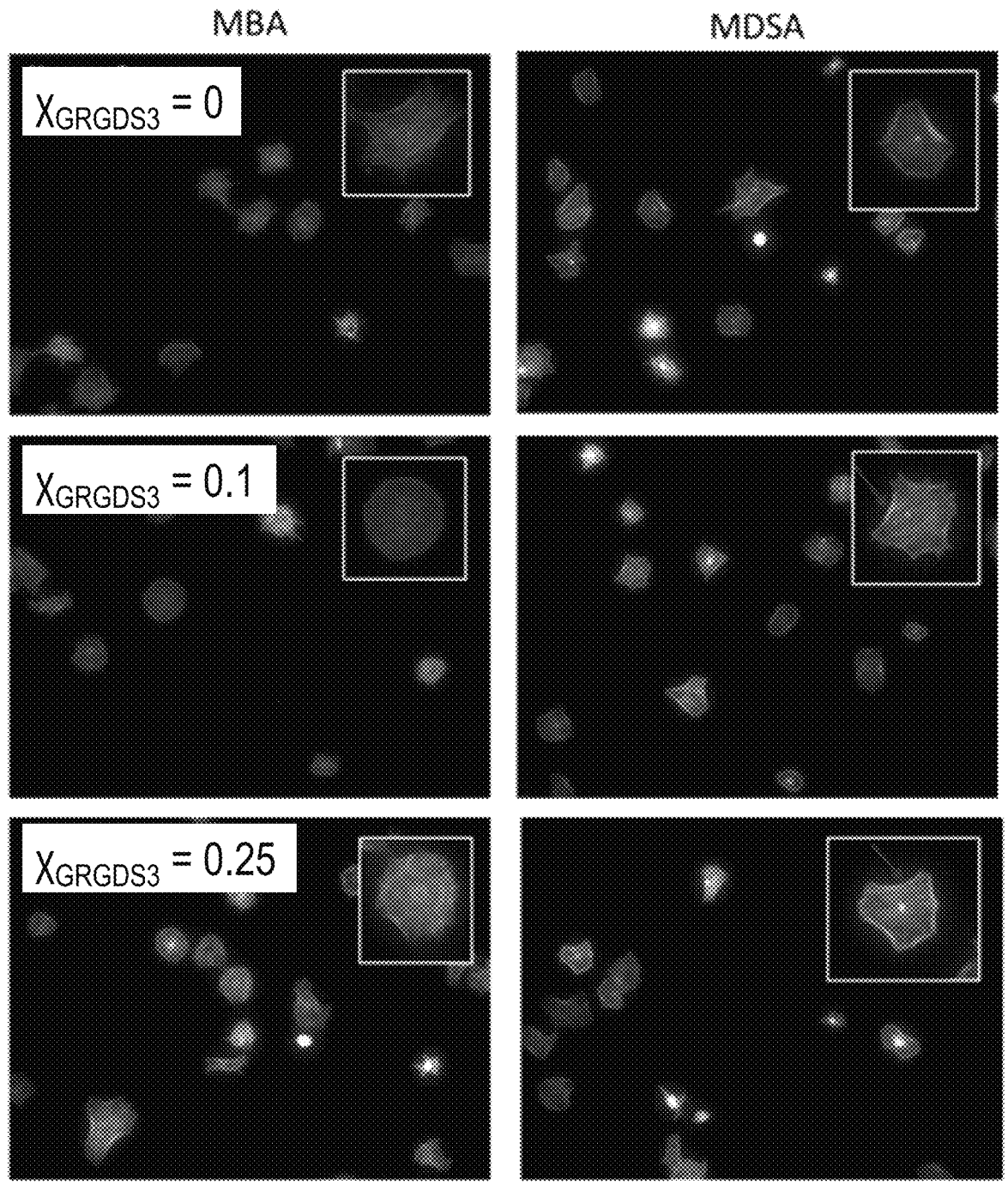

FIG. 33 shows fluoresence micrographs of FTIC-phalloidin stained MC3T3-E1 adhered on surfaces modified with varying mole fraction of GRGDS3 in filler 1, $X_{GRGDS3}$ on either MBA or MDSA SAMs.

Figure 34:
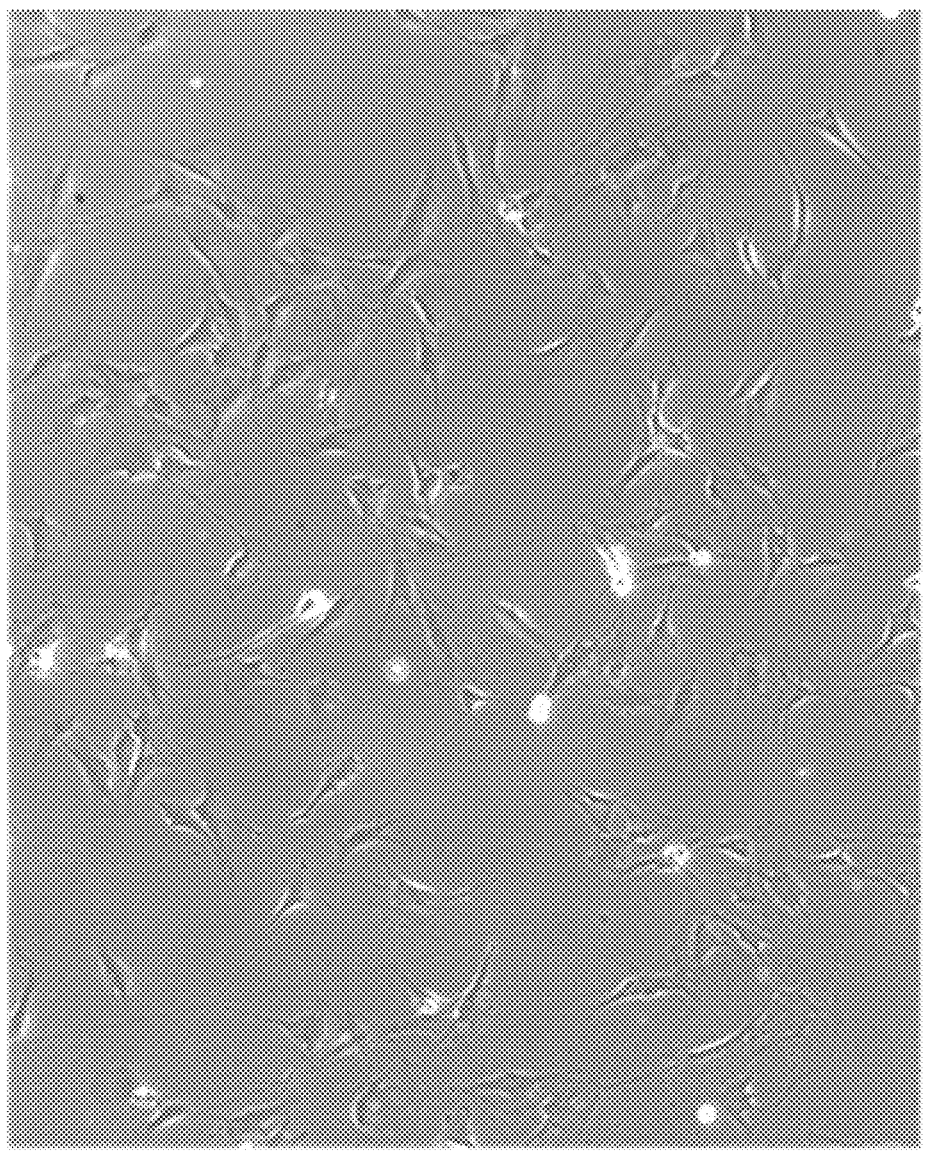

FIG. 34 shows brightfield micrographs of MC3T3-E1 after 100 µM exposure to filler 2.

Figure 35:
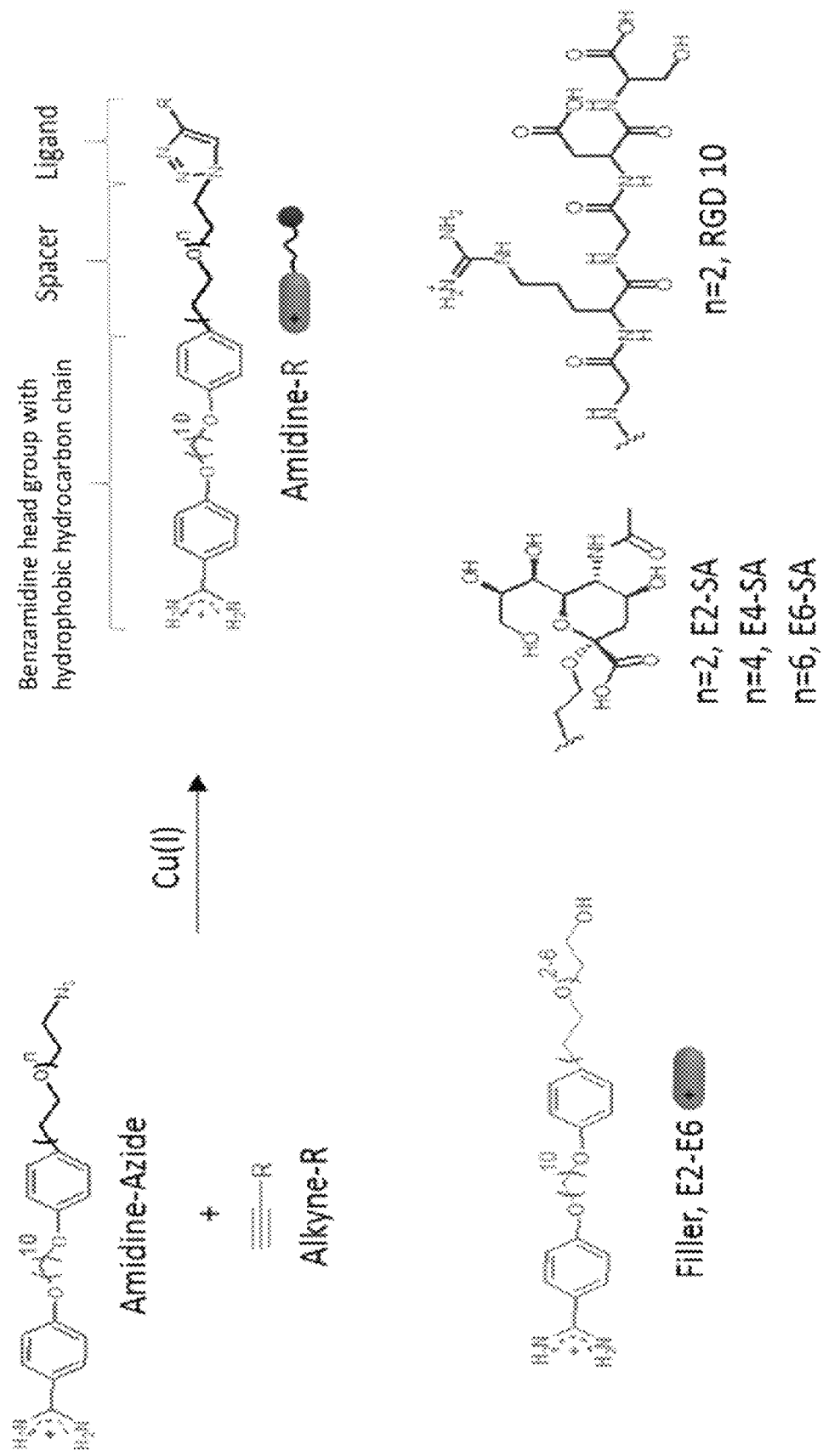

FIG. 35 shows modular construction α-benzamidine ω-ligand substituted bola amphiphiles and method for their synthesis by cupper (I) catalyzed click coupling from amidine-azides andalkyne substituted ligands. Also shown are examples of amphiphiles synthesized.

Figure 36:
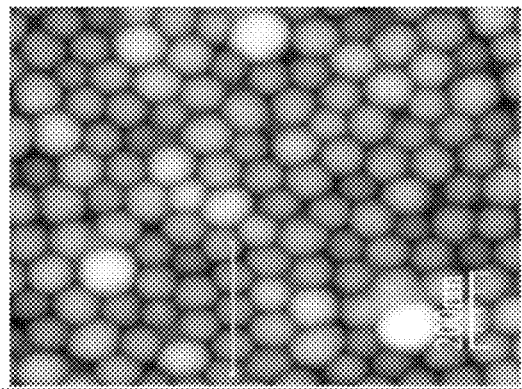
Figure 36:
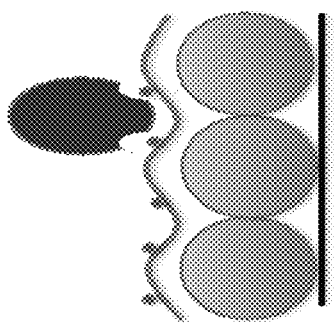
Figure 36:
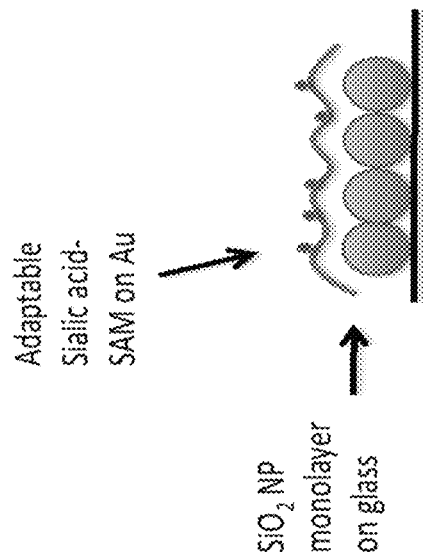

FIG. 36 illustrates principle of surface design along two lengths scales for glycan based virus sensing with an AFM image of a SAM of 100 nm silica nanospheres containing a sputtered gold film (right side).

DETAILED DESCRIPTION OF THE INVENTION

The present invention provides reversible self-assembled monolayers (rSAMs) of Bola-form amphiphiles featuring fluidity similar to biological lipid bilayer membranes. The properties is manifested in a strongly enhanced multivalent binding affinity for target or analytes like biopolymers (proteins, saccharides, nucleic acids), cells, virus, bacteria and other pathogens, full reversibility of the monolayer formation and a diffusion coefficient of the layer components similar to that measure for LBL-membranes.

The term Bola-form amphiphiles, also known as Bolaamphiphiles bolaform surfactants, bolaphiles, or alpha-omega-type surfactants, are amphiphilic molecules that have hydrophilic groups at both ends of a sufficiently long hydrophobic hydrocarbon chain.

The term lipid bilayer mimic relates to that there are no lipids in these films but the rSAMs are made of Bola-form amphiphiles which mimic membranes or lipid layers.

FURTHER EMBODIMENTS OF THE PRESENT INVENTION

The amphiphile or amphiphiles are bound to an underlying surface by polar interactions between cationic groups of the amphiphile and anionic groups of the surface;

The polar interaction between the amphiphile and surface is pH dependent;

The amphiphile is selected from amidines;

The amphiphile is selected from benzamidines;

The amphiphile is an ω-substituted α-(4-amidinophenoxy)alkane.

The amphiphile is substituted at the ω-position with an affinity ligand

The amphiphile is substituted at the ω-position with a biotin-containing head group.

The amphiphile is substituted at the ω-position with 4-(2-hydroxyethane)phenoxy.

The amphiphile is substituted at the ω-position with oligo-ethylenglycol.

The amphiphile is substituted at the ω-position with a monosaccharide containing head group.

The amphiphile is substituted at the ω-position with a disaccharide containing head group.

The amphiphile is substituted at the ω-position with a glycan containing head group.

The amphiphile is substituted at the ω-position with a sialic acid containing head group.

The amphiphile is substituted at the ω-position with a neuraminidase inhibitor containing head group such as zanamivir, oseltamivir or peramivir.

The amphiphile is substituted at the ω-position with a Siaα2-6GalNAc (Sialyl Tn) containing head group The amphiphile is substituted at the ω-position with a Siaα 2-3Galβ 1-3GalNAc (Sialyl T) containing head group The amphiphile is substituted at the ω-position with a Siaα2,3-Galβ containing head group.

The amphiphile is substituted at the ω-position with a Siaα2,6-Galβ containing head group.

The amphiphile is substituted at the ω-position with a Siaα2,3-N-acetyllactosamine containing head group.

The amphiphile is substituted at the ω-position with a Siaα2,6-N-acetyllactosamine containing head group.

The amphiphile is substituted at the ω-position with a N-acetylneuraminic acid (Neu5Ac, human form of sialic acid (SA)) containing head group.

The amphiphile is substituted at the ω-position with a N-glycolylneuraminic acid (Neu5Gc, animal form of sialic acid) containing head group.

The amphiphile is substituted at the ω-position with a GlcA2SO$_3$-1,4-Glc2NSO$_3$ or GlcA2SO$_3$-1,4-Glc2NSO$_3$6SO$_3$ containing head group.

The amphiphile is substituted at the ω-position with a peptide

The amphiphile is substituted at the ω-position with a peptide containing the amino acid sequence RGD.

The rSAM is formed from one amphiphile or mixtures of two or more amphiphiles on the underlying surface.

The rSAM feature lateral diffusion coefficients of 0.1-10 $\mu m^2 s^{-1}$

The rSAM feature lateral diffusion coefficients similar to lipid bilayers.

The rSAM is formed from mixtures of two or more amphiphiles on the underlying surface followed by streptavidine.

The rSAM is formed from mixtures of two or more amphiphiles on the underlying surface followed by streptavidine followed by a biotinylated antibody.

The underlying surface is a SAM on gold

The underlying surface is a SAM of mercaptobenzoic acid (MBA) on gold

The underlying surface is a SAM of mercaptohexadecanoic acid (MHA) on gold

The underlying surface is a SAM of mercaptoundecane sulfonic acid (MDSA) on gold The underlying surface is a SAM of benzoic acid on glass or quartz The underlying surface is a SAM of decanoic acid on glass or quartz The analyte is a protein The analyte is prostate specific antigen The analyte is human serum albumin The analyte is hemagluttinine The analyte is a microorganism The analyte is a cell The analyte is a cancer cell The analyte is a stem cell The analyte is a virus The analyte is an influenza virus The analyte is an influenza virus of the type H5N1

Detection of the analyte is performed by fluorescence measurements

Detection of the analyte is performed using an optical technique

Detection of the analyte is performed by ellipsometry

Detection of the analyte is performed by surface plasmon resonance

Detection of the analyte is performed electrochemically

Detection of the analyte is performed gravimetrically

The rSAM is used as a sensor to detect any of the analytes

The rSAM is used to control the adhesion of cells

The rSAM is used as dynamic supports for glycans in glycan arrays.

The rSAM glycan arrays are used for surveillance of influenza strains, identification of biomarkers for cancer and infection, and profiling of immune responses to vaccines.

The invention will be described in more detail giving a number of nonrestricting examples. Reversible self-assembled monolayers (rSAMs) are pH-switchable monolayers allowing a reversible and ordered introduction of affinity reagents on sensor surfaces. The principal layer building blocks consist of bola-amphiphiles comprising a hydrocarbon chain with hydrophilic end-groups at both the termini i.e at the α- and ω-ends. Preferably these are α-(4-amidinophenoxy)alkanes decorated at the ω-position with phenoxy substituted at the 3 or 4 position with a chain or spacer of repeating units of ethylene glycol (Filler) which can be optionally terminated with affinity ligands (Amidin-R) (FIG. 35). The alkane can be an acyclic hydrocarbon chain preferably with a number of carbons ranging from 2-16. These spontaneously self-assemble on top of oxo acid terminated SAMs to form reversible homo- or mixed monolayers (rSAMs) that are tunable with respect to the nature of the end-group and layer order and stability while featuring pH responsiveness and the dynamic nature of non-covalently build assemblies.

1. General Design and Synthesis of α-Benzamidine ω-Ligand Substituted Bola Amphiphiles and Method for their Synthesis by Cupper (I) Catalyzed Click Coupling from Amidine-Azides and Alkyne Substituted Ligands.

In order to develop rSAMs of bola-form amphiphiles into platforms suitable for biological applications such as biosensing and cell studies, analogous to SAMs but with lateral mobility and stimuli-responsiveness the following design strategy is adopted. Designing SAMs for molecular recognition require an upright orientation of the amphiphile molecules in the assembly with the bioactive ligands facing the external environment. With the well-established alkanethiol SAMs, this is achieved by substituting the ω-position with the ligand of interest. A versatile procedure consists of a Sharpless/Huisgen click coupling of ω-azide-substituted bola amphiphiles and alkyne substituted ligands as outlined in FIG. 35. Accessibility to ligand binding is promoted by inserting spacers of ethylenglycol, with a number of repeat units preferably ranging between 1 and 5, between the glycan and the hydrophobic hydrocarbon chain. Examples of the azide-substituted amidines are described in the accompanying examples. One example is amino(4-(10-(4-(2-(2-(2-azidoethoxy)ethoxy)ethyl)phenoxy)decyloxy) phenyl)methan iminium azide (11) (amidine-azide in FIG. 35 with n=2). The alkyne substituted ligand can be any of those described in the accompanying examples such as and alkyne substituted biotin, monosaccharide, disaccharide, glycan, ω-galactose, mannose, sialic acid (e.g. N-acetylneuraminic acid (Neu5Ac, human form of sialic acid) or N-glycolylneuraminic acid (Neu5Gc, animal form of sialic acid)), neuraminidase inhibitor (e.g. zanamivir, oseltamivir, peramivir), Siaα2-6GalNAc (Sialyl Tn), Siaα 2-3Galβ 1-3GalNAc (Sialyl T), Siaα2,3-Galβ, Siaα2,6-Galβ, Siaα2, 3-N-acetyllactosamine, Siaα2,6-N-acetyllactosamine, GlcA2SO$_3$-1,4-Glc2NSO$_3$, GlcA2SO$_3$-1,4-Glc2NSO$_3$6SO$_3$ or a peptide preferably containing the amino acid sequence RGD e.g. GRGDS.

For development of functional biomaterials such as SAMs, filler amphiphiles are commonly mixed with the amphiphiles containing the bioactive ligands during layer formation to allow stoichiometric control over ligand surface density and insertion between the ligand amphiphiles to reduce steric hindrance of the large ligand end-groups. The ideal filler molecule is inert towards non-specific interactions. As such, we utilized a common approach for SAMs formation by introducing repeating units of ethylene glycol at the ω-position. A series of w-(ethylene glycol),α-(4-amidinophenoxy)decane with 2 to 6 even repeating units of ethylene glycol, E2-6 was synthesized from intermediate 7 with hydroxyl substitution and a final Pinner conversion.

2. Design, Synthesis and Characterization of a Glycan rSAM

Figure 1:
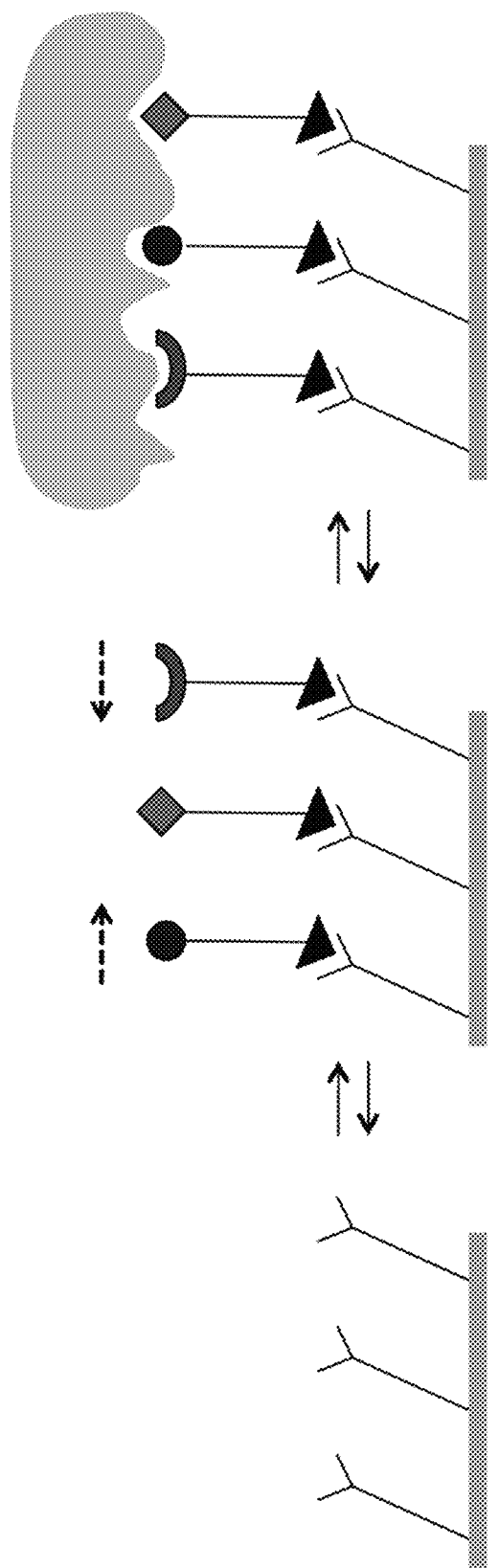
FIG. 1 is a schematic drawing of the concept of reversible self-assembled monolayers using two or more layer components to produce robust lipid bilayer membrane (LBL) mimicking surfaces.
Figure 2A:
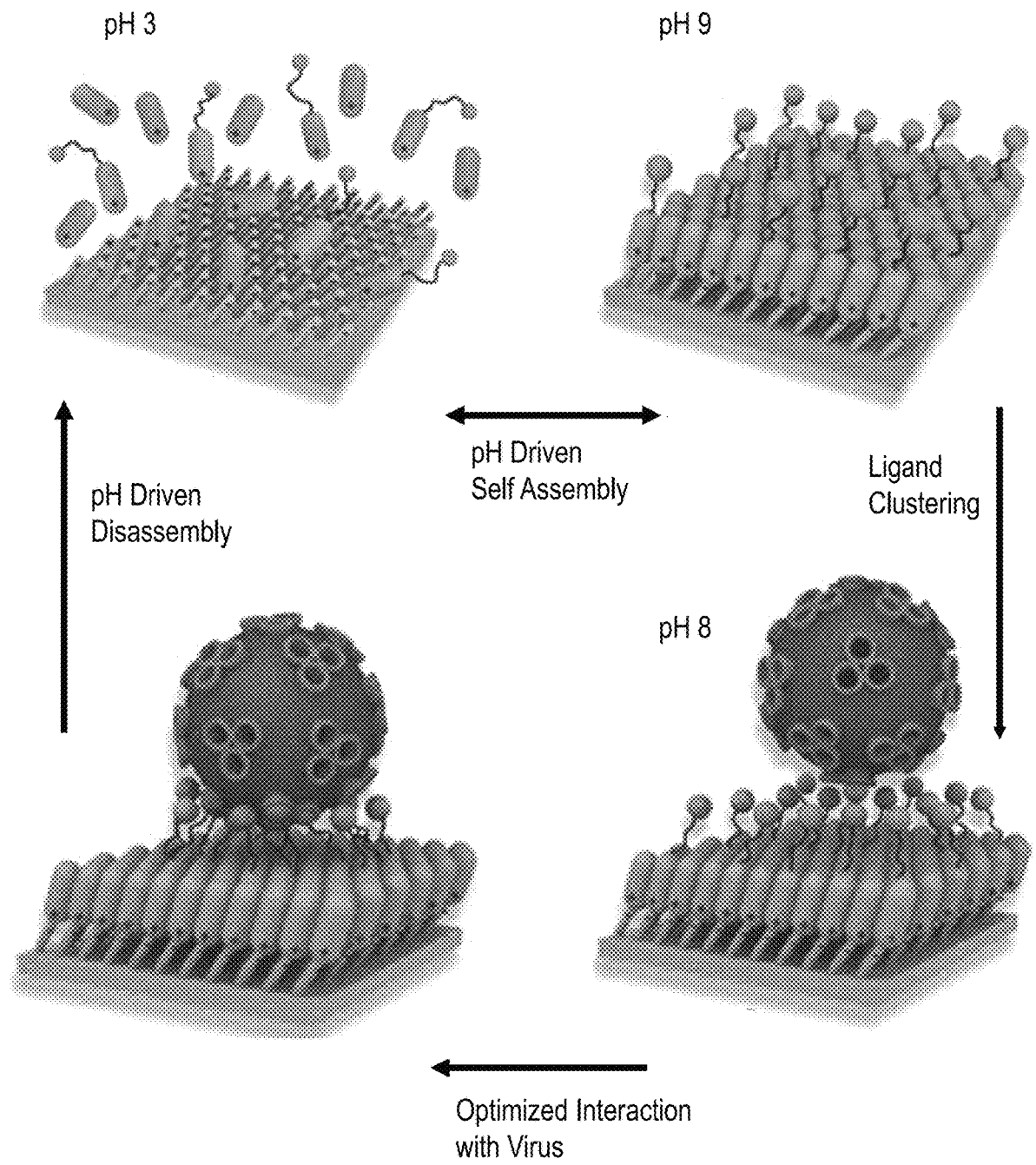
FIGS. 2A-2B are schematic drawings of an LBL-mimicking surface applied to the recognition and sensing of lectins and virus particles. The structures of the OH-terminated amidine 1 and sialic acid terminated amidine 2 have been drawn.
Figure 2B:
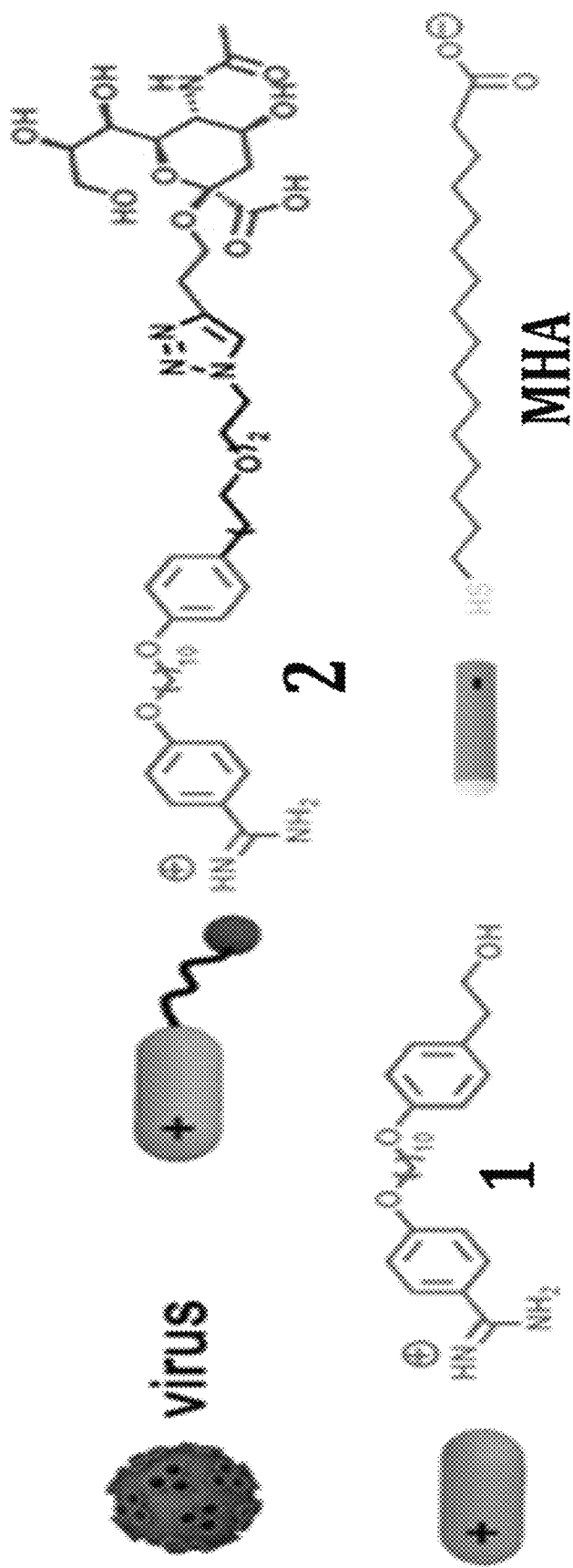
Figure 25:
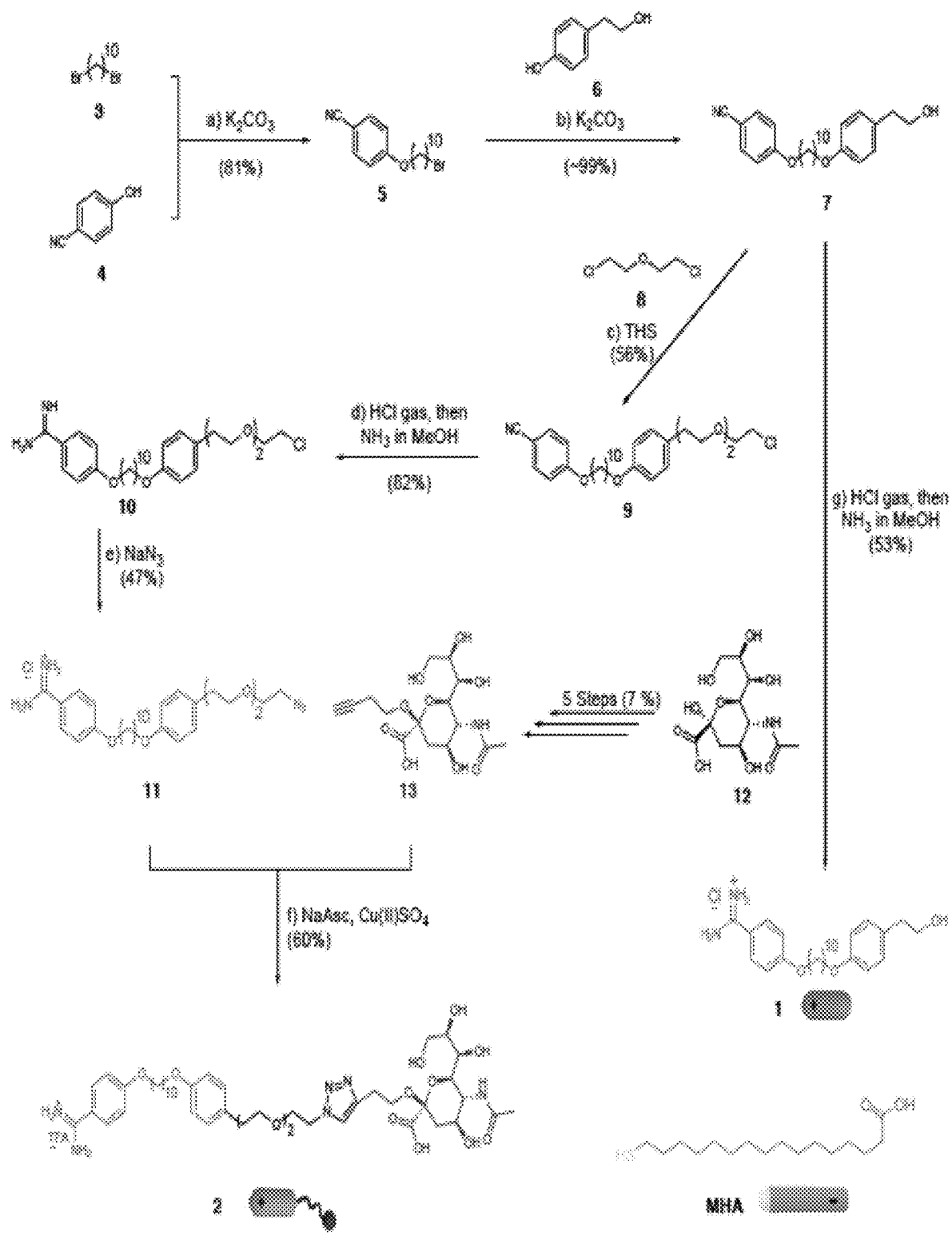

In order to extend the rSAM concept from homo- to heterodifunctionalized amphiphiles we aimed at appending biologically active ligands such as sialic acid at their ω-position and to investigate the affinity of the dynamic surfaces for lectins and virus particles (FIGS. 1-2B). The design of such surfaces requires attention to the geometrical constraints governing the receptor ligand interactions. Critical parameters are the surface density of ligands, the flexibility and polarity of the spacer and the distance separating the ligand from the underlying surface of the SAM. Mixed SAMs, polymers, or liposomes have been extensively studied for this purpose. Binary mixtures of amphiphiles typically containing 1-20% of sialic acid terminated amphiphile have proven optimal for inhibiting agglutination, infection or for sensing. Accessibility to lectin binding is promoted by inserting spacers of 2-3 ethylenglycol repeat units between the glycan and the SAM or liposome surface. Taking these criteria into consideration we designed a convergent synthesis strategy (FIG. 25) ending in the alkyne sialic acid 13 and the azide-terminated amidine fragment 11 which were joined by a final Sharpless/Huisgen click coupling to afford 2. Preceeding the coupling, 11 was prepared in five steps by sequential Williamson ether synthesis followed by Pinner conversion and azide substitution in an overall yield of 17%. The a alkyne sialic acid 13 was synthesized in 5 steps as recently reported whereas 1 was obtained by direct Pinner conversion of 7.

In situ ellipsometry To confirm formation, structure and properties of adsorbed films we used in situ ellipsometry, IRAS, contact angle and AFM. In situ ellipsometry was first used to verify formation of the thiol SAM used as rSAM anchor. We have previously shown that ordered SAMs of the long chain alkanoic acid MHA on gold are well suited for this purpose. The results collectively agree with previous findings which support a fast spontaneous assembly resulting in ordered monolayers with the alkane chains slightly tilted with respect to the surface normal. We then investigated the adsorption mode of the amidine amphiphiles 1 and 2 alone or as mixtures on this SAM. FIG. 26 shows the average film thickness and amount adsorbed during adsorption of the amphiphiles from 50 μM solutions in pH 9 sodium borate buffer.

The adsorption kinetics, the limiting film thickness and the stability to rinsing depended strongly on the type of amphiphile system. Considering first OH terminated amphiphile 1, this showed a relatively slow adsorption while forming a stable film with a thickness of 46 Å, hence exceeding the amphiphile molecular length (28 Å) assuming an extended chain conformation (Table 1). This agrees with our previous study of the adsorption mode of a homologous series of bis-benzamidines on negatively charged surfaces and indicates formation of bilayered structures featuring an underlying layer of high order and a less ordered top layer. In contrast, 2 displayed a very fast adsorption and a final film thickness of 54 Å prior to rinsing, exceeding only slightly the theoretical value of 47 Å. The layer thickness dropped significantly upon rinsing with pH 8 buffer levelling off at 19 Å. As seen in FIG. 26B, this layer can be rapidly destabilized/restabilized by cycling the pH between 3 and 9 showing that the process is fully reversible.

TABLE 1

Characterisation results of the SAMs in the study.

Self assembled monolayers

|  | MHA | 14[g] | 1 | 1 + 2 (x$_2$ = 0.2) | 2 |
|---|---|---|---|---|---|
| Contact Angle (°) [a] | 22 ± 2 | 27 ± 4 | 47 ± 11 | 29 ± 0 | 40 ± 2 |
| d (Å) [b] | 21 | 26 | 28 | — | 47 |
| d$_{ads}$ (Å) [c] | — | — | 44 ± 0 | 58 ± 0 | 54 ± 1 |
| d$_{rinse}$ (Å) [c] | 21 ± 1 | 7 ± 2 [h] | 46 ± 0 | 49 ± 2 | 19 ± 1 |
| ν CH$_2$ CH asym (cm$^{-1}$) [d] | 2920 ± 1 | 2918 | 2929 ± 1 | 2919 ± 1 | 2923 ± 1 |
| ν CH$_2$ CH sym (cm$^{-1}$) [d] | 2851 ± 0 | 2850 | 2853 ± 1 | 2851 ± 1 | 2855 ± 2 |

TABLE 1-continued

Characterisation results of the SAMs in the study.
Self assembled monolayers

|  | MHA | 14[g] | 1 | 1 + 2 ($x_2 = 0.2$) | 2 |
|---|---|---|---|---|---|
| Tilt angle (°)[e] | 37 ± 4 | — | 13 ± 3 | 19 ± 4 | 19 ± 0 |
| Roughness, $R_{RMS}$ (nm)[f] | 0.21 (0.01) | 0.38 (0.04) | 1.33 (0.02) | 2.44 (0.30) | 0.29 (0.05) |

The surfaces were rinsed with pH 8 HEPES buffer (0.01M) prior to analysis unless stated otherwise. All reported values are the average of min. 2 experiments on different substrates unless indicated otherwise.
[a] The static contact angle was taken at 3 different positions.
[b] Theoretical film thickness (d) assuming a densely packed layer of molecules oriented perpendicularly to the surface with the alkyl chains in an all-trans arrangement.
[c] Adsorbed thickness of MHA, $d_{rinse}$ was estimated using in situ ellipsometry after the adsorption of MHA onto cleaned gold surfaces in EtOH and rinsing with EtOH. The adsorbed thickness, $d_{ads}$ of rSAMs 1, 1 + 2 and 2 on MHA modified gold surfaces were estimated using in situ ellipsometry after the system reached steady state or for a maximum duration of 5000 s after introduction of the amphiphiles in pH 9 borate buffer (0.01M). Thickness after rinsing, $d_{rinse}$ of rSAMs 1, 1 + 2 and 2 were estimated after rinsing the surfaces with pH 8 HEPES buffer (0.01M) for 1000 s followed by equilibration until steady state or for a maximium duration of 5000 s.
[d] IR band positions corresponding to the $CH_2$ C—H asym and $CH_2$ C—H sym stretch.
[e] The average tilt angles, θ of the phenyl group relative to the surface perpendicular for rSAMs adsorbed on MHA. The tilt angles were calculated on the basis of the relative intensity of the bands corresponding to two perpendicular ring modes-the $(C=C)_{1,4}$ stretch band at 1611 cm$^{-1}$ and the C—H out-of plane bending mode at ca. 843 cm$^{-1}$. The spectra were subjected to base-line correction prior to analysis.
[f] The roughness, $R_{RMS}$ was calculated based on the 500 μm × 500 μm using Gwyddion. Each substrate was sampled in two areas. The bracketed values indicate the standard deviation.
[g] Results for the covalently anchored sialic acid SAM.
[h] Results from ex-situ ellipsometry in air.

The contrasting behaviour of these amphiphiles is likely related to their water solubility. 2 with its hydrophilic carbohydrate end-group is highly water soluble and we anticipate a SAM with a low surface energy with respect to the borate buffer media. This stabilizing contribution is however counteracted by the bulkiness of the end-group, which together with charge repulsion likely hinder close packing of the amphiphile chains and a monolayer of perpendicularly oriented amphiphiles to form. OH-terminated 1 is on the other hand poorly water-soluble and may therefore adsorb in the form of aggregates—this can explain the slower adsorption kinetics and formation of bilayered structures. We therefore went on to study a mixed rSAM. Adsorption in presence of a mixture of the two amphiphiles 1 and 2 ($\chi_2$=0.2) occurred at a rate that was intermediate between that of 1 and 2 alone. The resulting layer featured a film thickness close to that of 2 alone but in contrast to the latter, this layer was completely stable to rinsing. The data supports the formation of a mixed assembly but does not offer any insight into the structure of the films and stoichiometry of the layer components.

IRAS and AFM. To obtain further insight into the nature of these films we used infrared reflection absorption spectroscopy (IRAS) and atomic force microscopy (AFM). All IRAS spectra were compared with the attenuated total reflectance (ATR) spectra of the corresponding bulk samples in order to draw conclusions concerning layer stoichiometry and the order and orientation of the amphiphile molecules. As an example, FIGS. 27A-27H show the spectra of rSAMs and a SAM of MHA on gold together with the ATR spectrum of their respective hydrochloride and trifluoroacetate salt forms. Inspection of the spectra of the modified MHA-SAMs leads to identification of all significant peaks present in the ATR spectrum. This provides evidence for the presence of the amidines on the acid monolayer. Compared to the ATR spectra, however, the spectra of the rSAMs exhibit different relative band intensities and band-widths which are informative about the order and orientation of the layer components. Particularly striking are the relative intensities of the benzene $(C=C)_{1,4}$ stretch at 1611 cm$^{-1}$ and the C—O—C asymmetric stretch at 1247 cm$^{-1}$ relative to the intensities of the aromatic C—H out-of-plane bending mode at 841 cm$^{-1}$ and the amidine N—C=N asymmetric stretch found around 1690 cm$^{-1}$, the latter coinciding with the amide I and C=O stretch of the sialic acid end-group. The former have transition dipole vectors oriented along the 1,4-axis of the benzene ring and the longitudinal axis of the alkyl chain, respectively, whereas the latter have transition dipole vectors perpendicular to the 1,4-axis. The gain in intensity of the former signals and the concomitant decrease of the latter indicate a near upright position of the benzamidine end-group. Hence, the average tilt angles of the benzamidine group relative to the surface normal are small in all layers (13-19°) with rSAM-1 featuring the most upright groups (13°) (Table 1).

The position of the $CH_2$ asymmetric and symmetric stretch vibration (<2920 cm$^{-1}$ and 2850 cm$^{-1}$ respectively for ordered SAMs) as well as the band widths in the low-frequency region of the spectra are informative of the order of the monolayer structure. Whereas rSAM-1 feature these bands at positions indicating liquid like ordering (FIG. 27B), the mixed rSAM-1+2 appears more ordered (FIG. 27C). However, as indicated by in situ ellipsometry (vide supra) and AFM (vide infra) 1 tends to form bilayered structures. The top layer in these assemblies is presumably less dense and/or less ordered than the underlying layer contributing in turn to the high frequency of this band. The stoichiometry of layer components of mixed SAMs have been deduced based on component characteristic signals. 2 features an ethylene glycol linker and a sialic acid end-group with characteristic bands at 3345 cm$^{-1}$ (amide N—H stretch, carboxylic acid, hydrogen bonded OH stretch), 1694 cm$^{-1}$ (carboxylic acid, amide C=O stretch), 1431 cm$^{-1}$ (carboxylic acid, C—OH bend) and 1115 cm$^{-1}$ (aliphatic ethers, C—O—C stretch and secondary OH, C—C—O stretch). The normalized peak areas of these characteristic bands increase with increasing content of 2 showing that both amphiphiles coexist on the MHA SAM. More precise conclusions in terms of stoichiometry and mixing can not be drawn at this point.

Figure 3A:
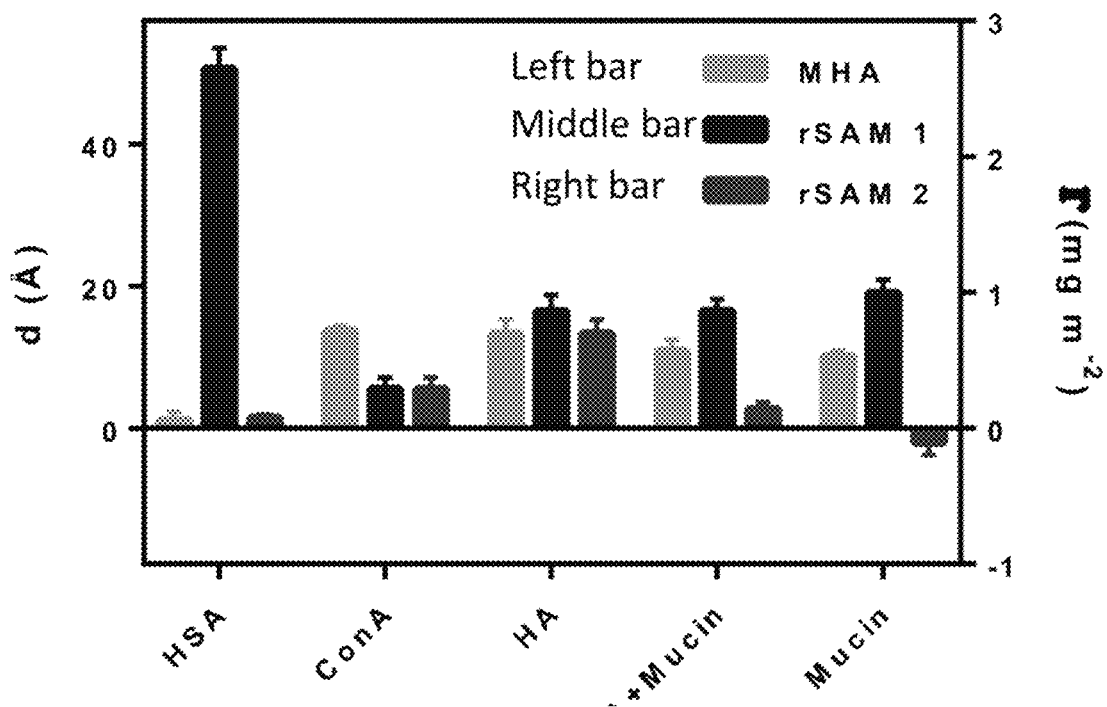

Instead we turned to AFM to obtain information concerning the lateral structure of the layers. The AFM image of a SAM of MHA is shown in FIG. 27E. This surface is relatively smooth with a roughness factor $R_{RMS}$ of 0.21. The image obtained after the assembly of 1 on this surface in a pH 9 borate buffer revealed large (>50 nm) domains (FIG. 27F) with a height of ca 3 nm, in close agreement with the molecular length of 1. Assuming a ca 60% surface coverage this should contribute roughly 2 nm to the layer thickness estimated using laterally averaging ellipsometry. However, in situ ellipsometry showed a layer thickness of 4.6 nm (Table 1), which exceeds this value by more than 2.5 nm. From these observations we conclude that 1 is near perpendicularly oriented with respect to the surface (vide supra) and that the AFM height profile in this case depicts the less densely packed top layer. The bottom rSAM-1 on the other hand appears densely packed. The domain structure prevails in the mixed rSAM (FIG. 27G), which shows a larger height contrast compared to the rSAM of 1 alone. On the contrary, rSAM-2 lacked domains and appeared as smooth as the SAM of MHA (FIG. 27H). A static control for the rSAM-2 surface, featuring covalently anchored sialic acid groups, was prepared by coupling sialic acid via an oligoethyleneglycol tether to a SAM of MHA. The resulting sialic acid SAM was characterised by FTIR, air ellipsometry and AFM (Table 1). The results indicate the formation of a smooth, well ordered SAM with a sialic acid coverage of 27%, the latter in the same range as the estimated sialic acid coverage of rSAM-2 of 40% (estimates based on the $d_{rinse}$ values).

rSAM interactions with viral proteins. In order to probe the rSAMs with respect to their affinity for the influenza lectin hemagglutinin (HA) we compared the adsorption of three proteins, the target lectin HA, concanavalin A (ConA) as a reference lectin and human serum albumin (HSA), representing the predominant blood protein. After assembly and rinse of rSAMs of 1 and 2 or a bare MHA SAM in pH 8 buffer, protein was added (21 nM) and the film thickness followed in real time by ellipsometry until a stable reading was obtained. As seen in FIG. 3A, the negatively charged MHA-SAM was resistant to HSA adsorption at this concentration whereas both lectins, ConA and HA, bound to reach approximately equal submonolayer thicknesses. The selectivity correlates to some extent with the isoelectric point pI of the proteins which increases in the order: HSA<ConA<HA. A different picture emerged when testing the two rSAMs prepared from 1 or 2. Whereas rSAM-2, in accordance with the bare MHA SAM, completely resisted HSA, the protein bound strongly to rSAM-1 resulting in a 52 Å film. Moreover, rSAM-2 displayed affinity for HA while showing a low crossreactivity for the two other proteins and was thus the only surface displaying the targeted selectivity.

This result was confirmed by IRAS of rinsed surfaces subjected to the different proteins. The relative intensities of the amide I and II bands increased in the order HSA<ConA<HA. To prove that HA binding to rSAM-2 was driven by the anticipated sialic acid-HA interactions we performed an additional control experiment. Mucin is an epithelial glycoprotein abundant in sialic acids. Among other functions it acts as a virus barrier by binding with high affinity ($K_i=2\times10^{-6}$ M) to HA. By preincubating HA with mucin we expected the lectin binding sites to be masked and adsorption driven by sugar lectin interactions to be suppressed. On the other hand, adsorption driven by nonspecific effects will not be affected in this experiment. FIG. 3A demonstrates the anticipated effect. Hence, mucin effectively suppressed binding of HA to rSAM-2 only, whereas it had no effect on binding to rSAM-1 or the MHA-SAM. Moreover, mucin alone adsorbs nonspecifically to rSAM-1 whereas rSAM-2 appeared completely resistant vis a vis this protein.

Figure 3B:
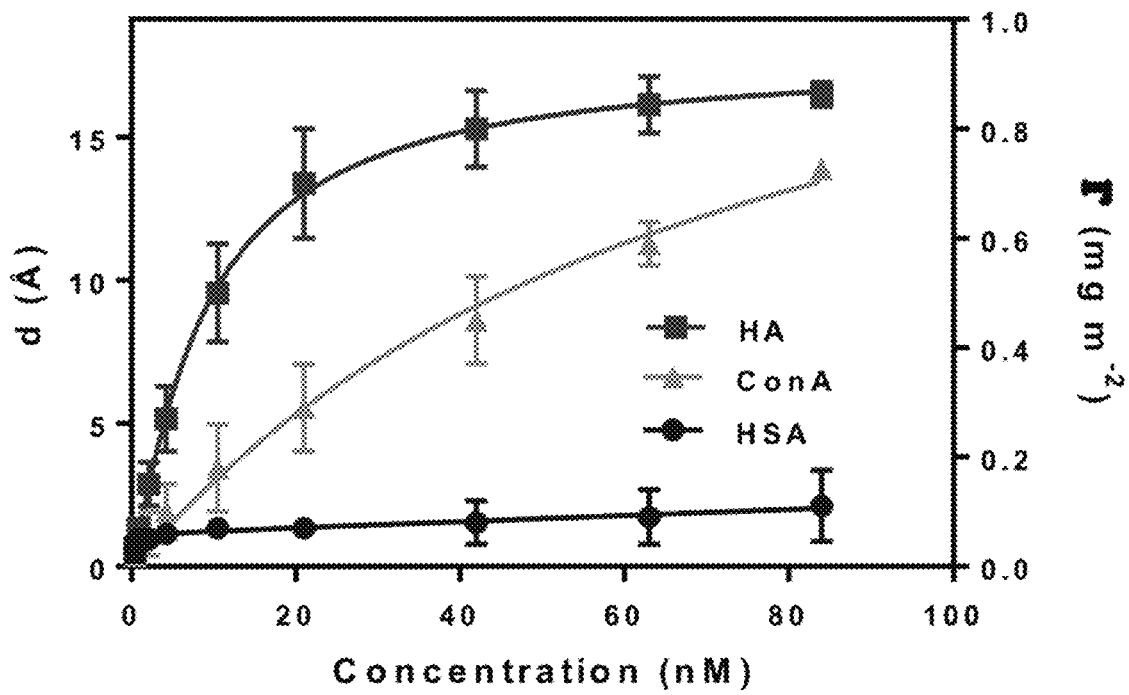

Given the nonspecific binding exhibited by the rSAM-1 (FIG. 3A) we refrained from studies of mixed rSAM based on this amphiphile but instead we decided to study the rSAM of pure 2 in more detail. FIG. 3B shows the equilibrium binding curves obtained after titrating freshly rinsed rSAM-2 with HA, ConA and HSA. This experiment fully confirms the functional properties of the glycan rSAM. Titration with HA resulted in a binding curve showing a steep initial portion followed by a clear saturation at concentrations exceeding 20 nM. This curve was best fitted with the Hill equation resulting in an overall equilibrium dissociation constant, $K_d^{multi}$ of 5.1 nM and an estimated detection limit of 0.84 nM. These results contrasted with the behaviour of rSAM-1 and the SAM of MHA. The corresponding binding curves were shallower and did not reach saturation within the investigated concentration interval. The weakly sigmoidal shape is in agreement with the glycan clustering effect and multivalent binding. The ConA binding curve however was shallow and showed no evidence of cooperativity, nor was saturation reached within the probed concentration interval. Hence, the results agree with the relative glycan specificity of the two lectins. Finally, as indicated by the lack of HSA binding, the surface appeared resistant to nonspecific binding of plasma proteins. Remarkably, each substrate could be used repeatedly by carrying out a pH induced regeneration. The complete removal of the rSAM was confirmed by ellipsometry, IRAS and contact angle measurements.

rSAMs interaction with influenza virus H5N1. As exemplified by the "bird flu" certain strains of the H5N1 influenza A virus subtype can be highly pathogenic and its pathogenicity is expected to rise. In order to probe the affinity of our dynamic rSAMs for this virus we subjected them to inactivated particles provided by the World Health Organisation (WHO). We started by carrying out a titration experiment identical to the one performed for the proteins (FIG. 3C) using three different surfaces, rSAM-2, a SAM featuring covalently attached sialic acids (SAM-14) and the anchoring MHA-SAM.

Figures 3C, 3D:
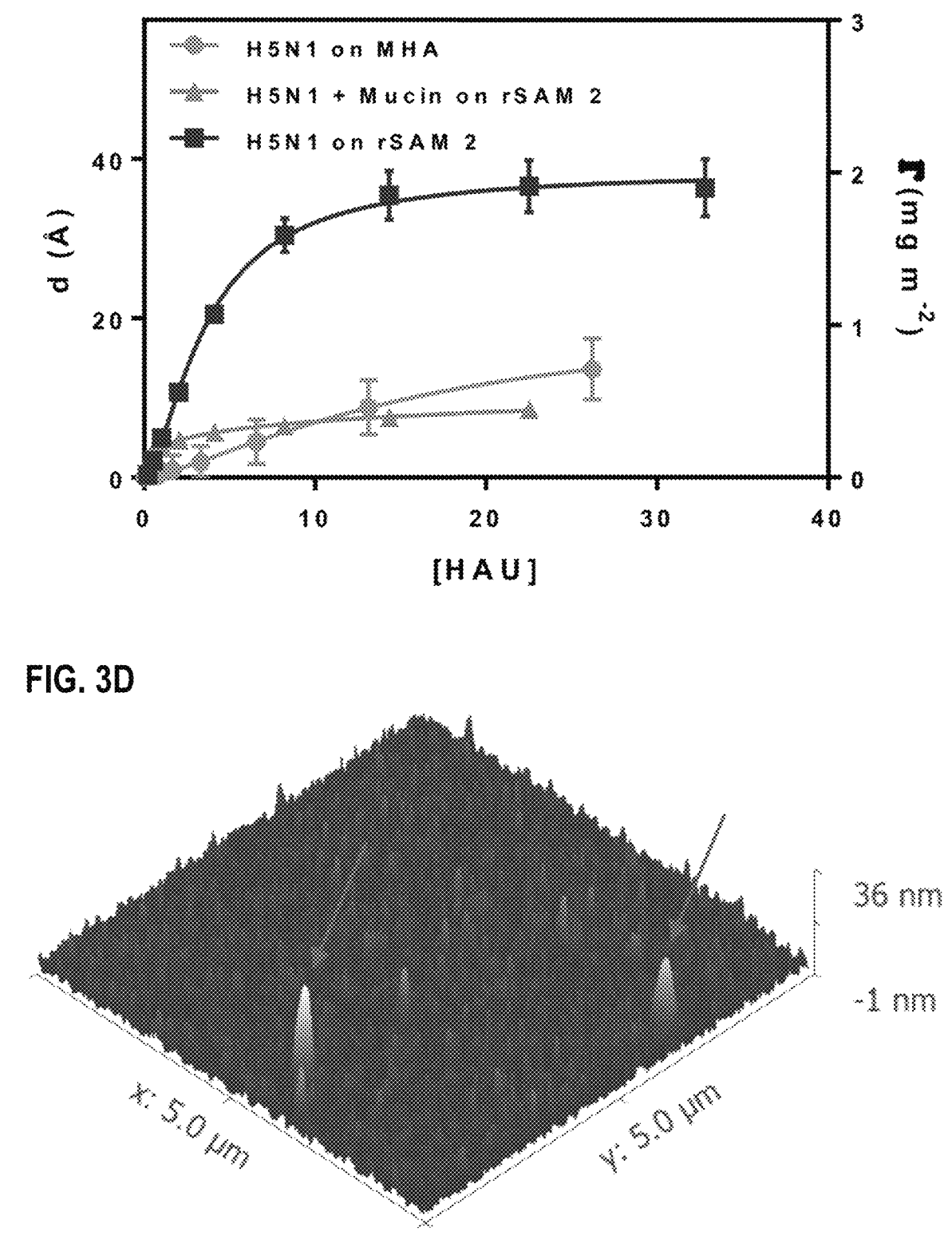

In analogy with the HA binding results (vide supra), the virus bound strongly to rSAM-2 with a clear cooperative binding behaviour while showing very weak affinity for SAM-14 and the underlying MHA-SAM. Fitting the curve with the Hill equation resulted in a $K_d^{multi}$ (M. Mammen, S.-K. Choi and G. M. Whitesides, Angewandte Chemie International Edition, 1998, 37, 2754-2794) of $2.1\times10^{-13}$ M and a detection limit of 0.5 HAU (46 fM), the latter corresponding to a mass sensitivity (assuming a virus molecular weight of $2.5\times10^8$ g/mol) of ca 11 ug/L. Adsorption of the virus was effectively suppressed by the mucin induced masking of HA (FIG. 3C).

In order to assess the influence of potential errors due to nonequilibrium binding we also performed a kinetic multicycle interaction analysis. The rate constants for virus adsorption and desorption were calculated from the adsorption and desorption rate profiles. The dissociation constants, $K_d$, determined by this method were in good agreement with the equilibrium analysis.

The high affinity displayed by rSAM-2 stand in striking contrast to the weak virus adsorption on SAM-14. The two SAMs feature near identical tethers but different ligand densities (40% and 27% respectively). Although this makes an unambiguous comparison difficult, it should be noted that mixed thiol SAMs with lower ligand densities typically show higher lectin/virus affinities. Hence, surfaces with less than 20% of the end-groups being glycans are more effective binders whereas binding drops with increasing ligand density. Moreover, we note that comparable sialic acid modified SAMs also display low affinity e.g. in the uM range towards hemagglutinin. All in all, this strongly indicates that dynamic interactions in rSAMs play an important role in enhancing influenza virus detection.

Figure 4:
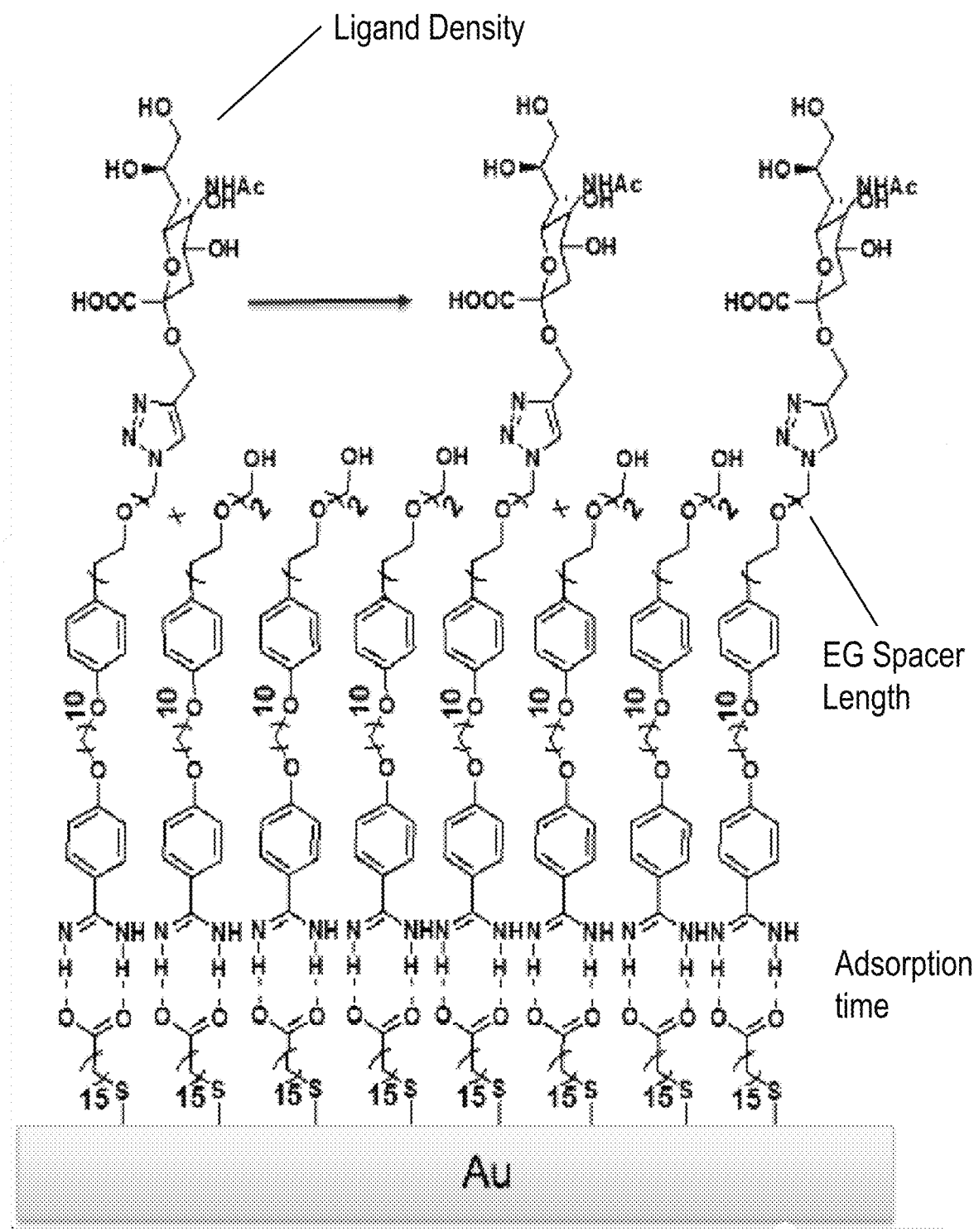
FIG. 4 shows a general strategy for optimizing multivalent binding affinity by tuning ligand density, ligand presentation and time of adsorption.

AFM images recorded for a rinsed rSAM-2 exposed to the virus are shown in FIG. 4. The virus particles could be discerned as spikes with a height of ca. 40 nm that were absent in images of rSAM-2 prior to virus exposure. The surface roughness after virus exposure ($R_a$=2.3 nm) agreed with results reported for a glycan modified thiol SAM. pH-induced restoration of the MHA-SAM was proven by IRAS and contact angle measurements of the surface prior to and post acidification. Hence the MHA-SAM was stable and the sensor could be reused several times.

Optimization of ligand density and presentation. We recall that the above results were obtained for an rSAM of 2 only and that efforts to use mixed rSAMs were hampered by excessive nonspecific binding on rSAM-1. We therefore set out to prepare more protein resistant surfaces based on oligoethylene glycol (EG) terminated rSAMs and accordingly to optimize the sialic acid tether length (FIG. 4).

Here we demonstrate rSAMs for quantitative fluidic immobilization of glycans for multivalent interaction studies. Using the trimeric binding of sialic acid to hemagglutinin as example, using rSAMs as scaffolds for sialic acid display strongly enhanced binding affinity compared to static immobilization. Quantitative immobilization of sialic acid amphiphiles were achieved by doping varying mole fraction of sialic acid amphiphiles in ω-(ethylene glycol)$_2$α-(4-amidinophenoxy)decanes. Ellipsometry, IRAS and AFM results directly correlated with the concentration of amphiphiles used. Length of sialic acid linker, surface density of sialic acid were found to be crucial parameters in determining binding affinity.

Influenza viruses bind optimally to surfaces presenting <20% sialic acid. Slides were modified with the desired surface density by incubating MHA-modified surfaces in the corresponding mole fraction of E4-SA in E2 amphiphile. After 18 hrs the surfaces were carefully rinsed in pH 8 buffer and characterized by ellipsometry, FTIR and AFM to give conclusion regarding the sialic acid surface density.

The incorporation of sialic acid amphiphiles with the E2 amphiphiles was first investigated via real-time in situ ellipsometry by comparing between homogenous sialic acid or E2 amphiphiles with the mixed solution. The initial assembly kinetics of spacer and sialic acid are similar. Both samples slows down in kinetics at around 100s with the spacer reaching a height more than a monolayer, whereas, the sialic acid a height less than a monolayer. This could be due to the bulkiness of the sialic acid end-group that prevents close packing of the molecules. Both surfaces then start to slow down at the second stage. The spacer molecule has a sharper transition between the initial and second stage organization than the sialic acid, which could also be attributed due the bulky end-group that interfered with the closer packing of molecules.

This was further supported by the kinetics of the mixed monolayers. First of all, the initial kinetics of mixed monolayers kinetics were similar to both pure amidine and sialic acid. This slows down at around 100 s. Moreover, the mixed monolayers have a larger thickness as compared to both pure amidine and sialic acid. This could only be attributed to the spacer that allows improved spatial arrangement of the molecules. This kinetics between the 3 samples tell us that during the adsorption phase, the sialic acid is incorporated onto the surface and the spacer molecule is crucial for packing of the surfaces. However, information regarding the composition of sialic acid and spacer on surface in relation to the composition of mixture used for immobilization is unknown.

Ellipsometry. The surfaces were then allowed to incubate overnight and rinsed with pH 8 HEPES buffer to remove the loosely bound molecules and blow dried. The thickness of the monolayers were then measured using ex situ ellipsometry. Spacer molecules give a monolayer thickness, while the sialic acid amidine gives a sub-monolayer thickness. With increasing mole fractions of sialic acid, E4-SA used, the ellipsometric thickness increases and plateaus at X=0.15. This results suggest that dilution of the sialic acid with spacer molecule improved rinse stability and the linear correlation from 0-0.15 suggest a direct relation of sialic acid surface composition and the solutions composition. However, the thickness stop increasing at X=0.2.

A few questions come to mind. Is the surface filled with the sialic acid amidine at X=0.15 that precludes the close packing at X=0.2, that makes it less rinse stable to rinsing or is it the limitation of ellipsometric model? To give an insight to these questions, the surfaces were further studied using FTIR and AFM.

IRAS. Comparison between the bulk and layer spectra of sialic acid amphiphile, the layers formed were less ordered assuming laying down orientation the surface by comparison of 1611 and 840 ratio. Layers that were formed by mixing sialic acid amphiphiles with the spacer however exhibit relative bands intensity and bandwidth corresponding to well-ordered amphiphiles. In the high frequency region, the $CH_2$ stretch vibration at 2918 cm$^{-1}$ (asym) and 2850 cm$^{-1}$ (sym) and sharpness of these bands of the layer spectra indicate the presence of trans extended closely packed amphiphiles. The pronounced increase of $(C=C)_{1,4}$ at ca. 1611 cm$^{-1}$ and concomitant decrease of aromatic C—H out-of-plane bending mode at 840 cm$^{-1}$ suggests a near upright position of the amphiphiles assemblies. Taking the peak intensity ratio of the layer and bulk spectra of aromatic C—H out-of-plane bending mode at ca. 840 cm$^{-1}$ and $(C=C)_{1,4}$ at 1611 cm$^{-1}$, the phenyl group of the amphiphiles are determined to have a tilt angle of ca. 18-20° relative to the surface perpendicular.

To obtain information regarding the incorporation of sialic acid amphiphiles in the layers, we compared the layer spectra of the spacer and sialic acid assemblies, the prominent signals derive from the sialic acid at ca. 3350 (bonded OH and mono substituted amide), 1440 and 1200 C—O—C and C—OH, which corresponded excellently with literature observations. Comparison between the integrated area below these sialic acid peaks and the mole fraction of sialic acid amphiphile used suggest linear incorporation of sialic acid on the surface. The questions remaining is the exact orientation of sialic acid molecules. To answer this questions, we turned to studying the surfaces using atomic force microscopy.

Figure 6A:
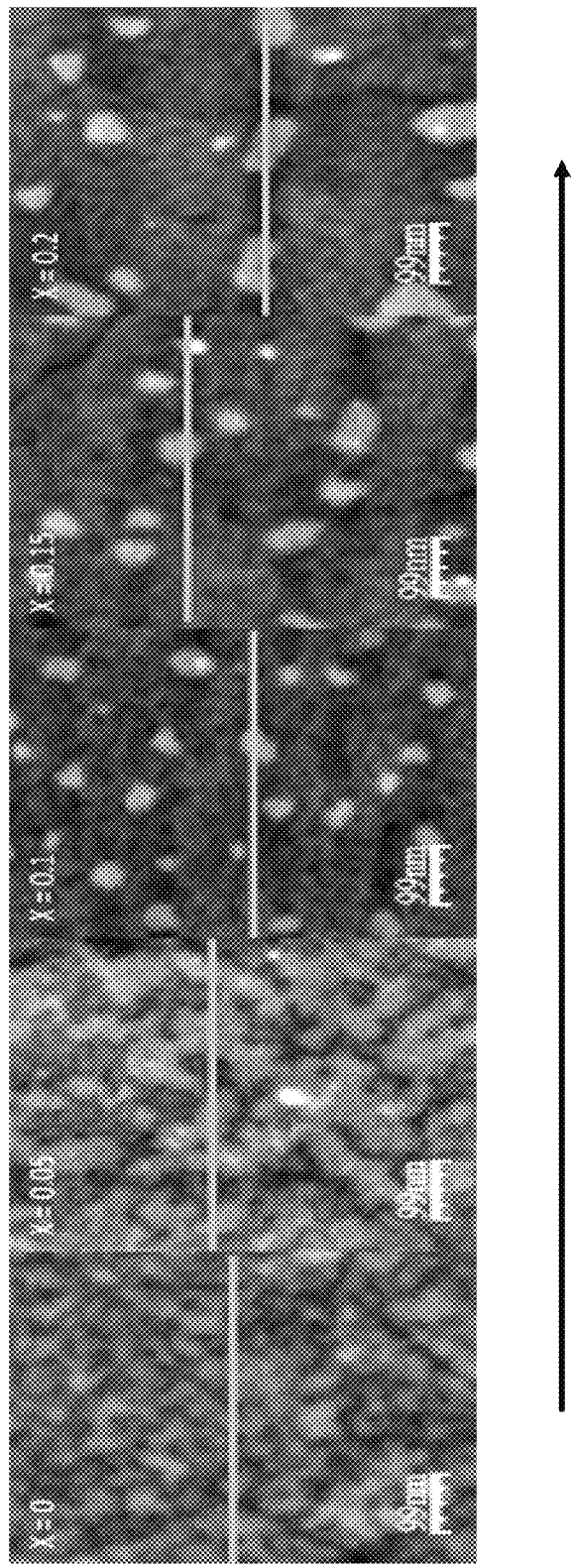
FIGS. 6A-6C show a AFM topography image and a profile of rSAMs prepared from different EG4 sialic acid 14 mole fractions (in presence of 15) ranging from 0 to 0.2, and plot of area covered by taller domains vs mole fraction of sialic acid used, respectively.
Figure 6B:
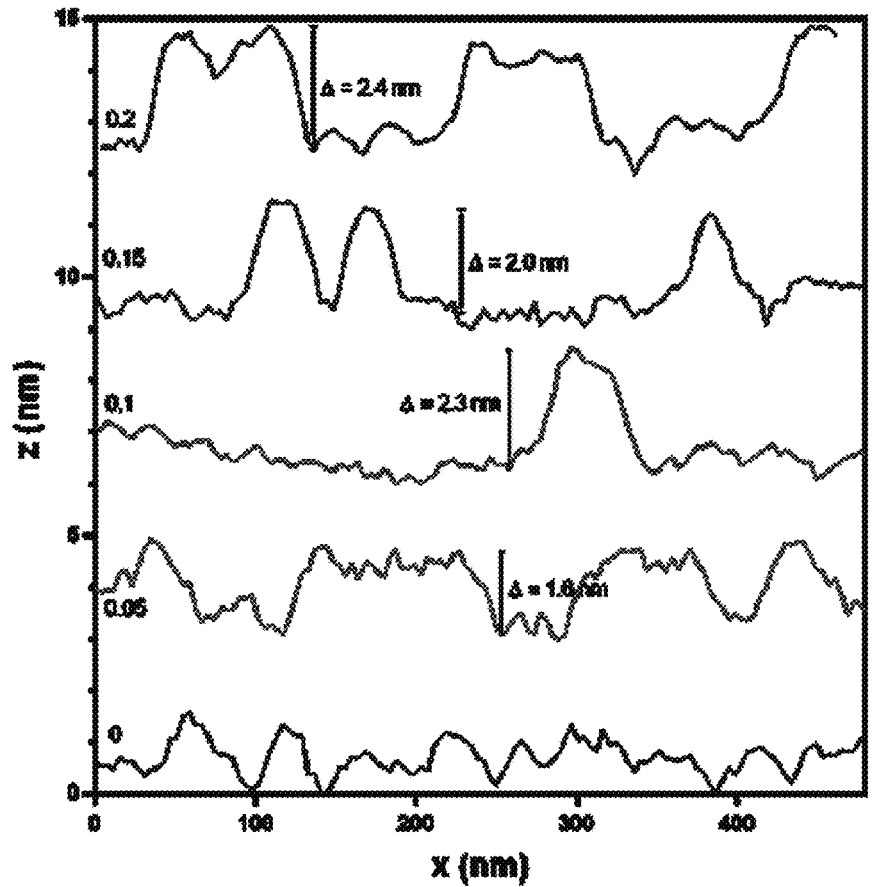
Figure 6C:
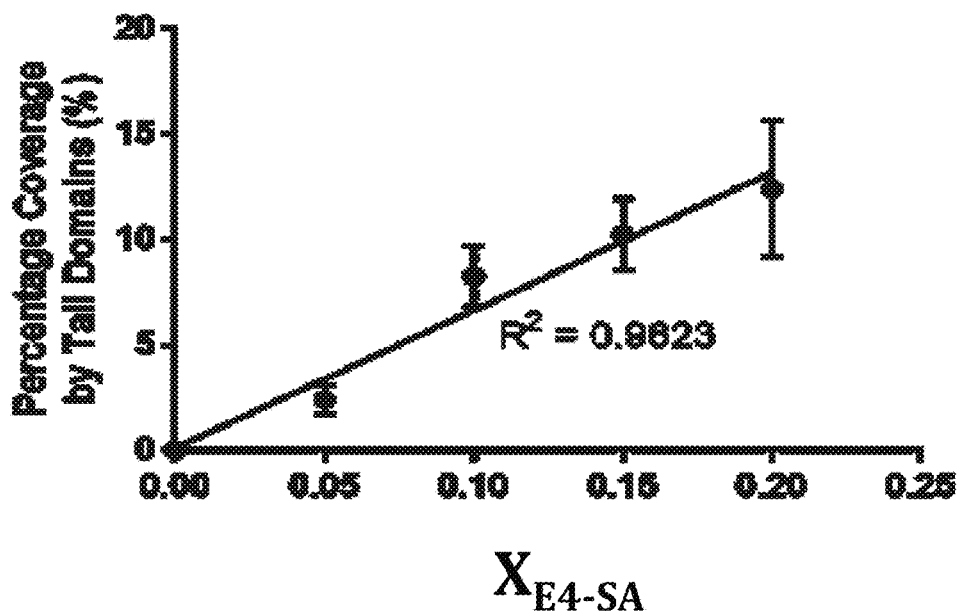

AFM. The pure spacer layers were rather featureless, suggesting monolayer formation as supported by the ellipsometric results. When sialic acid amphiphiles is introduced (χ=0.2), the topography of the shorter domains resembles the E2 layers, while taller domains of approximate 2 nm appeared. This coincides with the theoretical difference between the spacer and sialic acid amphiphiles and suggests ordered clusters of sialic acid amphiphiles formed on the surfaces. With increasing mole fractions of sialic acid amphiphiles used, the size of the 2 nm taller domains increases (FIGS. 6A-6C). Correlating the surface area covered by the taller domains with the ratio of sialic acid amphiphile used, we suggest a stoimetric incorporation of sialic acid in the layers within the probed sialic acid range. With the successful ordered immobilization of the sialic acid amphiphiles with varying density, the surfaces were then subjected to varying concentration of hemagglutinin to obtain information regarding binding affinity and surface density of sialic acid using fluidic rSAMs.

Hemagglutinin binding to static vs dynamic sialic acid platform. For optimal sialic acid and glycan binding, the chain length of the sialic acid protruding out of surface and the glycan density are two crucial parameters for optimizing. Here we analysed, the chain length of 2 and 4 (6 sialic acid was unable to formed stable monolayers) and the glycan density between 0.05 to 0.2. Parameters crucial for optimal hemagglutinin binding includes, duration of rSAMs assembly, chain length of sialic acid protruding out of sauce and ligand density. The results obtain were in conjunction with literature results, where optimal glycan density was between $\chi_{e4-SA}$=0.1 and 0.15. Interestingly, the surface was resistance towards hemagglutinin adsorption at $\chi_{e4-SA}$=0.2, strongly suggest that glycan density is crucial. This coincides with literature results where it was shown that formation of larger clusters appear to reduce receptor binding. At $\chi_{e4-SA}$=0.05, the rSAMs surface shows a binding mode with two distinctive KD.

Figure 5:
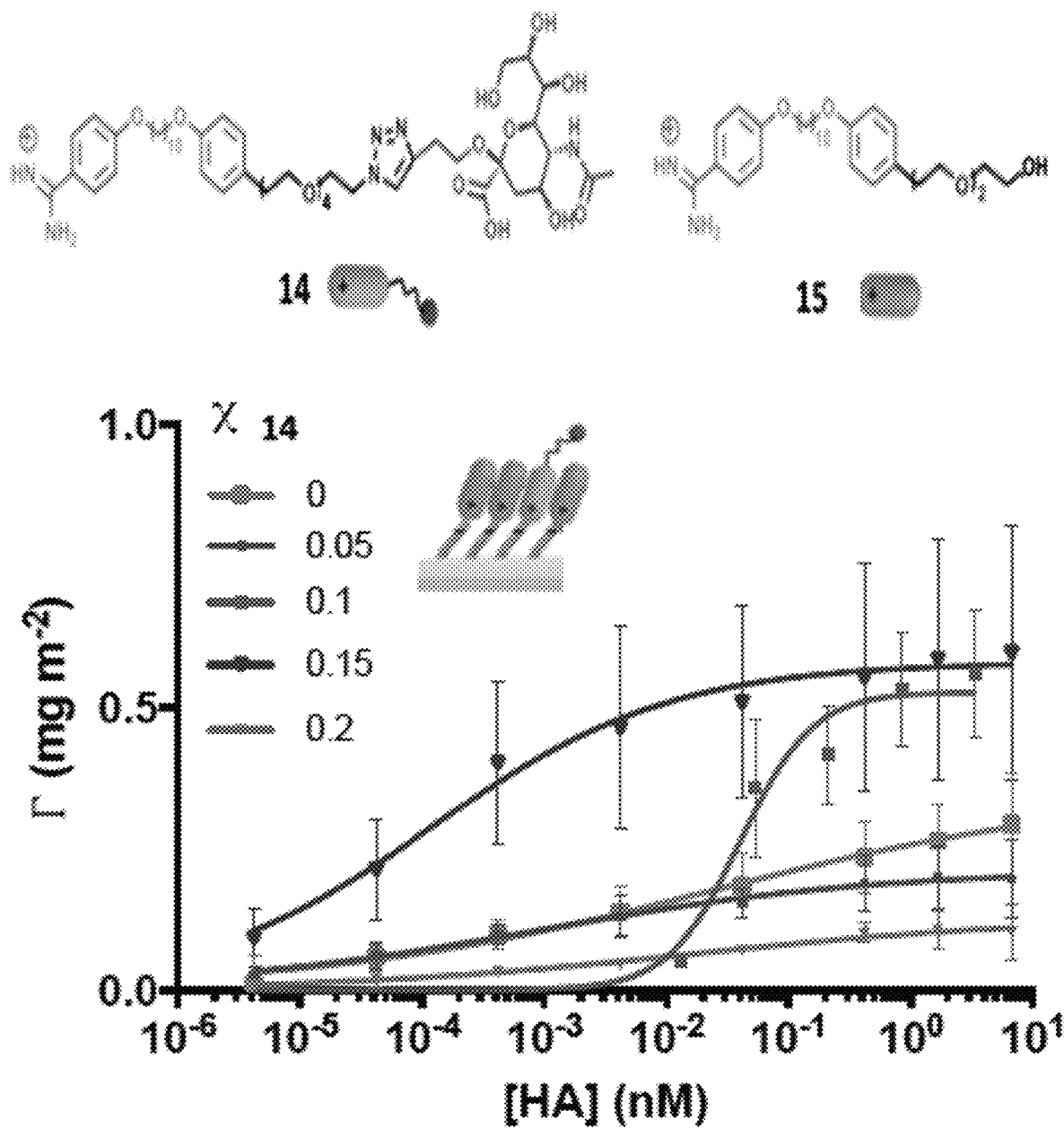
FIG. 5 shows Hemagglutinin binding isotherms of rSAMs formed with varying density of EG4-sialic acid 14 ($\chi$14) in mixed rSAMs of 14 and 15.

As shown in FIG. 5 a careful tuning of ligand presentation and ligand density leads to a strongly enhanced affinity for hemagglutinin (HA). Based on four EG repeats in the sialic acid tether as in 14 and two repeats in the OH-terminated amidine 15, the affinity for HA peaks at rather low ligand densities. For a surface prepared from 15% sialic acid amidine 14 it can be seen that the affinity has increased dramatically resulting in a $K_d^{multi}$ of $1.2 \times 10^{-13}$ M i.e. four orders of magnitude lower $K_d$ than the nM affinity reported for rSAM-2. The latter is nevertheless on a par with the best binders reported to date. These results are also in agreement with literature results, where optimal glycan densities are typically in the same range as we report here.

Figure 7:
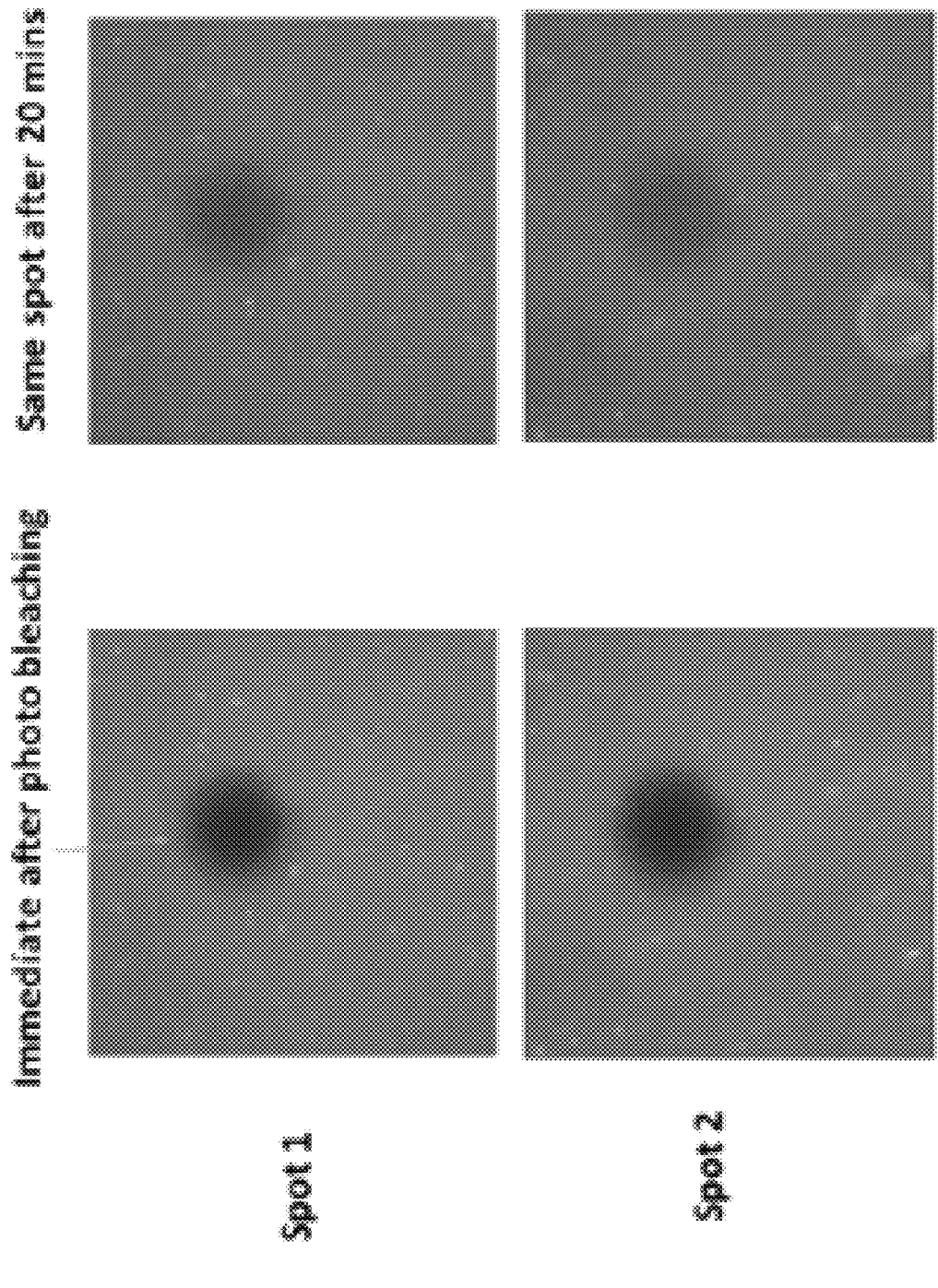
FIG. 7 shows Fluorescence recovery after photobleaching of a carboxylic acid SAM on quartz modified with the EG2 rSAM 15 doped with 1 mol % of FAM (fluorescein) terminated amphiphile. Bleaching was performed at 488 nm at full power for 30s and images recorded every 30 s for 20 minutes.

Lateral dynamics of layer components. As noted above, the high affinities displayed by the rSAMs likely stems from the dynamic nature of the films. To back up this hypothesis, we have used fluorescence recovery after photobleaching (FRAP) as a means to study monolayer fluidity. As shown in FIG. 7, dye doped rSAMs of 15 on quartz display fluorescence recovery in a time span similar to that observed for supported lipid bilayers. This clearly suggests layer dynamics to be the major cause of the enhanced affinities observed using the rSAM platform.

Comparison with literature. As a mean to compare the affinity of our assemblies with literature, we have summarized the affinity data of a series of assemblies based on α-sialoside groups (Table 2) and calculated the equilibrium dissociation constants, $K_d$, per sialic acid or monomeric HA. Making the assumption that each trimeric hemagglutinin has 3 sialic acid binding sites, the $K_d$ of our system towards HA was estimated to $1.5 \times 10^{-8}$ M for rSAM-2 and $3.6 \times 10^{-13}$ M for rSAM-14+15 per monomeric hemagglutinin, $HA_{mono}$ basis. Likewise, assuming each virus to contain 1500 sialic acid binding sites the $K_d$ towards H5N1 was estimated to $3.2 \times 10^{-10}$ M per monomeric hemagglutinin. To the best of our knowledge, α-sialoside glycopolymers has the highest reported affinity towards influenza viruses with an inhibition constant, $K_i$ of $10^{-10}$ M and a dissociation constant, $K_d$<$10^{-8}$ M per sialic acid unit. The tightest inhibitor for hemagglutinin is however a small molecule trivalent sialic acid with a $K_d$ of $1.3 \times 10^{-6}$ M. A comparison with other dynamic platforms such as liposomes and lipid bilayers are of particular relevance. These feature fluid bilayers where the sialic acids can diffuse laterally, in this respect ressembling the dynamic rSAM concept. An inhibition constant $K_i$ of $2 \times 10^{-8}$ M was reported for a liposome based multivalent inhibitor whereas polymerized liposomes bound influenza virus with a limit of detection of 4 HAU. Dissociation constants in the range $K_d^{multi}$=$10^{-10}$-$10^{-11}$ M were measured for H5N3 and H3N2 interacting with gangliosides (with intrinsically higher lectin affinity) in lipid bilayers. Although different techniques may have been used to determine the $K_d$:s, we can conclude that the affinity of our sialic acid rSAMs is on par with or exceeds the most potent binders reported.

TABLE 2

Comparison of mono-saccharide based sensors and inhibitors

| Lectin binder | Target | $K_d$ ($K_i$) (M) [a] | Reference |
|---|---|---|---|
| rSAM-2 | HA | $1.5 \times 10^{-8}$ | This work |
| rSAM-14 + 15 | HA | $3.6 \times 10^{-13}$ | This work |
| rSAM-2 | H5N1 | $3.2 \times 10^{-10}$ | This work |
| α-methyl sialoside | HA | $2.0 \times 10^{-3}$ | 39 |
| Trivalent inhibitor | HA | $1.3 \times 10^{-6}$ | 14 |
| Linear polymers [b] | H3N2 | <$10^{-8}$ | 15 |
| Gold nanoparticles | H3N2 | ($10^{-9}$) | 18 |
| Polymerized bilayers | H3N2 | $10^{-9}$ [c] | 40 |
| Liposomes [d] | H3N2 | ($2 \times 10^{-8}$) | 17 |

[a] $K_d$ = dissociation constant per SA or HA monomer unit. Inhibition constants, $K_i$, are given in parantheses.
[b] $K_d$ tabulated are based on the best performing polymers.
[c] Estimated graphically based on reported binding curve.
[d] Polymerized liposomes show a limit of detection of ca 4 HAU/mL.

We have demonstrated a new generic supramolecular concept for multivalent recognition and proven its benefits for enhancing recognition in affinity biosensors. Our results consistently show an overall enhanced affinity for both lectin and virus with respect to previous reports, which we attribute to a unique lipid bilayer like ligand adaptability. Another advantage of this glycan-based sensor is the simple architecture. Only three components are used to set up this sensor for detection. It can be built up in two immersion steps and is ready for detection with the significant advantage of substrate reusability. Further work will address the specificity of the sensor in terms of virus subtype recognition and extention of the operational pH range. Moreover, we will show in forthcoming reports the generic nature of the rSAM concept to boost biosensor affinity and restorability.

3. rSAMs as Air and Protein Exchange Stable Fluidic Lipid Bilayer Mimics

Figure 8:
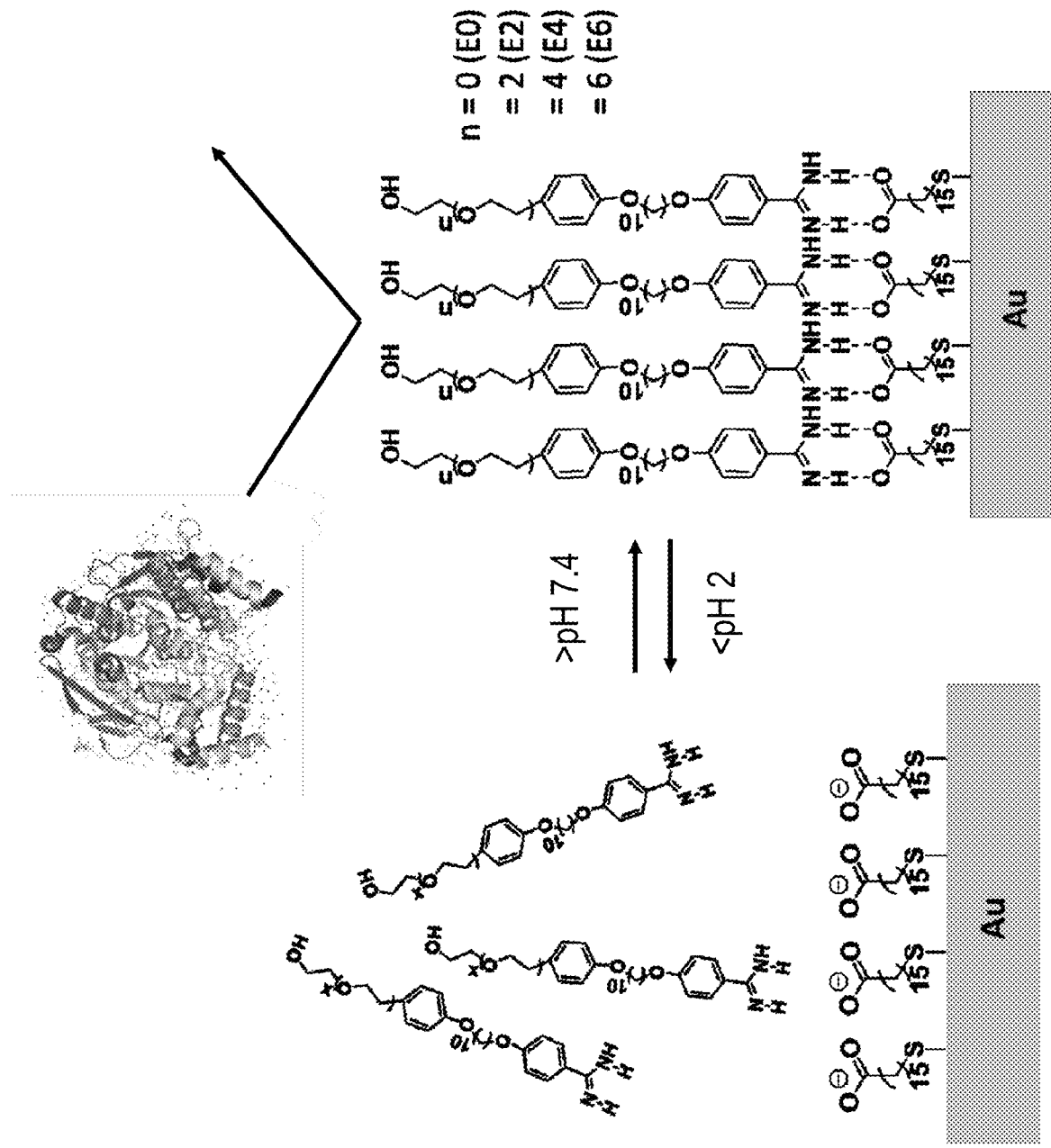
FIG. 8 is a schematic illustration of $\omega$-(ethylene glycol)$_{0\text{-}6}$-$\alpha$-(4-amidinophenoxy)decanes, E0-6 rSAMs on MHA modified gold and their use to suppress nonspecific protein adsorption.

We report on the design and characterization of reversible self-assembled monolayers (rSAMs) featuring terminal oligoethylene glycol chains imparting pH switchable protein resistance (FIG. 8). A series of ω-(ethylene glycol)$_{0-6}$-α-(4-amidinophenoxy)decanes, E0-6 were synthesized as described in the Examples.

The assembly kinetics and rinse stability of E0-6 were first evaluated using in situ ellipsometry at pH 9 borate buffer followed by pH 8 HEPES buffer rinsing. Using IRAS and AFM, further information regarding the molecular order of the formed layers were subsequently obtained.

Assembly and surface characteristics of E0-6 rSAMs on MHA modified gold. The rSAM film thickness on MHA modified gold surfaces were measured in real time upon exposure to 50 μM E0-6 in pH 9 borate buffer solution. The assembly rates, $K_{on}$ of amphiphiles increases with the number of ethylene glycol units, with E0, featuring only the terminal hydroxyethyl functionality adsorbing distinctively slower than the other 3 ethylene glycol tethered amphiphiles. Equilibration of the surfaces with the amphiphilic solution gave the limiting equilibrium thickness, $D_{ads}$ shown in FIG. 9B. E0-E4 were stable and formed layers with thickness exceeding the theoretical length of the amphiphiles. As we recently concluded this agrees with the formation of bilayered assemblies. The behavior of E0-E4 contrasted with E6 that spontaneously desorbed after the adsorption phase.

The enhanced water solubility of the ethylene glycol terminated amphiphiles implies that they are present predominantly in monomeric form and can rapidly diffuse to the surface, this is in contrast to E0 which is poorly water soluble and is likely to adsorb in the form of aggregates. Hydrophilic end-groups will also contribute to a lowering of the surface tension but may on the other hand be more sterically demanding, compromising rSAM close packing. Indeed, for surfaces that formed stable layers (E0-E4), the equilibrium thickness, $D_{ads}$ correlated inversely with the theoretical length of its corresponding amphiphiles. This indicates that steric repulsion from the ethylene glycol addition prevent close packing or bilayer formation. The odd behavior of E6 can be explained by the presence of two competing processes distinguished by different kinetics. Possibly, a fast surface assembly is here competing with a slower formation of a thermodynamically more stable supramolecular assembly (e.g. micelle).

Figure 9A:
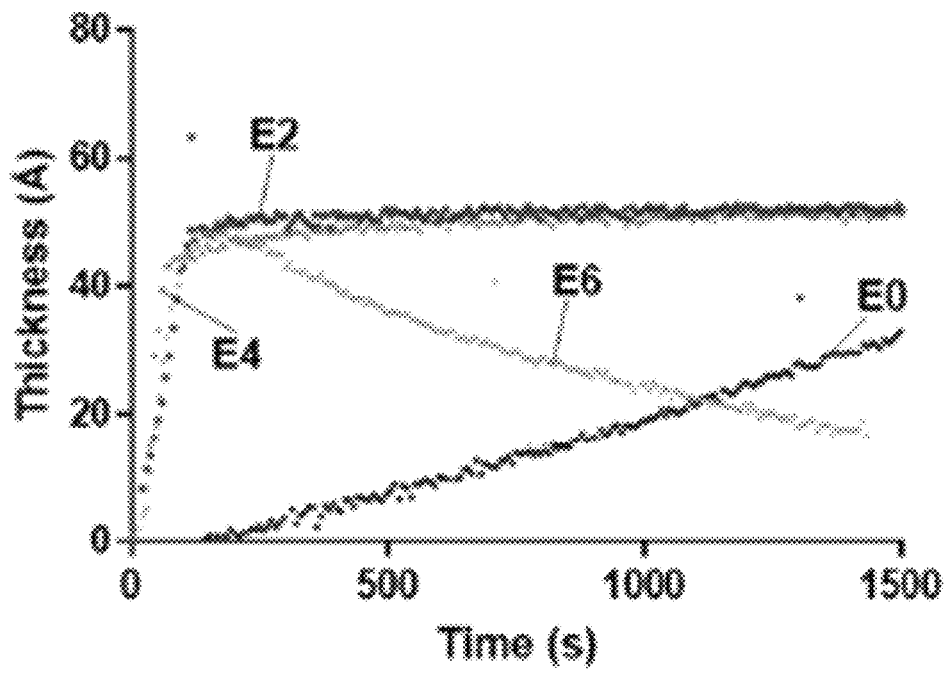
FIGS. 9A-9D generally illustrate characterization of $\omega$-(ethylene glycol)$_{0\text{-}6}$-$\alpha$-(4-amidinophenoxy)decanes, E0-6 rSAMs on MHA modified gold.
Figure 9B:
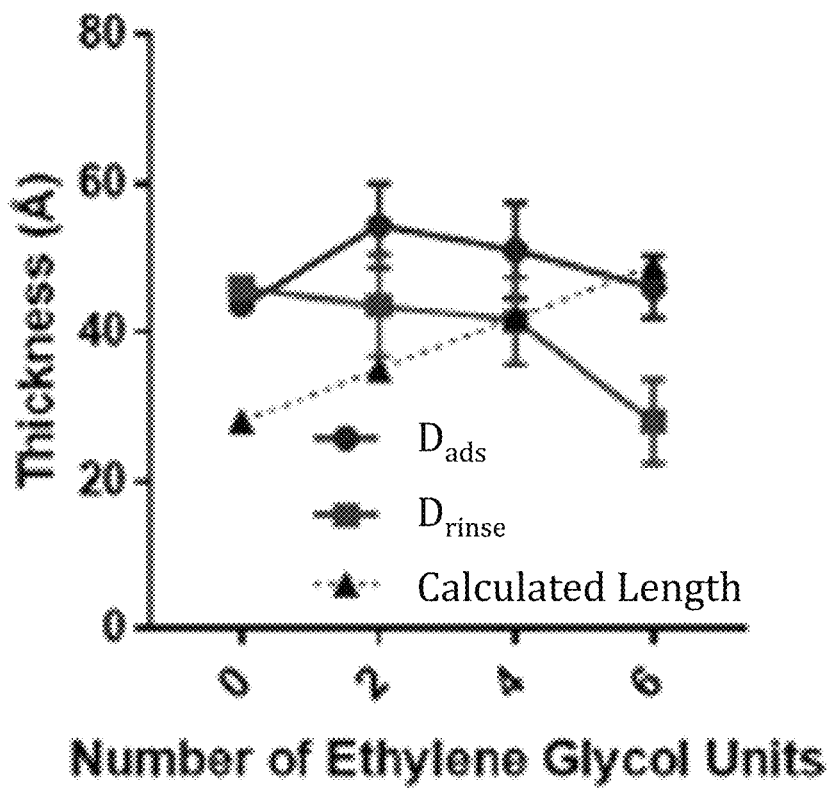

The surfaces were then rinsed in situ in a continuous system with pH 8 HEPES buffer to improve biological compatibility. The rinse stability of the layers inversely correlated with the ethylene glycol chain length (FIG. 9B). Nevertheless, $D_{rinse}$ of E0-4 layers is still larger than the theoretical length of the molecules, indicating the presence of a stable monolayer.

To gain further insight into the layers' molecular order and orientation, the E2 and E4 rSAMs were dried under a nitrogen stream and the IRAS spectra were collected. Comparing the layer IRAS spectra with the bulk ATR spectra of E2 and E4 (FIG. 9C), the layer spectra exhibit different relative bands intensity and bandwidth. In the high frequency region, the $CH_2$ stretch vibration at 2918 $cm^{-1}$ (asym) and 2850 $cm^{-1}$ (sym) and sharpness of these bands of the layer spectra indicate the presence of trans extended closely packed amphiphiles. The pronounced increase of $(C=C)_{1,4}$ at ca. 1611 $cm^{-1}$ and concomitant decrease of aromatic C—H out-of-plane bending mode at 840 $cm^{-1}$ suggests a near upright position of the amphiphiles assemblies. Taking the peak intensity ratio of the layer and bulk spectra of aromatic C—H out-of-plane bending mode at ca. 840 $cm^{-1}$ and $(C=C)_{1,4}$ at 1611 $cm^{-1}$, the phenyl group of the amphiphiles are determined to have a tilt angle of ca. 18-20° relative to the surface perpendicular.

Figure 9D:
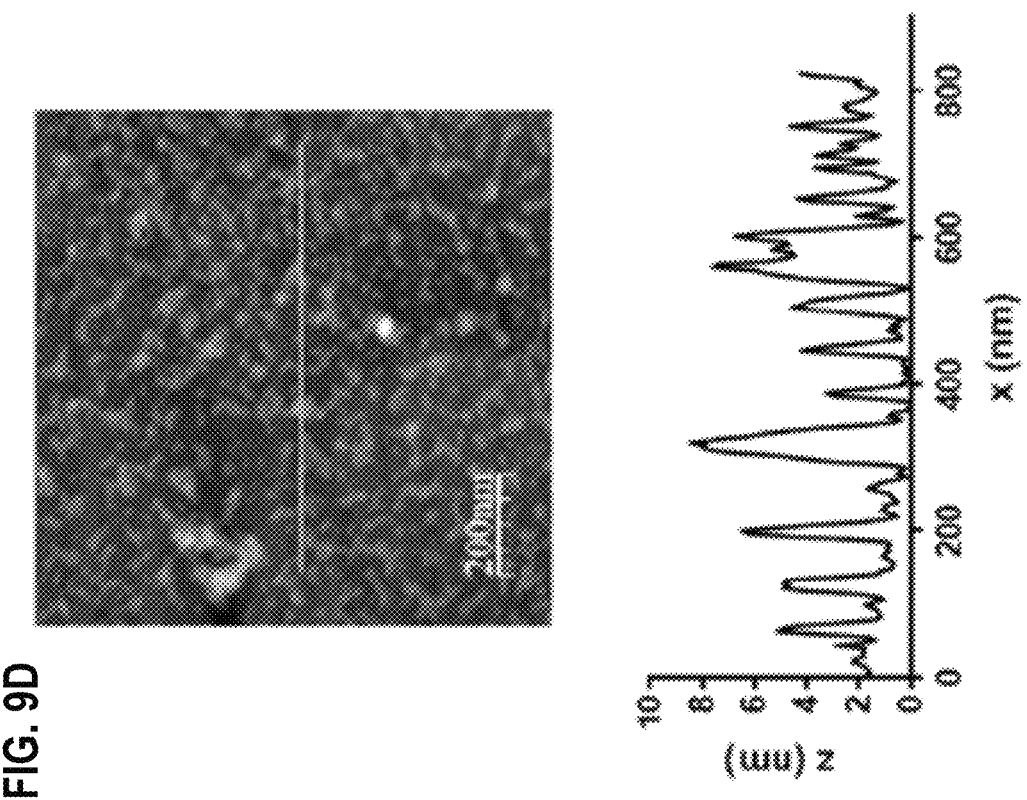
Figure 9C:
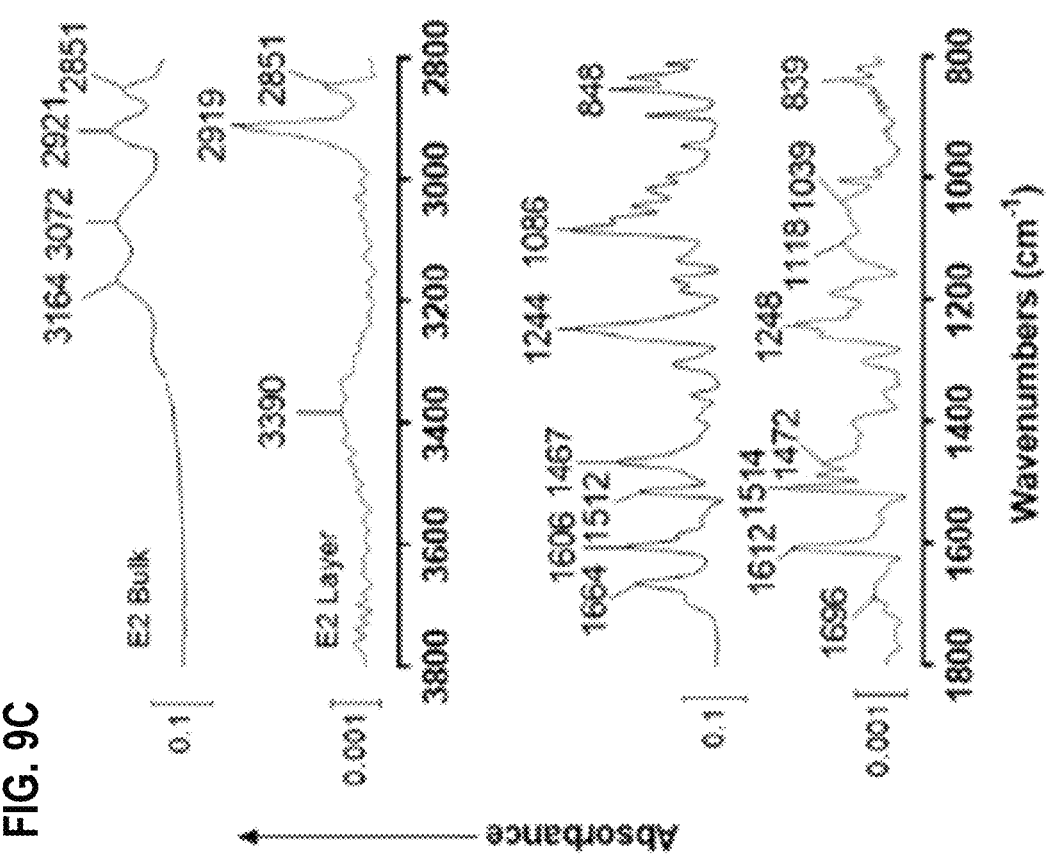

To obtain statistical information, each surface was sampled twice at different areas and the experiments were duplicated on a separate substrates. The $CH_2$ asym and sym stretch vibration decreases in wavenumbers with increasing ethylene glycol repeating units (E0<E2<E4). This contradicts the general consensus that ethylene glycol causes steric repulsion and prevents close packing of amphiphilic assemblies. As IRAS is an averaging technique, these results can also be attributed to the interference from a loosely packed 2nd layer. The ellipsometric thickness reported in FIG. 9B suggests a decrease in top layer coverage with increasing ethylene glycol chain length (E4<E2<E0). Presence of a loosely packed top layer in E0 and E2 results in $CH_2$ stretch vibrations corresponding to lower molecular order as compared to E4 showing bands at frequencies corresponding to highly ordered alkanes, the latter suggesting that only ordered monolayers are formed. This was confirmed by AFM topographic imaging of the E0 and E2 layers (FIG. 9D). A reduction of surface coverage of the taller domains was observed in the E2 layers and the estimated surface coverage corresponded with the ellipsometry values. All the characterization data strongly suggests the presence of a loosely packed 2nd layer in E2.

Monolayer reproducibility in terms of molecular order and stability appeared lower for the amphiphiles showing bilayer formation. For instance, after sampling a large number of E2 surfaces, spectra with differing peak intensities indicating both high and low degree of order and stability were observed. The most distinctive is the disappearance of the band at 1696 $cm^{-1}$ and the appearance of two new bands at 1575 and 1542 $cm^{-1}$. The former corresponds to the amidine I band i.e. the N=C—N stretch with a transition dipole vector directed perpendicular to the 1,4 axis of the aryl group whereas the latter are assigned to their in plane bending vibration. The concomitant increase in the aryl group tilt angle ($I_{1612}/I_{833}$) to 51±1° collectively suggests a near flat orientation of the benzamidine groups.

This suggests changes in amidine complexation, possibly resulting from adsorption of aggregates on the surface. Deciphering the exact molecular order of the 2nd layer and mechanism of assembly is beyond the scope of this publication and it was not investigated further. It however strongly suggests that control of the layer formation is crucial and concomitant bilayer formation should be avoided. Keeping these objectives in mind, the layer formation was investigated at different conditions.

Parameters controlling layer formation. Physical properties of self-assembled monolayers or surfactant layers can be controlled via optimization of immobilization conditions such as amphiphile concentration, solution pH, charge density of substrate and duration of assembly. Herein the assembly of E2 and/or E4 was systematically optimized with respect to these parameters.

Concentration. Referring back to FIG. 9A, the fast initial phase at 50 μM was similar for both E2 and E4. Both amphiphiles reach similar equilibrium thickness disregarding the difference in theoretical length. The contrast lies in the inflection point of the two layers. Upon reaching its theoretical length, E4 showed a gradual decrease in the rate of adsorption prior to reaching the limiting equilibrium thickness, while E2 featured a sharp inflection point at a film thickness beyond its theoretical length. In both cases, an equilibrium thickness exceeding a theoretical monolayer suggest that both amphiphiles are above their critical micelle concentration (CMC) at 50 μM. The assembly kinetics indicates that E2 assembles directly to the bilayer, while E4 goes through a monolayer stage before bilayer formation.

Their differing assembling behavior is even more pronounced at 5 μM. At the fast initial phase, the thickness of E2 linearly increased with time with a sharp inflection point above its theoretical length. E4 displayed a logarithmic curve that gradually tapers off to approximate theoretical length. This indicates that the E4 CMC is approximately 5 μM, while E2 is still above its CMC. At a further 10-fold decrease in E2 concentration (0.5 μM, pH 9 buffer), the layer did not reach monolayer thickness within the probed time. These observations suggest that E4 has a CMC at ca. 5 μM, while E2 has a CMC between 0.5 μM and 5 μM. These results agree with the finding that presence of ethylene glycol units increases CMC of amphiphiles.

pH. To adapt rSAMs to biological applications, an enhanced stability of the layers closer to physiological pH are of relevance. The driving force and stability of rSAMs is thought to be governed by the protonation state of the carboxylic acid self-assembled monolayer. MHA surfaces have a broad pKa-distribution averaging at 7.9 and it is crucial to determine how the rSAMs formation and stability would be affected at physiological pH of 7.4.

Figure 10B:
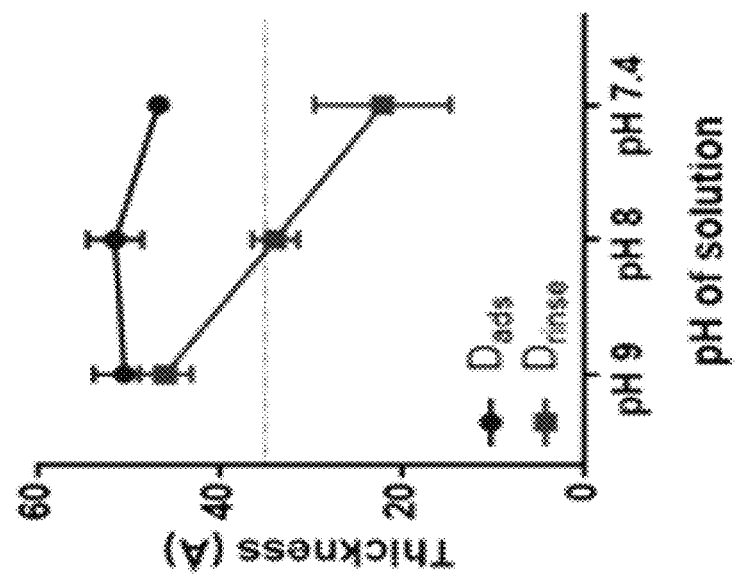
FIGS. 10A-10C generally illustrate adsorption kinetics and IRAS spectra of E2 rSAMs on 16-mercaptohexa decanoic acid (MHA) modified gold prepared at pH 9, 8 and 7.4.
Figure 10A:
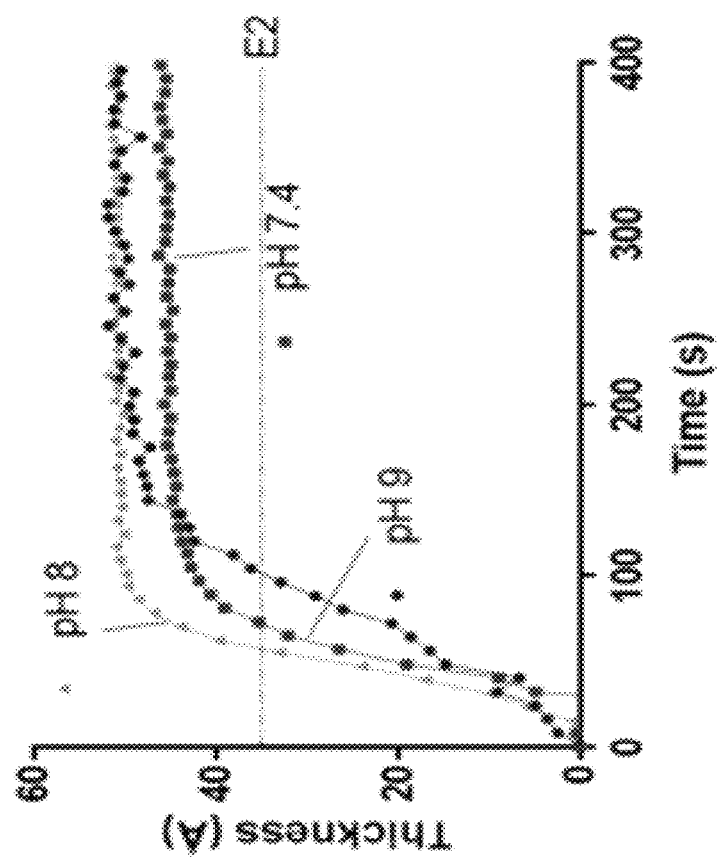
Figure 10C:
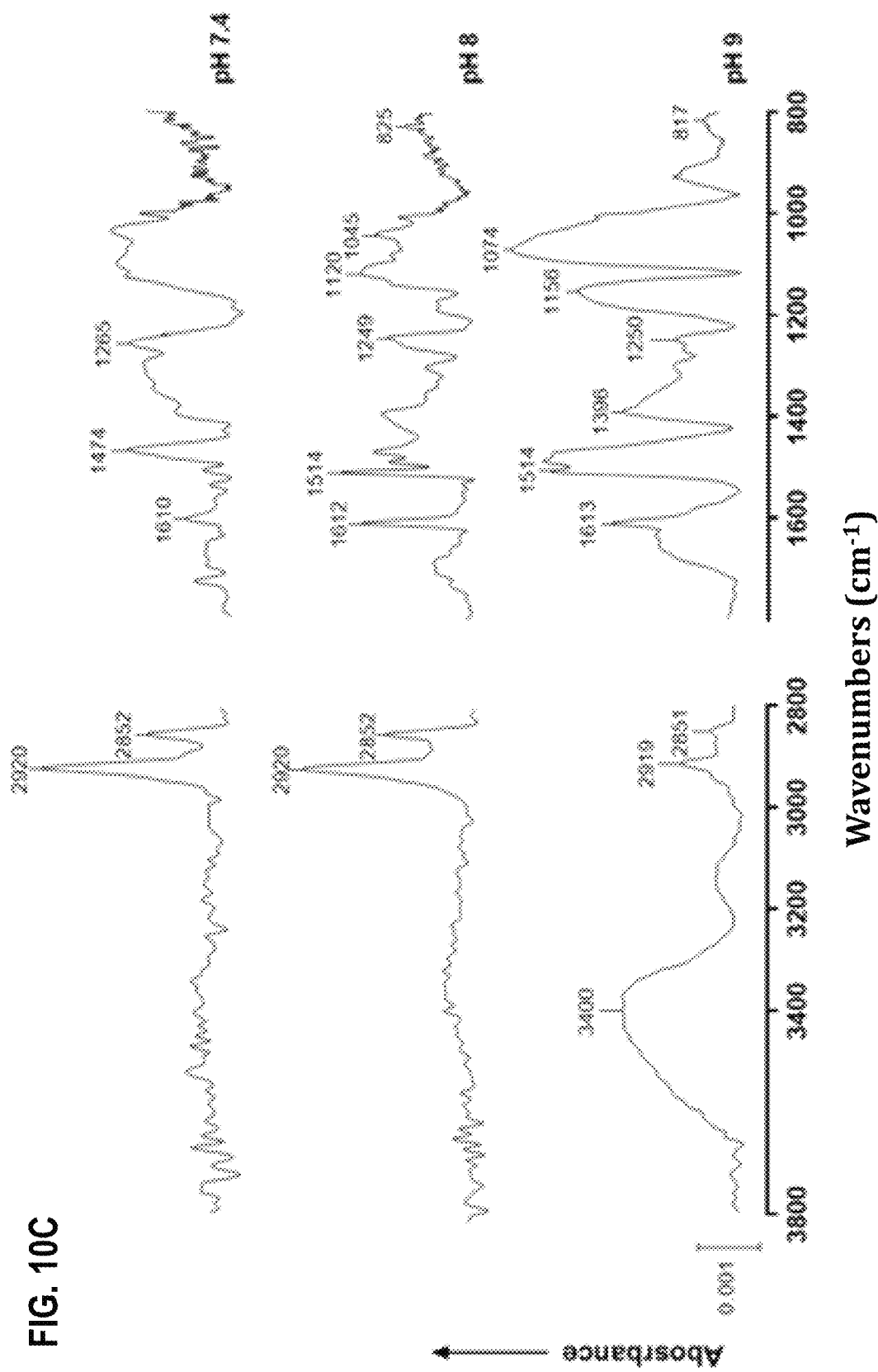

Interestingly, the rate constant, $K_{on}$ of E2 at pH 8 and 7.4 is higher than at pH 9 whereas the equilibrium thickness appeared to be independent of pH (FIGS. 10A-10B). Assuming the initial fast adsorption phase to be driven by electrostatic attraction, lowering of the pH should on the contrary result in a slower adsorption phase. Given the near identical equilibrium thickness values, we believe the effect is related to the nature of the buffer salt. This cause is also more likely given the direct correlation between pH and thickness after rinsing, $D_{rinse}$ (pH 7.4<pH 8<pH9) and rinse stability (FIG. 10B). This agrees with the $D_{rinse}$ results and indicates that the protonation state of the carboxylic acid is crucial for the stability of the layers.

Underlying order of monolayer and duration of assembly. We recently found that rSAM stability and order can be enhanced by optimizing the concentration of MHA used for MHA-modified gold preparation and thereby by increasing the charge density and order of the anchoring carboxylic acid SAM. The former can be enhanced by raising the pH of rSAM formation (vide supra) whereas the latter by extending the thiol on gold adsorption time. To address the latter factor we investigated thiol SAMs prepared at conditions reported to enhance layer order. These modifications resulted in highly ordered MHA SAMs. The E2 layers on the more ordered MHA SAM displayed enhanced rinse stability and molecular order in accordance with the position of the $CH_2$ stretch vibrations. Similar improvements were also observed by allowing the E2 layers to incubate for a longer period of time.

Hence, both an increased pH of rSAM formation and the use of MHA-SAMs displaying enhanced order, lead to increased rSAM rinse stability and molecular order. The equilibrium thickness correlates with the concentration of the amphiphiles. With this in mind, we optimized the conditions for immobilization of the amphiphiles, E0-6 and used ex situ ellipsometry and IRAS to investigate the rSAM stability and resistance to common plasma proteins.

Protein stability and resistivity of E0-6 rSAMs on MHA modified gold. The E0-6 layers on MHA-gold and their subsequent stability in pH 8 HEPES buffer were evaluated using ex situ ellipsometry and IRAS. Similar to the in situ experiments, the layers using the optimized protocol displayed a decrease in film thickness with increasing ethylene glycol units. This agrees with the general consensus that steric repulsion of ethylene glycol units precludes close packing of organized assemblies but may also be the result of competing formation of solution supramolecular assemblies, given the presumably low CMC of the OEG terminated amidines.

An extreme example of the latter is given by E6 which only showed a transient monolayer lacking permanent stability. This was confirmed by the ex-situ measurements showing a film thickness less than half of the E6 molecular length, hence the corresponding film was the least stable among the rSAMs. It is also important to note that E0 again promoted bilayer formation, while the ethylene glycol terminated amphiphiles, E2-6 formed monolayers (E2) or submonolayers. The $2^{nd}$ top E0 layer however can be destabilized via extended buffer rinse and resulted in large error bar during thickness acquisition.

For biomimietic biosensing application, layers have to be protein resistant and stable towards protein exchange. The formed layers were tested against human serum albumin (HSA) and lysozyme (LYZ), two common plasma proteins chosen in view of their contrasting isoelectric points (pI=4.7 and 11.4 respectively). At 1 mg/mL, both proteins adsorbed onto the MHA-SAM with the positively charged LYZ reaching a larger film thickness than HSA despite its considerably smaller size (LYZ: 28×28×50 Å; HSA: 80×80×30 Å).

The protein adsorption was compared with respect to the ellipsometric thickness and the IRAS intensity of the protein amide I band at ca. 1690 $cm^{-1}$. As not all the formed layers were homogenous monolayers, IRAS was the preferred method for comparison. The most pronounced protein adsorption was observed on the E0 films whereas the E2 films consistently displayed more than 50% reduced protein adsorption based on the amide I band intensity. (Chart 12B) Longer OEG chains as in E4 and E6 gave rise to rSAMs appearing less resistant. This was suggested by a constant or reduced film thickness accompanied by an increase in the amide I band intensity. The fact that this effect was especially pronounced for LYZ may reflect the enhanced affinity of the latter for the MHA-SAM.

Figure 11:
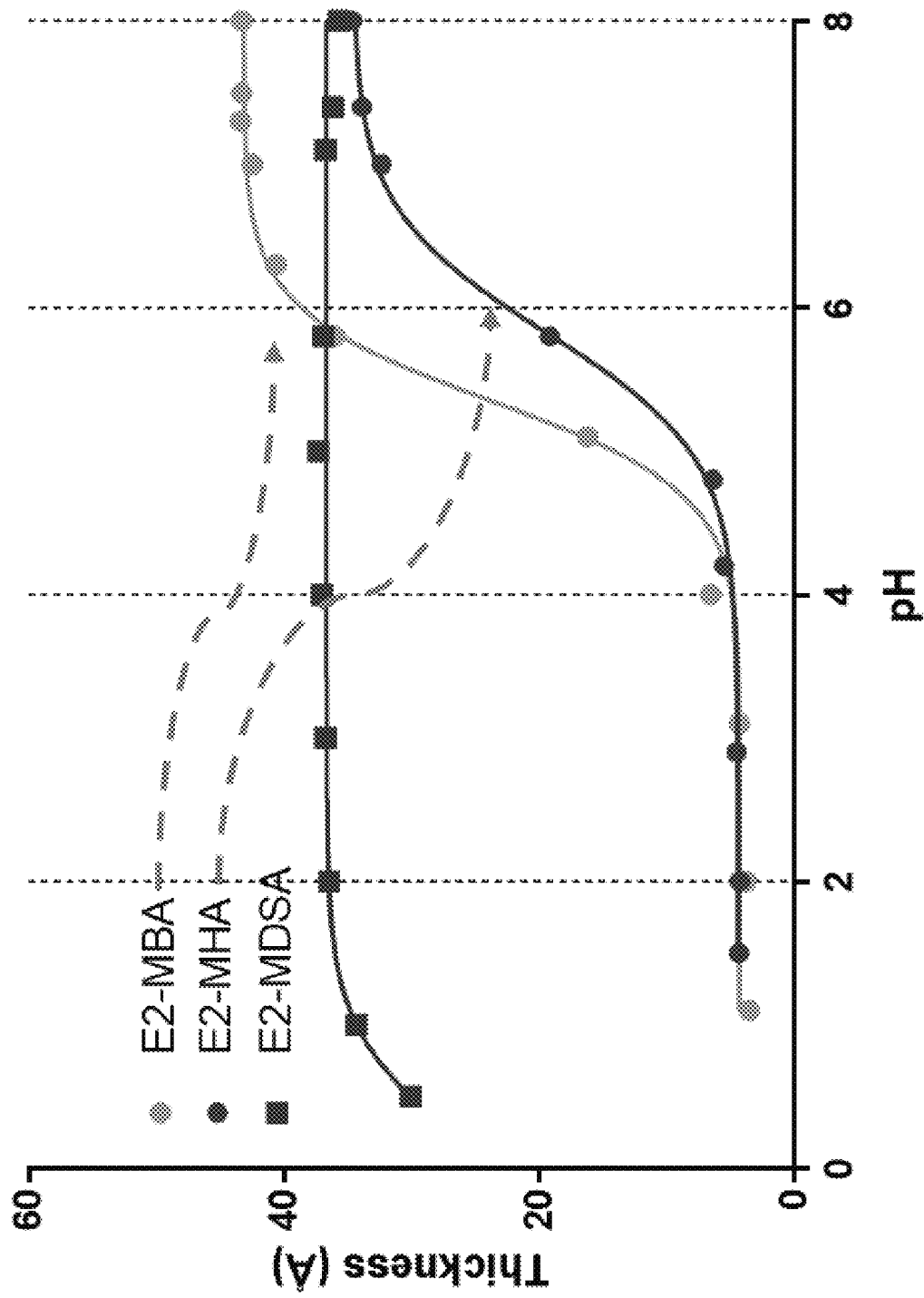
FIG. 11 generally illustrates ellipsometric thickness after rinsing versus pH for rSAMs of E2 amidine 15 on different oxoacid functionalized SAMs on gold. MBA=mercaptobenzoic acid, MHA=mercaptohexadecanoic acid, MDSA=mercaptodecylsulfonic acid.

Stability enhancement via optimization of underlying anchor. To counteract the instability of ethylene glycol rSAMs towards positively charged proteins, we looked into stronger oxoacids anchors, e.g. 4-mercaptobenzoic acid (MBA) and mercapto-decane sulfonic acid (MDSA). As seen in FIG. 11 these anchoring SAMs can dramatically extend and fine tune the pH stability range for the rSAMs in order of decreasing pKa of the anchoring acid groups. The benzoic acid terminated SAMs feature lower and narrow range surface pKa resulted in rSAMs with pH resistance up to 6 (FIG. 11) and enhanced protein stability and resistivity (FIGS. 12A-12F).

Using the E2 amphiphiles as an example, the pH titration curve of rinsed E2 layers on MBA SAMs showed pH resistance up to 6. IRAS of the E2-MBA layers before and after LZY or HSA (1 mg/ml) exposure (FIG. 12C) demonstrated the retention of the peak intensities after HSA or LYZ exposure. Astonishingly, a decrease in amide I intensity and ellipsometric thickness also supported a non specific protein interaction reduction. Nevertheless, both COOH-terminated surfaces could be regenerated with 0.1 M HCl after the protein adsorption test leaving them ready for a second adsorption experiment on the same substrate.

Figure 12A:
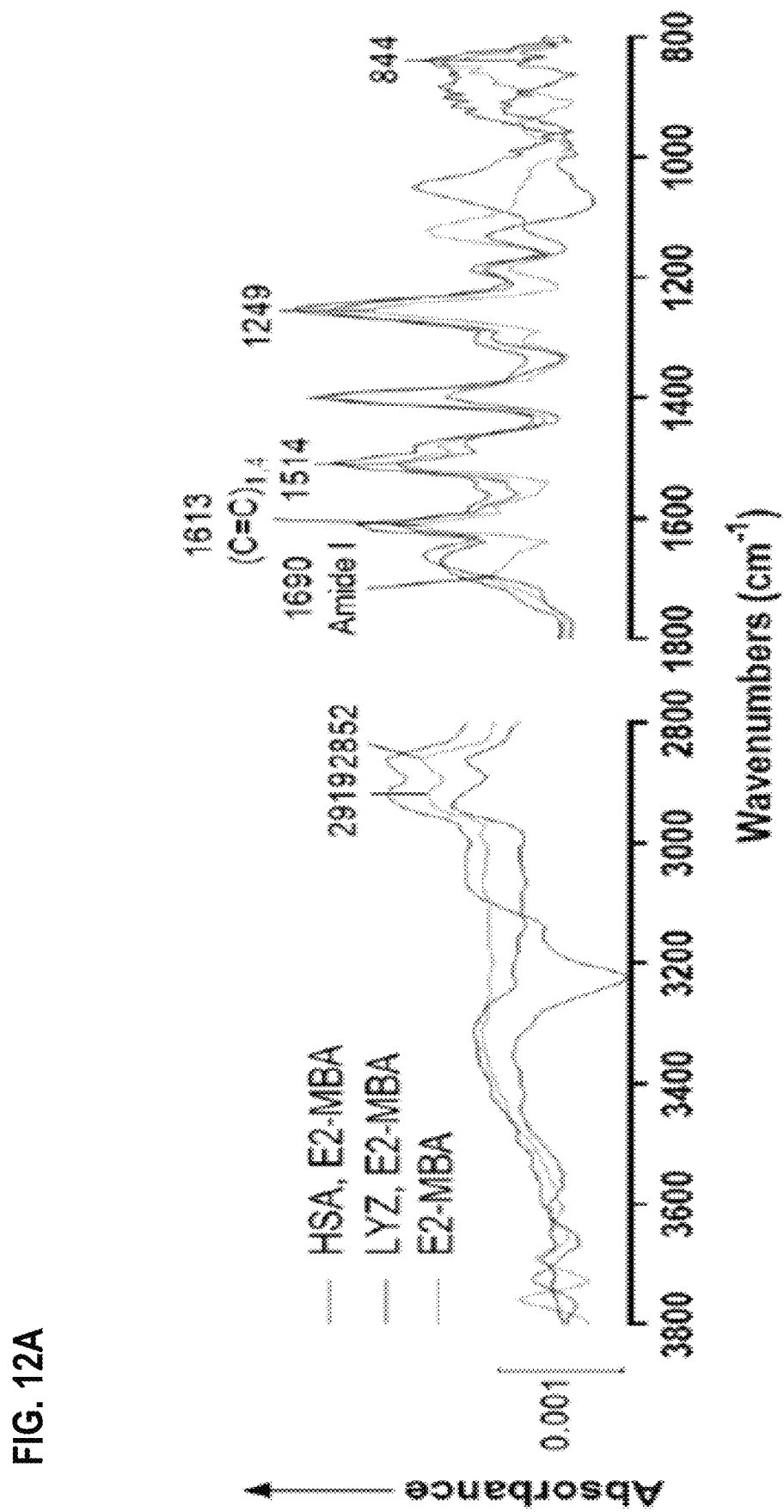
Figure 12B:
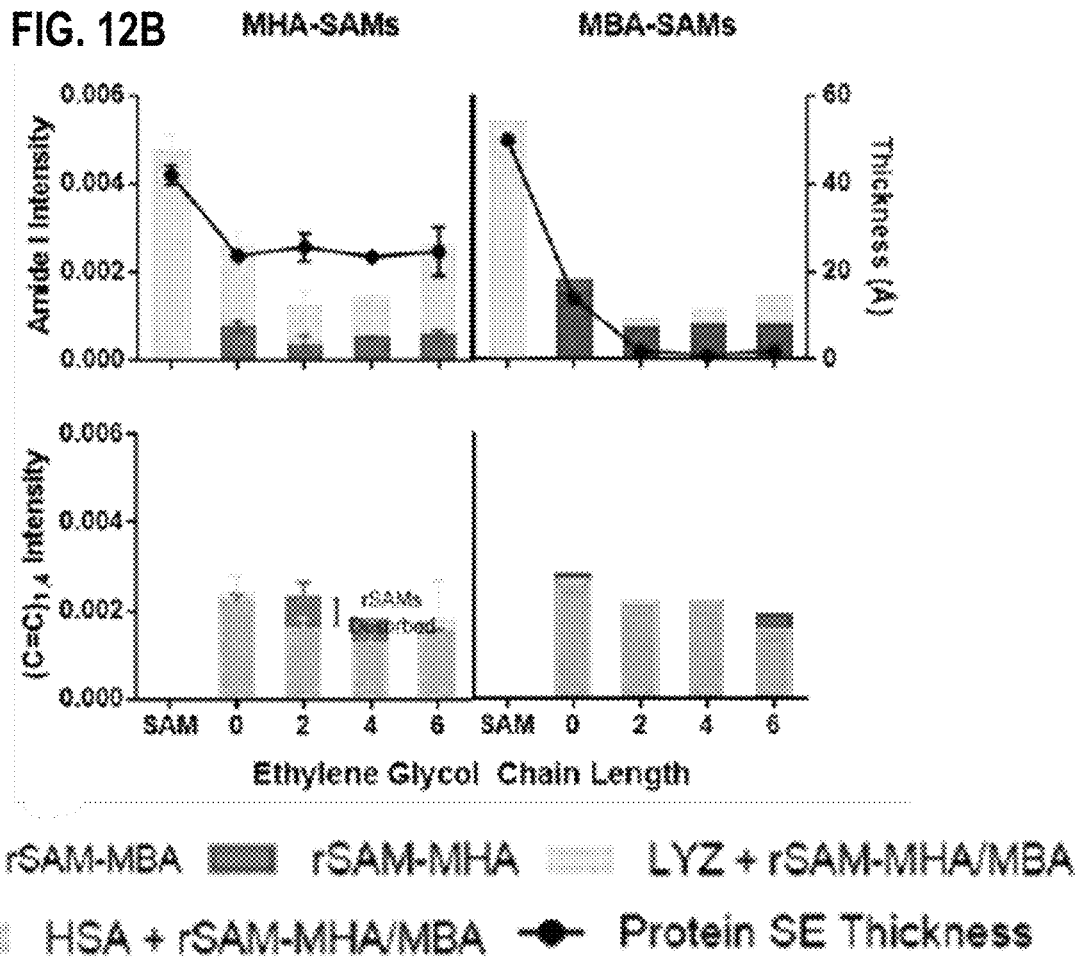
Figure 12C:
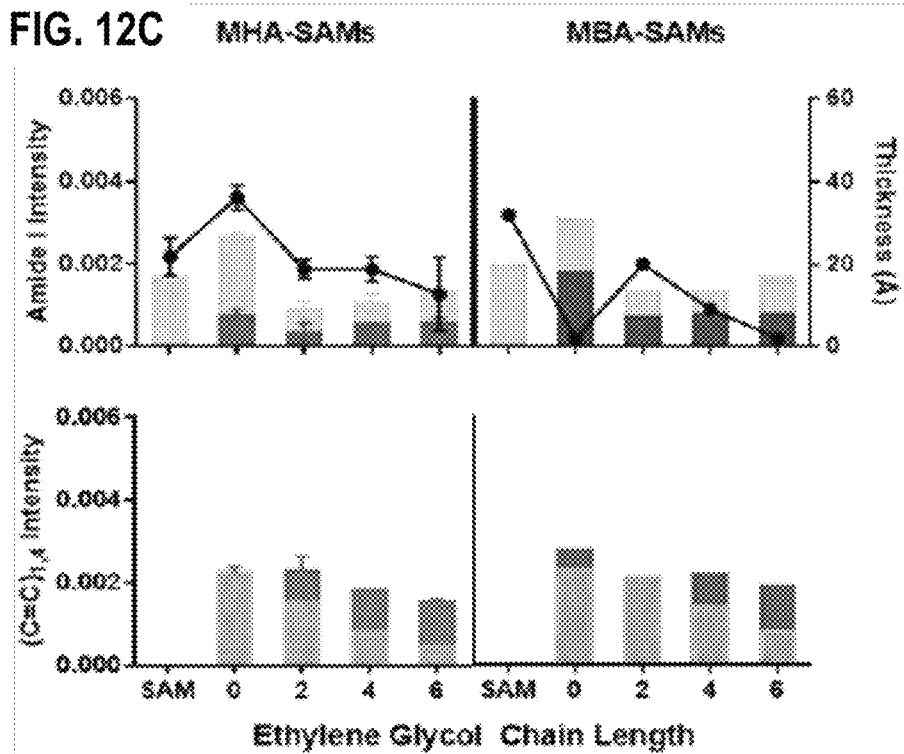

In view of using the rSAMs at physiological conditions, the amphiphiles were immobilized on the MHA modified gold at pH 7.4 for 18 hrs. In contrast with the results with short immobilization durations, these layers showed increase rinse resistance with ellipsometric E0-6 rSAMs thickness similar to those immobilized at pH 8. IRAS spectra also showed similar molecular order according to $CH_2$ C—H asym and sym stretch and tilt angle for E0 and E2 surfaces. The E2 layers displayed a reduction towards proteins resitvity and stability (FIG. 12B).

Figure 13A:
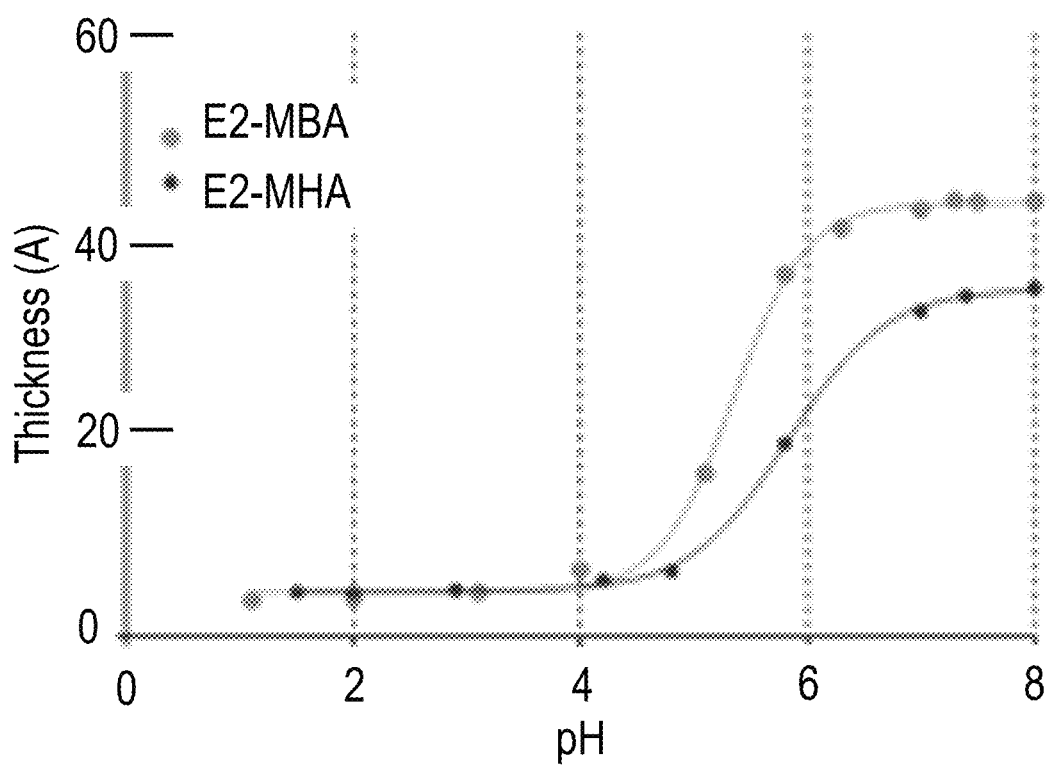
FIGS. 13A-13C generally illustrate pH and air stability and fluidity of rSAM on MHA-Gold.
Figure 13B:
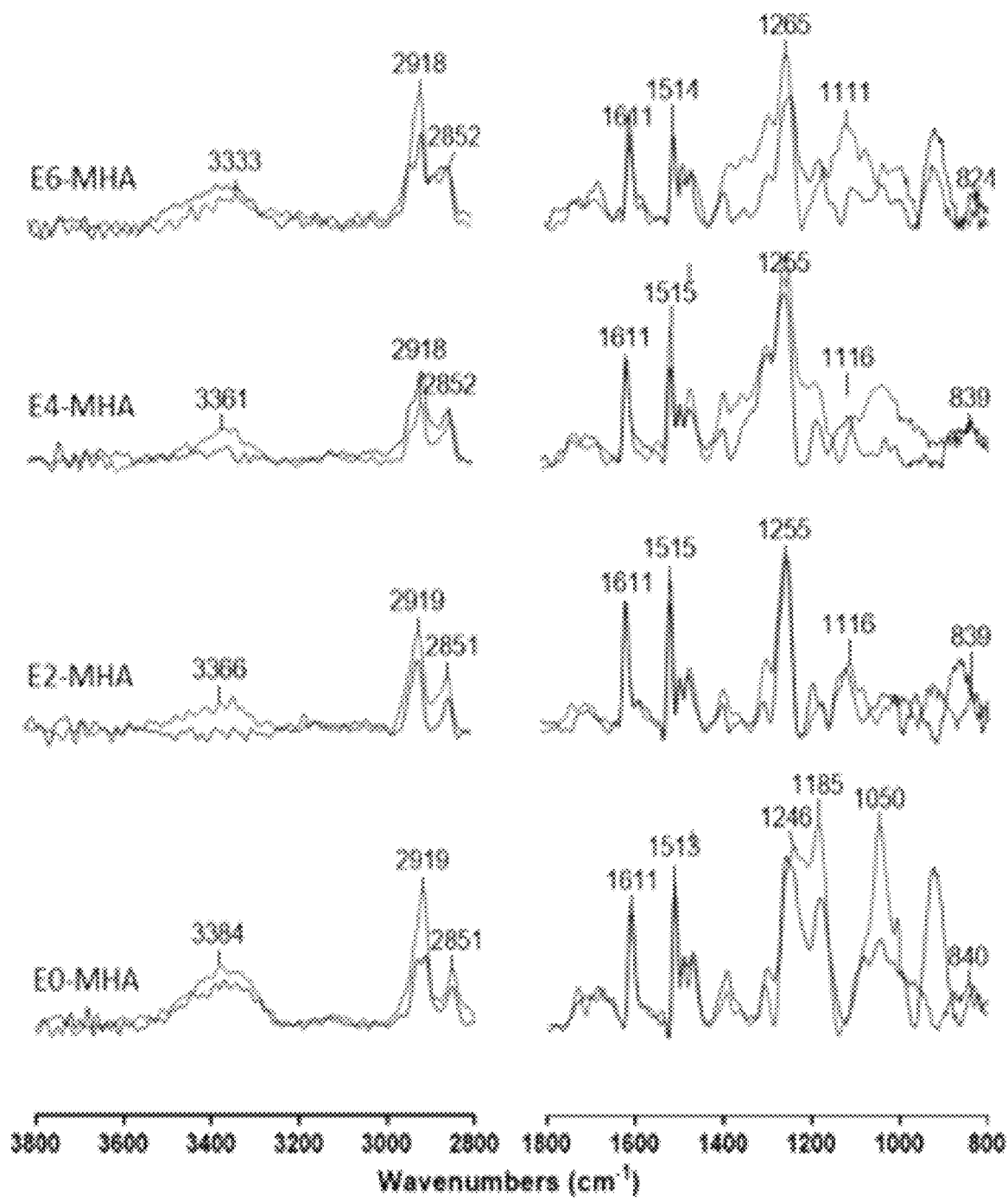
Figure 13C:
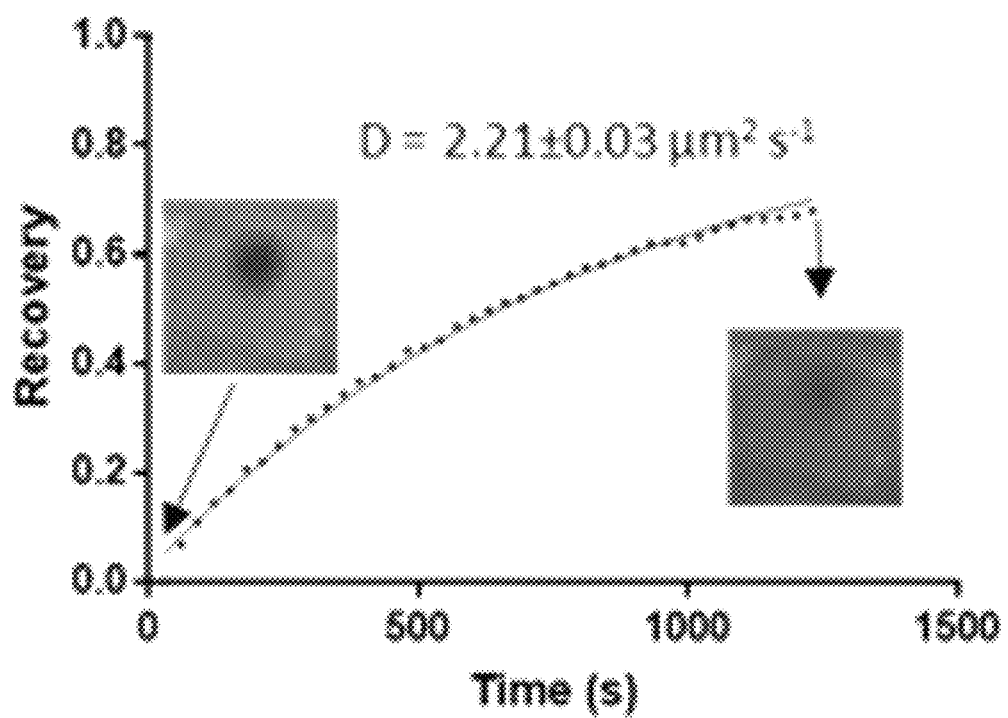

Stability of rSAMs in buffer and air. To evaluate air stability of the layers, the ellipsometric thickness and IRAS after 1 and 2 cycle of rinsing with pH 8 buffer and drying under a nitrogen stream were compared (FIG. 13A-13C). No decrease in layer thickness was observed for E0-4, whereas E6 displayed a 9 Å thickness decrease. Although a decrease in peak intensities was observed for E6, all IRAS spectra displayed similar band positions and relative intensities at $CH_2$ C—H asym and sym stretch (2918 and 2850 $cm^{-1}$), aromatic (C=C)1,4 stretch (1611 and 1515 cm$^{-1}$), aromatic ethers aryl-O asym stretch (1255 cm$^{-1}$) and aromatic C—H out of plane stretch (840 cm$^{-1}$) as prior at the 1$^{st}$ cycle (FIG. 13B). These results indicate that rinsed layers were structurally stable towards rinsing, long term exposure to buffer and in air.

Lipid bilayers liked fluidity of E2 terminated rSAMs on MHA modified gold. To demonstrate rSAMs lateral fluidity, fluorescence recovery after photobleaching (FRAP) measurements of 1 mol % FAM tagged amidine in E2 on COOH quartz surfaces were taken (FIG. 13C). The bleached spots show significant recovery after 20 mins with the rate of diffusion coefficient matching literature values of supported lipid bilayers.

The present invention demonstrates that rSAMs featuring terminal oligoethylene glycol chains allows reversible formation with enhanced protein resistant surfaces at close to physiological pH. This new surface modification utilizes noncovalent amidinium carboxylate ion pairs for building up stable 2 dimensional assemblies, akin to lipid bilayers but with strongly enhanced air and rinsing stability with fast on/off rates. In general, such surfaces capable of resisting nonspecific adsorption of biomacromolecules, cells or microorganisms, while retaining fluidity is of key importance in several applications in medicine and biotechnology. Apart from the reversibility, the air stability, fluidic nature and ease of preparation of these films we believe will impact robust biomimetic biosensor design.

4. rSAMs Assembled on Optically Transparent Surfaces

Figure 14A:
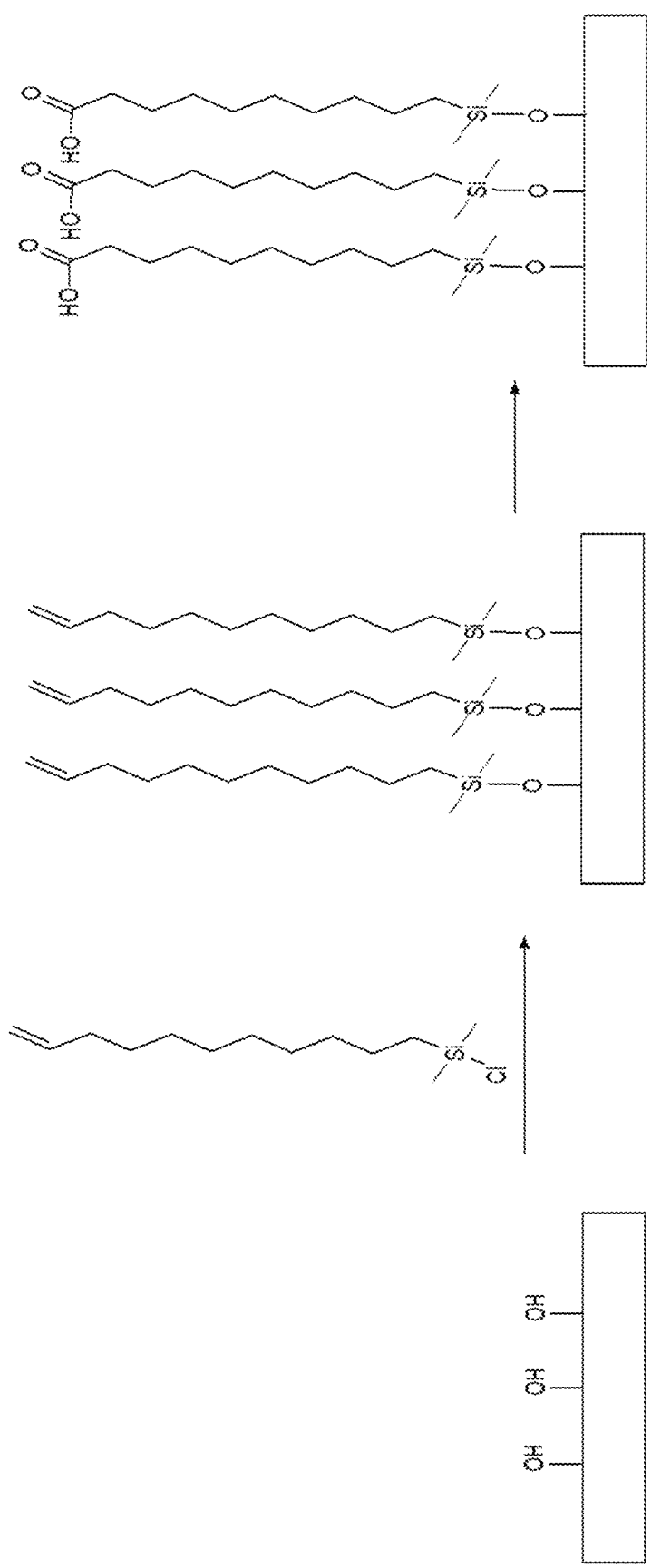
FIGS. 14A-14B show synthesis of decanoic acid and benzoic acid SAMs on glass and quartz surfaces, respectively.
Figure 14B:
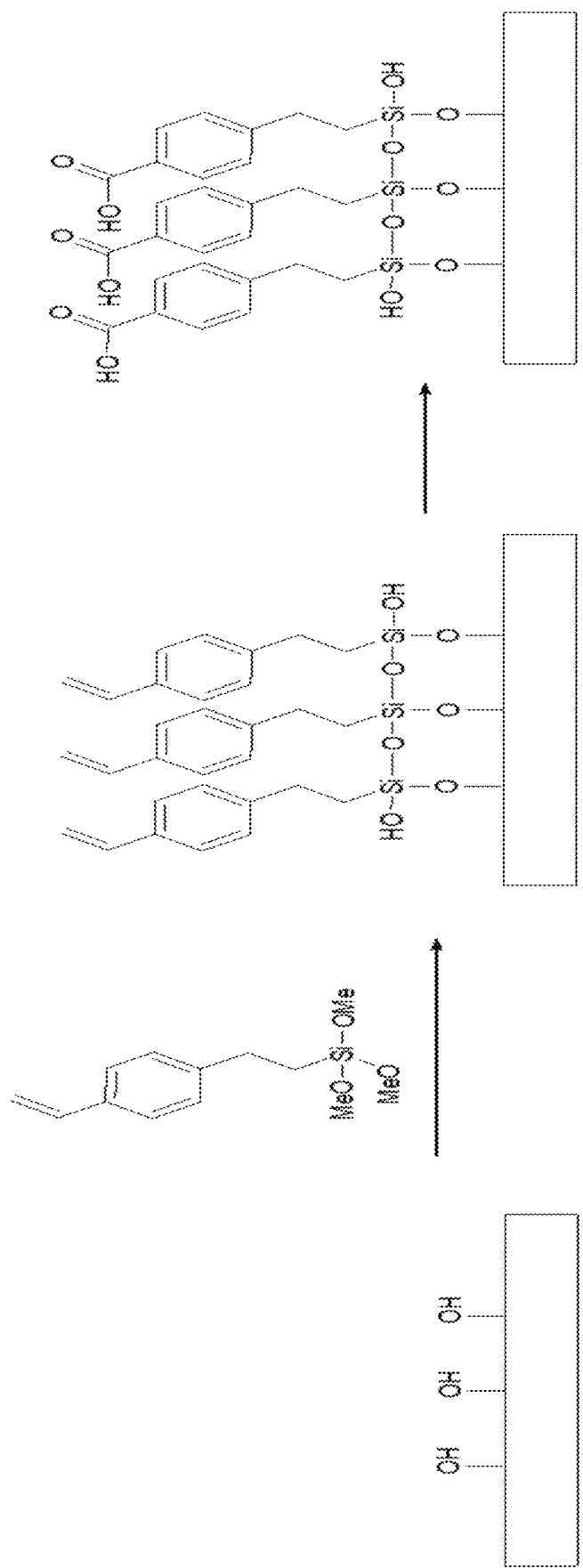
Figure 15:
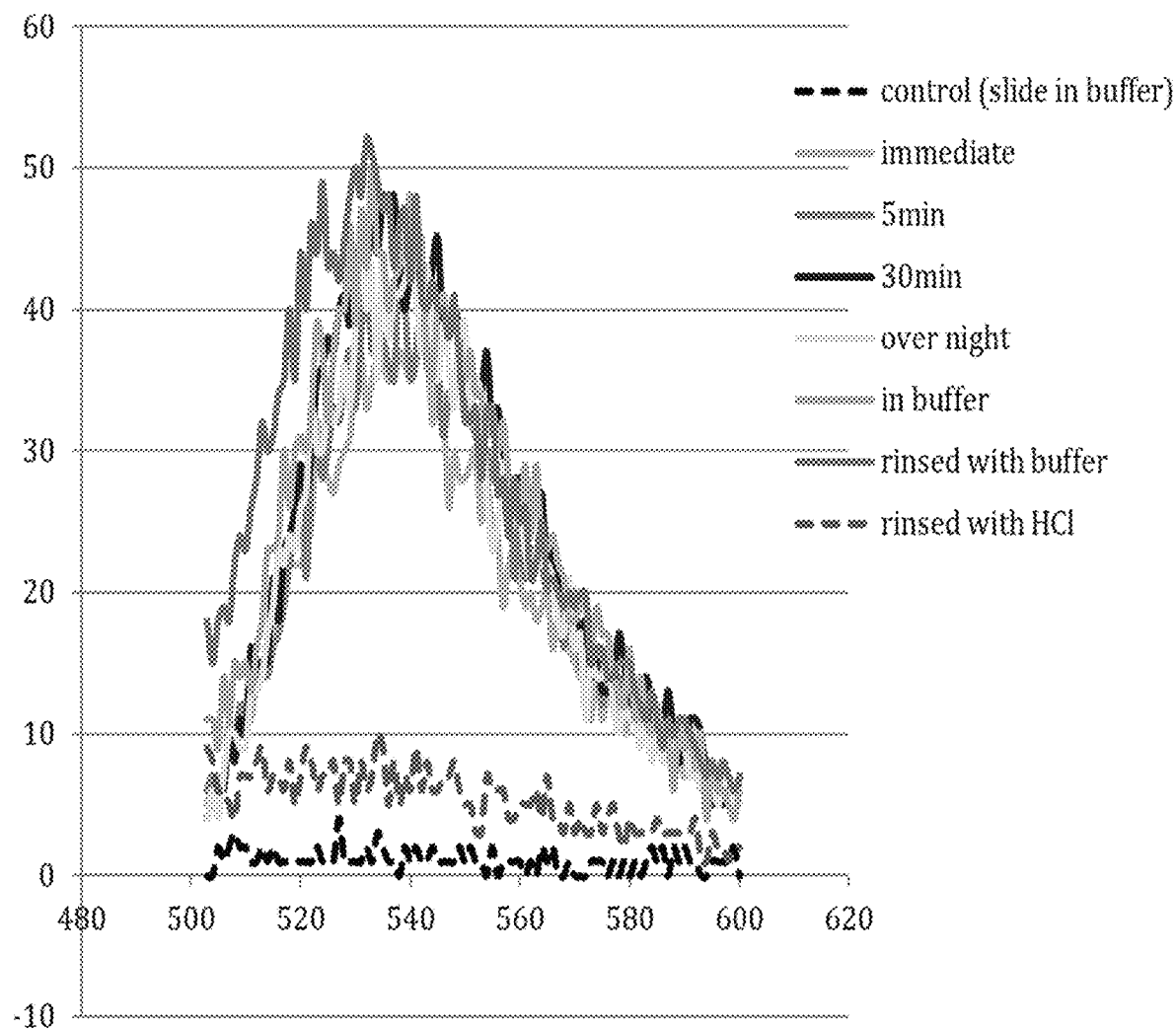
FIG. 15 generally shows fluorescence detection of rSAM formation and surface recognition events using FITC doped rSAMs.

In order to exploit rSAMs in optical sensing applications, transparent substrates such as glass, quartz or optical waveguides are required. Examples of anchoring SAMs formed from silanes are shown in FIGS. 14A-14B. FIG. 15 shows fluorescence emission spectra of a FAM doped E2 rSAM on a SAM prepared as in FIG. 14A over time and in response to rinsing at different pH values. This shows that the rSAM is stable and functional. Sensing of binding events occurring on the surface is possible using the doped rSAM.

5. Use of rSAMs with Tunable Surface Dynamics for Modulation of Cell Adhesion Behaviour Cells adhering onto a surface can sense and respond to a wide variety of chemical and physical features of the adhesive surface, including the molecular nature of the adhesive ligands, their local densities and mobility and the surrounding environment. These responses towards external cues regulate key cellular processes including tissue formation, cell survival, differentiation, migration, growth and apoptosis. Integrins, the main cellular receptors for the extracellular matrix, have a key role in mediating these activities. One of the highly conserved peptide sequence present in the ECM recognized by the integrins is the RGD peptide. Since its discovery, this peptide sequence and its variations have been integrated into and onto a variety of scaffolds to interrogate the role of cell adhesion molecules during cell adhesion processes and fabrication of biomaterials for cell culture, tissue engineering and regenerative medicine.

Figure 17:
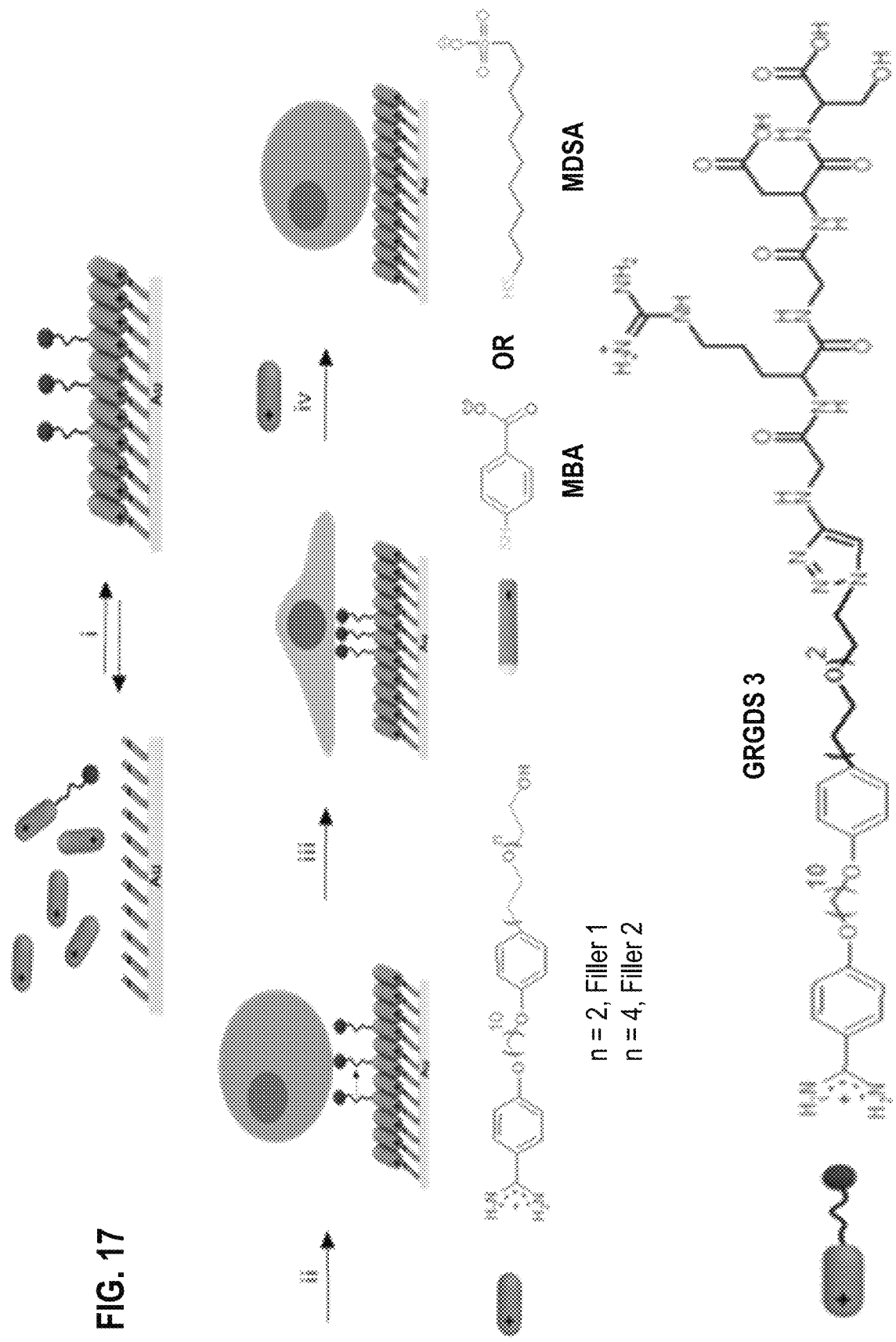

Mixed rSAMs functionalized with an RGD peptide can be used for modulating cell adhesion behaviour. In addition, molecular exchange of RGD functionalized rSAMs with the inert filler amphiphiles enables dynamic reversal of cell adhesion (FIG. 17).

6. Introducing Neuraminidase Inhibitor-Amidine as a Virus Type-Selective Anchor.

Figure 16:
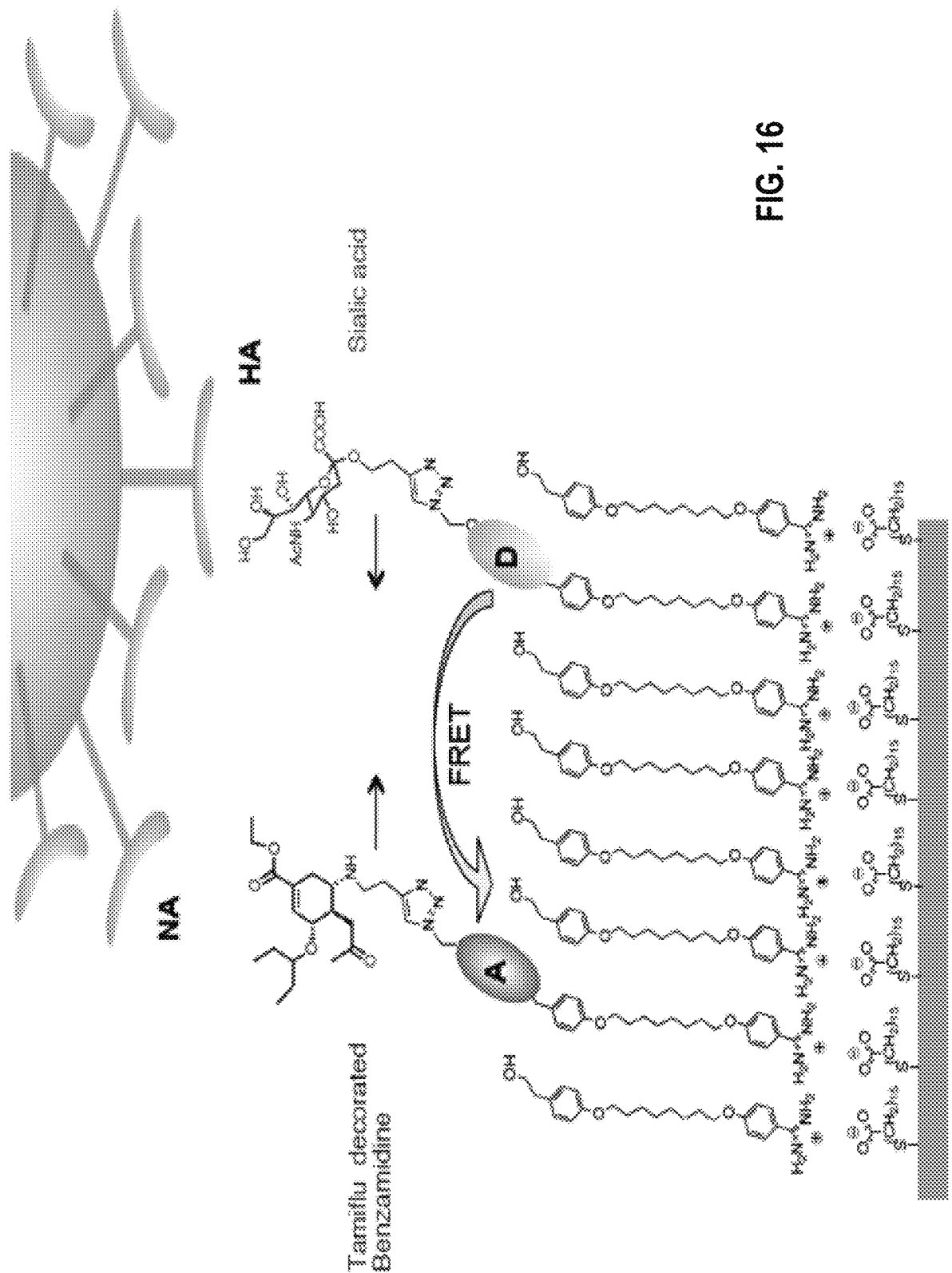
FIG. 16 generally illustrates a dual ligand mixed rSAM comprising a neuraminidase inhibitor and sialic acid ligand for enhanced binding affinity and selectivity for influenza virus particles. Also shown is a FRET (fluorescence resonance energy transfer) detection principle based on incorporation of fluorescence donor and acceptor dyes in the ligand decorated amidines.

Neuraminidase inhibitors bind strongly to NA exceeding typically the affinity between SA and HA. A range of inhibitors exist today targeting different NA subtypes. We have prepared inhibitor-decorated amidines via click chemistry. Mixed rSAMs impart an enhanced affinity and selectivity for virus subtypes within A or B strains (FIG. 16). By incorporating fluorescent donor (D) and acceptor (A) groups the spatial relationship can be detected by fluorescence resonance energy transfer.

7. Tuning Surface Roughness and Imprinting

In view of the pronounced role of surface roughness and topography on the adhesion of cells and microorganisms such as bacteria and virus particles we introduce this parameter in a two length scale design concept (See FIG. 36)—virus size and curvature as well as receptor distribution. As a straightforward approach we use the Langmuir Blodgett technique to prepare SAMs of monodisperse silica nanoparticles of different sizes. These are subsequently covered with gold films of different thicknesses by a sputter coating process. The AFM image demonstrates a successful example of a nanosphere monolayer formed from 200 nm particles. This is in the same size range as the targeted influenza virus particles and we anticipate therefore a stronger adhesion. In reference to FIG. 36, principle of surface design along two lengths scales for glycan based virus sensing. In reference to FIG. 36; Right: AFM image of a SAM of 100 nm silica nanospheres containing a sputtered gold film.

For monolayer imprinting in presence of guests, we add deactivated H5N1 particles to mixed monolayers formed from different mixing ratios of the three amidines forming the monolayer. The first alternative consists in the utilization of the uniquely tunable stability and order of the rSAMs. Longer mesogens or sulfonic acid anchored SAMs enhance the layer stability extending it to lower pH values. The first and most simple templating strategy consists in a layer system which is thermally freezable. We herewith refer to a monolayer where the layer amphiphiles can freely diffuse at higher temperatures whereas they would feature much limited diffusivity and even crystallinity at room temperature—in a way similar to the so called "main transition" of lipids. These tests need methods for measuring lateral mobility of the SAM amphiphiles such as FRAP (fluorescence recovery after photobleaching).

As an extention of the adaptability test templating of surfaces for virus-particles is possible. The nonfixed SAM should be exposed to a template (virus particle) and at thermodynamic equilibrium it will be fixed according to the fixation approach. Removal of the template will leave behind a surface selective for the template or a group of template analogs. The removal can be triggered by pH, salt, or addition of a displacing ligand (e.g. sialic acid, tamiflu etc).

8. A Dynamic Platform for Building Close Packed Protein Multilayers and Ultrasensitive Biosensors (FIG. 18)

Figure 19:
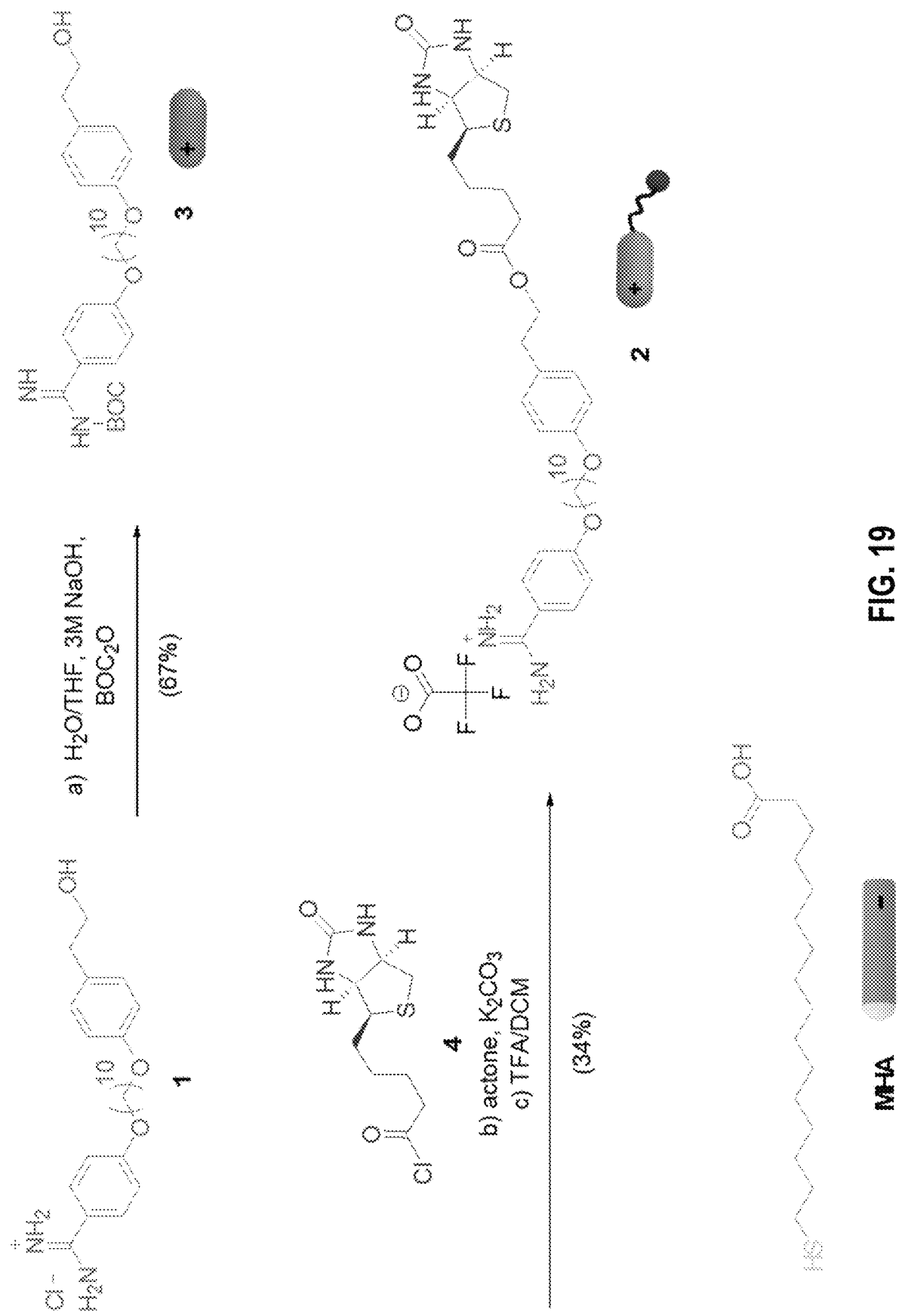

Design and synthesis We have previously shown that α,ω-bis(4-amidinophenoxy)alkanes form mono- and bi-layers on carboxylic acid functionalized alkanethiols, pre-assembled on gold. Layer order increased with alkane chain length and crystalline order was observed for layers formed from molecules with chains exceeding 7 carbons. In order to extend the rSAM concept from homo- to heterodifunctionalized amphiphiles we aimed at appending biologically active ligands at their ω-position. The design of such surfaces based on chemisorbed SAMs is well established and requires fine tuning of the ligand density and the size and flexibility of the spacer separating the bioactive ligand from the SAM end-groups. Hence, mixed SAMs containing 1-20% of biotin terminated amphiphile have proven optimal for adsorbing SA. In contrast to chemisorbed SAMs however, fluid supported lipid bilayers (SLB) promotes dense SA films exhibiting crystalline order. Taking these criteria into consideration we designed the synthetic strategy shown in FIG. 19 starting from 1 via amidine N-protection and O-biotinylation to yield 2 in a 23% overall yield.

Characterisation of rSAMs of 1 and 2. The adsorption of 1 and 2 on a SAM of chemisorbed mercaptohexadecanoic acid (MHA) on gold was studied by in situ ellipsometry whereas structure and properties of the films were characterized by a combination of infrared reflection absorption spectroscopy (IRAS), goniometry and atomic force microscopy (AFM) as outline in the Supplementary section (Figure S1). In situ ellipsometry data can be used to calculate the change in thickness and mass of a thin film and thus to monitor adsorption/desorption processes. As previously reported the order of the SAM used as anchor for the rSAM has a strong influence on the assembly kinetics, order and stability of the rSAMs. To enhance these parameters we turned to SAMs of MHA which are known to be stable and highly ordered. Thus, immersing a gold covered microscope slide in a dilute solution of MHA in ethanol gave rise to a fast adsorption process and a limiting film thickness near 22 Å in close agreement with the end to end distance of the molecule in an extended conformation. IRAS of the same substrate after drying revealed band positions of the $CH_2$ asymmetric and symmetric stretch vibration below 2920 $cm^{-1}$ and 2850 $cm^{-1}$ respectively, supporting the formation of a highly ordered monolayer (Table 3) in agreement with previous findings.

We then investigated the adsorption mode of the amidine amphiphiles 1 and 2 alone or as mixtures on this SAM.

TABLE 3

Characterisation results of the SAMs in the study.
Self assembled monolayers

|  | MHA | 1 | 2 |
|---|---|---|---|
| Contact Angle (°) [a] | 22 ± 3 | 22 ± 5 | 23 ± 1 |
| d (Å) [b] | 21 | 28 | 36 |
| $d_{air}$ (Å) [c] | — | 29 ± 2 | 34 ± 3 |
| $d_{rinse}$ (Å) [d] | 21 ± 1 | 29 ± 3 | 33 ± 3 |
| v $CH_2$ CH asym ($cm^{-1}$) [e] | 2918 | 2918 | 2918 |
| v $CH_2$ CH sym ($cm^{-1}$) [e] | 2850 | 2848 | 2850 |
| Tilt angle (°) [f] | 37 | 61 | 48 |

The surfaces were rinsed with pH9 borate buffer (0.01M) prior to analysis unless stated otherwise.
[a] The static contact angle was taken at 3 different positions as indicated in Supplementary section.
[b] Theoretical film thickness (d) assuming a densely packed layer of molecules oriented perpendicularly to the surface with the alkyl chains in an all-trans arrangement.
[c] Results from ex-situ ellipsometry in air.
[d] The thickness after rinsing, $d_{rinse}$, of the MHA-SAM was estimated after rinsing the surfaces with EtOH. $d_{rinse}$ of rSAMs 1, 1 + 2 and 2 were estimated after rinsing the surfaces with pH 9 borate buffer (0.01M).
[e] IR band positions corresponding to the $CH_2$ C—H asym and $CH_2$ C—H sym stretch.
[f] The average tilt angles, θ of the phenyl group relative to the surface perpendicular for rSAMs adsorbed on MHA. The tilt angles were calculated on the basis of the relative intensity of the bands corresponding to two perpendicular ring modes-the $(C=C)_{1,4}$ stretch band at 1611 $cm^{-1}$ and the C—H out-of plane bending mode at ca. 843 $cm^{-1}$. The spectra were subjected to base-line correction prior to analysis.

Both amphiphiles displayed a fast adsorption and a final film thickness, confirmed by air ellipsometry, agreeing in the case of 1 closely with the theoretical length of the molecule (assuming an extended chain conformation) whereas the rSAM of 2 was either incomplete or slightly tilted. IRAS and atomic force microscopy (AFM) were used to investigate the identity, structure and order of the films. A comparison of the IRAS spectra with transmission mode spectra (KBr) of the corresponding bulk samples is informative about layer stoichiometry, order and orientation of the monolayer components. The spectra of the rSAMs show all significant peaks present in the transmission spectra indicating presence of the amidine. Comparing the band intensities and band-widths of the two aquisation modes provide further structural information. The position of the $CH_2$ asymmetric and symmetric stretch vibration (2919 $cm^{-1}$ and 2849 $cm^{-1}$ for both rSAMs) as well as the sharpening of the bands in the low-frequency region of the spectra are signs indicating an ordered layer. Molecular orientation however is reflected in the relative intensities of the benzene $(C=C)_{1,4}$ stretch at 1612 $cm^{-1}$ and 1512 $cm^{-1}$ and the C—O—C asymmetric stretch at 1240-1250 $cm^{-1}$ relative to the intensities of the aromatic C—H out-of-plane bending mode at ca 840 $cm^{-1}$ and the amidine N—C=N asymmetric stretch found around 1690 $cm^{-1}$. The former bands have transition dipole vectors oriented along the 1,4-axis of the benzene ring and the longitudinal axis of the alkyl chain, respectively, whereas the latter have transition dipole vectors perpendicular to the 1,4-axis. We note with interest that the amidine band at 1690 $cm^{-1}$ is much weakened in rSAM-1 and also to a significant extent in rSAM-2 whereas the relative intensity of the benzene 1611 $cm^{-1}$ band increases. This indicates a near upright position of the anchoring benzamidine group. However, the out of plane signal at 841 $cm^{-1}$ is still rather intense. We attribute this ambiguity to a different average tilt of the two aryl groups, with the uppermost benzene group being significantly more tilted than the underlying benzamidine group. (Table 3).

Figure 20:
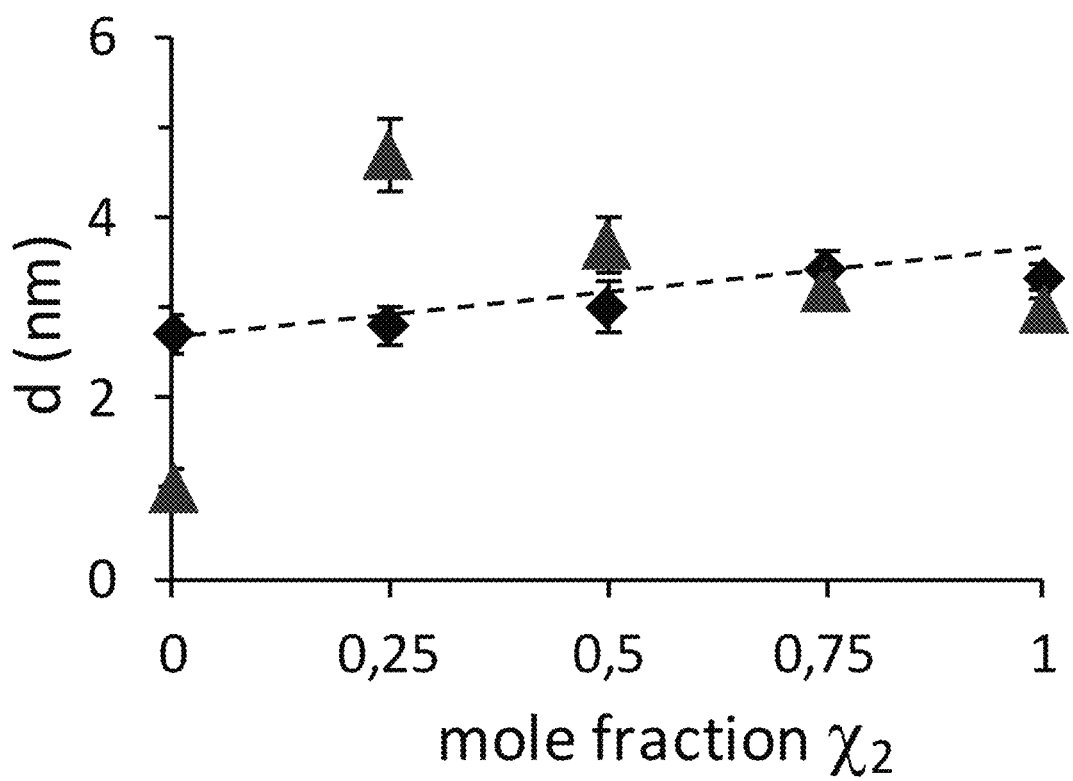

To achieve optimum surface density of the ω-biotinylated amidine (2) for streptavidin recognition, we studied the formation of mixed rSAMs of 1 and 2 formed using five different mixing ratios. The mixtures were prepared (total amidine concentration=50 μM) and the adsorption allowed to proceed for 1 hour or until a stable reading was observed. The surfaces were thereafter rinsed and dried and then characterized by air ellipsometry yielding an estimate of the film thickness in the dry state (FIG. 20, Table 3).

With the exception of rSAM-2 the film thickness corresponds closely to the molecular mechanics estimates of the molecular dimensions of 1 and 2 and their weighted average for the mixed rSAMs. This indicates that 1 and 2 form well ordered statistically mixed rSAMs. IRAS-spectra of all rSAMs reveal band positions of the $CH_2$ asymmetric and symmetric stretch vibration below 2920 $cm^{-1}$ and 2850 $cm^{-1}$ showing that the monolayers feature high, possibly crystalline, order (Table 3). Moreover, the intensity of bands characteristic for 2, notably the ester carbonyl stretch vibration at 1726 $cm^{-1}$ increases with the content of 2 in the mixed rSAM.

Adsorption of Streptavidine, Biotinylated Antibodies and their Antigens on Mixed rSAMs Having concluded that 1 and 2 form stoichiometrically mixed monolayers, we went on to test them as anchor for SA. The same surfaces used to characterize the mixed rSAMs were hence exposed to dilute solutions of SA (5 μM in pH 8, borate buffer) followed by rinsing and drying. The air ellipsometry measurements led to the results shown in FIG. 20, revealing a maximum of adsorbed SA at the lowest biotin level (25%) of 2. On this rSAM the SA thickness was estimated to 3.9±0.1 nm which is only slightly lower than the reported dimension of this protein and in agreement with previous reports on biotinylated thiol SAMs. IRAS was then used to study the nature of the adsorbed film. Apart from the bands corresponding to the amphiphile functional groups, three new bands appeared; ~1718 cm-1, ~1673 cm-1 and ~1546 cm-1. These can be assigned to the protein carbonyl stretch and to the amide I and amide II vibration respectively. All in all, the above results provide unequivocal evidence for the anticipated 3-layer assembly comprising an upper closely packed protein layer, the latter in support of data reported elsewhere. The above surfaces were subsequently immersed in a pH 3 solution to destabilize the anchoring amidinium carboxylate interactions. IRAS of the surfaces indicate that the rSAM and SA layers were effectively removed by this treatment leaving behind the MHA SAM ready for a subsequent adsorption experiment.

Similar studies in buffer indicated slightly enhanced SA adsorption for rSAMs with biotin levels of 10% ($\chi_2$=0.1), hence this level was used in subsequent experiments.

To probe the functionality of the SA modified rSAMs we investigated the immobilization of biotinylated antibodies targeting the prostate cancer biomarker, prostate-specific antigen (PSA) and human serum albumin (HSA). Numerous SPR based immunosensors for these analytes have been reported which may serve as benchmarks for the rSAM system. The SA modified mixed rSAM was hence used as an anchor layer for biotinylated anti-human-serum-albumin (anti-HSA) or anti-prostate specific antigen (anti-PSA). Monitoring the adsorption of both antibodies from dilute solutions (5 µM) by in situ ellipsometry (FIGS. 21A-21B) showed fast on rates and limiting film thicknesses of 3.4 nm (anti-HSA) and 4 nm (anti-PSA) respectively. The latter thickness is close to the short axial length of the antibody molecule, indicating that the molecules here adopt a "flat-on" orientation, in agreement with several previous reports.

Figure 21A:
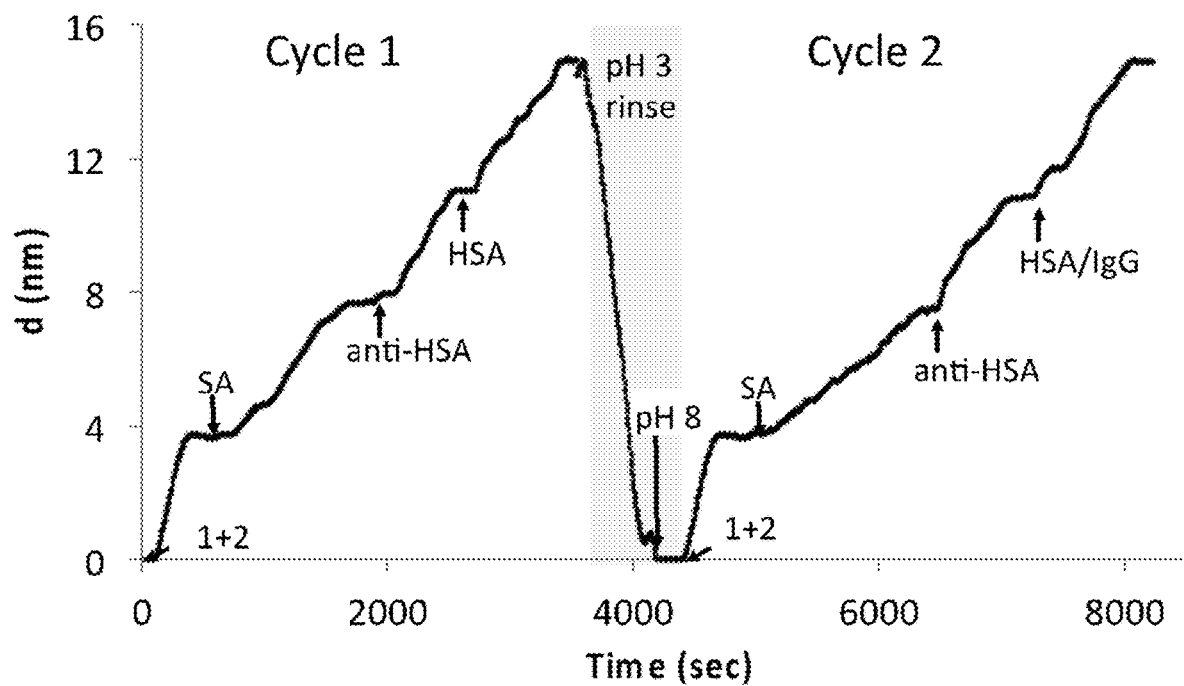
Figure 21B:
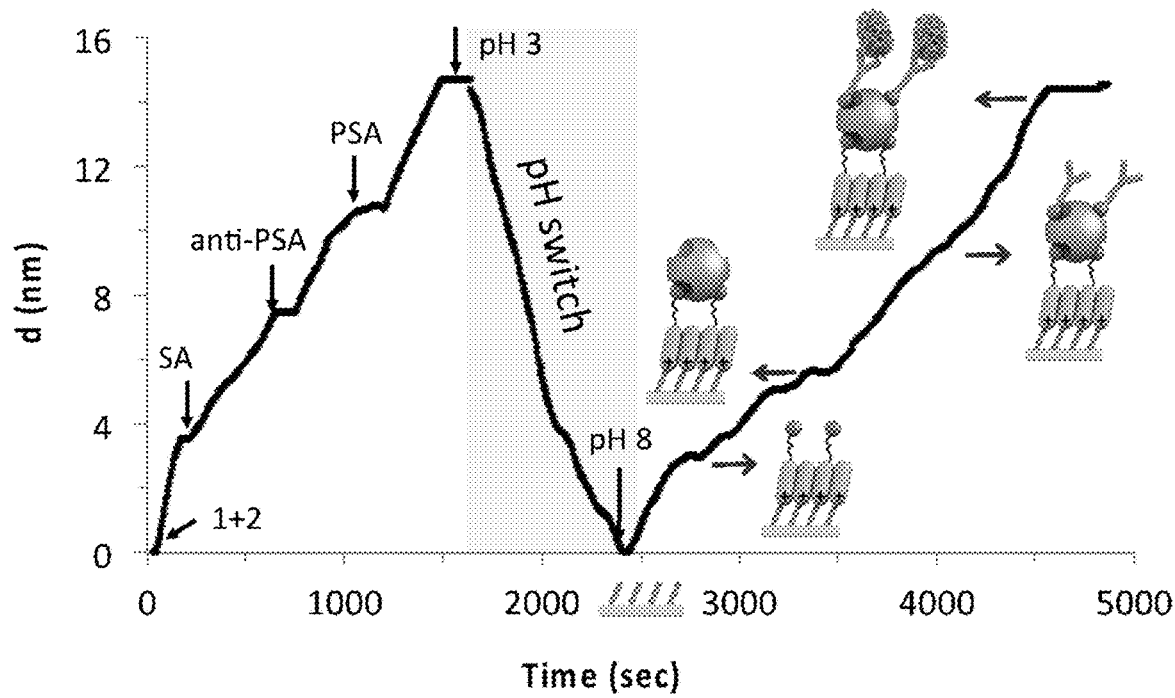

We subsequently incubated the immunosensors with dilute solutions (100 pM antigens in borate buffer, pH 8) of the corresponding antigens PSA and HSA. As seen in FIGS. 21A-21B, this resulted in sharply increased film thicknesses levelling off at near 4 nm, again in the range of the corresponding protein short axial length. Identical experiments performed using rSAMs made from pure 1 or 2 resulted in only small thicknesses.

Looking more closely at the rate curves it can be seen that the films build up at a near constant rate i.e. the thickness versus time plots depict nearly straight lines. The curves are then abruptly ended once the limiting thickness has been reached. This characterises processes governed by pseudo zero order kinetics with a rate of adsorption that is independent of the number of free unreacted surface sites. In fact, all layers appeared to adhere to this odd adsorption kinetics which we believe reflects an adsorption process driven by a strong tendency towards spontaneous self-assembly.

Next we investigated whether the multilayered system could be destabilized and reconstructed by repeating the sequential additions. FIG. 21A shows two such cycles preceeded by formation of the anchoring MHA SAM on bare gold. The second cycle was preceeded by a surface regeneration step by pH adjustment with acid to pH 3. Evidently the five layer assembly, attaining a total thickness of ca 17 nm prior to acidification, is fully reversible apart from the anchoring thiol SAM i.e. fully functional sensor surfaces can be repeatadly prepared using one single substrate. By performing the pH switch in absence of the rinsing step gave the intriguing result shown in FIG. 21B. All layers were here constructed as in the first cycle in FIG. 21A, hence including a buffer rinse. Destabilization of the layers at pH 3 was however in this case followed by a direct pH change in situ without exchanging the solution. Amazingly, in spite of a now exceedingly low concentration of the layer components, the layers seemed to spontaneously reassemble in the same order and at a similar rate as in the first cycle. Hence, plateaus were observed at thicknesses near those corresponding to the respective layers in cycle 1. Moreover, the final limiting thickness was identical to the one of the first cycle. This level of supramolecular self-assembly, akin to the well known reconstruction of tobacco mosaic virus, is to our knowledge unprecedented in synthetic supramolecular chemistry.

TABLE 4

Size corresponding to crystal unit cell dimensions of amphiphiles or proteins used in the quadruple layer construction

| TOP LAYER | Molecular size | Top layer thickness (nm) | Reference |
| --- | --- | --- | --- |
| rSAM $x_2$ = 0.1 | 2.8 | 2.9 ± 0.1 | |
| SA | 4.2 × 4.2 × 5.6 nm$^3$ | 3.9 ± 0.1 | 12 |
| anti-HSA | 14 × 8.5 × 3.8 nm$^3$ | 3.4 ± 0.1 | 30 |
| HSA | 8 × 8 × 3 nm$^3$ | 3.9 ± 0.1 | 33 |
| anti-PSA | 14 × 8.5 × 3.8 nm$^3$ | 4.0 ± 0.1 | 27 |
| PSA | 6 nm $^a$ | 4.0 ± 0.3 | 14, 34 |

Figure 22:
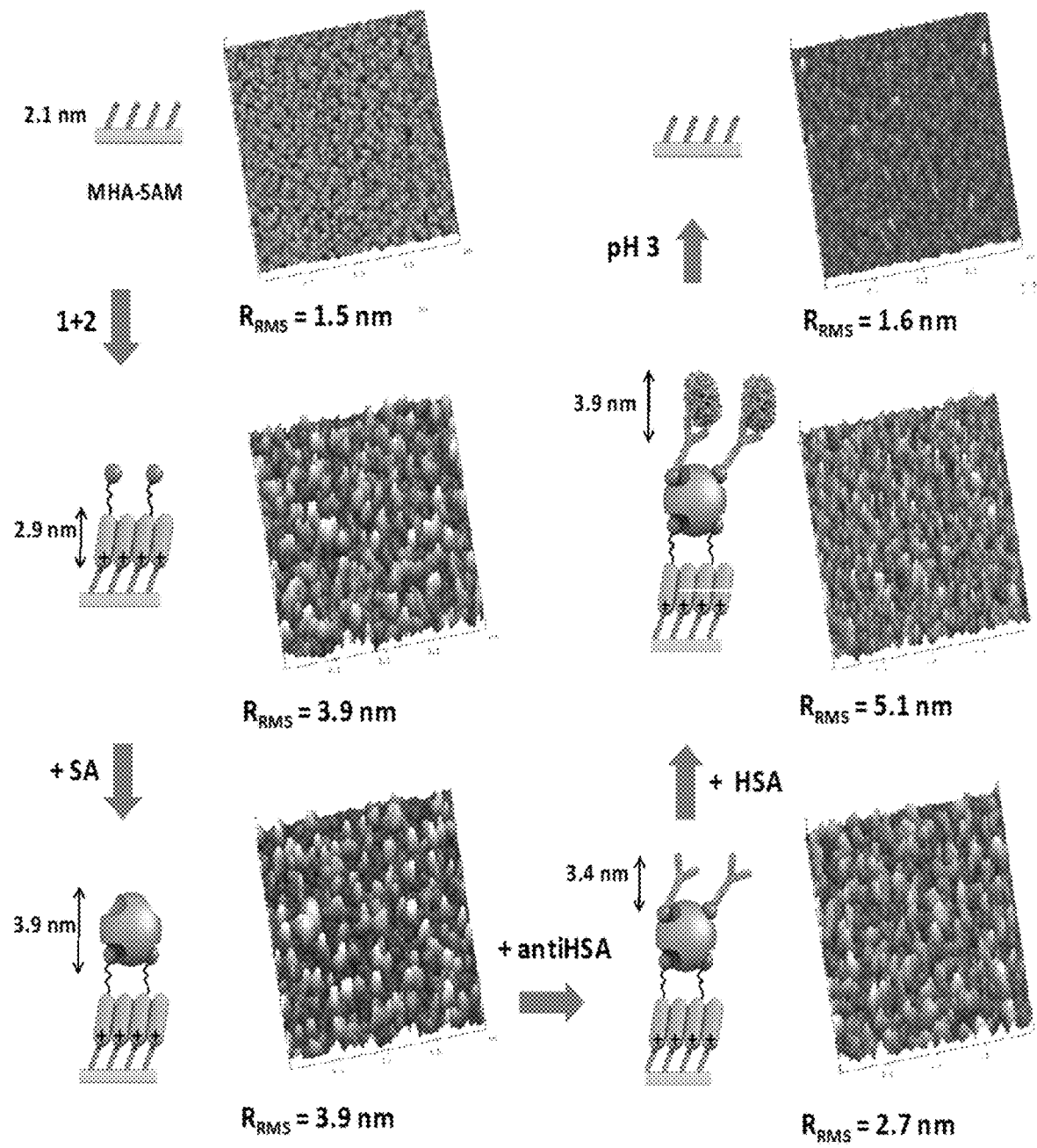
Figure 23:
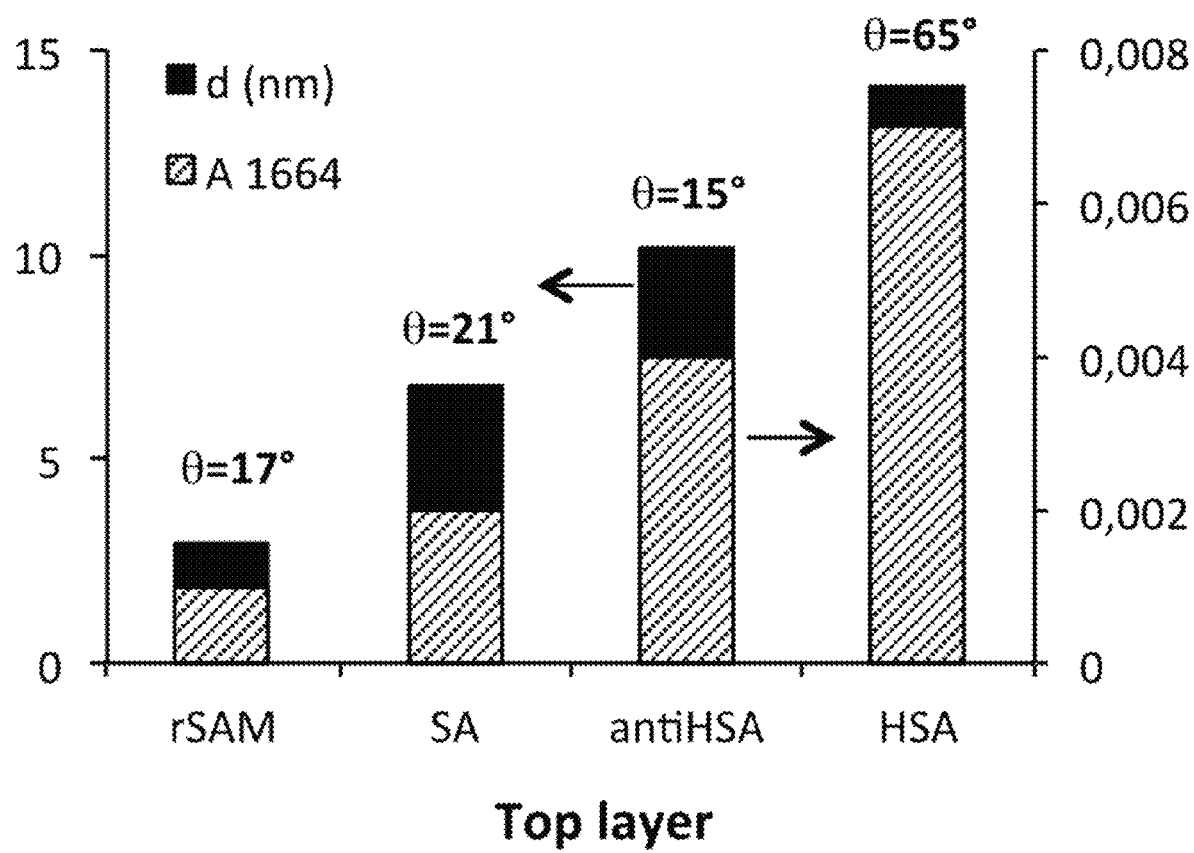

The layer thickness corresponding to flat protein orientations have been indicated in bold.
a) Hydrodynamic diameter Characterisation of the multi-layer assembly by AFM, IRAS and contact angle measurements. To gain insight into surface topography and lateral structure of the multilayered assembly we deposited the layers on MICA-surfaces modified with electron-sputtered gold and studied them by atomic force microscopy (AFM) in the dynamic contact mode. The morphology of this surface and that of bare gold (not shown) reveal ca 100 nm wide grains of gold, with a height of ca 2-3 nm. This texture is common for surfaces prepared using electron sputtering as deposition method. Higher magnifications did not reveal any crystalline areas although, based on other studies, they are known to be present. This was also the case for the subsequently deposited rSAM and protein layers. Instead we compared the overall surface texture and roughness of the surfaces during the successive buildup of the multilayered structure ending with anti-HSA and HSA followed by a final treatment with acid pH 3 (FIG. 22). As can be seen in FIG. 22 the surface texture changed for each deposited layer. The most distinct effect was observed upon formation of the rSAM ($\chi_2$=0.1). This showed disappearance of the gold texture, a clear increase in the size of the islands as well as their height and a more than doubling of the surface roughness from 1.5 to 3.9. These features were similar for the SA modified rSAM whereas adsorption of the biotinylated anti-HSA appeared to smoothen the surface given the lower roughness factor ($R_{RMS}$=2.7). This contrasted with the texture of the surface after the final antigen adsorption which showed a near twofold increase in the roughness factor. A final rinse with pH 3 buffer resulted in reappearance of the original gold topography except for some bright spots, possibly caused by residual amidine or salt. Overall, the results agree with the ellipsometry data in FIG. 4 and demonstrate that the original surface can be regenerated. Nevertheless, given the lack of absolute height profiles, the results may be due to surface displacement reactions and are hence not proving the existance of the multilayered structure. In order to address this we attempted to scratch the surface applying an excessive cantilever force. An AFM image with both scratched and unscratched areas revealed a height difference between these two areas of 5.2 nm which is less than the total thickness (ca 15 nm) estimated for the multilayered assembly by ellipsometry. This suggest that scratching only led to removal of the one or two uppermost protein layers. Support for this is given by the absence of gold features in the zoomed in AFM image of the scratched area. We therefore turned to IRAS and contact angle measurements to further confirm the identity and quantity of the adsorbed components. FIG. 23 shows the amide I band intensity, stemming from adsorbed protein, the ellipsometric thickness measured in air as well as the corresponding advancing contact angle measured for each layer of the multilayered assembly. The increase in film thickness during buildup correlates with the amide I band intensity in agreement with the assumption that protein multilayers are formed. The contact angles on the other hand, reflecting the surfaces wettability, change in a less predictable manner. First the mixed rSAM shows a lower contact angle compared to the pure amphiphiles (Table 3) likely as a result of the different mesogenic lengths of the molecules and the polarity of the biotin end-group. The contact angles remain low until the final adsorption of the HSA antigen, where a strong increase was observed. This is in agreement with previous studies of HSA films on charged surfaces prepared from highly concentrated solutions (1 mg/mL) and reflect the hydrophobic nature of this protein. Interestingly however, the rSAM anchored films were in our case prepared from highly dilute solutions (100 pM). Thus, dense protein films appear to form also at very low concentrations. This suggest that the driving force behind the self-assembly is exceedingly strong in these systems. Regeneration of the original MHA-SAM by rinsing the protein treated surface in pH 3 buffer resulted in return of the contact angles to the original values.

Sensing of HSA and PSA by in situ ellipsometry using antibody-modified rSAMs. As model diagnostic antigens PSA and HSA were chosen. HSA is the most abundant protein in the human blood and a low HSA concentration is a hint for liver disease. Therefore it is important to be able to detect HSA and distinguish it from other proteins present in the blood such as IgG. Different concentrations of HSA (1.5 μM to 5 μM) were used to test the sensor response (FIGS. 24A-24B) with the second most abundant plasma protein IgG used as reference.

Up to a concentration of 50 μM the ellipsometric angles did not change within the time frame of the measurement (1500 s). However, starting at 70 μM films appeared to form as judged by the near linear change in the ellipsometric angles with time. As expected the slopes of these curves increased with concentration. We noted with interest that the thickness versus time curves always levelled off at the same value (ca 4 nm) as when testing the original assembly using higher protein concentrations (5 μM) where monolayers are formed. This contrasts with the behaviour of traditional biosensors where instead a correlation between the analyte concentration and the film thickness, i.e. the adsorbed amount, is observed. We attribute this effect to the dynamic nature of the rSAMs rendering them adaptable for promoting an optimal packing of the adsorbed molecules. No binding of IgG was observed which proves the function of the HSA antibody and its high affinity for HSA ($K_d < 10^{-8}$ M).

Figure 24C:
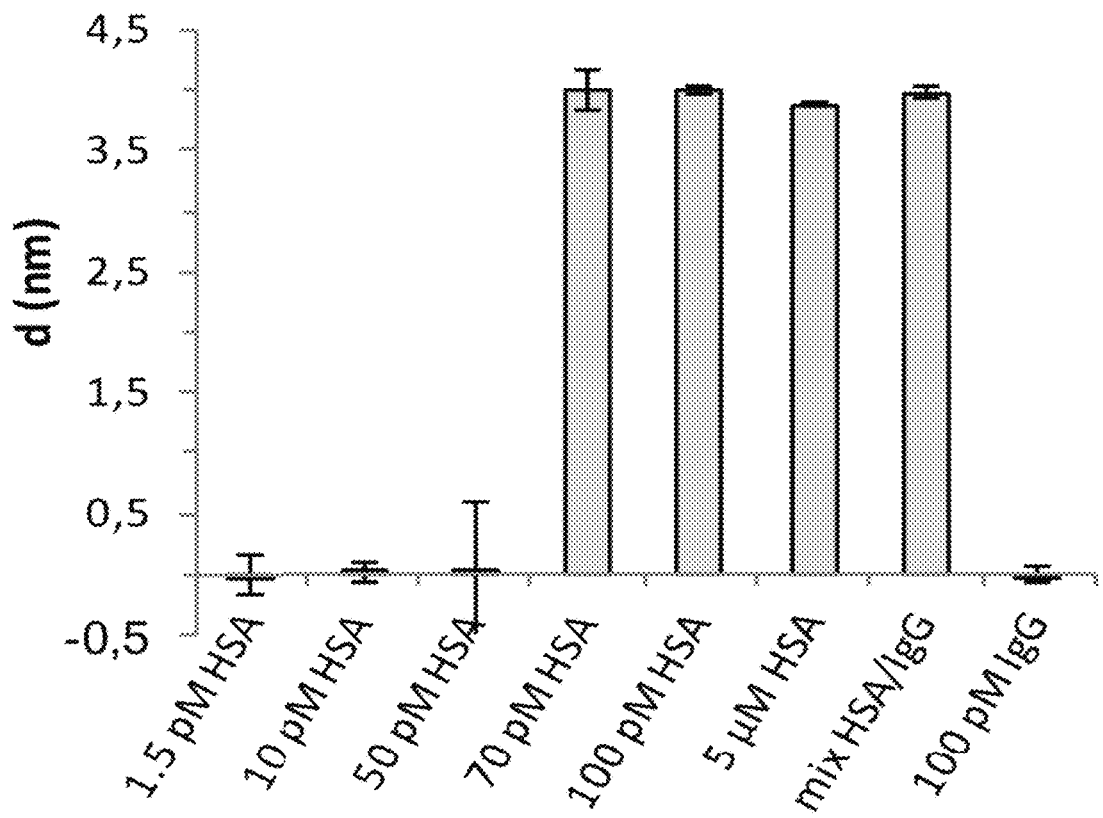

To estimate the amount of protein (Γ) adsorbed on the surfaces the Feijter equation was applied. The amount of HSA adsorbed on the antibody modified surfaces is shown in FIG. 24A. The maximum surface coverage of HSA on the anti-HSA modified rSAMs varied between 2.3-2.7 mg/m². The maximum amount HSA adsorbed on a poly(2-vinylpyridine) covered surface was determined to be 7.2 mg/m² but this was attributed to multilayer formation. Monolayers on hydrophobic substrates such as methylated silica surfaces, vary between 0.8 and 0.9 mg/m². Hence we conclude that the protein packing density of rSAM-based immunosensors is on a par or higher than protein SAMs formed on conventional surfaces.

Prostate cancer is a major cancerous disease in male population and accounts for about 10% of deaths from cancers. Its early detection can save millions of lives. Monitoring the prostate-specific antigen (PSA) level in serum is by far the most commonly used approach. PSA is a 34 kDa serine protease synthesized by the prostate gland and has been used as a premier oncological marker due to the lack of real alternative markers of prostate cancer. However, the low cutoff limit of the PSA (2.5±4 ng/ml) challenges current detection methods.

Figure 24D:
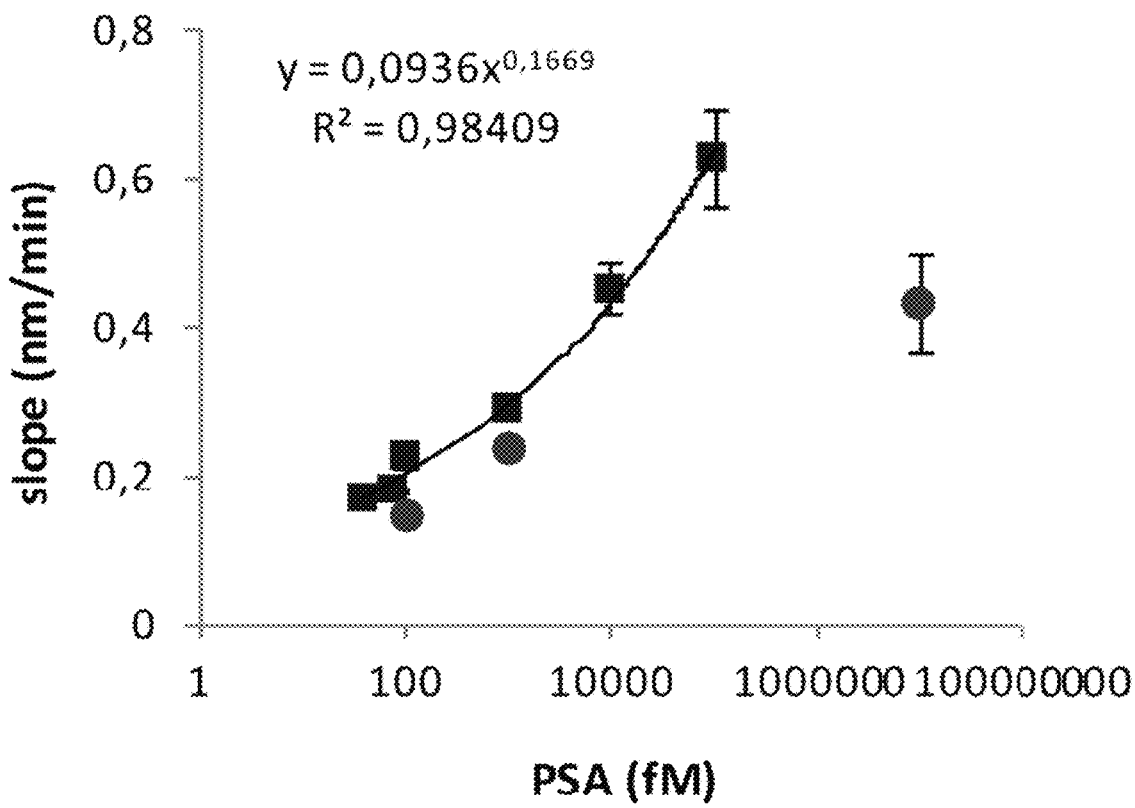

The PSA-sensor was build up identically to the HSA counterpart apart from the specific recognition layer consisting in this case of biotinylated anti-PSA. Probing the detection limit we noted that the sensor could detect PSA in buffer down to a concentration of 40 fM (FIG. 24B,D). As for HSA, we could not correlate the equilibrium thicknesses observed with the added amount of protein simply because the thickness consistently levelled off at a value indicating presence of a protein monolayer. Hence we once more adopted kinetic analysis for this purpose. FIG. 24D shows the assembly kinetics of PSA on an anti-PSA modified rSAM versus PSA concentration. The amount of bound protein can be estimated from this graph. The maximum surface coverage achieved for PSA from buffer media is 2.4 mg/m²±0.1 mg/m² again in the same range as HSA bound to the HSA sensor. To test the selectivity of the PSA sensor the non-target protein HSA was added to the system. This did not result in any significant change in the ellipsometric angles.

To test the utility of the sensor to detect PSA in presence of biological matrix, we first prepared the PSA sensor resulting in a increased film thickness of ca 12 nm. As before, this corresponds to the rSAM-SA-antiPSA triple layer. Dilute serum samples was then prepared by diluting human serum (commercially available AB plasma) 200 times with pH 8 HEPES buffer followed by spiking of PSA to three different levels (100 fM, 1 pM and 10 nM) while recording film formation by ellipsometry. This would correspond to serum PSA levels of 20 pM, 200 pM and 2 pM. As the case for the pure protein standards the thickness increased from 11 nm to 15 nm, hence an increase of ca 4 nm, again in support of a dense protein layer. Spiking lower levels led to similar behaviour i.e. attainment of monolayer thicknesses, but at slower rates. The slope versus the logaritm of the spiking level for both standards and spiked serum have been plotted in FIG. 24D. This indicates that serum levels down to ca 20 pM can in principle be detected using this sensor.

The concept of reversible self-assembled monolayers (rSAM) offers a unique opportunity to combine the dynamic nature of biological membranes with the robustness of chemisorbed self assembled monolayers. By introducing biologically active ligands such as biotin or glycans reversible mixed monolayers can be prepared with multiple tuning opportunities using one single substrate. Thus a partially biotinylated monolayer of an ω-functionalized α-benzamidine Bola amphiphile can in principle be used to anchor any biotinylated protein receptor with a positive effect on packing density and order. This translates into immunosensors with significantly higher sensitivities compared to benchmarks based on covalently linked biotins. Moreover, based on spontaneous self-assembly of multilayered systems, the sensors can be repeatedly reconstructed using one single substrate or used to sense alternative targets.

EXAMPLES

Example 1. Synthesis of Sialic Acid Amidine

The synthesis of the sialic-acid derivatized amidine was done by convergant synthesis ending by the coupling of the molecule body and the sialic acid ligand using 1,3 dipolar cycloaddition. 1,3 dipolar cycloaddition of amidine azide and α-alkyne sialic acid. resulting in 87% yield of pure product.

Example 2. Formation of an rSAM of a Sialic Acid Amidine

A gold surface modified with mercaptohexadecanoic acid was immersed in borate buffer adjusted to pH 9. The sialic acid amidine according to Example 1 was added to this solution to make up a 50 µM solution of the amidine. The self assembly was monitored by in-situ ellipsometry allowing values of film thickness to be estimated. A thickness of 54±1 Å of the amidine-sialic acid was measured. Rinsing of the rSAM with pH 8 buffer resulted in a film thickness of 19+1 Å. The layer could be completely removed by acidifying the solution to pH 3.

Example 3. Detection of Hemaglutinine and Influenza Virus Using the Sialic Acid rSAM To test the sialic acid rSAMs according to Example 2 for stability, selectivity and sensitivity towards its specific lectins, they were tested by adding either trimeric H5N1 hemagglutinin (pI 3.5), concanavalin A (pI 4.5-5.5, lectin specific to mannose), human serum albumin (protein abundant in human serum) or H5N1 virus in a pH 7.5 buffer and monitoring the change in film thickness by in situ ellipsometry. The analyte concentration was varied between 0.4 nM to 84 nM. After adsorption the surface could be restored by acidifying the solution to pH3 and reimmersion in the pH 7.5 buffer.

Example 4. Glycan rSAMs

Preparation of protein and virus solutions. Influenza A H5N1 (A/Anhui/2005) hemagglutinin (HA) was purchased from Sino Biological Inc. Concanavalin A (ConA), human serum albumin (HSA) and mucin from porcine stomach (Type III, bound sialic acid 0.5-1.5%) were obtained from Sigma Aldrich. Stock solution of HA, ConA, HSA (4.2 µM) and mucin (1% w/v) were prepared in milli q water or pH 8 HEPES buffer (0.01 M) and stored at −80° C. prior to usage.

Influenza A (H5N1) Surveillance Antigen, BPL-Inactivated Influenza A Virus, A/Anhui/01/2005(H5N1)-PR8-IBCDC-RG6, FR-918, were generously provided through the Influenza Reagent Resource, Influenza Division, WHO Collaborating Center for Surveillance, Epidemiology and Control of Influenza, Centers for Disease Control and Prevention, Atlanta, GA, USA and were used without further treatment. The hemagglutination titer of the influenza virus was 512 HAU and the estimated concentration (mol $L^{-1}$) was determined using equation 1.

$$\text{Concentration of Virus (mol } L^{-1}) = \frac{C \times B \times 10^3}{L} \quad (1)$$

where C is concentration of the virus in HAU, [HAU] $mL^{-1}$, B is the estimated number of virus particles per HAU, $5.5 \times 10^7$ units $HAU^{-1}$,[41] L is the Avogadro constant, 6.022× 1023 units $mol^{-1}$. For the inhibitory studies, the solutions were prepared by shaking H5N1 (512 HAU) or HA (4.2 µM) with equal volume of 1% mucin in pH 8 HEPES buffer for min. 30 mins prior to absorption studies.

Adsorption Experiments. The adsorption process of amidine, protein or virus was monitored using in situ null ellipsometry. The instrument used was a Rudolph thin film ellipsometer (type 43603-200E, Rudolph Research, USA) using an angle of incidence of 68° and automated according to Cuypers et al.[42] The light source was a xenon lamp, filtered to λ=442.9 nm. The thiol SAMs prepared as described in the Supplementary Information were immersed vertically into an ellipsometric quartz cuvette with ordinary microscopic cover glass windows containing 5 ml of sodium borate buffer (0.01 M, pH 9.0, prepared from boric acid). The cuvette was thermostated to 25° C. and equipped with a magnetic stirrer at constant stirring rate of 350 rpm. Before each measurement, the refractive index of the MHA gold substrate was determined by a 4-zone surface calibration in pH 9 HEPES solution.

Amidine addition. After a stable baseline was obtained, 100 μL of stock solution containing 1, 2, or a mixture of 1 and 2 ($\chi$=0.2) (2.5 mM) were added to the cuvette. Kinetics data was collected until stabilization or for a maximum duration of 5000 s. The system was then rinsed with pH 8 HEPES buffer for a maximum of 1000 s (11 mL min$^{-1}$) in a continuous system. The surface was later allowed to stabilize till steady state or 5000 s (whichever came first).

Protein addition. After the adsorption of rSAMs (vide supra) the selectivity of the surfaces was tested by by measuring the adsorption of 21 nM or 5.3 nM (ConA) solutions (HEPES-buffer, 0.01 M, pH 8) of the proteins HA, ConA and HSA by in situ ellipsometry. Binding curves were recorded by adding incremental amounts of the respective protein (0.42-84 nM) or virus (0.2-33 HAU) to the cuvette and monitoring the adsorption by in situ ellipsometry.

The additions were made every 2000 s using the respective stock solution prepared as described above. The surfaces were subsequently either regenerated by 0.1 M HCl or blown dry using nitrogen and subjected to further characterisation by IRAS, contact angle or AFM. Calculations of thickness and adsorbed amounts. A homogenous 3-layer model was used to determine the average thickness, d and adsorbed amount, Γ from the ellipsometric data according to (Equation 2).[43,44]

$$\Gamma = d_A \frac{n - n_0}{dn/dc} \quad (2)$$

where $d_A$ is the thickness of the adsorbed layer, n is the refractive index of the molecules, and $n_0$ is the refractive index of the ambient and dn/dc is the refractive index increment for the molecules in the layer. The thickness of the rSAMs was calculated using a homogenous 3 layer model (MHA Au-rSAM-buffer solution) with assumed refractive index of 1.45 and 1.34 for rSAMs and ambient respectively. The ellipsometric determined thickness of rSAMs using this model has been previously verified using neutron reflectivity.[20] Refractive index increment, dn/dc of 0.22 mg ml$^{-1}$ was used to determine the amount of rSAMs adsorbed.[45] Relative adsorbed protein thickness was calculated based on a homogenous 3-layer model (rSAMs-protein-buffer solution) with refractive index of 1.45 for protein. It assumed that minimum penetration or exchange occurred between the interface and analyte during the adsorption process. The thicknesses obtained are relative values to describe trends in the protein adsorption.[46] A refractive index increment, dn/dc of 0.19 mg ml$^{-1}$ was used to determine the adsorbed amount of protein.[47]

Statistical methods. Equilibrium binding analysis based on successive injections (single cycle measurement)[48] was used to determine the dissociation constant, $K_d$, limiting adsorbed amount, $\Gamma_{max}$ and Hill slope, h. The technique requires a way to accurately determine the steady state value of thickness, d, and adsorbed amount, Γ. We considered the latter to have reached a plateau within 2000s. If this was not the case, the curves were extrapolated to steady state values by nonlinear curve fitting.

The limit of detection (LoD) was estimated as the concentration producing a signal corresponding to a minimum of three times the standard deviation (SD) of the blank signal. The binding curves were fitted to the Hill equation using Graphpad Prism v7.0. Error bars are standard error of mean (S.E.M) describe the range between the values obtained unless stated otherwise. All values are averages of a minimum of two experiments on different substrates. Raw plots and details of fitting are shown in the supplementary information. Molecular length of the compounds was estimated after minimizing the energy of the corresponding compound using molecular mechanics calculations with the MM2 force field (ChemDraw 3D, CambridgeSoft).

Reagents. All solvents were purchased from Acros Organics (Geel, Belgium) unless otherwise stated. Acetonitrile (ACN) was obtained from Merck (Darmstadt, Germany). Ethanol (99.5%) was obtained from CCS Health Care (Borlänge, Sweden). Boric acid, (4-(2-hydroxyethyl)-1-piperazineethanesulfonic acid (HEPES) and NaCl were obtained from VWR Chemicals (Leuven, Belgium). MgSO$_4$, anhydrous were purchased from JT Baker (Japan). Sialic acid was purchased from Carbosynth (Berkshire, UK). Deionized water was used for chemical reactions. All other reagents were purchased from Sigma Aldrich (Sweden) or Merck (Sweden) and used as supplied unless otherwise stated. Details concerning the synthesis and characterisation of EG4-SA and EG2 terminated amidines 14 and 15 and resulting rSAMs will be published separately.

Apparatus and methods. Thin layer chromatography (TLC) was carried out using Merck aluminium backed sheets coated with 60F254 silica gel. Visualization of the silica plates was achieved using a UV lamp (max=254 nm), and/or 5% ethanolic H$_2$SO$_4$.

HPLC analysis was carried out on a Waters 2695 Alliance HPLC system equipped with autosampler, inline degasser, Waters 2996 PDA detector and MassLynx 4.0 software, using a Phenomenex Luna C18(2) column (4.6 mm (i.d.)× 150 mm, 5 μm, 110 Å) and a guard column (4.6×20 mm) at ambient temperature. The mobile phase, as indicated in the procedure (vide infra), was pumped at a flow rate of 1.0 mL min$^{-1}$.

Flash column chromatography was carried out using Sigma Aldrich silica gel (Merck grade 9385, 60 Å). Reversed phase column chromatography was performed using an Agilent Bond Elute C18 column. The mobile phase used is as specified in the procedure (vide infra). Proton and carbon nuclear magnetic resonance spectra were recorded using an Agilent (Varian) Mercury 400 MHz instrument operating at 400 or 101 MHz and evaluated using Mestre Nova software. Chemical shifts (δ) are reported in parts per million (ppm) with respect to tetramethylsilane (TMS) using the manufacturers indirect referencing method. All chemical shifts are quoted on the δ scale in ppm using residual solvent as the internal standard. (1H NMR: CDCl$_3$=7.26, CD$_3$OD=4.87; DMSO-d$_6$=2.50 and $^{13}$C NMR: CDCl$_3$=77.0; CD$_3$OD=49.0; DMSO-d$_6$=39.5). Coupling constants (J) are reported in Hz with the following splitting abbreviations: s=singlet, d=doublet, t=triplet, q=quartet, quin=quintet, and m=mutiplet.

Low resolution mass spectra (LRMS) were conducted using a Waters ZQ2000 MS system with 2795 LC and 2996 PDA. High resolution mass spectra (HRMS) were recorded by MALDI-MS analysis performed on a hybrid MALDI LTQ Orbitrap XL (Thermo Fisher Scientific, Germany) instrument. Nominal and exact m/z values are reported in Daltons.

FTIR (ATR) spectra were recorded on a Nicolet 6700 instrument with a SmartITR accessory using 64 scans, a standard KBr beamsplitter, a spectral range of 5000-400 cm$^{-1}$, and a resolution of 4 cm$^{-1}$. All spectra were processed and analysed using the OMNIC 8 software. Elemental analysis of carbon, nitrogen and sulphur contents were determined by analysis at the Department of Organic Chemistry, Johannes Gutenberg Universität Mainz using a Heraeus CHN-rapid analyser (Hanau, Germany).

Synthesis of OH-Terminated Amphiphiles 4-(10-Bromo-decyloxy)-benzonitrile (5) was synthesized according to a modified literature protocol.[1] 1,10-dibromodecane 3 (25 mL, 111 mmols, 10 eq), 4-cyanophenol 4 (1.31 g, 11 mmol, 1 eq) and anhydrous K$_2$CO$_3$ (3.00 g, 22 mmols, 2 eq) in dry acetone (7 mL) was stirred at 80° C. under N$_2$ atmosphere for 24 hrs. The resulting slurry was cooled, filtered and washed with acetone. The filtrate was collected and concentrated at 40° C. in vacuo. The crude product was later purified using flash chromatography (hexane to 10% ethylacetate in hexane) to give the nitrile 5 as a white amorphous solid (3.05 g, 81% yield).

TLC (EtOAc:Hexane, 1:9 v/v): R$_F$=0.49; $^1$H-NMR (500 MHZ, CDCl$_3$) δ 7.60-7.52 (m, 2H), 6.96-6.88 (m, 2H), 3.99 (t, J=6.5 Hz, 2H), 3.40 (t, J=6.8 Hz, 2H), 1.90-1.68 (m, 4H), 1.50-1.33 (m, 12H); $^{13}$C{$^1$H} NMR (126 MHZ, CDCl$_3$) δ 162.6, 134.1, 119.4, 115.3, 103.8, 68.5, 34.2, 32.9, 29.5, 29.5, 29.4, 29.1, 28.9, 28.3, 26.0; LRMS (m/z): [M]$^+$ calcd for C$_{17}$H$_{24}$BrNO, 338.28; found, 337.82, 339.83.

4-(10-(4-(2-hydroxyethyl)phenoxy)decyloxy)benzonitrile (7) was synthesized according to a modified literature protocol.[1] Dry acetone (85 ml) was added to 4-(10-bromo-decyloxy)benzonitrile 5 (1.70 g, 5.0 mmols, 1 eq), 4-(2-hydroxyethyl)phenol 6 (1.40 g, 10 mmols, 2 eq) and K$_2$CO$_3$, anhydrous (1.40 g, 10 mmols, 2 eq) under N$_2$ atmosphere at 80° C. After 24 hrs, additional 4-(2-hydroxyethyl)phenol 6 (0.31 g, 2.3 mmols, 0.5 eq) and K2CO$_3$, anhydrous (0.38 g, 2.3 mmols, 0.5 eq) was added and the reaction was left to stir at 80° C. for a further 48 hrs. The resulting slurry was cooled, filtered and washed with acetone. The filtrate was collected and concentrated at 40° C. in vacuo. The crude product was purified using flash chromatography (30% ethyl acetate in hexane to 100% ethyl acetate) to give nitrile 7 as white crystalline solid (~99%, 75% purity) and the sample was used in the next step without further purification. A sample was purified to give the analytical data.

TLC (EtOAc:Hexane, 3:7 v/v): R$_F$=0.23; $^1$H-NMR (400 MHZ, CDCl$_3$) δ 7.56 (d, J=8.9 Hz, 2H), 7.13 (d, J=8.6 Hz, 2H), 6.93 (d, J=8.9 Hz, 2H), 6.84 (d, J=8.6 Hz, 2H), 3.99 (t, J=6.5 Hz, 2H), 3.93 (t, J=6.5 Hz, 2H), 3.82 (t, J=6.6 Hz, 2H), 2.80 (t, J=6.5 Hz, 2H), 1.85-1.70 (m, 4H), 1.49-1.23 (m, 12H); $^{13}$C{$^1$H}-NMR (101 MHZ, CDCl$_3$) δ 162.57, 157.95, 134.07, 130.34, 130.05, 119.44, 115.29, 114.75, 103.74, 68.52, 68.11, 63.95, 38.40, 29.58, 29.56, 29.47, 29.42, 29.40, 29.09, 26.17, 26.03; analysis (% calcd, % found for C$_{25}$H$_{33}$NO$_3$): C (75.91, 75.86), H (8.41, 8.59), N (3.54, 3.40).

Amino(4-(10-(4-(2-hydroxyethyl)phenoxy)decyloxy) phenyl)methaniminium chloride (1) was synthesized based on a modified literature protocol.[2] HCl gas was bubbled into a stirred solution 4-(10-(4-(2-hydroxyethyl)phenoxy)decyloxy)benzonitrile 7 (1.0 g, 2.5 mmols) in 1,4 dioxane, dry (30 mL) and dry methanol (2.6 mL) at 0° C. under N$_2$ atmosphere. The solution was then left to warm to room temperature and stirred for further 72 hrs. The clear solution was concentrated in vacuo at 40° C. and the crude imino ester was precipitated in diethyl ether in the freezer overnight. The white precipate was collected via filtration under N$_2$ atmosphere and reacted with 7M methanolic ammonia (10 mL) and dry methanol (10 mL) at 70° C. for 48 hrs. The crude amidine was concentrated in vacuo at 40° C., precipitated using diethyl ether and filtered to give amidine 1 (0.59 g, 53%) as a white amorphous solid. The product was recrystallized from 2M methanolic HCl prior to characterization and analysis.

m.p.: 206-209° C.; $^1$H-NMR (400 MHZ, DMSO) δ 9.23 (s, 2H), 9.04 (s, 2H), 7.84 (d, J=8.8 Hz, 2H), 7.11 (dd, J=18.6, 8.6 Hz, 4H), 6.80 (d, J=8.5 Hz, 2H), 4.60 (t, J=5.2 Hz, 1H), 4.07 (t, J=6.4 Hz, 2H), 3.90 (t, J=6.4 Hz, 2H), 3.54 (dt, J=12.4, 6.3 Hz, 2H), 2.63 (t, J=7.1 Hz, 2H), 1.78-1.62 (m, 4H), 1.47-1.22 (m, 12H); $^{13}$C{$^1$H}-NMR (101 MHz, DMSO) δ 164.69, 163.07, 156.91, 131.21, 130.14, 129.72, 119.21, 114.73, 114.10, 68.08, 67.28, 62.43, 38.15, 28.91, 28.74, 28.71, 28.44, 25.52, 25.38; analysis (% calcd, % found for C$_{25}$H$_{37}$ClN$_2$O$_3$): C (66.87, 67.19), H (8.31, 8.41), N (6.24, 6.03).

Synthesis of α-Alkyne Sialic Acid 13

α-alkyne sialic acid 13 was synthesized based on a modified literature procedure giving an overall yield of 7% over 5 steps.

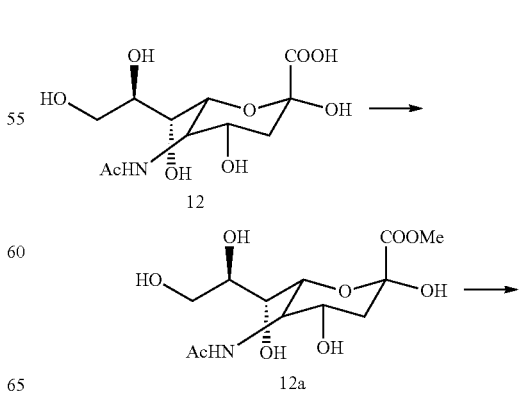

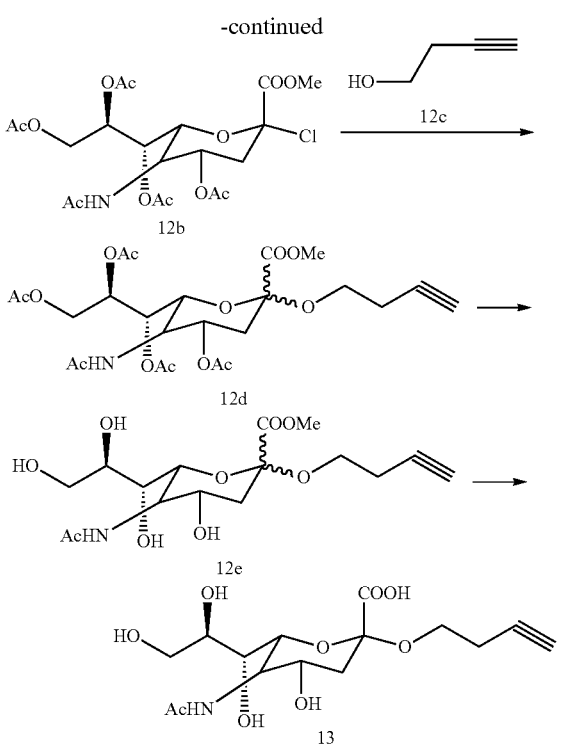

Methyl 5-acetamido-2,4-dihydroxy-6-((1R,2R)-1,2,3-trihydroxypropyl)tetrahydro-2H-pyran-2-carboxylate (12a) was synthesized as reported elsewhere.[4] The ester 12a was isolated as a white amorphous solid (92% yield).

1H-NMR (400 MHZ, CD$_3$OD) δ 4.03 (m, 2H), 3.87-3.79 (m, 3H), 3.78 (d, J=3.7 Hz, 3H), 3.73-3.66 (m, 1H), 3.62 (dd, J=11.2, 5.7 Hz, 1H), 3.48 (dd, J=9.1, 1.3 Hz, 1H), 2.22 (dd, J=12.9, 4.9 Hz, 1H), 2.02 (s, 3H), 1.89 (dd, J=12.8, 11.5 Hz, 1H); $^{13}$C {$^{1}$H}-NMR (101 MHZ, CD$_3$OD) δ 175.10, 171.75, 96.66, 72.07, 71.64, 70.18, 67.84, 64.83, 54.31, 53.14, 40.69, 22.66.

4-Acetoxy-5-acetylamino-2-chloro-6-(1,2,3-triacetoxypropyl)-tetrahydro-pyran-2-carboxylic acid methyl ester (12b) was synthesized based on a literature procedure.[3] Ester 12a (2.00 g, 6.19 mmols) was added to a stirred solution of fresh acetyl chloride (50 mL) and acetic acid (15 mL) cooled in a NaCl ice bath. The reaction mixture was left to warm to room temperature and stirred for 24 hrs. The excess acetyl chloride and acetic acid was then removed in vacuo at 40° C. by co-evaporating with toluene. The crude mixture was subjected to flash chromatography (ethyl acetate) to afford the protected sialic acid 12b as a white foam (1.97 g, 62%). The proton and carbon NMR confirmed the presence of protected 12b in >80% purity. It was used in the next step without further purification.

1H-NMR (400 MHZ, CDCl$_3$) δ 5.94 (d, J=10.1 Hz, 1H), 5.44 (dd, J=6.6, 2.4 Hz, 1H), 5.40-5.32 (m, 1H), 5.13 (td, J=6.3, 2.7 Hz, 1H), 4.41 (dd, J=12.5, 2.7 Hz, 1H), 4.34 (dd, J=10.8, 2.4 Hz, 1H), 4.18 (q, J=10.4 Hz, 1H), 4.03 (dd, J=12.5, 6.2 Hz, 1H), 3.83 (s, 3H), 2.74 (dd, J=13.9, 4.8 Hz, 1H), 2.22 (dd, J=13.9, 11.2 Hz, 1H), 2.08 (s, 3H), 2.04 (s, 3H), 2.01 (d, J=1.0 Hz, 6H), 1.86 (s, 3H); $^{13}$C{$^{1}$H}-NMR (101 MHZ, CDCl$_3$) δ 170.99, 170.70, 170.50, 170.00, 169.89, 165.68, 96.73, 74.03, 70.26, 68.86, 67.03, 62.20, 53.84, 48.64, 40.71, 23.13, 20.98, 20.89, 20.83, 20.80.

4-Acetoxy-5-acetylamino-2-but-3-ynyloxy-6-(1,2,3-triacetoxy-propyl)-tetrahydro-pyran-2-carboxylic acid methyl ester (12d) was synthesized based on a modified procedure.[4] The protected sialic acid 12b (1.59 g, 3.11 mmols, 1 eq) and 4 Å molecular sieves (4.00 g) were evacuated and back filled with nitrogen 3 times. 3-Butyn-1-ol, 12c (1.60 mL, 21.8 mmols, 7 eq) and anhydrous·acetonitrile (50 mL) was then added under N$_2$ atmosphere and stirred at room temperature. After 1 hr, silver triflate (2.40 g, 9.36 mmol, 3 eq) was added and the resulting reaction was left to stir in the dark at 40° C. for 24 hrs. The resulting suspension was filtered, concentrated in vacuo at 40° C. and reconstituted in CHCl$_3$ (100 ml). The organic mixture was later washed with sat. NaHCO$_3$ (100 mL), brine (100 ml), dried over Na$_2$SO$_4$ and concentrated in vacuo at 40° C. The crude mixture was purified using flash chromatography (3% MeOH in DCM) to give a mixture of a and B 12d as an off-white foam (58%, 945 mg) in approximate 65% purity. The product 12d was used without further purification in the next step. TLC (MeOH:DCM, 3:97 v/v): R$_F$=0.28; 1H-NMR (400 MHZ, CD$_3$OD) δ 5.41 (dd, J=5.3, 2.1 Hz, 1H), 5.40-5.36 (m, 1H), 5.33 (d, J=2.1 Hz, 1H), 5.32-5.27 (m, 1H), 5.21 (td, J=11.2, 4.9 Hz, 1H), 4.81 (dd, J=4.5, 1.6 Hz, 2H), 4.73 (dd, J=12.4, 2.5 Hz, 1H), 4.31 (dd, J=12.4, 2.6 Hz, 1H), 4.22 (dd, J=10.6, 2.1 Hz, 1H), 4.15 (dd, J=10.8, 2.0 Hz, 1H), 4.13-4.06 (m, 2H), 4.04-3.92 (m, 2H), 3.87-3.85 (m, J=6.7 Hz, 1H), 3.83 (s, 3H), 3.81 (s, 3H), 3.66-3.56 (m, 1H), 3.53-3.43 (m, J=9.1, 6.2 Hz, 1H), 3.43-3.34 (m, J=9.4, 7.0 Hz, 1H), 2.64 (dd, J=12.7, 4.6 Hz, 1H), 2.54-2.45 (m, 3H), 2.41 (ddd, J=12.7, 6.9, 4.0 Hz, 4H), 2.27 (t, J=2.6 Hz, 1H), 2.14 (s, 3H), 2.11 (s, 6H), 2.07 (s, 3H), 2.01 (s, 6H), 1.99 (s, 3H), 1.98 (s, 4H), 1.85 (s, 3H), 1.84 (s, 3H), 1.83-1.81 (m, 1H); $^{13}$C {$^{1}$H}-NMR (101 MHZ, CD$_3$OD) δ 173.40, 173.36, 172.31, 172.28, 171.91, 171.81, 171.71, 171.62, 171.50, 171.45, 169.45, 168.76, 100.05, 99.88, 81.82, 81.63, 73.23, 72.54, 72.23, 71.51, 70.68, 70.62, 70.34, 69.57, 69.44, 68.57, 64.35, 63.48, 63.38, 63.34, 53.32, 53.31, 50.07, 50.02, 38.94, 38.35, 22.70, 22.65, 21.23, 21.14, 20.87, 20.82, 20.80, 20.74, 20.69, 20.61, 20.28; LRMS (m/z): [M]$^+$ calcd for C$_{24}$H$_{33}$NO$_{13}$, 543.52, found 543.86.

5-Acetylamino-2-but-3-ynyloxy-4-hydroxy-6-(1,2,3-trihydroxy-propyl)-tetrahydro-pyran-2-carboxylic acid methyl ester (12e) was synthesized based on the modified literature procedure.[3,4] Alkyne 12d (829 mg, 1.53 mmols) was stirred in NaOMe in MeOH (0.5 M, 0.8 mL) and anhydrous MeOH (20 mL) for 24 hrs. The resulting reaction was neutralized using Amberlite IR 120 (H$^+$) and filtered. The filtrate was concentrated in vacuo at 40° C. and purified using flash chromatography (13% to 20% MeOH in CH$_2$Cl$_2$) to give the α and β product 12e as an off-white foam (166 mg, 29%).

TLC (EtOAc): R$_F$=0.28; $^1$H-NMR (400 MHZ, CD$_3$OD) δ 3.92-3.78 (m, 8H), 3.75 (d, J=10.2 Hz, 1H), 3.69-3.61 (m, 3H), 3.57 (dd, J=10.4, 1.7 Hz, 1H), 3.55-3.48 (m, 3H), 2.69 (dd, J=12.8, 4.7 Hz, 1H), 2.44-2.38 (m, 3H), 2.26 (t, J=2.7 Hz, 1H), 2.00 (s, 3H), 1.73 (dd, J=12.8, 11.8 Hz, 1H); $^{13}$C {1H}-NMR (101 MHZ, CD$_3$OD) δ 175.19, 170.84, 100.22, 81.50, 74.95, 72.39, 70.60, 70.17, 68.51, 64.75, 63.72, 53.79, 53.40, 41.62, 22.66, 20.63; analysis (% calcd, % found for $C_{16}H_{25}NO_9$): C (51.20, 51.16), H (6.71, 6.74), N (3.73, 3.60).

B-alkyne sialic acid (13) was synthesized based on a modified literature procedure.[3] Ester 12e (540 mg, 1.44 mmols) in aqueous NaOH solution (0.2M, 8 mL) was stirred at room temperature for 24 hrs. The resulting solution was neutralized using amberlyst IR-120 ($H^+$), filtered and purified using flash chromatography (DCM/MeOH/$H_2O$, 65:35: 0.5) to give the α-product 13 as an off-white solid (112 mg, 22%). The E1-anomer was confirmed using 1H-NMR.[3]

TLC (EtOAc:iPrOH:$H_2O$, 2:2:1 v/v): $R_F$=0.5; 1H-NMR (400 MHZ, $CD_3OD$) δ 3.90-3.80 (m, 3H), 3.74-3.54 (m, 6H), 3.49 (dd, J=9.1, 1.8 Hz, 1H), 2.83 (dd, J=12.3, 4.3 Hz, 1H), 2.41 (td, J=7.6, 2.6 Hz, 2H), 2.19 (d, J=2.7 Hz, 1H), 2.01 (s, 3H), 1.62-1.50 (m, 1H); $^{13}C$ {$^1H$}-NMR (101 MHz, $CD_3OD$) δ 175.55, 174.21, 101.91, 81.70, 74.40, 72.95, 70.39, 70.34, 69.48, 64.49, 63.75, 54.20, 42.71, 22.57, 20.77; HRMS (m/z): $[M+Na]^+$ calcd for $C_{15}H_{21}DNNaO_9$, 384.1254; found, 384.1279.

Synthesis of Sialic Acid Terminated Amphiphile (2)

4-(10-(4-(2-(2-(2-chloroethoxy)ethoxy)ethyl)phenoxy) decyloxy)benzonitrile (9) was synthesized based on a modified literature procedure.[5] Aqueous NaOH (50% w/w, 2.5 mL) was added to a stirred solution of nitrile 7 (200 mg, 0.51 mmols, 1 eq), tetrabutylammonium hydrogen sulfate (343 mg, 1.01 mmols, 2 eq) and 2-chloroethyl ether 8 (2.5 mL, 22 mmols, 43 eq) and left to stir at room temperature for 18 hrs. The resulting two-phase suspension was reconstituted in chloroform (15 mL) and washed with water (3×25 mL). The organic layer was dried over $MgSO_4$ and the excess solvent removed in vacuo at 40° C. Purification of the crude product using flash column chromatography (20 to 40% ethyl acetate in hexane) afforded the chloride 9 as an amorphous white solid (143 mg, 56%).

TLC (EtOAc:Hexane, 3:7 v/v): $R_F$=0.55; 1H-NMR (400 MHZ, $CDCl_3$) δ 7.57 (d, J=8.8 Hz, 2H), 7.12 (d, J=8.5 Hz, 2H), 6.93 (d, J=8.8 Hz, 2H), 6.81 (d, J=8.5 Hz, 2H), 3.95 (dt, J=27.4, 6.5 Hz, 4H), 3.73 (t, J=5.9 Hz, 2H), 3.70-3.54 (m, 8H), 2.84 (t, J=7.3 Hz, 2H), 1.92-1.70 (m, 4H), 1.38 (d, J=48.3 Hz, 12H); $^{13}C${$^1H$}-NMR (101 MHz, $CDCl_3$) δ 162.53, 157.68, 134.08, 130.75, 129.93, 119.52, 115.25, 114.42, 103.65, 72.75, 71.47, 70.73, 70.34, 68.48, 68.02, 42.87, 35.43, 29.59, 29.57, 29.49, 29.41, 29.07, 26.17, 26.03 LRMS (m/z): $[M+Na]^+$ calcd for 525.08, found 524.26, 526.26.

Amino(4-(10-(4-(2-(2-(2-chloroethoxy)ethoxy)ethyl) phenoxy)decyloxy)phenyl)methan iminium chloride (10) was synthesized based on a modified literature procedure.[2] HCl gas (150 ml of sulfuric acid to 135 g of NaCl) was bubbled into a stirred solution of 9 (1 g, 1.99 mmols, 1 eq) in MeOH, anhydrous (50 mL) cooled in a NaCl-ice bath. After the bubbling had ceased, the reaction was warmed to room temperature and left to stir for 24 hrs. The excess solvent was removed in vacuo and methanolic $NH_3$ (7 N, 50 mL) was added. The reaction mixture was further stirred at room temperature for 24 hrs. The resulting product was then concentrated and recrystallized in 1M HCl in EtOH to give the amidine 10 as an off-white amorphous solid (0.59 g, 53%).

1H-NMR (400 MHz, DMSO) δ 9.20 (s, 2H), 8.96 (s, 2H), 7.83 (d, J=8.7 Hz, 2H), 7.20-7.04 (m, 4H), 6.87-6.74 (m, 2H), 4.07 (t, J=6.5 Hz, 2H), 3.90 (t, J=6.5 Hz, 2H), 3.72-3.60 (m, 4H), 3.53 (tdd, J=5.8, 4.8, 2.4 Hz, 6H), 2.72 (t, J=7.0 Hz, 2H), 1.79-1.59 (m, 4H), 1.49-1.20 (m, 12H). $^{13}C$-NMR (101 MHZ, DMSO) δ 164.69, 163.06, 157.01, 130.65, 130.13, 129.71, 119.20, 114.72, 114.13, 71.53, 70.52, 69.61, 69.45, 68.07, 67.27, 43.56, 34.63, 28.91, 28.91, 28.73, 28.70, 28.43, 25.51, 25.38. LRMS (m/z): $[M]^+$ calcd for 520.12, found 519.62, 521.6165.

Amino(4-(10-(4-(2-(2-(2-azidoethoxy)ethoxy)ethyl)phe-noxy)decyloxy)phenyl)methan iminium azide (11) was synthesized based on a modified procedure.[6] Chloride 10 (248 mg, 0.48 mmols, 1.0 eq), sodium azide (124 mg, 1.91 mmols, 4.0 eq.) in DMF, anhydrous (4 mL) was stirred at 60° C., N2 for 24 hrs. The crude reaction mixture was then concentrated in vacuo, dissolved in chloroform and filtered. The filtrate was purified using flash chromatography (10% MeOH in DCM) to give the product as an off-white amorphous solid (127 mg, 47%). The product was acidified with 1M HCl in methanol before the next step.

TLC (MeOH:DCM, 1:9 v/v): $R_F$=0.43; 1H-NMR (400 MHZ, $CD_3OD$) δ 7.82-7.74 (m, 2H), 7.15-7.08 (m, 4H), 6.83-6.77 (m, 2H), 4.09 (t, J=6.4 Hz, 2H), 3.93 (t, J=6.4 Hz, 2H), 3.71-3.55 (m, 8H), 3.33 (d, J=5.2 Hz, 2H), 2.79 (t, J=7.0 Hz, 2H), 1.86-1.69 (m, 4H), 1.55-1.31 (m, 12H); $^{13}C${$^1H$}-NMR (101 MHZ, $CD_3OD$) δ 167.62, 165.49, 159.03, 132.23, 131.03, 130.85, 120.64, 116.20, 115.40, 73.57, 71.47, 71.37, 71.12, 69.66, 68.97, 51.77, 36.30, 30.58, 30.57, 30.44, 30.43, 30.38, 30.13, 27.15, 27.03; HRMS (m/z): $[M]^+$ calcd for $C_{29}H_{44}N_5O_4^+$, 526.3393, found 526.3395.

5-Acetylamino-2-[2-(1-{2-[2-(2-{4-[10-(4-carbamim-idoyl-phenoxy)-decyloxy]-phenyl}-ethoxy)-ethoxy]-ethyl}-1H-[1,2,3]triazol-4-yl)-ethoxy]-4-hydroxy-6-(1,2,3-trihy-droxy-propyl)-tetrahydro-pyran-2-carboxylic acid (2). Amidine azide precursor 11 (74 mg, 0.13 mmol, 1 eq), α-linked alkyne sialic acid 13 (47 mg, 0.13 mmol, 1 eq), sodium ascorbate (77 mg, 0.39 mmol, 3 eq) and copper (II) sulphate (19 mg mmol, 0.3 eq) in water/2-butanol (1:2, 1 mL) was sonicated and stirred at room temperature for 4 hrs. The reaction mixture was concentrated in vacuo and purified using C18 flash chromatography (35% AcCN, 0.1% TFA in $H_2O$). The purified fractions were then concentrated in vacuo at 30° C. and the residual water was lyophilized to give the TFA salt of sialic acid terminated amphiphile 2 as an amorphous white powder (69 mg, 60%).

HPLC (C-18 column, mobile phase: 10%-90% ACN in water (0-30 mins) 90% ACN in water (30-35 mins)): k=10.6 (see chromatogram in Supplementary section 1.12). 1H-NMR (400 MHZ, $CD_3OD$) δ 7.86 (s, 1H), 7.80-7.73 (m, 2H), 7.10 (dt, J=3.4, 2.2 Hz, 4H), 6.82-6.76 (m, 2H), 4.48 (t, J=5.1 Hz, 2H), 4.08 (t, J=6.4 Hz, 2H), 4.02 (s, 1H), 3.91 (t, J=6.4 Hz, 2H), 3.86-3.80 (m, 3H), 3.80-3.66 (m, 4H), 3.65-3.46 (m, 10H), 2.92 (d, J=6.0 Hz, 2H), 2.79-2.67 (m, 3H), 2.00 (s, 3H), 1.86-1.67 (m, 5H), 1.55-1.30 (m, 12H); $^{13}C${$^1H$}-NMR (101 MHZ, $CD_3OD$) δ 175.34, 167.65, 165.49, 159.02, 132.26, 131.03, 130.88, 120.69, 116.21, 115.42, 75.03, 73.46, 72.82, 71.44, 71.32, 70.40, 70.12, 69.65, 68.97, 68.72, 64.57, 63.99, 53.89, 51.38, 49.85, 49.71, 49.50, 49.28, 41.84, 36.29, 30.56, 30.54, 30.42, 30.36, 30.11, 27.31, 27.14, 27.02, 22.63; HRMS (m/z): [M]+ calcd for $C_{44}H_{67}N_6O_{13}$, 887.4766, found 887.4788.

Synthesis and Sialic Acid Tether (14) for Covalent Immobilization

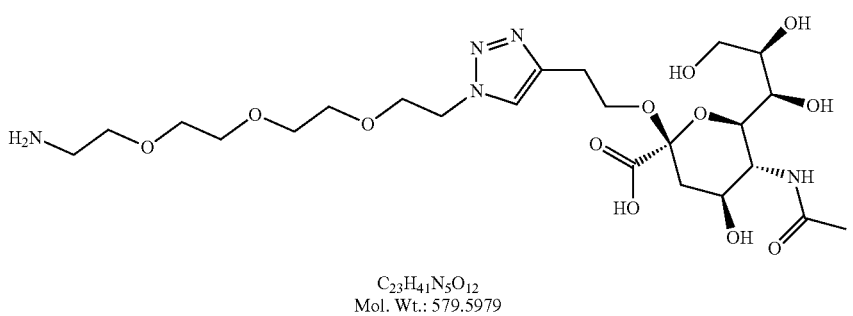

$C_{23}H_{41}N_5O_{12}$
Mol. Wt.: 579.5979

Alkyne sialic acid 13 (20 mg, 0.055 mmol, 1 eq) and 11-Azido-3,6,9-trioxaundecan-1-amine (11 μl, 0.055 mmol, 1 eq) were dissolved in butanol:water (2:1, 900 μl). Ascorbic acid (sodium salt) (1.1 mg, $5.5 \times 10^{-3}$ mmol, 0.1 eq) and Cu(II) sulphate hydrate (0.14 mg, $5.5 \times 10^{-4}$ mmol, 0.01 eq) predissolved in butanol:water (2:1, 100 μl) was added. The reaction mixture was stirred at 40° C. for 2 hrs. The crude mixture was then dried in vacuo at 40° C. and methanol (1 mL) was added. The MeOH mixture was left in the freezer for 1 hr and the resulting precipitate was centrifuged and the supernantant was collected and dried. The dried filtrate was redissolved in water and passed through a C18 column. The collected monolayer was dried in vacuo to give 14 as a light yellow solid (27 mg, 84%).

$^1$H NMR (400 MHZ, CD$_3$OD) δ 7.99 (s, J=16.3 Hz, 1H), 4.55 (t, J=5.1 Hz, 2H), 4.05 (dd, J=16.1, 6.7 Hz, 1H), 3.90 (t, J=5.1 Hz, 2H), 3.83 (dt, J=6.5, 2.5 Hz, 2H), 3.79-3.53 (m, 17H), 3.49 (dd, J=8.9, 1.6 Hz, 1H), 2.94 (t, J=6.5 Hz, 2H), 2.84 (dd, J=12.4, 4.1 Hz, 1H), 2.02 (s, J=7.7 Hz, 3H), 1.59 (t, J=11.6 Hz, 1H). $^{13}$C NMR (101 MHz, CD$_3$OD) δ 175.56, 124.85, 74.44, 73.14, 71.60, 71.56, 71.54, 71.48, 71.47, 71.39, 71.24, 71.08, 70.43, 70.36, 69.46, 64.67, 63.83, 54.24, 51.76, 51.26, 42.73, 27.50, 22.59. ESI-MS (M−H)$^−$: calculated 578.2679; found: 578.3762.

Kinetic Interaction Analysis

In situ ellipsometry, in analogy with surface plasmon resonance (SPR), allows real time monitoring of adsorption and desorption events at solid surfaces. The latter technique has been extensively used to analyse ligand-receptor association dissociation kinetics and for assessing binding constants.[7] We have here used the former technique for the same purpose.

Under pseudo first order conditions where the free target concentration is held constant in the cuvette, the binding can be described by Eq. 1:

$$d\Gamma/dt = k_a C(\Gamma_{max}-\Gamma) - k_d\Gamma \qquad (1)$$

where Γ=the measured adsorbed amount per unit area (mg/m$^2$), $\Gamma_{max}$=the maximum adsorbed amount per unit area, C is the injected concentration (M) of the virus or protein, $k_a$ is the association rate constant or on-rate (M$^{-1}$s$^{-1}$) and $k_d$ is the dissociation rate or off-rate (s$^{-1}$). The dissociation constant may be calculated according to equation 2 as:

$$K_d = k_d/k_a (M) \qquad (2)$$

Equation [1] may be rearranged as:

$$d\Gamma/dt = k_a C\Gamma_{max} - (k_a C + k_d)\Gamma \qquad (3)$$

thus plotting dΓ/dt against Γ for each cycle of association dissociation (Supplementary FIG. 12B) give rise to straight lines with slope $S=k_aC+k_d$. A plot of S against C will in turn be a straight line with slope $k_a$ (Supplementary FIG. 12C). The dissociation rate constant, $k_d$, was determined by the average of direct measurements of the dissociation from saturated binding sites into a buffer solution by nonlinear curve fitting to the dissociation rate equation (4) (Supplementary FIG. 12D-G).

$$d\Gamma/dt = k_d\Gamma_0 \qquad (4)$$

The result of the analysis is summarized in Supplementary Table 7.

Substrates. For ellipsometry, IRAS and contact angle, the gold surfaces were prepared by electron beam (e-beam) evaporation of gold (2000 Å thickness) onto precleaned glass slides (76×26×1 mm) containing adhesive layers (25 Å) of titanium. Prior to thiol adsorption, these gold surfaces were rinsed with ethanol, water and treated with plasma cleaner. Gold on mica for atomic force microscopy was purchased from Phasis and used without further processing. The MHA SAMs were prepared by immersing the cleaned or freshly prepared gold substrate in 1 mM 16-mercaptohexadecanoic acid (MHA) in ethanol (99.5%) for 12 hrs followed by rinsing with copious amount of ethanol and drying under a nitrogen stream.

The covalently anchored sialic acid monolayer the MHA functionalized slides were activated using 200 mM EDC and 50 mM NHS in water for 15 mins (see reference 8 of main manuscript). The slides were then rinsed thoroughly with water. The activated slides were then left in an aqueous solution of 14 (100 μM) at room temperature for 1.5 hrs. It was then rinsed again and the unreacted NHS-esters were then hydrolysed in 1 M NaOH solution for mins. The final slides were then rinsed thoroughly with water. Immobilization of 14 was 15 confirmed by contact angle, FTIR and ellipsometry. Ellipsometry suggested a surface coverage of 14 of 27%.

Scheme 1. Schematic view of a covalently anchored mixed SAM of 14 and MHA on gold.

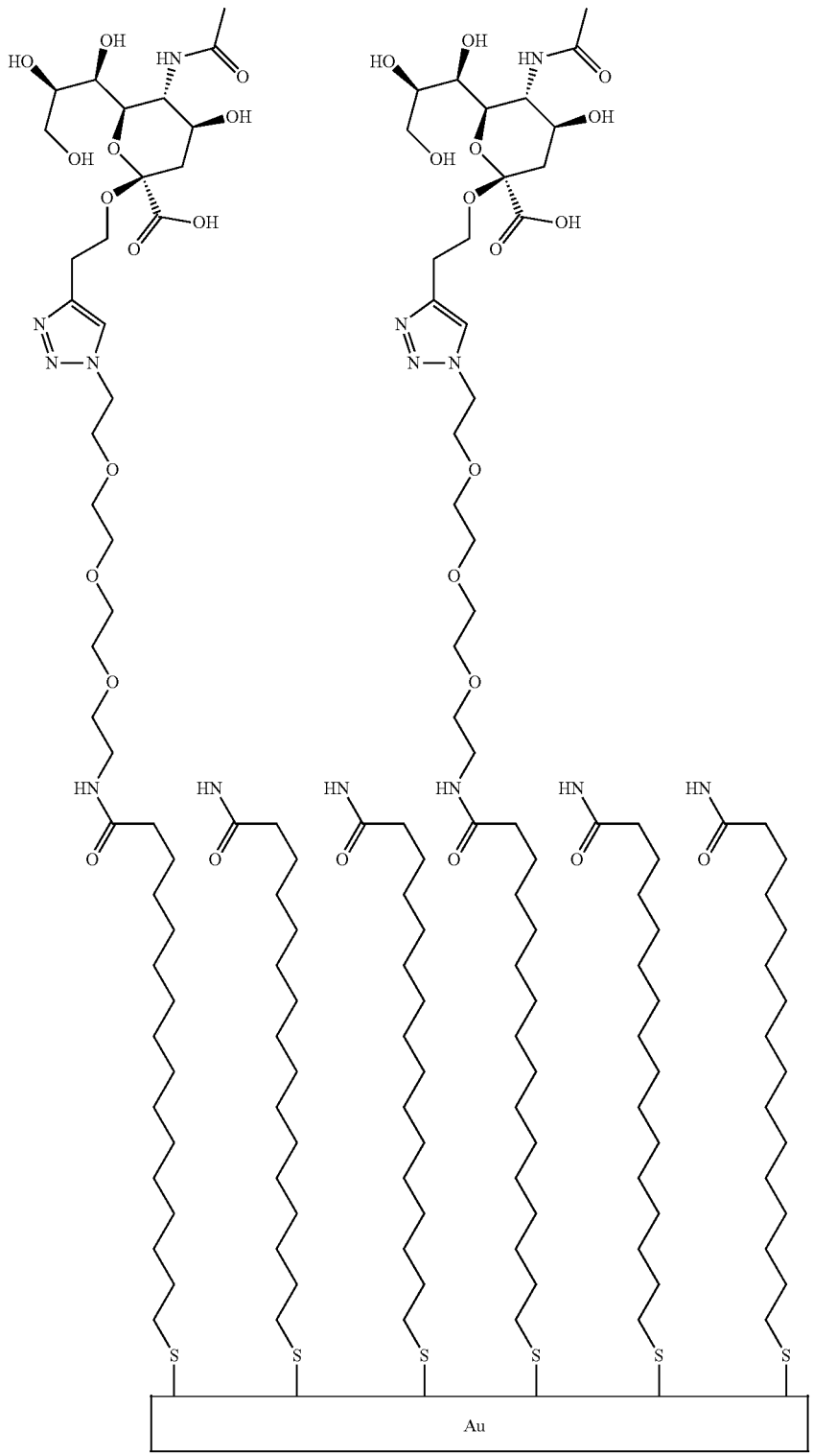

Infrared reflection-adsorption spectroscopy (IRAS). The measurements were made using a Nicolet 6400 instrument equipped with a liquid nitrogen-cooled MCT-A detector operating at a resolution of 4 cm$^{-1}$. Data was collected with a smart Saga accessory operating at an angle of incidence of 80°. The instrument was purged with nitrogen before and during measurements. Each spectrum is the sum of 512 scans on the modified surfaces using an unreacted, cleaned gold substrate as reference. Each spectrum was processed using OMINIC software and baselined corrected.

Atomic Force Microscopy. The surfaces were modified as described in the Methods section using freshly deposited gold on mica and dried under a stream of nitrogen prior to measurement unless stated otherwise. The surfaces were examined with a commercial Atomic Force Microscope (AFM) (MultiMode 8 SPM with a NanoScope V control unit, Bruker AXS) in air at room temperature in PeakForce Tapping® mode. Cantilevers with nominal spring constant 0.5819 N m$^{-1}$ were employed. Analysis and processing of AFM images were performed using the Gwyddion software. Each substrate was scanned at min. 2 points.

Contact Angle. A milli Q water droplet was formed at the end of the needle and lowered onto the surface. The needle was raised as soon as the water droplet touches the surface and the contact angle analysed using drop shape analysis was recorded immediately. Measurements were taken consecutively on different areas on the surface and averaged based on a minimum of 3 measurements.

Example 5. rSAMs as Air and Protein Exchange Stable Fluidic Lipid Bilayer Mimics Preparation of E0-6 or protein stock solutions. E0 was synthesized as previously reported. Synthesis of E2-6 are described in supporting information. 2.5 mM E0-E6 stock solutions were prepared in 3% ethanolic pH 9 borate or pH 8 HEPES buffer. Albumin from human serum (HSA) and lysozyme from chicken egg white (LYZ) were obtained from Sigma Aldrich. HSA or LYZ (50 mg/ml or 50 ug/mL) stock solutions were prepared in pH 8 HEPES buffer. All unused samples were stored at −20° C.

In situ ellipsometry. The adsorption process of the amphiphiles was monitored using in situ null ellipsometry. The instrument used was a Rudolph thin film ellipsometer (type 43603-200E, Rudolph Research, USA) using an angle of incidence of 68° and automated according to Cuypers et al. The light source was a xenon lamp, filtered to λ=442.9 nm. The thiol SAMs prepared as described in supporting information were immersed vertically into an ellipsometric quartz cuvette with ordinary microscopic cover glass windows containing 5 ml of buffer solution. The cuvette was thermostated to 25° C. and equipped with a magnetic stirrer at constant stirring rate of 350 rpm. Before each measurement, the refractive index of the MHA gold substrate was determined by a 4-zone surface calibration in buffer solution. After a stable baseline was obtained, 100 µL of stock solution containing E0-E6 (2.5 mM) were added to the curvette. Kinetics data was collected until equilibrium or for a maximum duration of 5000 s. The system was then rinsed with the respective buffer for a maximum of 1000 s (11 ml min$^{-1}$) in a continuous system. The surface was later allowed to stabilize till steady state or 5000 s (whichever came first). The surfaces were either dried under a nitrogen stream for IRAS measurement or reused after pH 1 HEPES buffer rinsing. The thickness of the rSAMs layer was calculated using a homogenous 3 layer model (MHA Au-rSAMs-buffer solution) with assumed refractive index of 1.45 and 1.34 for rSAMs and ambient respectively. The ellipsometric determined thickness of rSAMs using this model has been previously verified using neutron reflectivity. Average in situ ellipsometric thickness at equilibrium, $D_{ads}$ or after rinsing, $D_{rinse}$ are based on 30 data points at steady state.

Ex situ immobilization of E0-E6 on MHA gold surface. The gold surfaces modified using 0.02 mM MHA in 10% acetic acid ethanol solution as described above were fully immersed into an E0-6 (50 µM, pH 8 or 7.4 HEPES buffer) solution. After 18 hrs, the modified surfaces were taken out from the solution, rinsed with pH 8 or 7.4 HEPES buffer and dried under a stream of nitrogen before spectroscopic ellipsometer and/or IRAS measurement(s).

Adsorption of protein on E0-E6 layers. The E0-E6 modified rSAMs surface as described above were rehydrated in 2.5 mL pH 8 or 7.4 HEPES buffer for 1 hr. 50 µL of HSA or LYZ stock solution (50 mg/ml or 50 ug/mL) was then added and the solution was gently mixed. After 2 hrs, the slides were removed from solution, rinsed with pH 8 or 7.4 HEPES buffer and dried under nitrogen stream before spectroscopic ellipsometric and/or IRAS measurement(s).

Spectroscopic ellipsometry. Ex situ ellipsometric measurements were taken using UVISEL HORIBA spectroscopic ellipsometer covering a wavelength range of 200-820 nm, incidence angle of 70° at room temperature in air. Optical constants of substrates (MHA or E0-6 rSAMs) were determined before adsorption of the amphiphiles or proteins and each surface was sampled at random at 3-4 points. Relative rSAMs and protein thickness were modelled based on a homogenous 2-layer model (MHA-rSAM or rSAM-protein) using Cauchy layer, where extinction coefficient, k is 0 and an assumed refractive index, n of 1.45. To verify the accuracy of ellipsometric measurements, thickness of MHA on gold was determined. Experiment thickness of 19±1 Å corresponded well to literature values.[29]

IRAS. The measurements were made using a Nicolet 6400 instrument equipped with a liquid nitrogen-cooled MCT-A detector operating at a resolution of 4 cm$^{-1}$. Data was collected with a Smart SAGA™ accessory operating at an angle of incidence of 80°. The instrument was purged with nitrogen before and during measurements. Each spectrum is the sum of 512 scans on the modified surfaces using an unreacted, cleaned gold substrate as reference. Each spectrum was processed using OMINIC software and baseline corrected. Average tilt angles, θ were calculated on the basis of the relative intensity of the bands at 1611 and ~843 cm$^{-1}$ assigned to two perpendicular ring mode as previously reported.[20]

Statistical methods. Error bars are standard deviations describe the range between the values obtained unless stated otherwise. All values are averages of minimum two experiments on different substrates. Details of fitting are indicated in the supporting information. Molecular length of the compounds were estimated after minimizing the energy of the corresponding compound using a molecular mechanics calculations with MM2 force field (ChemDraw 3D, CambridgeSoft).

Reagents. All solvents were purchased from Acros Organics (Geel, Belgium) unless otherwise stated. Ethanol (99.5%) was obtained from CCS Health Care (Borlänge, Sweden). Boric acid, (4-(2-hydroxyethyl)-1-piperazineethanesulfonic acid (HEPES) and NaCl were obtained from VWR Chemicals (Leuven, Belgium). MgSO$_4$, anhydrous was purchased from JT Baker (Japan). 10-undecenyldimethylchlorosilane was purchased from Gelest. Deionized water was used for chemical reactions. Milli Q water was purified with a Thermo Scientific Barnstead NANOpure Diamond Water Purification Systems to give a minimum resistivity of 18.2 MΩ cm$^{-1}$. All other reagents were purchased from Sigma Aldrich (Sweden) or Merck (Sweden) and used as supplied unless otherwise stated. pH 8 and 7.4 HEPES buffers (0.01 M) were prepared from HEPES and pH 9 borate buffers (0.01 M) were prepared from boric acid.

Apparatus and methods. Thin layer chromatography (TLC) was carried out using Merck aluminium backed sheets coated with 60F254 silica gel. Visualization of the silica plates was achieved using a UV lamp (max=254 nm). Flash column chromatography was carried out using Sigma Aldrich silica gel (Merck grade 9385, 60 Å). The mobile phase used is as specified in the procedure (vide infra).

Proton and carbon nuclear magnetic resonance spectra were recorded using an Agilent (Varian) Mercury 400 MHz instrument operating at 400 or 101 MHz and evaluated using Mestre Nova software. Chemical shifts (δ) are reported in parts per million (ppm) with respect to tetramethylsilane (TMS) using the manufacturers indirect referencing method. All chemical shifts are quoted on the δ scale in ppm using residual solvent as the internal standard. (1H NMR: $CDCl_3$=7.26, $CD_3OD$=4.87; DMSO-$d_6$=2.50 and $^{13}C$ NMR: $CDCl_3$=77.0; $CD_3OD$=49.0; DMSO-$d_6$=39.5). Coupling constants (J) are reported in Hz with the following splitting abbreviations: s=singlet, d=doublet, t=triplet, q=quartet, quin=quintet, and m=mutiplet.

Low resolution mass spectra (LRMS) were conducted using a Waters ZQ2000 MS system with 2795 LC and 2996 PDA. High resolution mass spectra (HRMS) were collected on a LTQ Orbitrap XL (ThermoScientific, San Jose, CA), calibrated following instructions of the brand using a mixture of caffeine, methionine-arginine-phenylalanine-alanine-acetate (MRFA), and Ultramark 1621 in a solution of acetonitrile, methanol and acetic acid. Nominal and exact m/z values are reported in Daltons.

FTIR (ATR) spectra were recorded on a Nicolet 6700 instrument with a SmartITR accessory using 16 scans, a standard KBr beamsplitter, a spectral range of 5000-400 $cm^{-1}$, and a resolution of 4 $cm^{-1}$. All spectra were processed and analysed using the OMNIC 8 software.

Synthesis and Characterization of ω-(Ethylene Glycol)$_{0-6}$-α-(4-Amidinophenoxy)Decanes, E2-6.

4-[10-(4-{2-[2-(2-Hydroxy-ethoxy)-ethoxy]-ethyl}-phenoxy)-decyloxy]-benzamidine E2 to 40% ethyl acetate in hexane) afforded 3 as a white amorphous solid (710 mg, 41%).

STEP II Chloride 3 (700 mg, 1.03 mmol, 1.0 eq) and sodium iodide (1000 mg) in acetone (10 mL) was stirred at reflux for 48 hours. The resulting solution was filtered and the filtrate was concentrated in vacuo. The crude product was reconstituted with ethyl acetate and washed with brine. The organic layer was collected and dried over $MgSO_4$ to give product 4A (755 mg, 95%) that was used in the next step without further purification.

4A (755 mg, 0.98 mmol, 1.0 eq) was stirred with $AgNO_3$ (200 mg, 1.17 mmol, 1.2 eq) in acetone (2 mL) and water (1 mL) for 18 hrs. The resulting reaction mixture was concentrated, reconstituted in ethyl acetate and washed with brine. The organic layer was then concentrated in vacuo to give the crude product (610 mg) as a mixture of nitric ether and alkanol (5:1). Acetic acid (2 ml) and Zn powder (1 g) were then added at 0° C. and the resulting suspension was stirred at room temperature for 2 hrs. The reaction mixture was reconstituted in DCM and washed with water. The organic layer was then concentrated in vacuo and purified using silica gel (10% methanol in dichloromethane) to afford the desired product 4B as white semi-solid (530 mg, 82%).

STEP III HCl gas was bubbled into a stirred solution 4B (520 mg, 1.1 mmol) in anhydrous 1,4 dioxane, dry (2 mL) and anhydrous methanol (0.5 mL) at 0° C. under $N_2$ atmosphere. After 72 hrs, the intermediate was concentrated in vacuo at 40° C. and precipitated using anhydrous diethyl ether in the freezer overnight. The resulting imide ester white precipitate was collected via filtration under $N_2$ atmosphere and dried in vacuo. The imide ester intermediate was reacted with 7N methanolic ammonia (50 mL) at 20° C. for 16 hours. The crude product was then concentrated in vacuo at 40° C. and purified using silica gel (5 to 10% MeOH in DCM) to afford the desired product E2 as a white amorphous solid (220 mg, 63%). 1H NMR (400 MHz, dmso) δ 9.20 (s,

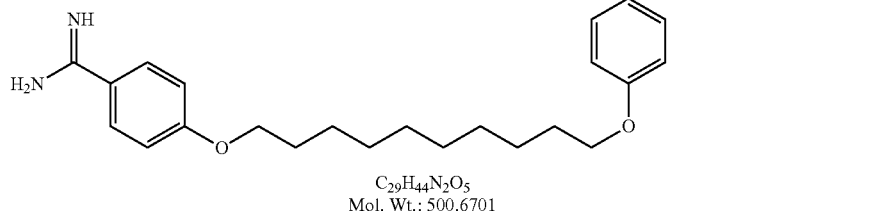

E2
$C_{29}H_{44}N_2O_5$
Mol. Wt.: 500.6701

STEP I1 was synthesized as previously reported.[1] Aqueous NaOH (50% w/w, 2.5 mL) was added to a stirred solution of 1 (1000 mg, 2.6 mmol, 1.0 eq), tetrabutylammonium hydrogen sulfate (1715 mg, 5.1 mmol, 2.0 eq) and 1-chloro-2-(2-chloro-ethoxy)-ethane 2 (16 g, 51 mmol, 20 eq) and left to stir at room temperature for 18 hrs. The resulting 2 phase suspension was reconstituted in chloroform and washed with water 3 times. The organic layer was dried over $MgSO_4$ and the excess solvent was removed in vacuo. Purification of the crude product using silica gel (20

2H), 8.97 (s, 2H), 7.83 (d, J=8.9 Hz, 2H), 7.17-7.09 (m, 4H), 6.81 (d, J=8.6 Hz, 2H), 4.07 (t, J=6.5 Hz, 2H), 3.90 (t, J=6.5 Hz, 2H), 3.63-3.35 (m, 10H), 2.72 (t, J=7.1 Hz, 2H), 1.81-1.60 (m, 4H), 1.52-1.20 (m, 12H). $^{13}C$ NMR (101 MHZ, dmso) δ 164.66, 163.08, 157.02, 130.64, 130.14, 129.71, 119.23, 114.74, 114.15, 72.33, 71.55, 69.72, 69.49, 68.08, 67.28, 60.20, 34.64, 28.91, 28.74, 28.71, 28.69, 28.43, 25.52, 25.38. LRMS (m/z): $[M+H]^+$ calcd for 501.33, found 501.69. HRMS (m/z): $[M+H]^+$ calcd for 501.33, found 501.33.

4-(10-{4-[2-(2-{2-[2-(2-Hydroxy-ethoxy)-ethoxy]-ethoxy}-ethoxy)-ethyl]-phenoxy}-decyloxy)-benzamidine E4

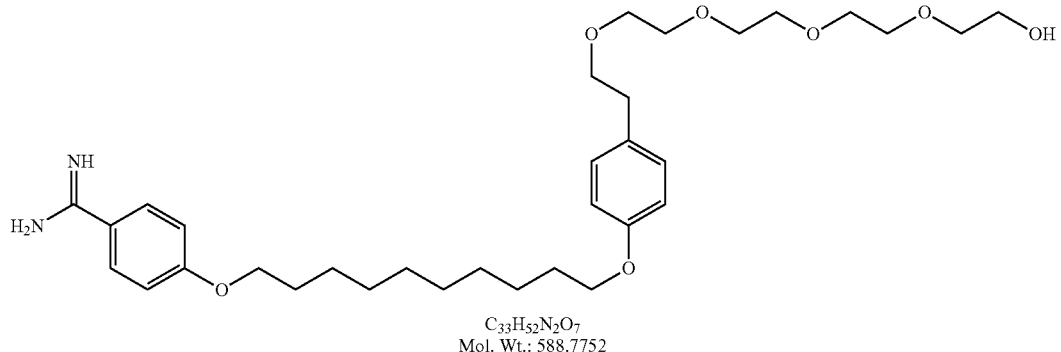 [SMILES: N=C(N)c1ccc(OCCCCCCCCCCOc2ccc(CCOCCOCCOCCOCCO)cc2)cc1]

C$_{33}$H$_{52}$N$_2$O$_7$
Mol. Wt.: 588.7752

E4 was synthesized based on the above general procedure using 1-chloro-2-{2-[2-(2-chloro-ethoxy)-ethoxy]-ethoxy}-ethane 2 with n=3. $^1$H NMR (400 MHZ, dmso) δ 9.20 (s, 2H), 8.96 (s, 2H), 7.83 (d, J=8.9 Hz, 2H), 7.13 (t, J=8.6 Hz, 4H), 6.81 (d, J=8.6 Hz, 2H), 4.58 (t, J=5.4 Hz, 1H), 4.07 (t, J=6.5 Hz, 2H), 3.90 (t, J=6.5 Hz, 2H), 3.59-3.37 (m, 18H), 2.72 (t, J=7.1 Hz, 2H), 1.83-1.60 (m, 4H), 1.52-1.25 (m, 12H). $^{13}$C NMR (101 MHz, dmso) δ 164.65, 163.07, 157.01, 130.65, 130.14, 129.70, 119.23, 114.73, 114.14, 72.32, 71.53, 69.78, 69.75, 69.73, 69.47, 68.08, 67.28, 60.18, 34.63, 28.91, 28.74, 28.70, 28.69, 28.43, 25.52, 25.38. LRMS (m/z): [M+H]$^+$ calcd for 589.34, found 589.67. HRMS (m/z): [M+H]$^+$ calcd for 589.34, found 589.38.

4-{10-[4-(2-{2-[2-(2-{2-[2-(2-Hydroxy-ethoxy)-ethoxy]-ethoxy}-ethoxy)-ethoxy]-ethoxy}-ethyl)-phenoxy]-decyloxy}-benzamidine E6

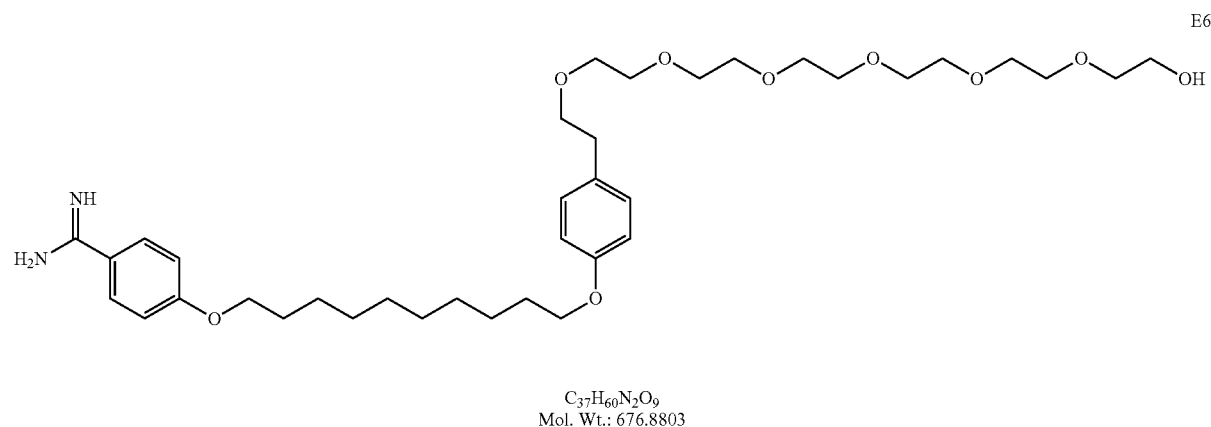 [SMILES: N=C(N)c1ccc(OCCCCCCCCCCOc2ccc(CCOCCOCCOCCOCCOCCOCCO)cc2)cc1]

C$_{37}$H$_{60}$N$_2$O$_9$
Mol. Wt.: 676.8803

E6 was synthesized based on the above general procedure using 1-Chloro-2-[2-(2-{2-[2-(2-chloro-ethoxy)-ethoxy]-ethoxy}-ethoxy)-ethoxy]-ethane 2 with n=5. $^1$H NMR (400 MHZ, dmso) δ 9.15 (s, 2H), 8.81 (s, 2H), 7.81 (d, J=8.9 Hz, 2H), 7.19-7.08 (m, 4H), 6.81 (d, J=8.6 Hz, 2H), 4.57 (t, J=5.3 Hz, 1H), 4.07 (t, J=6.5 Hz, 2H), 3.90 (t, J=6.5 Hz, 2H), 3.58-3.39 (m, 26H), 2.72 (t, J=7.1 Hz, 2H), 1.79-1.62 (m, 4H), 1.46-1.27 (m, 12H). $^{13}$C NMR (101 MHz, dmso) δ 164.57, 163.08, 157.01, 130.65, 130.16, 129.70, 119.26, 114.74, 114.13, 72.32, 71.54, 69.79, 69.77, 69.75, 69.47, 68.09, 67.28, 60.18, 52.76, 34.63, 28.91, 28.91, 28.74, 28.70, 28.69, 28.43, 25.52, 25.38. LRMS (m/z): [M+H]$^+$ calcd for 677.44, found 677.69. HRMS (m/z): [M+H]$^+$ calcd for 677.44, found 677.43.

Fluorescein (FAM) Tagged Amidine 7

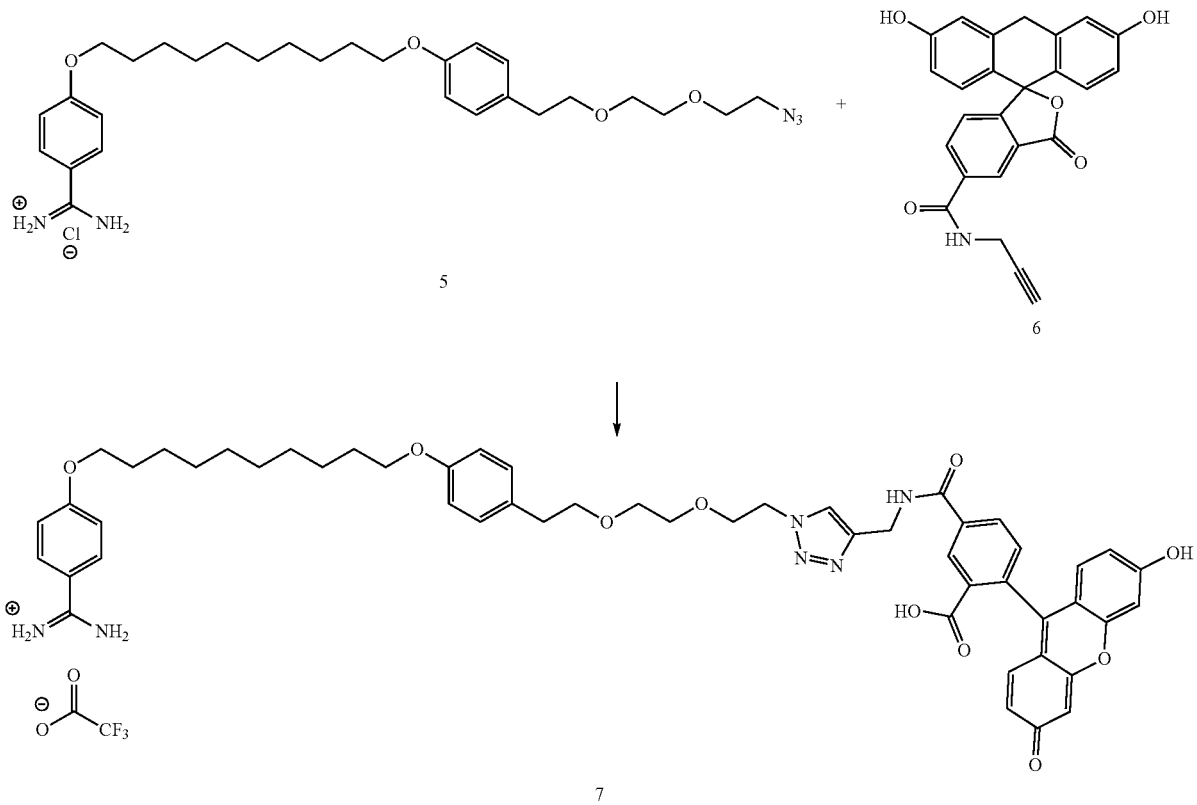

Amidine azide 5 was synthesized as previously reported.[1] FAM-alkyne 6 (1 mg, 2.42 μmol) was dissolved in minimal amount of DMF and concentrated in vacuo. The resulting waxy residue and amidine azide 5 (1.4 mg, 2.42 μmol) were dissolved in 2-butanol (800 μL). 75 μl of 61 mM aqueous sodium ascorbate and 400 μL of 60 mM aqueous copper sulphate were then added and the resulting 2 phase suspension was stirred at 40° C. After 1 hr, an additional 25 μL of 61 mM aqueous sodium ascorbate and 133 μl of 60 mM aqueous copper sulphate were added. After the reaction was deemed completed by HPLC, the reaction mixture was concentrated in vacuo and purified using C18 column (50-100% AcCN, 0.1% TFA in H$_2$O). The purified fractions were concentrated in vacuo and the residual water was lyophilized to give the TFA salt of FAM tagged amidine 7 as an amorphous yellow solid (2.2 mg, 86%). The purity and identity of the compound was confirmed via HPLC and ESI-MS respectively. HPLC (C-18 column, mobile phase: 10%-90%, 0.1% TFA in H$_2$O (0-15 mins): k=21.0 (see chromatogram in supporting section). LRMS (m/z): [M+H]$^+$ calcd for 939.43, found 939.77.

Preparation and Characterization of Surfaces

Preparation of COOH functionalized gold substrates. For ellipsometry, IRAS and contact angle, the gold surfaces were prepared by electron beam (e-beam) evaporation of gold (2000 Å thickness) onto precleaned glass slides (76× 26×1 mm) containing adhesive layers (25 Å) of titanium. Prior to thiol adsorption, these gold surfaces were cut with a diamond cutter, rinsed with ethanol and water, dried under a stream of nitrogen and treated with plasma cleaner. Gold on mica for AFM were purchased from Phasis and used without further processing. The 16-mercaptohexadecanoic acid (MHA) SAMs were prepared by immersing the cleaned or freshly prepared gold substrates in 1 mM MHA in ethanol or 0.02 mM MHA in 10% acetic acid ethanol solution for a minimum of 12 hrs followed by rinsing with copious amount of ethanol and drying under a nitrogen stream.

Preparation of COOH functionalized quartz substrates. COOH terminated quartz surfaces were prepared following modified procedure as reported by Faucheux et al.[2] Quartz slides were cleaned in freshly prepared piranha solution (Piranha solution: 1:3 H$_2$O$_2$ (30%)/H$_2$SO$_4$ (conc.) reacts violently with organic materials and should not be stored) for 30 mins at room temperature, rinsed with copious amount of milli-Q water and ethanol and dried with N2. The cleaned slides were immersed immediately into 1% (v/v) solution of 10-undecenyldimethylchlorosilane in ethanol overnight at room temperature. After 18 hours, the surfaces were rinsed with ethanol, milli-Q water and dried with N2. COOH group were generated by modifying the vinyl end group by oxidation with permanganate-periodate (0.5 mM KMnO$_4$, 19.5 mM NaIO$_4$, 1.8 mM K$_2$CO$_3$ pH 7.7) for 48 hours with gentle stirring. The materials were rinsed with 0.3 M NaHSO$_3$ solution, 0.1 M HCl solution, water and ethanol and dried with N2. Static contact angles obtained of vinyl terminated (77±2°) and COOH terminated (44+6°) surfaces corresponded to literature values.

Atomic Force Microscopy Measurements. The surfaces were modified as described in experimental above using freshly deposited gold on mica and dried under a stream of nitrogen prior to measurement unless stated otherwise. The surfaces were examined with a commercial Atomic Force Microscope (AFM) (MultiMode 8 SPM with a NanoScope V control unit, Bruker AXS) in air at room temperature in PeakForce Tapping® mode. Cantilevers with nominal spring constant 0.5819 N m$^{-1}$ were employed. Analysis and processing of AFM images were performed using the WSxN 5.0 Develop 8.2.[3] Each substrate was scanned at min. 3 points.

Fluoresence recovery after photobleaching (FRAP). The COOH terminated quartz slide was then incubated in 1 mol % FAM tagged amphiphile 7 in E2 (50 µM, pH 8 buffer) for 18 hrs. The modified slides were then rinsed with pH 8 buffer, dried under a nitrogen stream and rehydrated in pH 8 buffer prior to measurements. FRAP measurements were performed with a Nikon Eclipse Ti-E inverted microscope with a photoactivation unit. The sample was bleached for 30 s using a multiwavelength 40 mW argon ion laser using the 488 nm emission. Epifluorescence images were acquired using an Intensilight (Hg) lamp (Nikon) and filters for excitation/emission at 480/535 nm. Monochrome images were recorded at 30 s intervals with an Andor DU-897 camera at either 256 or 512 px resolution. The thicknesses of the quartz substrate did not allow greater than 20× magnification objectives to be used, resulting in a large illuminated area (radius 76 µm), and ensuing long bleaching times. Collected images were normalized to the background fluorescence, and Gaussian functions fitted to the intensities across the bleached areas. Peak intensities after bleaching were plotted versus acquisition time and fitted to recovery functions of the form.

$$f(t)=A_0+A(1-e^{-t\tau})$$

The equilibration half-time, $\Gamma_{1/2}$ is obtained as $\Gamma_{1/2}=-\ln 0.5/\tau$, and the diffusion coefficient, D (for bleaching via a Gaussian beam) is calculated from Axelrod et al., where w is the bleached radius.[4]

$$D = 0.88\left(\frac{w^2}{4\tau_{1/2}}\right)$$

Example 6. rSAMs on Glass and Quartz

Materials: Piranha 3:1—concentrated $H_2SO_4$+30% $H_2O_2$ solution (obtained from Sigma Aldrich); 10-undecenyldimethylchlorosilane (obtained from Gelest); Ethanol (99.5%); $KMnO_4$ (old bottle, dark purple powders); $NaIO_4$ (white powders, purity 99.8%, Merck); $K_2CO_3$ (white powders); 39% $NaHSO_3$ solution in water (obtained from Sigma Aldrich); 0.1M HCl (made by diluting 1M HCl solution).
Sample Preparation:
1) Slides were placed in Piranha solution for 24 h (or longer). Slides were taken out of Piranha solution, washed with Milli-Q water and ethanol (3 times each side), EtOH being the last rinse, dried with $N_2$.
2) 1% (v/v) 10-undecenyldimethylchlorosilane was prepared using 10 ml ethanol, absolute+100 µl silane for 10 slides in 10 mL container. Slides were placed in glass tubes (each slide in separate tube) and 1 ml of 1% silane solution was filled on the slides.
3) Reaction was carried out over the night (~18h).
4) After that time slides were rinsed with Milli-Q water and ethanol (3 times each side), dried with $N_2$. Contact angle of two slides was measured:3 spots were measured on each slide (contact angle 70-80°).
5) 0.5 mM $KMnO_4$, 19.5 mM $NaIO_4$, 1.8 mM $K_2CO_3$ pH 7.5 solution was prepared in 100 ml flat-bottom flask by adding 7 mg $KMnO_4$, 0.417 g $NaIO_4$, 24.5 mg $K_2CO_3$ and diluting it to 100 ml with Milli-Q water. pH was corrected to 7.5 by adding 1 drop of 10 M NaOH solution.
6) Slides were placed in 250 ml round bottom flask (5 slides in one flask), 50 ml permanganate solution was filled in. The reaction was carried out 48 h with gentle magnetic stirring (over head).
7) After that time the slides were rinsed with 39% $NaHSO_3$ solution, 0,1M HCl solution, Milli-Q water and ethanol (by this order), dried with nitrogen flow. Contact angle of two slides was measured:3 spots were measured on each slide (contact angle 40-60°).

Example 7. A Dynamic Platform for Building Close Packed Protein Multilayers and Ultrasensitive Biosensors Chemicals. Biotinylated prostate specific antigen antibody (ABIN 192197) and prostate specific antigen (ABIN572980) were purchased from Antikoerper-online.de. Di-tert-butyl dicarbonate (Boc$_2$O), D(+)-Biotin, anhydrous acetonee, $K_2CO_3$, trifluoracetic acid, tetrahydrofuran, were obtained from Merck (Darmstadt, Germany). Ethanol was purchased from J. T. Baker (Griesheim, Germany). Dichloromethane, sodium sulfate, sodium hydroxide, ethyl acetate and, HEPES dry powder were purchased from Applichem (Münster, Germany). All other reagents were purchased from Sigma Aldrich (Steinheim, Germany) and used as supplied unless otherwise stated.

Apparatus. Proton and carbon nuclear magnetic resonance spectra were recorded using a Bruker Advance DRX spectrometer 400 MHz instrument operating at 400 or 101 MHz and evaluated using Mestre Nova software. Chemical shifts (δ) are reported in parts per million (ppm) with respect to tetramethylsilane (TMS) using the manufacturers indirect referencing method. All chemical shifts are quoted on the δ scale in ppm using residual solvent as the internal standard. (1H NMR: CDCl$_3$=7.26, CD$_3$OD=4.87; DMSO-d$_6$=2.50 and $^{13}$C NMR: CDCl$_3$=77.0; CD$_3$OD=49.0; DMSO-d$_6$=39.5). Coupling constants (J) are reported in Hz with the following splitting abbreviations: s=singlet, d=doublet, t=triplet, q=quartet, quin=quintet, and m=mutiplet.

MALDI TOF MS, was performed using a MALDI reflector time-of-flight mass spectrometer (Autoflex II massspectrometer, Brucker-Daltonics GmbH, Bremen, Germany.) Nominal and exact m/z values are reported in Daltons. Thin layer chromatography (TLC) was carried out using Merck aluminium backed sheets coated with 60F254 silica gel. Visualization of the silica plates was achieved using a UV lamp (max=254 nm).

FTIR (ATR) spectra were recorded on a Nexus instrument with a Smart ITR accessory using 32 scans, a standard KBr beam splitter, a spectral range of 5000-400 and a resolution of 4 cm$^{-1}$. All spectra were processed and analysed using the OMNIC 8 software.

Hydroxy-terminated amphiphile (1). OH-terminated amphiphile 1 (4-10-[4-(2-hydroxyethyl)phenoxy]decoxybenzamidine hydrochloride) was prepared as reported elsewhere in three steps by sequential Williamson ether synthesis followed by Pinner conversion in an overall yield of 69%.

[(4-{10-[4-(2-Hydroxy-ethyl)-phenoxy]-decyloxy}-phenyl)-imino-methyl]-carbamic acid tert-butyl ester (3). Hydroxy-terminated amphiphile 1 (0.051 g, 0.11 mmol) was dissolved in a mixture of deionized water (20 mL), 2 mL NaOH (3N) and THF (22 mL). The solution was cooled to 0° C. and boc anhydride ($Boc_2O$) (0.25 g, 1.1 mmol) was added drop wise followed by stirring of the solution for 3 hours. The reaction mixture was then concentrated in vacuo and extracted with EtOAc and $H_2O$. The organic phase was dried with sodium sulfate and concentrated in vacuo to yield the product as a yellowish solid (0.039 g, 67%). The product was used without further purification.

$^1$H NMR (400 MHZ, DMSO-d6) δ 7.84 (dd, J=44.5, 8.5 Hz, 1H), 7.68 (d, J=8.5 Hz, 2H), 7.05 (d, J=8.5 Hz, 2H), 6.92 (d, J=8.4 Hz, 2H), 6.76 (d, J=8.5 Hz, 2H), 3.96 (t, J=6.40 Hz, 2H), 3.86 (t, J=6.40 Hz, 2H), 3.51-4.47 (m, 3H), 2.61-2.47 (m, 2H), 2.49 (m, 4H), 1.70-1.33 (m, 9H), 1.33-1.13 (m, 12H). $^{13}$C NMR (101 MHz, Chloroform-d) δ 162.37, 157.70, 130.03, 129.81, 128.97, 114.50, 114.25, 68.10, 67.87, 63.72, 38.15, 29.32, 29.18, 28.97, 28.10, 25.91, 25.83. HR-ESI-MS: calc $C_{30}H_{44}N_2O_5$ $[M+H]^+$ m/z 513.3323 found 513.3330.

5-(2-Oxo-hexahydro-thieno[3,4-d]imidazol-6-yl)-pentanoic acid 2-{4-[10-(4-carbamimidoyl-phenoxy)-decyloxy]-phenyl}-ethyl ester·trifluoroacetate (2)

To a stirred solution of protected benzamidine 3 (0.40 g, 0.78 mmol) in anhydrous acetone (10 mL) and toluene (10 mL), biotin chloride (0.23 g, 0.86 mmol) and $K_2CO_3$ (0.70 g, 5.1 mmol) in anhydrous acetone (5 mL) was added under $N_2$ atmosphere. The resulting reaction mixture was then left to stir at 50° C. After 12 hrs, the K2CO3 was filtered off and the organic layer was concentrated in vacuo to afford the crude product (0.21 g, 52%). This crude material was immediately reconstituted in anhydrous DCM (10 mL) and cooled to 0° C. TFA (3 mL) was then added drop wise to the solution to give a light orange solution, which was stirred at room temperature for 2 hrs. The resulting reaction mixture was then concentrated in vacuo, recrystallized in ethanol (20 mL) to afford the product 2 as a light yellow solid (60 mg, 35%).

$^1$H NMR (400 MHZ, DMSO-d6) δ 9.08 (s, 2H), 8.68 (s, 2H), 7.76 (d, J=8.8 Hz, 2H), 7.20-7.04 (m, 4H), 6.80 (d, J=8.5 Hz, 2H), 6.41 (s, 1h), 6.33 (s, 1H), 4.26 (t, 8.0 Hz, 1H), 4.10-4.01 (m, 4H), 3.87 (t, 8.0 Hz, 2H), 3.39 (d, J=13.8 Hz, 2H), 2.77-2.74 (m, 4H), 2.16 (t, J=8.0 Hz, 2H), 1.71-1.62 (m, 6H), 1.44-1.14 (m, 14H). (FAB/LR) Exact Mass: 638.35 Found: 638.33. HR-ESI-MS: calc $C_{35}H_{51}N_4O_5S$ $[M+H]^+$ m/z 639.869, found 639.3580.

Preparation of gold substrates. Glass slides (1.4×1.8 cm$^2$) were cleaned by sonication in a 2% Hellmanex solution for 15 min, following an additional sonication step for 15 minutes in absolute ethanol. The slides were rinsed 10 times with Milli-Q water prior to each treatment and finally dried under nitrogen flow. Chromium (20 nm) was deposited by plasma sputtering at a pressure of 0.133 Pa followed by gold (99.99%) (200 nm thickness). For further sample processing, all slides were immersed in thiol solution as described below.

Preparation of self assembled monolayers of mercaptohexadecanoic acid (MHA). Gold slides prepared as described above were immersed in freshly prepared piranha solution (Caution: "Piranha" solution: 1:3 $H_2O_2$ (30%)/concentrated $H_2SO_4$ 1:3 reacts violently with organic materials and should not be stored) for 1 min, washed with copious amounts of Milli-Q water, and dried under nitrogen flow. Subsequently, the gold slides were immersed in a 0.02 mM MHA in absolute ethanol for ≥18h. The slides were removed from the thiol solution, rinsed with ethanol and then dried under a nitrogen flow.

In situ Ellipsometry. The thiol SAMs were prepared as described above and stored dry prior to use. All surfaces were washed consecutively in ethanol, water, 0.1M HCl, 0.1M NaOH, and water. They were then immersed in a teflon-coated fluid cell containing sodium borate buffer (2 mL, 0.01M, pH 9, prepared from boric acid) thermostated to 25° C. The cell was equipped with a small magnetic stirrer and a pH electrode. Prior to the addition of the amphiphiles or proteins, the starting ellipsometric angles were recorded by in-situ ellipsometry (ELX-1 Precisionellipsometer (DRE-Ellipsometerbau, Ratzeburg, DE, angle of incidence: 70°, HeNe laser: wavelength=632.8 nm) as the average of 30 data points. The adsorption of compounds was then monitored until stable angle values were obtained. A homogenous 3-layer model was used to determine the average thickness, d and adsorbed amount, Γ from the ellipsometric data according to (Equation 1).

$$\Gamma = d_A \frac{n - n_0}{dn/dc} \tag{1}$$

where $d_A$ is the thickness of the adsorbed layer, n is the refractive index of the molecules, and $n_0$ is the refractive index of the ambient and dn/dc is the refractive index increment for the molecules in the layer. The thickness of the rSAMs was calculated using a homogenous 3 layer model (MHA Au-rSAM-buffer solution) with assumed refractive index of 1.45 and 1.33 for rSAMs and ambient respectively. Relative adsorbed protein thickness was calculated based on a homogenous 3-layer model (rSAMs-protein-buffer solution) with refractive index of 1.45 for protein. It assumed that minimum penetration or exchange occurred between the interface and analyte during the adsorption process. A refractive index increment, dn/dc of 0.19 mg ml$^{-1}$ was used to determine the adsorbed amount of protein.

Adsorption of amphiphiles 1 and 2. The OH— or biotin-terminated amiphiphiles (1 and 2) or mixtures of 1 and 2 were added to make up a final concentration of 50 μM, if not otherwise indicated. After addition of the amidine amphiphiles, the adsorption process was allowed to proceed for up to 5 h. After adsorption, the surfaces were rinsed with pH 9 buffer by allowing≈10 cell volumes of fresh buffer to pass the cell by simultaneous filling and emptying of the cell. This was followed by continued measurements in pH 9 buffer, unless otherwise stated. After rinsing, the ellipsometric angles were then calculated as averages of 30 data points and the film thickness (d) was calculated from the ellipsometric angles as outlined above.

Consecutive adsorption of streptavidine and biotinylated antibodies. Prior to streptavidine addition, the mixed rSAM modified surfaces were rinsed with pH 8 buffer (0.01M borate) as described above. Thereafter 0.5 ml of a streptavidine stock solution (12.5 μM in 0.01 M borate buffer pH 8) was added to the cuvette and borate buffer added (0.75 mL) to make up a final protein concentration of 5 μM. The adsorption process was allowed to proceed for at least 30 min or until stable ellipsometric angles were obtained. After adsorption, the surfaces were rinsed with pH 8 buffer by allowing ~10 cell volumes of fresh buffer to pass the cell by simultaneous filling and emptying of the cell. The addition of biotinylated antibodies was performed in an identical manner.

Sensing of the proteins HSA and PSA using the multi-layered rSAM-SA-antibody sensor Prior to protein addition, the antibody modified surfaces were rinsed with pH 8 buffer (0.01M borate) as described above. Protein solutions (1.25 mL) of different concentrations (40 fM to 5 µM in 0.01 M borate buffer, pH 8) were added to the cuvette and the adsorption process monitored for at least 30 min or until stable ellipsometric angles were obtained. After adsorption, the surfaces were rinsed with pH 8 buffer as above.

To test the detection of PSA in dilute serum, rSAM-SA-antiPSA multilayered sensors were first prepared as described and rinsed in pH 8 HEPES buffer (10 mM). To prepare the serum samples, AB type human serum from male (Sigma Aldrich, Germany) was filtered through a 0.45 µm syringe filter, diluted with pH 8 HEPES buffer (0.01 M) 200 times and then spiked with PSA to different concentrations (100 fM-10 nM). These solutions were then added to the sensor and the adsorption process monitored for at least 30 min or until stable ellipsometric angles were obtained. After adsorption, the surfaces were rinsed with pH 8 buffer and thereafter restored by adjusting the pH to 2-3 with 0.1M HCl, for subsequent reuse.

Contact angle. An OCA 15 from Data-Physics was used to measure the contact angle. Analyses of adsorbed layers were carried out using a 2 cm×2 cm gold-coated glass substrate. A milli Q water droplet (?≥18 M?cm) was formed at the end of the needle and lowered onto the surface. The needle was raised as soon as the water droplet touches the surface and the contact angle analysed using drop shape analysis was recorded immediately.

Atomic Force Microscopy. Atomic force microscopy was carried out with a Nanoscope IIIa equipped with a 10 µm scanner from Veeco Instruments. The samples were examined with standard cantilevers equipped with a tip with 10 nm radius. The AFM samples were prepared in a similar way as described above for ellipsometry, but from MICA-substrates covered by electron sputtered gold (200 nm). MICA was obtained from "Ssenes", Netherlands. Each substrate was scanned at minimum 2 points.

Infrared reflection absorption spectroscopy (IRAS). The spectra were recorded on a Nicolet 5DXC-FTIR spectrometer equipped with a SpectraTech FT-80 grazing-angle setup at 80° angle of incidence in p polarization, a MCT-A detector cooled with liquid nitrogen, and a sample compartment purged with CO2 and moisture-free air. The monolayer spectra were recorded at 4 cm$^{-1}$ resolution in the external reflection mode accumulating 100 scans.

Example 8. Use of rSAMs with Tunable Surface Dynamics for Modulation of Cell Adhesion Behaviour Amphiphiles design and synthesis. Optimization of RGD-decorated surfaces for cell adhesion demands attention to parameters such as peptide sequence, length of the filler molecule, surface density of the ligands and lateral dynamics. For instance, increasing ethylene glycol repeating units in the filler molecule decreases cell adhesion and the degree of lateral dynamics of the ligand determines the area of adhered cells and focal adhesion formation (FIGS. 28A-D). Herein we compared GRGDS-terminated amphiphile 3 in combination with ethylene glycol (EG)-terminated amidine with either two or four EG repeats (Filler 1 and 2 respectively) to form stimuli-responsive layers. GRGDS-terminated amphiphile 3 was synthesised as described in the Supporting Information with the final step being the click coupling of the GRGDS 4 and the azide-terminated amidine fragment 5.

Influence of ligand presentation and density on fibroblast adhesion. The layers functionalized with GRGDS was immobilized by incubating MBA or MDSA SAMs in pH 8 HEPES buffer solution containing 50 µM of different mole fractions of GRGDS 3 in filler 1 or 2, $X_{GRGDS3}$=0-0.25 for 18 hrs. With the success incorporation of GRGDS 3 in the layers evidenced by the increase peak area ratio of the amide I (1680 cm$^{-1}$) to benzene $(C=C)_{1,4\ stretch}$ (1611 cm$^{-1}$) in the IRAS layer spectra, we evaluated the surfaces ability to regulate cell adhesive behaviour based on the mole fractions of GRGDS 3 in the assembling solution and the molecular length of filler. The coverage of adhered cells correlated with the increasing amount of GRGDS3 utilized for layer formation (FIGS. 28A-D) and conformed well with reported literature on cell adhesion on RGD functionalized SLBs. It is important to note that surface coverage on rSAMs with filler 2 assembled on MDSA-SAMs did not follow the same trend. With careful quantification of the average projected cell area using actin-stained cell, the average projected cell area is ca. 1.3 times larger on $X_{GRGDS3,filler2}$=0 (1634 µm$^2$) as compared to at $X_{GRGDS3,filler2}$=0.1 (1183 µm$^2$) or 0.25 (1282 µm$^2$) (FIG. 2B). Normalizing the results based on the average projected cell area, cells adhered on $X_{GRGDS3,filler2}$=0 would have 12% surface coverage, which is lower as compared to the cells adhered on $X_{GRGDS3,filler2}$=0.1 and 0.25. To determine that the increased cell adhesion was induced by specific interactions between the GRGDS peptide on GRGDS 3 with the integrins on the cells, the adhered cells on $X_{GRGDS3,filler2}$=0.25 surface were exposed to 100 µM GRGDS 4. After 2 hrs, a 50% decrease in average projected cell area (FIG. 28D) strongly suggested that the incorporation of GRGDS 3 introduce specific RGD-integrin mediated cell adhesion.

Influence of lateral dynamics on fibroblast morphology. In view of quantifying the average projected cell area and cell shape of the adhered cells, the cells adhered on the surfaces were rinsed and stained with FITC-phalloidin to visualize the F-actin structure. As our previous reports, one of the outstanding feature of rSAMs is its long-range lateral fluidity, akin to lipid bilayers. On the rSAMs on MBA-SAMs, the adhered fibroblasts consistently presented larger average projected cell area regardless of filler length and density of GRGDS 3 (FIG. 30A, FIG. 33). In view of controlling the lateral mobility of rSAMs and confirm the interplay of lateral dynamics on cell morphology, GRGDS 3 with either filler 1 or 2 were immobilized at the same conditions as above on MDSA SAMs. Sulfonic acid terminated SAMs featured lower pKa (−2.6), these SAMs presumably anchor the benzamidine amphiphiles tighter than MBA-SAMs and decreases the mobility of the amphiphiles. As the adhesion strength between the ligands and receptors correlates with binding affinity, the MBA and MDSA-SAMs were titrated with filler 2 via in situ ellipsometry to obtain the dissociation constant, $K_D$ of the benzamidine anchor towards the oxoacids on the surface (FIGS. 29A-29C). Fitting the binding isotherm with a Hill equation, the resulting binding affinity of filler 2 towards MBA ($2.1\times10^{-6}$) was one order of magnitude lower than MDSA ($2.3\times10^{-7}$).

Examination of the actin-stained cells on the rSAMs on MDSA SAMs confirmed these findings with distinct differences in cell morphology, as compared to the cells on the rSAMs assembled on MBA SAMs (FIGS. 30 and 33). These adhered cells on the rSAMs on MDSA SAMs had a decrease in average projected cell area. In the absence of the GRGDS 3 in the layer, the average projected cell area is sensitive to the length of ethylene glycol of the filler. For instance, filler 1 on MDSA demonstrated a 28% reduction in average projected cell area as compared to filler 1 assembled on MBA-SAMs, whereas filler 2 illustrated no significant differences between the two layers (FIG. 30 B,C and FIG. 33).

With the inclusion of GRGDS 3 in the rSAMs, the choice of oxoacid on the SAM, the type of filler used and the GRGDS 3 density influenced the average projected cell area. For example, with filler 1, no distinct differences was observed with the cells adhered on rSAMs with different GRGDS density on MDSA SAMs, whereas an increase in average projected cell area was observed at $X_{GRGDS3}=0.25$ on MBA SAMs as compared to the surface without GRGDS3 (FIG. 31B). With filler 2, there is no distinct differences between the cells adhered on rSAMs of different GRGDS density on MBA SAMs, whereas a decrease in average projected cell area was observed at $X_{GRGDS3}=0.1$ and 0.25 on MDSA SAMs as compared to the surface without GRGDS 3 (FIG. 31C).

Despite the contradicting results obtained between the relationship of cell morphology and lateral mobility in published literature, these observations coincide well with the report by Kocer et. al. demonstrating a 50% increase in average adhered human MSC (hMSC) area on the RGD functionalized DOPC SLBs as compared to the less mobile DPPC. All in all, it can be concluded that rSAMs with its tunable surface dynamics can be used as an alternative to SLBs for modulating and studying cell behaviour.

Reversible cell adhesion via molecular exchange. We then check the potential of the rSAMs to reverse cell adhesion. After adding 100 µM filler 2 in the medium to the adhered cells of $X_{GRGDS3,filler2}=0.25$ on MBA SAMs, a dramatic transition from a spread-out cell shape to a non-adhesive round shape (65% reduction in average projected cell area and increase in circularity of the cells) was clearly observed after incubation at 37° C. for 30 minutes (FIGS. 31A-D). Whereas, if the adhered cells were incubated with 100 µM L-Arginine, chosen in view of the similarity between the guanidine functionality to the amidine, most of the cells remained the spread-out shape after 30 minutes. Most striking was after replacing the filler 2 exposed cell culture medium with fresh medium and incubation at 37° C. for 24 hrs, the filler 2 exposed cells retain their adhesive characteristic (FIG. 34). Both of these observations indicate the suitability of rSAMs to reverse cell adhesion in a non-invasive manner.

Here it has been demonstrated the simple fabrication of dynamic lipid bilayer-like monolayers with tunable lateral dynamics and dynamic control over surface composition for modulating cell adhesion behaviour. Combined with the possibility of controlling viscosity of rSAMs with the variation in chain length of the amphiphiles, rSAMs would be an interesting platform for studying the effect of both adhesive force and viscosity on cell adhesion and differentiation. Coupled with its inherent controllable surface dynamics for cell release, rSAMs would have important implications as biomaterials for tissue engineering and regenerative medicine.

EXPERIMENTAL

Preparation of amphiphiles. Filler 1 and 2 were synthesized as previously reported. Synthesis of GRGDS 3 is described in the supporting information. 2.5 mM amphiphile stock solutions were prepared in 5% ethanolic pH 8 HEPES buffer.

Preparation of GRGDS3 in filler 1 or 2, $X_{GRGDS3}$ well plates. Gold-coated 24 well cell culture plates were prepared as previously reported. The freshly coated plates were incubated immediately with 1 mM MBA in 5% acetic acid ethanol solution for at least 24 hrs, in the dark, at room temperature. The surfaces were then rinsed with ethanol, sonicated with ethanol, rinsed with ethanol, dried under a nitrogen stream and stored in N2, in the dark. Prior to cell culture studies, the MBA modified surfaces were immersed into pH 8 HEPES buffer solution (0.01 M) containing the corresponding 50 µM GRGDS 3 in filler 1 or 2, $X_{GRGDS3}$ at ambient conditions for 12-18 hrs. The amphiphilic solution was then discarded and the wells were rinsed with pH 8 HEPES buffer 3 times.

Assay for cell attachment. MC3T3-E1 cells were cultured as previously reported. MC3T3-E1 cells were seeded onto the surfaces prepare above at a density of $1\times10^4$ cells/cm$^2$, and cultured at 37° C. under a humidified atmosphere of 5% $CO_2$ for 5 hours. For cell detachment experiments, 100 µM of the corresponding compound was added to the wells and incubated at the same conditions as above. Cell morphology was recorded under a microscope equipped with a digital camera at different time intervals.

For the staining of cells, the culture medium was removed after each experiment and the samples were washed with PBS and then fixed using a 4% paraformaldehyde and 1 mM $CaCl_2$) solution in PBS. After 30 minutes the slides were washed 2 times with PBS and incubated for minutes with 0.4% triton-X and 1 mM $CaCl_2$) in PBS at room temperature and washed two times with PBS. Subsequently, the cells were stained with FITC-phalloidin (for staining F-actin 10 stress fibers) for 1.5 hours. After staining, the samples were washed three times with PBS and examined under a fluorescence microscope.

Statistical Analysis. Cell culture experiments were based on minimum 3 independent seeding experiments. Average projected cell area and circularity were quantified by analysing a minimum of 100 cells. In all figures, the values are given as mean±SEM. Statistical analyses were performed using GraphPad Prism 7.0. For normally distributed data with equal variances, one-way ANOVA with Tukey's multiple comparison test was used. A p value<0.05 was considered significant.

Synthesis of GRGDS-Terminated Amidine 3

GRGDS-terminated amidine 3. GRGDS-terminated amidine 3 was synthesized from GRGDS 4 and azide-terminated amidine 5 based on a modified protocol as previously reported.[1] Amidine azide precursor 5 (20 mg, 0.036 mmol, 1 eq), GRGDS 4 (19 mg, 0.04 mmol, 1 eq), sodium ascorbate (21 mg, 0.1 mmol, 3 eq) and copper (II) sulphate (5 mg, 0.02 mmol, 0.6 eq) in water/2-butanol/MeOH (1:2:1, 1 mL) was sonicated and stirred at room temperature for 4 hrs. The reaction mixture was concentrated in vacuo and purified using C18 prep chromatography. The purified fractions were then concentrated in vacuo at 30° C. and the residual water was lyophilized to give the TFA salt of sialic acid terminated amphiphile 2 as an amorphous white powder (18 mg, 54%).

HPLC (C-18 column, mobile phase: 10%-90% ACN (0.1% TFA) in water (0.1% TFA) (0-15 mins)): k=4.3.
$^1$H-NMR (400 MHZ, CD$_3$OD) δ 8.41 (s, 1H), 7.77 (d, J=8.9 Hz, 2H), 7.11 (dd, J=7.7, 2.8 Hz, 4H), 6.80 (d, J=8.7 Hz, 2H), 4.62-4.57 (m, 2H), 4.47 (t, J=4.1 Hz, 1H), 4.39 (dd, J=7.7, 5.7 Hz, 1H), 4.09 (dd, J=8.8, 4.1 Hz, 4H), 3.92 (t, J=6.5 Hz, 4H), 3.64-3.54 (m, 7H), 3.20 (s, 2H), 2.88 (dd, J=17.2, 5.9 Hz, 1H), 2.77 (t, J=6.9 Hz, 3H), 1.94 (s, 1H), 1.87-1.63 (m, 8H). LRMS (m/z): [(M+2H)/2]$^+$ calcd for $C_{49}H_{75}N_{13}O_{14}{}^{2+}$, 535, found 535; $[(M+H)]^+$ calcd for $C_{49}H_{74}N_{13}O_{14}{}^{2+}$, 1069, found 1069.

What is claimed is:

1. Lipid bilayer mimic comprising self-assembled Bola-form amphiphiles on a surface, wherein the amphiphile comprises a hydrocarbon chain with hydrophilic end-groups at both the termini consisting of the α- and ω-ends, wherein the Bola-form amphiphile is an α-(4-amidinophenoxy)-ω-(3- or 4-substituted phenoxy) alkane.

2. Lipid bilayer mimic according to claim 1, wherein the hydrocarbon chain contains a number of carbons between 2 and 16.

3. Lipid bilayer mimic according to claim 1, wherein the Bola-form amphiphile has a spacer comprising from 1 through 5 repeating units of ethylene glycol.

4. Lipid bilayer mimic according to claim 1, wherein the terminus at the ω-end of the Bola-form amphiphile is a ligand selected from the group consisting of a monosaccharide, disaccharide, biotin, glycan, and peptide or the terminal ω-end is a neuramididase inhibitor group.

5. Kit of parts comprising:
   a. the lipid bilayer mimic according to claim 4;
   b. streptavidine;
   c. biotinylated antibody or biotinylated antibodies; and
   d. optionally a surface.

6. Lipid bilayer mimic according to claim 1, wherein the Bola-form amphiphile or amphiphiles are reversably bound to the surface by polar pH dependent interactions between cationic groups of the Bola-form amphiphile and anionic groups of the surface.

7. Lipid bilayer mimic according to claim 1, wherein the self-assembled Bola-form amphiphiles are comprising one single amphiphile, or a mixture of two or more amphiphiles.

8. Lipid bilayer mimic according to claim 1, wherein the surface comprises curved surfaces, of gold, silver, glass, or quartz surfaces, in the form of porous surfaces or in the form of micro or nanoparticles.

9. Lipid bilayer mimic according to claim 8 wherein the surface comprises gold coated with a self-assembled monolayer selected from the group consisting of mercaptobenzoic acid (MBA), mercaptohexadecanoic acid (MHA), and mercaptoundecane sulfonic acid (MDSA).

10. The Bola-form amphiphile of claim 1 substituted at the ω-end with a group selected from the group consisting of:
    N-acetylneuraminic acid,
    N-glycolylneuraminic acid,
    disaccharide Siaα2-6GalNAc (Sialyl Tn),
    Siaα2,3-Galβ,
    Siaα2,6-Galβ,
    GlcA2SO$_3$-1,4-Glc2NSO$_3$,
    GlcA2SO$_3$-1,4-Glc2NSO$_3$6SO$_3$,
    Siaα 2-3Galβ 1-3GalNAc (Sialyl T),
    Siaα2,3-N-acetyllactosamine,
    Siaα2,6-N-acetyllactosamine,
    a peptide group containing the amino acid sequence RGD,
    a biotin-containing group,
    the neuramididase zanamivir,
    the neuramididase oseltamivir, and
    the neuramididase peramivir.

11. Lipid bilayer mimic according to claim 10, wherein the hydrophilic biotin end-group at the ω-end of the Bola-form amphiphile interacts with streptavidine, which in turn can further interact with a biotinylated antibody.

12. Lipid bilayer mimic according to claim 8 wherein the surface comprises glass or quartz coated with a self-assembled monolayer selected from the group consisting of silane functionalized benzoic acid, silane functionalized decanoic acid and silane functionalized hexadecanoic acid.

13. Method for detecting a target by using the lipid bilayer mimic according to claim 1, wherein the target is a biological target selected from the group consisting of proteins, any of the human serum albumins, prostate specific antigen, hemagglutinin, neuraminidase, saccharides, nucleic acids, microorganisms, including viruses, and bacteria, cells, including cancer cells and stem cells.

14. Method according to claim 13, wherein the detection is performed by at least one of the techniques selected from the group consisting of fluorescence measurements, optical techniques, ellipsometry, surface plasmon resonance, electrochemical techniques, and gravimetry.

15. Use of the lipid bilayer mimic according to claim 1 as an antibacterial or antiviral agent to inhibit pathogen adhesion or as a vaccine.

16. Use of the lipid bilayer mimic according to claim 1 as dynamic supports for glycans in glycan arrays, wherein the glycan arrays are used for surveillance of influenza strains, identification of biomarkers for cancer and infection, and profiling of immune responses to vaccine; in cell and tissue engineering; or to control the reversible adhesion of cells.

17. Sensor comprising the lipid bilayer mimic according to claim 1, to detect biological targets.

18. The lipid bilayer mimic of claim 1 wherein the Bol-form amphiphile is selected from the group consisting of:
    Amino(4-(10-(4-(2-hydroxyethyl)phenoxy)decyloxy) phenyl)methaniminium chloride;
    4-[10-(4-{2-[2-(2-Hydroxy-ethoxy)-ethoxy]-ethyl}-phenoxy)-decyloxy]-benzamidine;
    4-(10-{4-[2-(2-{2-[2-(2-Hydroxy-ethoxy)-ethoxy]-ethoxy}-ethoxy)-ethyl]-phenoxy}-decyloxy)-benzamidine;
    4-{10-[4-(2-{2-[2-(2-{2-[2-(2-Hydroxy-ethoxy)-ethoxy]-ethoxy}-ethoxy)-ethoxy]-ethoxy}-ethyl)-phenoxy]-decyloxy}-benzamidine;
    5-Acetylamino-2-[2-(1-{2-[2-(2-{4-[10-(4-carbamimidoyl-phenoxy)-decyloxy]-phenyl}-ethoxy)-ethoxy]-ethyl}-1H-[1,2,3]triazol-4-yl)-ethoxy]-4-hydroxy-6-(1,2,3-trihydroxy-propyl)-tetrahydro-pyran-2-carboxylic acid;
    A glycan group @ end substituted 5-Acetylamino-2-[2-(1-{2-[2-(2-{4-[10-(4-carbamimidoyl-phenoxy)-decyloxy]-phenyl}-ethoxy)-ethoxy]-ethyl}-1H-[1,2,3]triazol-4-yl)-ethoxy]-4-hydroxy-6-(1,2,3-trihydroxy-propyl)-tetrahydro-pyran-2-carboxylic acid;
    (2S,5S,11S)-16-(1-((2-(4-((10-(4-carbamimidoylphenoxy)-decyl)oxy)phenethoxy)ethoxy)methyl)-1H-1,2,3-triazol-4-yl)-5-(carboxymethyl)-11-(3-guanidinopropyl)-2-(hydroxymethyl)-4,7,10,15-tetraoxo-3,6,9,12,13-pentaazahepta dec-16-enoic acid;
    RGD ω end substituted (2S,5S,11S)-16-(1-((2-(4-((10-(4-carbamimidoylphenoxy)-decyl)oxy)phenethoxy)ethoxy)methyl)-1H-1,2,3-triazol-4-yl)-5-(carboxymethyl)-11-(3-guanidinopropyl)-2-(hydroxymethyl)-4,7,10,15-tetraoxo-3,6,9,12,13-pentaazahepta dec-16-enoic acid;
    5-(2-Oxo-hexahydro-thieno[3,4-d]imidazol-6-yl)-pentanoic acid 2-{4-[10-(4-carbamimidoyl-phenoxy)-decyloxy]-phenyl}-ethyl ester trifluoroacetate; and
    Biotin ω end substituted 5-(2-Oxo-hexahydro-thieno[3,4-d]imidazol-6-yl)-pentanoic acid 2-{4-[10-(4-carbamimidoyl-phenoxy)-decyloxy]-phenyl}-ethyl ester trifluoroacetate.

* * * * *